United States Patent [19]
Grimm et al.

[11] Patent Number: 6,132,967
[45] Date of Patent: *Oct. 17, 2000

[54] RIBOZYME TREATMENT OF DISEASES OR CONDITIONS RELATED TO LEVELS OF INTERCELLULAR ADHESION MOLECULE-1 (ICAM-1)

[75] Inventors: Susan Grimm; Dan T. Stinchcomb; James McSwiggen; Sean Sullivan; Kenneth G. Draper, all of Boulder, Colo.

[73] Assignee: Ribozyme Pharmaceuticals, Inc., Boulder, Colo.

[*] Notice: This patent is subject to a terminal disclaimer.

[21] Appl. No.: 09/071,845

[22] Filed: May 1, 1998

Related U.S. Application Data

[63] Continuation of application No. 08/292,620, Aug. 17, 1994, Pat. No. 5,837,542, which is a continuation-in-part of application No. 08/008,895, Jan. 19, 1993, abandoned, which is a continuation-in-part of application No. 07/989,849, Dec. 7, 1992, abandoned.

[51] Int. Cl.[7] .............. C12Q 1/68; C07H 21/04; C12N 15/63; C12N 15/85
[52] U.S. Cl. ............ 435/6; 435/91.31; 435/320.1; 435/325; 435/366; 536/23.1; 536/24.5
[58] Field of Search .............. 435/6, 91.31, 320.1, 435/375, 325, 366; 514/44; 536/23.1, 23.2, 24.34, 29.5

[56] References Cited

U.S. PATENT DOCUMENTS

| | | | |
|---|---|---|---|
| 4,987,071 | 1/1991 | Cech | 435/91.31 |
| 5,168,053 | 12/1992 | Altman et al. | 435/91.31 |
| 5,225,337 | 7/1993 | Robertson et al. | 435/91.1 |

FOREIGN PATENT DOCUMENTS

| | | |
|---|---|---|
| 0 519 463 | 12/1992 | European Pat. Off. . |
| 91/03162 | 3/1991 | WIPO . |
| 91/15580 | 7/1991 | WIPO . |
| 91/18624 | 12/1991 | WIPO . |
| 91/18625 | 12/1991 | WIPO . |
| 91/18913 | 12/1991 | WIPO . |
| 92/07065 | 4/1992 | WIPO . |
| 92/00080 | 9/1992 | WIPO . |
| 93/15187 | 8/1993 | WIPO . |
| 93/23569 | 11/1993 | WIPO . |
| 94/02595 | 2/1994 | WIPO . |

OTHER PUBLICATIONS

Branch TIBS 23:45–50, Feb. 1998.
Crooke, Chi "Antisense Research and Application", Springer, N.Y., pp. 1–50, 1998.
Altmann et al., "Cotransfection of ICAM–1 and HLA–DR reconstitutes human antigen–presenting cell function in mouse L cells," *Nature* 338:512–514 (1989).
Ballantyne et al., "Nucloetide sequence of the cDNA for murine intercellular adhesion molecule–1 (ICAM–1)," *Nucleic Acids Research* 17:5853 (1989).
Baringa, "Ribozymes: Killing the messenger," *Science* 262:1512–1514 (1993).
Bowes et al., "Monoclonal antibody to the ICAM–1 adhesion site reduces neurological damage in a rabbit cerebral embolism stroke model," *Experimental Neurology* 119:215–219 (1993).
Boyd et al., "Intercellular adhesion molecule 1 (ICAM–1) has a central role in cell–cell contact–mediated immune mechanisms," *Proc. Natl. Acad. Sci. USA* 85:3095–3099 (1988).
Cech, "Ribozymes and their medical implications," *JAMA* 260:3030–3034 (1988).
Chen et al., "Multitarget–ribozyme directed to cleave at up to nine highly conserved HIV–1 env RNA regions inhibits HIV–1 replication–potential effectiveness against most presently sequenced HIV–1 isolates," *Nucleic Acids Research* 20:4581–4589 (1992).
Chiang et al., "Antisense oligonucleotides inhibit intercellular adhesion molecule 1 expression by two distinct mechanisms," *J. Biol. Chem.* 27:18162–18171 (1991).
Chin et al., "Role of cytokines in inflammatory synovitis," *Arthritis and Rheumatism* 33:1776–1786 (1990).
Chowrira et al., "Extensive phosphorothioate substitution yields highly active and nuclease–resistant hairpin ribozymes," *Nucleic Acids Res.* 20:2835–2840 (1992).
Collins et al., "Reaction conditions and kinetics of self–cleavage of a ribozyme derived from Neurospora vs RNA," *Biochemistry* 32:2795–2799 (1993).
Cosimi, et al., "In vivo effects of monoclonal antibody to ICAM–1 (CD54) in nonhuman primates with renal allografts," *Journal of Immunology* 144:4604–4612 (1990).
Cotton, "The in vivo application of ribozymes," *TIBTECH* 8:174–178 (1990).
Dang et al., "Role of ICAM–1 in antigen presentation demonstrated by ICAM–1 defective mutants," *Journal of Immunology* 144:4082–4091 (1991).
Dropulic et al., "Functional characterization of a U5 ribozyme: Intracellular suppression of human immunodeficiency virus type I expression," *Journal of Virology* 66:1432–1441 (1992).
Dustin et al., "Induction IL 1 and interferon–γ: Tissue distribution. Biochemistry, and function of a natural adherence molecule (ICAM–1)," *Journal of Immunology* 137:245–254 (1986).
Dustin et al., "Lymphocyte function–associated antigen–1 (LFA–1) interaction with intercellular adhesion molecule–1 (ICAM–1) is one of at least three mechanisms for lymphocyte adhesion to cultured endothelial cells," *J. Cell. Biol.* 107:321–331 (1988).

(List continued on next page.)

*Primary Examiner*—David Guzo
*Assistant Examiner*—Andrew Wang
*Attorney, Agent, or Firm*—Brobeck, Phleger & Harrison LLP

[57] ABSTRACT

Enzymatic RNA molecules which cleave ICAM-1 mRNA.

24 Claims, 6 Drawing Sheets

OTHER PUBLICATIONS

Edgington, "Ribozymes: Stop making sense," *Biotechnology* 10:256–262 (1992).

Elroy–Stein et al., "Cytoplasmic expression system based on constitutive synthesis of bacteriophage T7RNA polymerase in mammalian cells," *Proc. Natl. Acad. Sci. USA* 87:6743–6747 (1990).

Flavin et al., "Monoclonal antibodies against intercellular adhesion molecule 1 prolong cardiac allograft survival in cynomolgus monkeys," *Transplantation Proceedings* 23:533–534 (1991).

Fung et al., WO 91/1580 (Oct. 17, 1991) provided as WPI Abstract. Acc. #91–32522344.

Furukawa et al, "Transient depletion of T cells with bright CD11a/CD18 expression from peripheral circulation during acute kawasaki disease," *Scand. J. Immunol.* 37:377–380 (1993).

Furukawa et al., "Increased levels of circulating intercellular adhesion molecule 1 in kawasaki disease," *Arthritis and Rheumatism* 35:672–677 (1992).

Gao et al., "Cytoplasmic expression of a reporter gene by co–delivery of T7 RNA polymerase and T7 promoter sequence with cationic liposomes," *Nucleic Acids Res.* 21:2867–2872 (1993).

Griffiths et al., "Characterization of intercellular adhesion molecule–1 and HLA–DR expression in normal and inflammed skin: Modulation by recombinant gamma interferon and tumor necrosis factor," *J. Am. Acad. Dermatol.* 20:617–629 (1989).

Guerrier–Takada et al., "The RNA moiety of ribonuclease P is the catalytic subunit of the enzyme," *Cell* 35:849–857 (1983).

Gundel et al., *Clin. Exp. Allergy* 22:569–575 (1992).

Hampel et al., "Hairpin catalytic RNA model: Evidence for helices and sequence requirement for substrate RNA," *Nucleic Acids Research* 18:299–304 (1990).

Hampel et al., "'Hairpin' catalytic RNA model: Evidence for helices and sequence requirement for substrate RNA," *Nucleic Acids Research* 18:299 (1990).

Hampel et al., "RNA catalytic properties of the minimum (–)sTRSV sequence," *Biochemistry* 28:4929–4933 (1989).

Haseloff et al., "Simple RNA enzymes with new and highly specific endoribonuclease activities," *Nature* 334:585–591 (1988).

Haug et al., "A phase I trial of immunosuppression with anit–ICAM–1 (CD54) mAb in renal allograft recipients," *Transplantation* 55:766–773 (1993).

Hertel et al., "Numbering system for the hammerhead," *Nucleic Acids Res.* 20:3252 (1992).

Hession et al., WO 90/13300 (Nov. 15, 1990) provided as CA Abstr. Acc. #114(25): 292037g.

Jaeger et al., "Improved predictions of secondary structures for RNA," *Proc. Natl. Acad. Sci. USA* 86:7706–7710 (1989).

Jeffries et al., "A catalytic 13–mer ribozyme," *Nucleic Acids Research* 17:1371–1377 (1989).

Johnston et al., "Present status and future prospects for HIV therapies," Science 260:1286–1293 (1993).

Kakimoto et al., "The effect of anti–adhesion molecule antibody on the development of collagen–induced arthritis," *Cellular Immunology* 142:326–337 (1992).

Kashani–Sabet et al., "Reversal of the malignant phenotype by an anti–ras ribozyme," *Antisense Research & Development* 2:3–15 (1992).

Kellner et al., "Overexpression of extracellular matrix receptors (VLA–3, 5 and 6) on psoriatic keratinocytes," *British Journal of Dermatology* 125:211–216 (1991).

Kim et al., *Proc. Natl. Acad. Sci. USA* 84:8788 (1987).

Kita et al., "Sequence and expression of rat ICAM–1," *Biochem Biophys. Acta* 1131:108–110 (1992).

Koch et al., "Immunolocalization of endothelial and leukocyte adhesion molecules in human rheumatoid and osteoarthritic synovial tissue," *Laboratory Investigation* 64:313–320 (1991).

L'Huiller et al., "Cytomplasmic delivery of ribozymes leads to efficient reduction in α–lactalbumin mRNA levels in C1271 mouse," *EMBO J.* 11:4411–4418 (1992).

Leung et al., "Endothelial call activation and high interleukin–1 secretion in the pathogenesis of acute kawasaki disease," *The Lancet* 2:1298–1302 (1989).

Lieber et al., "Stable high–level gene expression in mammalian cells by T7 phage RNA polymerase," *Methods Enzymol.* 217:47–66 (1993).

Ligo et al., "ICAM–1 dependent pathway is critically involved in the pathogenesis of adjuvant arthritis in rats," *Journal of Immunology* 147:4167–4171 (1991).

Lisziewicz et al., "Inhibition of human immunodeficiency virus type I replication by regulated expression of a polymeric tat activation response RNA decoy as a strategy for gene therapy in AIDS," *Proc. Natl. Acad. Sci. USA* 90:8000–8004 (1993).

Ma et al., "Coronary endothelial and cardiac protective effects of a monoclonal antibody to intercellular adhesion molecule–1 in myocardial ischemia and reperfusion," *Circulation* 86:937–946 (1992).

Mamone et al., "Design of hammerhead ribozymes targeted to sequences in HIV, HSV and the RAT ANF gene," Abstract of Keystone, CO (May 27, 1992).

Mason et al., "Detection of increased levels of circulating intercellular adhesion molecule 1 in some patients with rheumatoid arthritis but not in patients with systemic lupus erythematosus," *Arthritis and Rheumatism* 36:519–527 (1993).

Nabel et al., "Site–specific gene expression in vivo by direct gene transfer into the arterial wall," *Science* 249:1285–1288 (1990).

Nickeloff et al., "Accessory cell function of keratinocytes for superantigens," *Journal of Immunology* 150:2148–2159 (1993).

Ohkawa et al., "Activities of HIV–RNA targeted ribozymes transcribed from a 'shot–gun' type ribozyme–trimming plasmid," *Nucleic Acids Symp. Ser.* 27:15–16 (1992).

Ojwang et al., "Inhibition of human immunodeficiency virus type 1 expression by a hairpin ribozyme," *Proc. Natl. Acad. Sci. USA* 89:10802–10806 (1992).

Pavco et al., "Regulation of self–splicing reactions by antisense RNA," Abstract of Keystone, CO (May 27, 1992).

Perrault et al., "Mixed deoxyribo–and ribo–oligonucleotides with catalytic activity," *Nature* 344:565–567 (1990).

Perrotta et al., "Cleavage of oligoribonucleotides by a ribozyme derived from the hepatitis δ virus RNA sequence," *Biochemistry* 31:16–21 (1992).

Pieken et al., "Kinetic characterization of ribonuclease–resistant 2'–modified hammerhead ribozymes," *Science* 253;314–317 (1991).

Rossi et al., "Ribozyme mediated intracellular immunity to HIV–1 in CD4," *J. Cell Biochem.* Suppl 14A:D428 (1990).

Rossi et al., "Ribozymes as Anti–HIV–1 therapeutic agents: principles, applications, and problems," *AIDS research and human retroviruses* 8:183 (1992).

Rothlein et al., "Induction of intercellular adhesion molecule 1 on primary and continuous cell lines by pro–inflammatory cytokines," *Journal of Immunology* 141:1665–1669 (1988).

Sarver et al., "Ribozymes as potential Anti–HIV–1 therapeutic agents," *Science* 247:1222–1225 (1990).

Saville et al., "RNA–mediated ligation of self–cleavage products of a Neurospora Mitochondrial plasmid transcript," *Proc. Natl. Acad, Sci. USA* 88:8826–8830 (1991).

Saville et al., "A site–specific self–cleavage reaction performed by a novel RNA in neurospora mitochondria," *Cell* 61:685–696 (1990).

Scanlon et al., "Ribozyme–mediated cleavage of c–fos mRNA reduces gene expression of DNA synthesis enzymes and metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl. Acids Res.* 18:5433–5441 (1990).

Schopf et al., "Soluble intercellular adhesion molecule–1 levels in patients with psoriasis," *British Journal of Dermatology* 128:34–37 (1993).

Simmons et al., "ICAM, an adhesion ligand of LFA–1, is homologous to the neural cell adhesion molecule NCAM," *Nature* 331:624–627 (1988).

Sioud et al., *J. Mol. Biol.* 223:831–835 (1992).

Springer et al., "The lymphocyte function–associated LFA–1, CD2, and LFA–3 molecules: Cell adhesion receptors of the immune system," *Ann. Rev. Immunol.* 5:223–252 (1987).

Stull et al., "Antigene, Ribozyme and Aptamer Nucleic Acid Drugs: Progress and Prospects," *Pharmaceutical Research* 12:465–483 (1995).

Taira et al., "Construction of a novel RNA–transcript–trimming plasmid which can be used both in vitro in place of run–off and (G)–free transcriptions in vivo as multisequences transcription vectors," *Nucleic Acids Res.* 19:5125–5130 (1991).

Tanabe et al., J. Biol. Chem. 262:16580 (1987),.provided as BIOSIS Abstr. 85047487.

Tsuji et al., "Soluble intercellular adhesion molecule–1 levels in sera of patients with kawasaki disease," *Arerugi* 41:1507–1514 (1992) (Japanese document with English Abstract).

Uhlenbeck, "A small catalytic oligoribonucleotide," *Nature* 328:596–600 (1987).

Usman et al., "Automated chemical synthesis of long oligoribonucleotides using 2'–O–silylated ribonucleoside 3'–O–phosphoramidtes on a controlled–pore glass support: Synthesis of a 43–nucleotide sequence similar to the 3'–half molecule of an *Escherichia coli* formylmethoionine tRNA," *J. Am. Chem. Soc.* 109:7845–7854 (1987).

Usman et al., "Exploiting the chemical synthesis of RNA," *TIBS* 17:334–339 (1992).

Ventura et al., "Activation of HIV–specific ribozyme activity by self–cleavage," *Nucleic Acids Research* 21:3249–3255 (1993).

Weerasinghe et al., "Resistance to human immunodeficiency virus type 1 (HIV–1) infection in human $CD4^+$ lymphocyte–derived cell lines conferred by using retroviral vectors expressing an HIV–1 RNA–specific ribozyme," *Journal of Virology* 65:5531–5534 (1994).

Wegner et al., "Intercellular adhesion molecule–1 (ICAM–1) in the pathogenesis of asthma," *Science* 247:456–458 (1990).

Willard et al., "Recombinant adenovirus in an efficient vector for in vivo gene transfer and can be preferentially directed at vascular endothelium or smooth muscle cells," *Circulation–Abstracts from the 6th Scientific Sessions,* New Orleans Convention Center, New Orleans, Louisana, Nov. 16–19, 1992, 86:I–473 at 1880.

Woolf et al., "Specificity of antisense oligonucleotides in vivo," *Proc. Natl. Acad. SCi. USA* 89:7305–7309 (1992).

Yoshida et al., "Anoxia/reoxygenation–induced neotrophil adherence to cultured endothelial cells," *Am. J. Physiol.* 262:H1891–H1898 (1992).

Yu et al., "A hairpin ribozyme inhibits expression of diverse strains of human immunodeficiency virus type 1," *Proc. Natl. Acad. Sci. USA* 90:6340–6344 (1993).

Zaug et al., "The tetrahymena ribozyme acts like an RNA restriction endonuclease," Nature 324:429–434 (1986).

Zhou et al., "Synthesis of functional mRNA in mammalian cells by bacteriophage T3 RNA polymerase," *Mol. Cell. Biol.* 10:4259–4537 (1990).

HAMMERHEAD RIBOZYME SUBSTRATE MOTIFS a b c d

HEPATITIS DELTA VIRUS RIBOZYME

NEUROSPORA VS RNA ENZYME

RNase H Assay

- Body-labeled transcript (not purified)
- DNA oligo (10 nM, 100 nM and 1000 nM)
- RNAse H (0.08 -1.0 u/μl)
- 37°C, 10 min

RIBOZYME TREATMENT OF DISEASES OR CONDITIONS RELATED TO LEVELS OF INTERCELLULAR ADHESION MOLECULE-1 (ICAM-1)

RELATED APPLICATIONS

This Application is a continuation of U.S. Ser. No. 08/292,620, filed Aug. 17, 1994, now U.S. Pat. No. 5,837,542, which is a continuation-in-part of U.S. Ser. No. 08/008,895, filed Jan. 19, 1993 now abandoned, which is a continuation-in-part of U.S. Ser. No. 07/989,849, filed Dec. 7, 1992, now abandoned, the entirety of each of these prior applications, including the drawings, are hereby incorporated by reference herein.

FIELD OF THE INVENTION

The present invention relates to therapeutic compositions and methods for the treatment or diagnosis of diseases or conditions related to ICAM-1 levels, such as transplant rejection, cancer, rheumatoid arthritis, asthma, reperfusion injury, and inflammatory or autoimmune disorders. For example, such treatments will be useful for transplant rejection, myocardial ischemia, stroke, psoriasis, and Kawasaki disease.

BACKGROUND OF THE INVENTION

The following is a brief description of the physiological role of ICAM-1. The discussion is not meant to be complete and is provided only for understanding of the invention that follows. This summary is not an admission that any of the work described below is prior art to the claimed invention.

Intercellular adhesion molecule-1 (ICAM-1) is a cell surface protein whose expression is induced by inflammatory mediators. ICAM-1 is required for adhesion of leukocytes to endothelial cells and for several immunological functions including antigen presentation, immunoglobulin production and cytotoxic cell activity. Blocking ICAM-1 function prevents immune cell recognition and activity during transplant rejection and in animal models of rheumatoid arthritis, asthma and reperfusion injury.

Cell—cell adhesion plays a pivotal role in inflammatory and immune responses (Springer et al., 1987 Ann. Rev. Immunol. 5, 223–252). Cell adhesion is required for leukocytes to bind to and migrate through vascular endothelial cells. In addition, cell—cell adhesion is required for antigen presentation to T cells, for B cell induction by T cells, as well as for the cytotoxicity activity of T cells, NK cells, monocytes or granulocytes. Intercellular adhesion molecule-1 (ICAM-1) is a 110 kilodalton member of the immunoglobulin superfamily that is involved in all of these cell—cell interactions (Simmons et al., 1988 Nature (London) 331, 624–627).

ICAM-1 is expressed on only a limited number of cells and at low levels in the absence of stimulation (Dustin et al., 1986 J. Immunol. 137, 245–254). Upon treatment with a number of inflammatory mediators (lipopolysaccharide, γ-interferon, tumor necrosis factor-α, or interleukin-1), a variety of cell types (endothelial, epithelial, fibroblastic and hematopoietic cells) in a variety of tissues express high levels of ICAM-1 on their surface (Sringer et. al. supra; Dustin et al., supra; and Rothlein et al., 1988 J. Immunol. 141, 1665–1669). Induction occurs via increased transcription of ICAM-1 mRNA (Simmons et al., supra). Elevated expression is detectable after 4 hours and peaks after 16–24 hours of induction.

ICAM-1 induction is critical for a number of inflammatory and immune responses. In vitro, antibodies to ICAM-1 block adhesion of leukocytes to cytokine-activated endothelial cells (Boyd, 1988 Proc. Natl. Acad. Sci. USA 85, 3095–3099; Dustin and Springer, 1988 J. Cell Biol. 107, 321–331). Thus, ICAM-1 expression may be required for the extravasation of immune cells to sites of inflammation. Antibodies to ICAM-1 also block T cell killing, mixed lymphocyte reactions, and T cell-mediated B cell differentiation, suggesting that ICAM-1 is required for these cognate cell interactions (Boyd et al., supra). The importance of ICAM-1 in antigen presentation is underscored by the inability of ICAM-1 defective murine B cell mutants to stimulate antigen-dependent T cell proliferation (Dang et al., 1990 J. Immunol. 144, 4082–4091). Conversely, murine L cells require transfection with human ICAM-1 in addition to HLA-DR in order to present antigen to human T cells (Altmann et al., 1989 Nature (London) 338, 512–514). In summary, evidence in vitro indicates that ICAM-1 is required for cell—cell interactions critical to inflammatory responses, cellular immune responses, and humoral antibody responses.

SUMMARY OF THE INVENTION

This invention relates to ribozymes, or enzymatic RNA molecules, directed to cleave mRNA species encoding ICAM-1. In particular, applicant describes the selection and function of ribozymes capable of cleaving this RNA and their use to reduce levels of ICAM-1 in various tissues to treat the diseases discussed herein. Such ribozymes are also useful for diagnostic uses.

Ribozymes that cleave ICAM-1 mRNA represent a novel therapeutic approach to inflammatory or autoimmune disorders. ICAM-1 function can be blocked therapeutically using monoclonal antibodies. Ribozymes have the advantage of being generally immunologically inert, whereas significant neutralizing anti-IgG responses can be observed with some monoclonal antibody treatments. Antisense DNA molecules have been described that block ICAM-1 expression (Chiang et al., 1991 J. Biol. Chem. 266, 18162–18171). However, ribozymes may show greater perdurance or lower effective doses than antisense molecules due to their catalytic properties and their inherent secondary and tertiary structures. Such ribozymes, with their catalytic activity and increased site specificity (as described below), represent more potent and safe therapeutic molecules than antisense oligonucleotides.

Applicant indicates that these ribozymes are able to inhibit expression of ICAM-1 and that the catalytic activity of the ribozymes is required for their inhibitory effect. Those of ordinary skill in the art, will find that it is clear from the examples described that other ribozymes that cleave target ICAM-1 encoding mRNAs may be readily designed and are within the invention.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992 *Proc. Natl. Acad. Sci. USA,* 89, 7305–7309). Thus, the specificity of action of a ribozyme is greater than that of an antisense oligonucleotide binding the same RNA site.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence). Examples of such hammerhead motifs are described by Rossi et al., 1992 *Aids Research and Human Retroviruses,* 8, 183, of hairpin motifs by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, 1989 *Biochemistry,* 28, 4929 and Hampel et al., 1990 *Nucleic Acids Res.earch* 18, 299, and an example of the hepatitis delta virus motif is described by Perrotta and Been, 1992, *Biochemistry* 31, 16, of the RNaseP motif by Guerrier-Takada et al., 1983 *Cell* 35, 849, of the Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

The invention provides a method for producing a class of enzymatic cleaving agents which exhibit a high degree of specificity for the RNA of a desired target. The enzymatic nucleic acid molecule is preferably targeted to a highly conserved sequence region of a target ICAM-1 encoding mRNA such that specific treatment of a disease or condition can be provided with either one or several enzymatic nucleic acids. Such enzymatic nucleic acid molecules can be delivered exogenously to specific cells as required. Alternatively, the ribozymes can be expressed from DNA vectors that are delivered to specific cells.

Synthesis of nucleic acids greater than 100 nucleotides in length is difficult using automated methods, and the therapeutic cost of such molecules is prohibitive. In this invention, small enzymatic nucleic acid motifs. (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eukaryotic promoters (e.g., Scanlon et al., 1991 *Proc. Natl. Acad. Sci. USA,* 88, 10591–5; Kashani-Sabet et al., 1992 *Antisense Res. Dev.* 2, 3–15; Dropulic et al., 1992 *J Virol.* 66, 1432–41; Weerasinghe et al., 1991 *J Virol.* 65, 5531–5534; Ojwang et al., 1992 *Proc. Natl. Acad. Sci. USA,* 89, 10802–10806; Chen et al., 1992 *Nucleic Acids Res.,* 20, 4581–1589; Sarver et al., 1990 *Science,* 247, 1222–1225). Those skilled in the art realize that any ribozyme can be expressed in eukaryotic cells from the appropriate DNA vector. The activity of such ribozymes can be augmented by their release from the primary transcript by a second ribozyme (Draper et al., PCT WO93/23569, and Sullivan et al., PCT WO94/02595, both hereby incorporated in their totality by reference herein; Ohkawa et al., 1992, *Nucleic Acids Symp. Ser.,* 27, 15–6; Taira et al., 1991 *Nucleic Acids Res.,* 19, 5125–5130; Ventura et al., 1993 *Nucleic Acids Res.,* 21, 3249–55).

Thus, in a first aspect, the invention features ribozymes that inhibit ICAM-1 production. These chemically or enzymatically synthesized RNA molecules contain substrate binding domains that bind to accessible regions of their target mRNAs. The RNA molecules also contain domains that catalyze the cleavage of RNA. The RNA molecules are preferably ribozymes of the hammerhead or hairpin motif. Upon binding, the ribozymes cleave the target ICAM-1 encoding mRNAs, preventing translation and protein accumulation. In the absence of the expression of the target gene, a therapeutic effect may be observed.

By "inhibit" is meant that the activity or level of ICAM-1 encoding mRNA is reduced below that observed in the absense of the ribozyme, and preferably is below that level observed in the presence of an inactive RNA molecule able to bind to the same site on the mRNA, but unable to cleave that RNA.

Such ribozymes are useful for the prevention of the diseases and conditions discussed above, and any other diseases or conditions that are related to the level of ICAM-1 activity in a cell or tissue. By "related" is meant that the inhibition of ICAM-1 mRNA and thus reduction in the level of ICAM-1 will relieve to some extent the symptoms of the disease or condition.

Ribozymes are added directly, or can be complexed with cationic lipids, packaged within liposomes, or otherwise delivered to target cells. The RNA or RNA complexes can be locally administered to relevant tissues or cells ex vivo or in vivo by injection or through the use of a catheter, infusion pump or stent, with or without their incorporation in biopolymers. In preferred embodiments, the ribozymes have binding arms which are complementary to the sequences in Tables II, III, VI–IX. Examples of such ribozymes are shown in Tables IV–VIII and X. Examples of such ribozymes consist essentially of sequences defined in these Tables. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target molecules and inhibit ICAM-1 activity are expressed from transcription units inserted into DNA, RNA, or viral vectors. Preferably, the recombinant vectors capable of expressing the ribozymes are locally delivered as described above, and transiently persist in target cells. Once expressed, the ribozymes cleave the target mRNA. The recombinant vectors are preferably DNA plasmids or adenovirus vectors. However, other mammalian cell vectors that direct the expression of RNA may be used for this purpose.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

Figure 1:
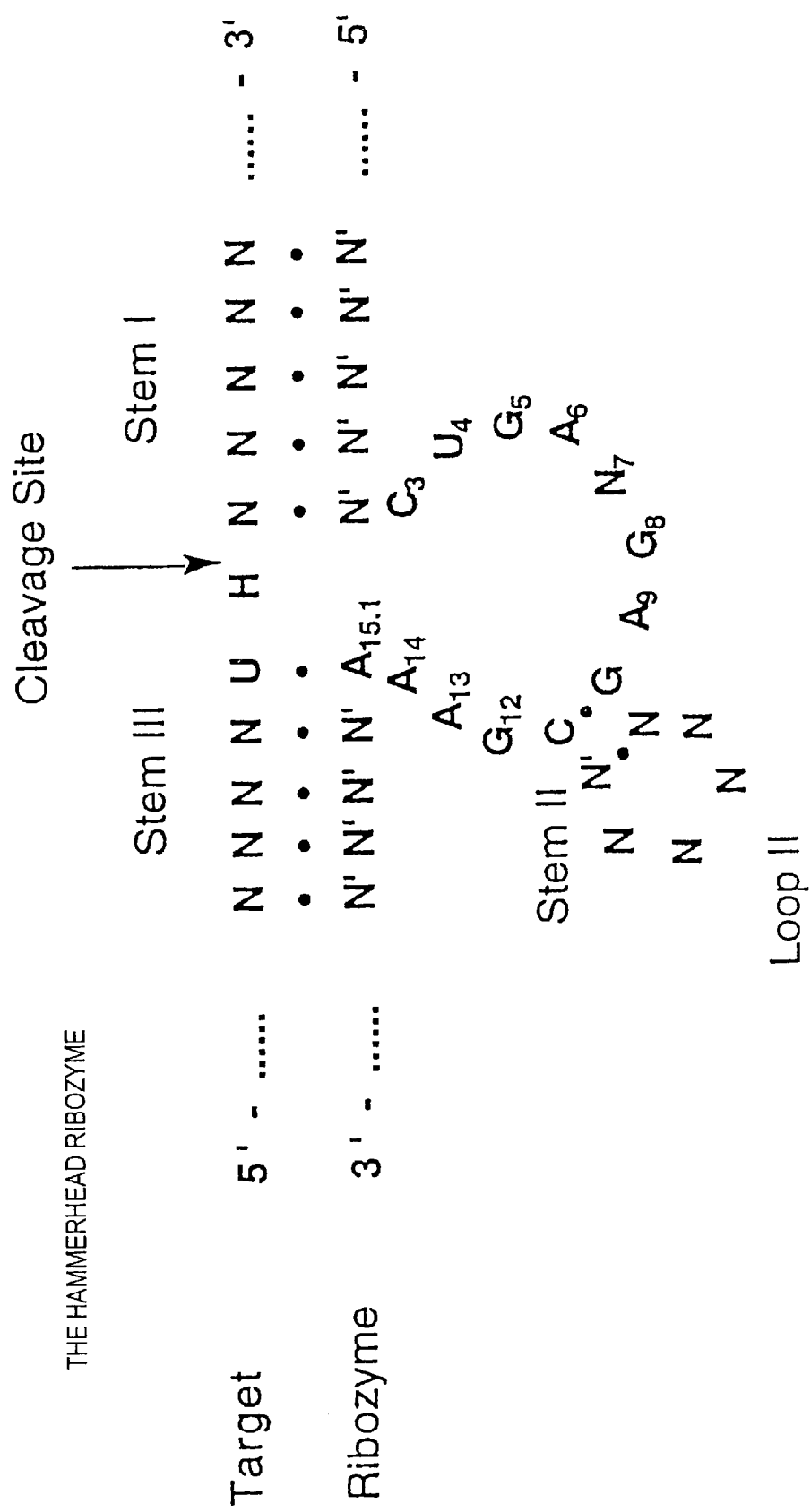
FIG. 1 is a diagrammatic representation of the hammerhead ribozyme domain known in the art.
Figure 2A:
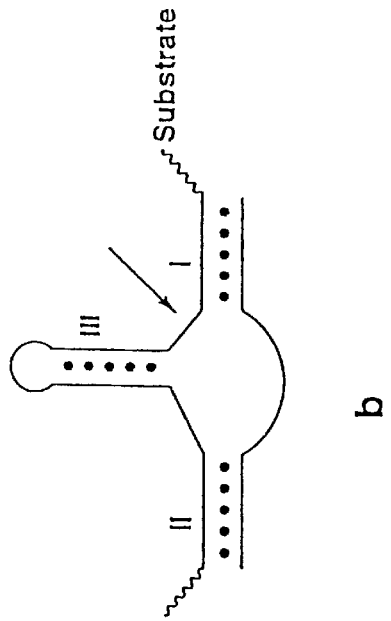
FIG. 2a is a diagrammatic representation of the hammerhead ribozyme domain known in the art.
Figure 2B:
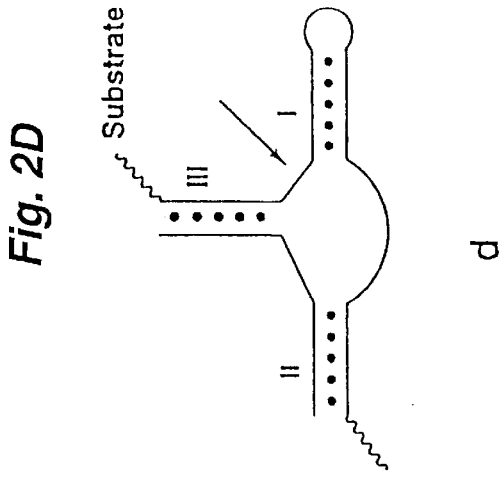
FIG. 2b is a diagrammatic representation of the hammerhead ribozyme as divided by Uhlenbeck (1987, Nature 327, 596–600) into a substrate and enzyme portion.
Figure 2C:
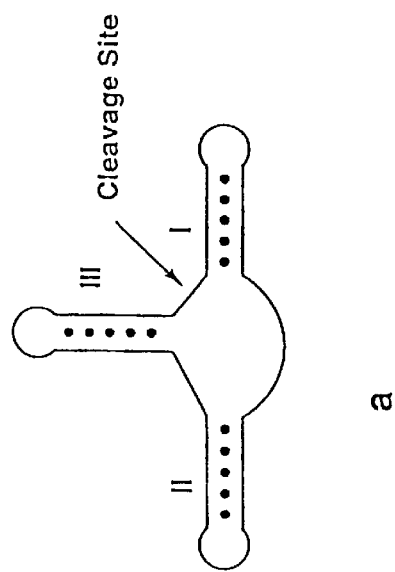
Figure 2D:
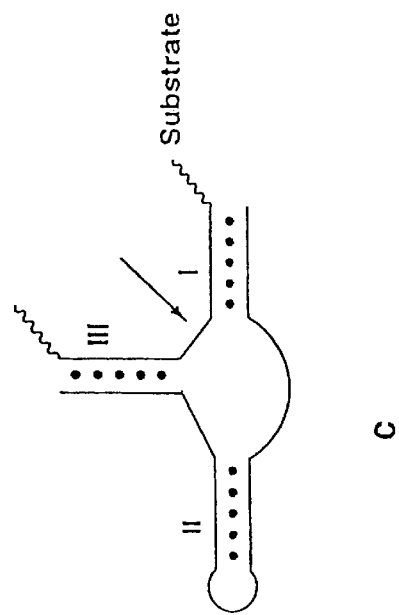

FIG. 2c is a similar diagram showing the hammerhead divided by Haseloff and Gerlach (1988, Nature 334, 585–591) into two portions; and FIG. 2d is a similar diagram showing the hammerhead divided by Jeffries and Symons (1989, Nucl. Acids. Res. 17, 1371–1371) into two portions.

Figure 3:
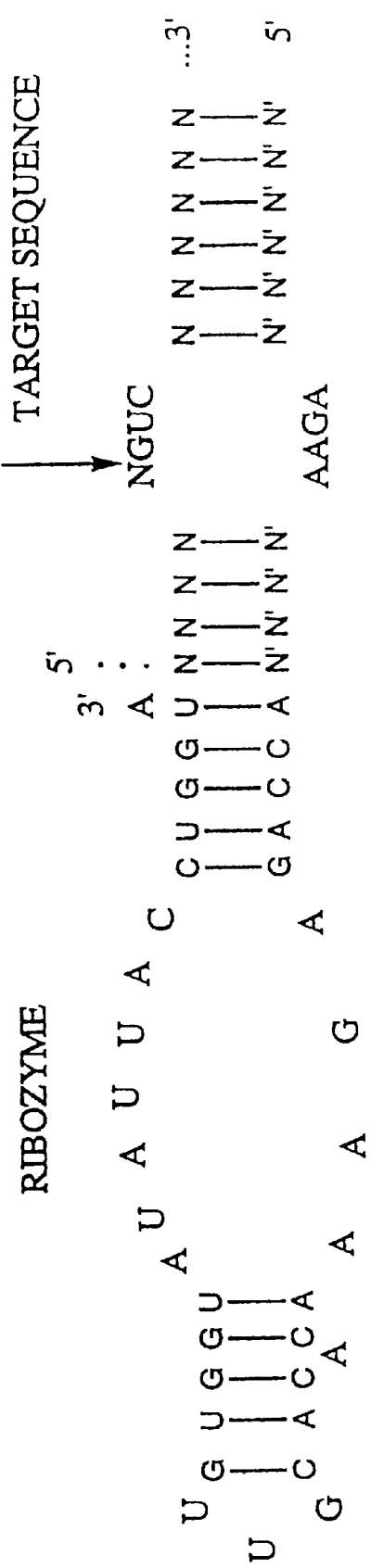

FIG. 3 is a representation of the general structure of the hairpin ribozyme domain known in the art.

Figure 4:
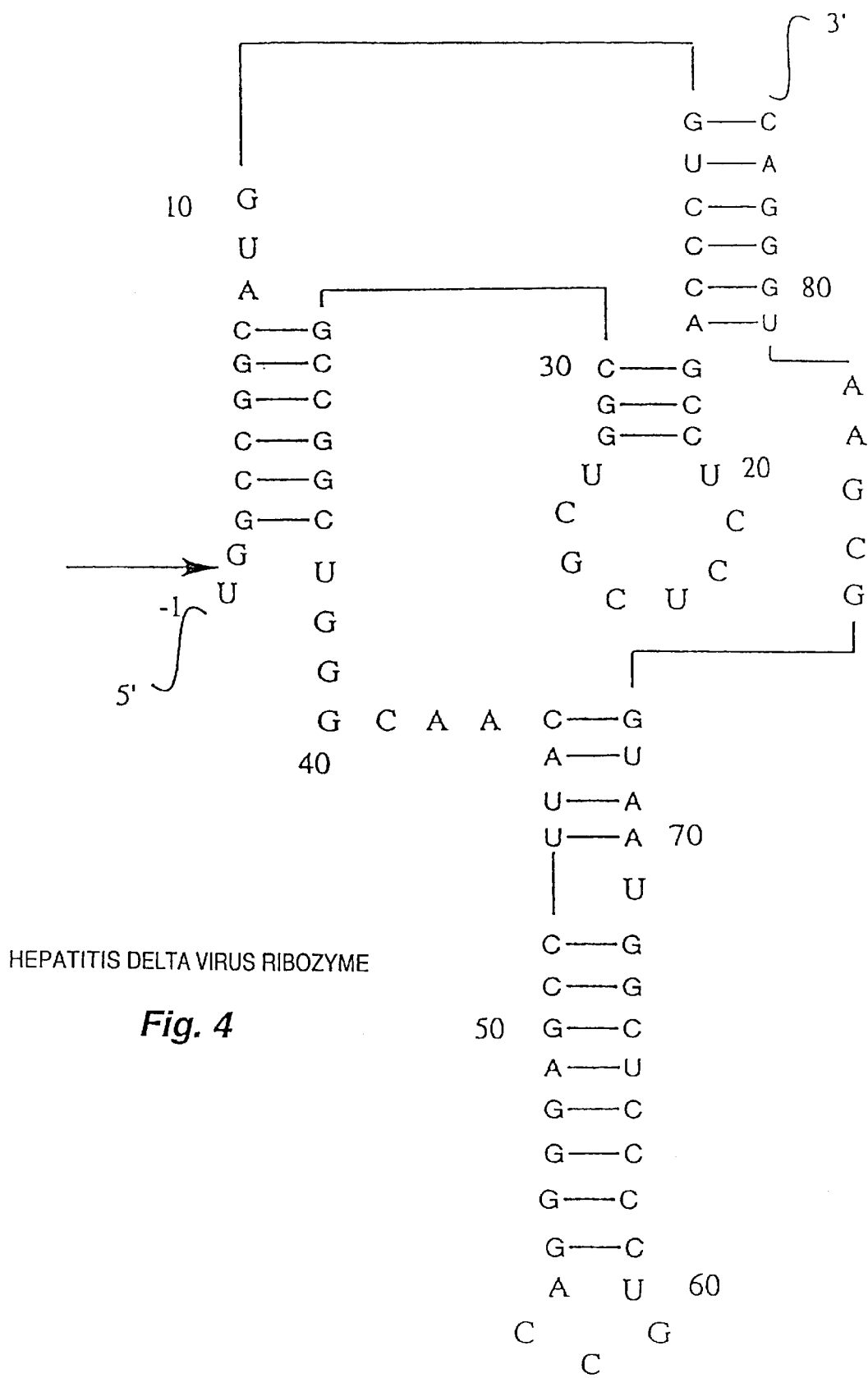

FIG. 4 is a representation of the general structure of the hepatitis delta virus ribozyme domain known in the art.

Figure 5:
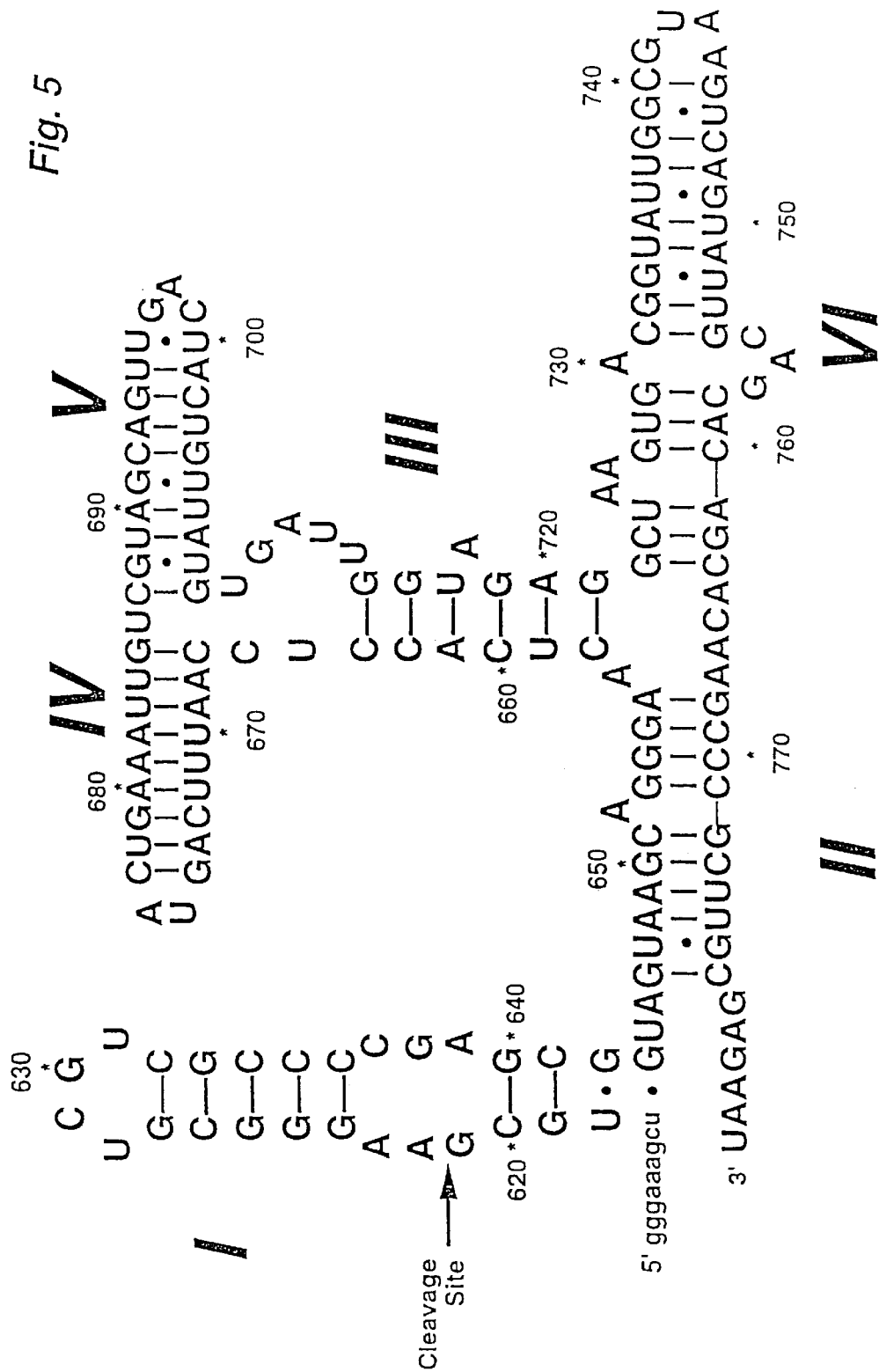

FIG. 5 is a representation of the general structure of the VS RNA ribozyme domain known in the art.

Figure 6B:
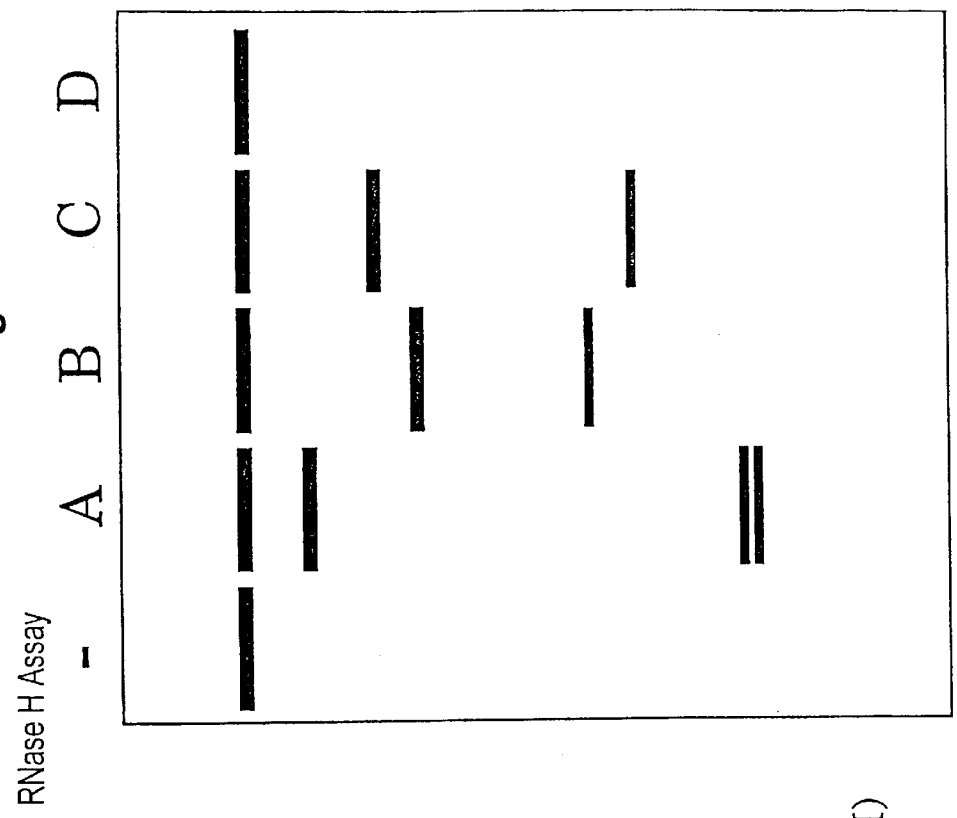
Figure 6A:
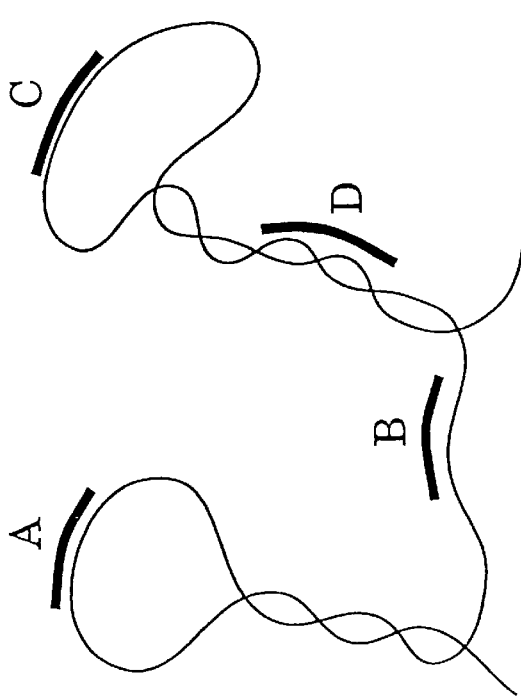

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

Ribozymes

Ribozymes of this invention block to some extent ICAM-1 expression and can be used to treat disease or diagnose such disease. Ribozymes will be delivered to cells in culture and to tissues in animal models of transplant rejection and rheumatoid arthritis. Ribozyme cleavage of ICAM-1 mRNA in these systems may prevent inflammatory cell function and alleviate disease symptoms.

Target sites

Targets for useful ribozymes can be determined as disclosed in Draper et al supra, Sullivan et al., supra, as well as by Draper et al., "Method and reagent for treatment of arthritic conditions" U.S. Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described. Such ribozymes can also be optimized and delivered as described therein. While specific examples to rat, mouse and human RNA are provided, those in the art will recognize that the equivalent human RNA targets described can be used as described below. Thus, the same target may be used, but binding arms suitable for targetting human RNA sequences are present in the ribozyme. Such targets may also be selected as described below.

The sequence of human, rat and mouse ICAM-1 mRNA can be screened for accessible sites using a computer folding algorithm. Regions of the mRNA that did not form secondary folding structures and that contain potential hammerhead or hairpin ribozyme cleavage sites can be identified. These sites are shown in Tables II, III and VI–IX. (All sequences are 5' to 3' in the tables.) While rat, mouse acid human sequences can be screened and ribozymes thereafter designed, the human targetted sequences are of most utility. However, as discussed in Stinchcomb et al. "Method and Composition for Treatment of Restenosis and Cancer Using Ribozymes," U.S. Ser. No. 08/245,466, filed May 18, 1994, and hereby incorporated by reference herein, rat and mouse targetted ribozmes are useful to test efficacy of action of the ribozyme prior to testing in humans. The nucleotide base position is noted in the Tables as that site to be cleaved by the designated type of ribozyme. (In Table III, lower case letters indicate positions that are not conserved between the Human and the Mouse ICAM sequences.)

To test whether the sites predicted by the computer-based RNA folding algorithm correspond to accessible sites in the target mRNA, hammerhead sites are selected for analysis. Hammerhead ribozymes are designed that could bind and are individually analyzed by computer folding (Jaeger et al., 1989, Proc. Natl. Acad. Sci. USA, 86, 7706–7710) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Referring to FIG. 6, mRNA is screened for accessible cleavage sites by the method described generally in Draper et al., WO/US93/04020 and McSwiggen, U.S. patent application Ser. No. 07/883,849 filed May 1, 1992, entitled "Assay for ribozyme target site," both hereby incorporated by reference herein. Briefly, DNA oligonucleotides representing potential hammerhead ribozyme cleavage sites are synthesized. A polymerase chain reaction is used to generate a substrate for T7 RNA polymerase transcription from human or murine ICAM-1 cDNA clones. Labeled RNA transcripts are synthesized in vitro from the two templates. The oligonucleotides and the labeled transcripts are annealed, RNAseH is added and the mixtures are incubated for the designated times at 37° C. Reactions are stopped and RNA separated on sequencing polyacrylamide gels. The percentage of the substrate cleaved is determined by autoradiographic quantitation using a phosphor imaging system. From these data, hammerhead ribozyme sites are chosen as the most accessible.

Ribozymes of the hammerhead motif are designed to anneal to various sites in the mRNA message. The binding arms are complementary to the target site sequences described above. The ribozymes were chemically synthesized. The method of synthesis used follows the procedure for normal RNA synthesis as described in Usman et al., 1987 J. Am. Chem. Soc., 109, 7845–7854 and in Scaringe et al., 1990 Nucleic Acids Res., 18, 5433–5441, and makes use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from (Hertel et al., 1992 Nucleic Acids Res., 20, 3252). Hairpin ribozymes are synthesized in two parts and annealed to reconstruct the active ribozyme (Chowrira and Burke, 1992 Nucleic Acids Res., 20, 2835–2840). All ribozymes are modified to enhance stability by modification of five ribonucleotides at both the 5' and 3' ends with 2'-O-methyl groups. Ribozymes are purified by gel electrophoresis using general methods or are purified by high pressure liquid chromatography (HPLC; See Usman et al., Synthesis, deprotection, analysis and purification of RNA and ribozymes, filed May 18, 1994, U.S. Ser. No. 08/245,736) the totality of which is hereby incorporated herein by reference) and were resuspended in water.

The sequences of the chemically synthesized ribozymes useful in this study are shown in Tables IV–VIII and X. Those in the art will recognize that these sequences are representative only of many more such sequences where the enzymatic portion of the ribozyme (all but the binding arms) is altered to affect activity and may be formed of ribonucleotides or other nucleotides or non-nucleotides. Such ribozymes are equivalent to the ribozymes described specifically in the Tables.

Optimizing Ribozyme Activity

Ribozyme activity can be optimized as described by Stinchcomb et al., supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al., Nature 1990, 344:565; Pieken et al., Science 1991, 253:314; Usman and Cedergren, Trends in Biochem. Sci. 1992, 17:334; Usman et al., International Publication No. WO 93/15187; and Rossi et al., International Publication No. WO 91/03162, as well as Usman, N. et al. U.S. patent application Ser. No. 07/829,729, and Sproat, B. European Patent Application 92110298.4 which describe various chemical modifications that can be made to the sugar moieties of enzymatic RNA molecules. All these publications are hereby incorporated by reference herein), modifications which enhance their efficacy in cells, and removal of stem II bases to shorten RNA synthesis times and reduce chemical requirements.

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. The RNA/vehicle combination is locally delivered by direct injection or by use of a catheter, infusion pump or stent. Alternative routes of delivery include, but are not limited to, intramuscular injection, aerosol inhalation, oral (tablet or pill form), topical, systemic, ocular, intraperitoneal and/or intrathecal delivery. More detailed descriptions of ribozyme delivery and administration are provided in Sullivan, et al., supra and Draper, et al., supra which have been incorporated by reference herein.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol I or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 Proc. Natl. Acad. Sci. USA, 87, 6743–7; Gao, and Huang, 1993 Nucleic Acids Res., 21, 2867–72; Lieber et al., 1993 Methods Enzymol., 217, 47–66; Zhou et al., 1990 Mol. Cell Biol., 10, 4529–37). Several investigators have demonstrated that ribozymes expressed from such promoters can function in mammalian cells (e.g. Kashani-Sabet, et al., 1992 Antisense Res. Dev. 2, 3–15; Ojwang et al., 1992 Proc. Natl. Acad. Sci. USA 89, 10802–6; Chen et al., 1992 Nucleic Acids Res., 20, 4581–9; Yu et al., 1993 Proc. Natl. Acad. Sci. USA 90, 6340–4; L'Huillier, et al., 1992 EMBO J. 11, 4411–8; Lisziewicz et al., 1993 Proc. Natl. Acad. Sci. U.S.A. 90, 8000–4). The above ribozyme transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral vectors).

In a preferred embodiment of the invention, a transcription unit expressing a ribozyme that cleaves ICAM-1 RNA is inserted into a plasmid DNA vector or an adenovirus DNA viral vector. Both vectors have been used to transfer genes to the intact vasculature of live animals (Willard et al., 1992 Circulation, 86, 1–473; Nabel et al., 1990 Science 249, 1285–1288) and both vectors lead to transient gene expression. The adenovirus vector is delivered as recombinant adenoviral particles. DNA may be delivered alone or complexed with vehicles (as described for RNA above). The DNA, DNA/vehicle complexes, or the recombinant adenovirus particles are locally administered to the site of treatment, e.g., through the use of a catheter, stent or infusion pump.

EXAMPLE 1

ICAM-1 Hammerhead ribozymes

By engineering ribozyme motifs we have designed several ribozymes directed against ICAM-1 mRNA sequences. These have been synthesized with modifications that improve their nuclease resistance. These ribozymes cleave ICAM-1 target sequences in vitro.

The ribozymes will be tested for function in vivo by exogenous delivery to human umbilical vein endothelial cells (HUVEC). Ribozymes will be delivered by incorporation into liposomes, by complexing with cationic lipids, by microinjection, or by expression from DNA vectors. Cytokine-induced ICAM-1 expression will be monitored by ELISA, by indirect immunofluoresence, and/or by FACS analysis. ICAM-1 mRNA levels will be assessed by Northern, by RNAse protection, by primer extension or by quantitative RT-PCR analysis. Ribozymes that block the induction of ICAM-1 protein and mRNA by more than 90% will be identified.

RNA ribozymes and/or genes encoding them will be locally delivered to transplant tissue ex vivo in animal models. Expression of the ribozyme will be monitored by its ability to block ex vivo induction of ICAM-1 mRNA and protein. The effect of the anti-ICAM-1 ribozymes on graft rejection will then be assessed. Similarly, ribozymes will be introduced into joints of mice with collagen-induced arthritis or rabbits with Streptococcal cell wall-induced arthritis. Liposome delivery, cationic lipid delivery, or adeno-associated virus vector delivery can be used. One dose (or a few infrequent doses) of a stable anti-ICAM-1 ribozyme or a gene construct that constitutively expresses the ribozyme may abrogate inflammatory and immune responses in these diseases.

Uses

ICAM-1 plays a central role in immune cell recognition and function. Ribozyme inhibition of ICAM-1 expression can reduce transplant rejection and alleviate symptoms in patients with rheumatoid arthritis, asthma or other acute and chronic inflammatory disorders. We have engineered several ribozymes that cleave ICAM-1 mRNA. Ribozymes that efficiently inhibit ICAM-1 expression in cells can be readily found and their activity measured with regard to their ability to block transplant rejection and arthritis symptoms in animal models. These anti-ICAM-1 ribozymes represent a novel therapeutic for the treatment of immunological or inflammatory disorders.

The therapeutic utility of reduction of activity of ICAM-1 function is evident in the following disease targets. The noted references indicate the role of ICAM-1 and the therapeutic potential of ribozymes described herein. Thus, these targets can be therapeutically treated with agents that reduce ICAM-1 expression or function. These diseases and the studies that support a critical role for ICAM-1 in their pathology are listed below. This list is not meant to be complete and those in the art will recognize further conditions and diseases that can be effectively treated using ribozymes of the present invention.

Transplant rejection

ICAM-1 is expressed on venules and capillaries of human cardiac biopsies with histological evidence of graft rejection (Briscoe et al., 1991 *Transplantation* 51, 537–539).

Antibody to ICAM-1 blocks renal (Cosimi et al., 1990 *J. Immunol.* 144, 4604–4612) and cardiac (Flavin et al., 1991 *Transplant. Proc.* 23, 533–534) graft rejection in primates.

A Phase I clinical trial of a monoclonal anti-ICAM-1 antibody showed significant reduction in rejection and a significant increase in graft function in human kidney transplant patients (Haug, et al., 1993 *Transplantation* 55, 766–72).

Rheumatoid arthritis

ICAM-1 overexpression is seen on synovial fibroblasts, endothelial cells, macrophages, and some lymphocytes (Chin et al., 1990 *Arthritis Rheum* 33, 1776–86; Koch et al., 1991 *Lab Invest* 64, 313–20).

Soluble ICAM-1 levels correlate with disease severity (Mason et al., 1993 *Arthritis Rheum* 36, 519–27).

Anti-ICAM antibody inhibits collagen-induced arthritis in mice (Kakimoto et al., 1992 *Cell Immunol* 142, 326–37).

Anti-ICAM antibody inhibits adjuvant-induced arthritis in rats (Iigo et al., 1991 *J Immunol* 147, 4167–71).

Myocardial ischemia, stroke, and reperfusion injury

Anti-ICAM-1 antibody blocks adherence of neutrophils to anoxic endothelial cells (Yoshida et al., 1992 *Am J Physiol* 262, H1891–8).

Anti-ICAM-1 antibody reduces neurological damage in a rabbit model of cerebral stroke (Bowes et al., 1993 *Exp Neurol* 119, 215–9).

Anti-ICAM-1 antibody protects against reperfusion injury in a cat model of myocardial ischemia (Ma et al., 1992 *Circulation* 86, 937–46).

Asthma

Antibody to ICAM-1 partially blocks eosinophil adhesion to endothelial cells and is overexpressed on inflamed airway endothelium and epithelium in vivo (Wegner et al., 1990 *Science* 247, 456–9).

In a primate model of asthma, anti-ICAM-1 antibody blocks airway eosinophilia (Wegner et al., supra) and prevents the resurgence of airway inflammation and hyper-responsiveness after dexamethosone treatment (Gundel et al., 1992 *Clin Exp Allergy* 22, 569–75).

Psoriasis

Surface ICAM-1 and a clipped, soluble version of ICAM-1 is expressed in psoriatic lesions and expression correlates with inflammation (Kellner et al., 1991 *Br J Dermatol* 125, 211–6; Griffiths 1989 *J Am Acad Dermatol* 20, 617–29; Schopf et al., 1993 *Br J Dermatol* 128, 34–7).

Anti-ICAM antibody blocks keratinocyte antigen presentation to T cells (Nickoloff et al., 1993 *J Immunol* 150, 2148–59).

Kawasaki disease

Surface ICAM-1 expression correlates with the disease and is reduced by effective immunoglobulin treatment (Leung, et al., 1989 *Lancet* 2, 1298–302).

Soluble ICAM levels are elevated in Kawasaki disease patients; particularly high levels are observed in patients with coronary artery lesions (Furukawa et al., 1992 *Arthritis Rheum* 35, 672–7; Tsuji, 1992 *Arerugi* 41, 1507–14).

Circulating LFA-1$^+$ T cells are depleted (presumably due to ICAM-1 mediated extravasation) in Kawasaki disease patients (Furukawa et al., 1993 *Scand J Immunol* 37, 377–80).

Diagnostic uses

Ribozymes of this invention may be used as diagnostic tools to examine genetic drift and mutations within diseased cells. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNA associated with an ICAM-1 related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., ICAM-1) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE I

Characteristics of Ribozymes

Group I Introns

Size: ~200 to >1000 nucleotides.
Requires a U in the target sequence immediately 5' of the cleavage site.
Binds 4–6 nucleotides at 5' side of cleavage site.
Over 75 known members of this class. Found in *Tetrahymena thermophila* rRNA, fungal mitochondria, chloroplasts, phage T4, blue-green algae, and others.

RNAseP RNA (M1 RNA)

Size: ~290 to 400 nucleotides.
RNA portion of a ribonucleoprotein enzyme. Cleaves tRNA precursors to form mature tRNA.

TABLE I-continued

Characteristics of Ribozymes

Roughly 10 known members of this group all are bacterial in origin.

Hammerhead Ribozyme

Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIGS. 1 and 2 show examples of various manifestations as used in the art).

Hairpin Ribozyme

Size: ~50 nucleotides.
Requires the target sequence GUC immediately 3' of the cleavage site.
Binds 4–6 nucleotides at 5' side of the cleavage site and a variable number to the 3' side of the cleavage site.
Only 3 known member of this class. Found in three plant pathogen (satellite RNAs of the tobacco ringspot virus, ararbis mosaic virus and chicory yellow mottle virus) which uses RNA as the infectious agent (FIG. 3).

Hepatitis Delta Virus (HDV) Ribozyme

Size: 50–60 nucleotides (at present).
Cleavage of target RNAs recently demonstrated.
Sequence requirements not fully determined.
Binding sites and structural requirements not fully determined, although no sequences 5' of cleavage site are required.
Only 1 known member of this class. Found in human HDV (FIG. 4).

Neurospora VS RNA Ribozyme

Size: ~144 nucleotides (at present)
Cleavage of target RNAs recently demonstrated.
Sequence requirements not fully determined.
Binding sites and structural requirements not fully determined. Only 1 known member of this class. Found in Neurospora VS RNA (FIG. 5).

Table II

Human ICAM HH Target sequence

| nt. Position | Target Sequences | nt. Position | Target Sequences |
|---|---|---|---|
| 11 | CCCCAGU C GACGCUG | 386 | ACCGUGU A CUGGACU |
| 23 | CUGAGCU C CUCUGCU | 394 | CUGGACU C CAGAACG |
| 26 | AGCUCCU C UGCUACU | 420 | CACCCCU C CCCUCUU |
| 31 | CUCUGCU A CUCAGAG | 425 | CUCCCCU C UUGGCAG |
| 34 | UGCUACU C AGAGUUG | 427 | CCCCUCU U GGCAGCC |
| 40 | UCAGAGU U GCAACCU | 450 | AGAACCU U ACCCUAC |
| 48 | GCAACCU C AGCCUCG | 451 | GAACCUU A CCCUACG |
| 54 | UCAGCCU C GCUAUGG | 456 | UUACCCU A CGCUGCC |
| 58 | CCUCGCU A UGGCUCC | 495 | CCAACCU C ACCGUGG |
| 64 | UAUGGCU C CCAGCAG | 510 | UGCUGCU C CCUGCGG |
| 96 | CCGCACU C CUGGUCC | 564 | CUGAGGU C ACGACCA |
| 102 | UCCUGGU C CUGCUCG | 592 | GAGAGAU C ACCAUGG |
| 108 | UCCUGCU C GGGGCUC | 607 | AGCCAAU U UCUCGUG |
| 115 | CGGGGCU C UGUUCCC | 608 | GCCAAUU U CUCGUGC |
| 119 | GCUCUGU U CCCAGGA | 609 | CCAAUUU C UCGUGCC |

Table II-continued

Human ICAM HH Target sequence

| nt. Position | Target Sequences | nt. Position | Target Sequences |
|---|---|---|---|
| 120 | CUCUGUU C CCAGGAC | 611 | AAUUUCU C GUGCCGC |
| 146 | CAGACAU C UGUGUCC | 656 | GAGCUGU U UGAGAAC |
| 152 | UCUGUGU C CCCCUCA | 657 | AGCUGUU U GAGAACA |
| 158 | UCCCCCU C AAAAGUC | 668 | AACACCU C GGCCCCC |
| 165 | CAAAAGU C AUCCUGC | 677 | GCCCCCU A CCAGCUC |
| 168 | AAGUCAU C CUGCCCC | 684 | ACCAGCU C CAGACCU |
| 185 | GGAGGCU C CGUGCUG | 692 | CAGACCU U UGUCCUG |
| 209 | AGCACCU C CUGUGAC | 693 | AGACCUU U GUCCUGC |
| 227 | CCCAAGU U GUUGGGC | 696 | CCUUUGU C CUGCCAG |
| 230 | AAGUUGU U GGGCAUA | 709 | AGCGACU C CCCCACA |
| 237 | UGGGCAU A GAGACCC | 720 | CACAACU U GUCAGCC |
| 248 | ACCCCCU U GCCUAAA | 723 | AACUUGU C AGCCCCC |
| 253 | GUUGCCU A AAAAGGA | 735 | CCCGGGU C CUAGAGG |
| 263 | AAGGAGU U GCUCCUG | 738 | GGGUCCU A GAGGUGG |
| 267 | AGUUGCU C CUGCCUG | 765 | CCGUGGU C UGUUCCC |
| 293 | AAGCUGU A UGAACUG | 769 | GGUCUGU U CCCUGGA |
| 319 | AGAAGAU A GCCAACC | 770 | GUCUGUU C CCUGGAC |
| 335 | AUGUGCU A UUCAAAC | 785 | GGGCUGU U CCCAGUC |
| 337 | GUGCUAU U CAAACUG | 786 | GGCUGUU C CCAGUCU |
| 338 | UGCUAUU C AAACUGC | 792 | UCCCAGU C UCGCAGG |
| 359 | GGGCAGU C AACAGCU | 794 | CCAGUCU C GGAGGGC |
| 367 | AACAGCU A AAACCUU | 807 | CCCAGCU C CACCUGG |
| 374 | AAAACCU U CCUCACC | 833 | CAGAGGU U GAACCCC |
| 375 | AAACCUU C CUCACCG | 846 | CCACAGU C ACCUAUG |
| 378 | CCUUCCU C ACCGUGU | 851 | GUCACCU A UGGCAAC |
| 863 | AACGACU C CUUCUCG | 1408 | UCGAGAU C UUGAGGG |
| 866 | GACUCCU U CUCGGCC | 1410 | GAGAUCU U GAGGGCA |
| 867 | ACUCCUU C UCGGCCA | 1421 | GGCACCU A CCUCUGU |
| 869 | UCCUUCU C GGCCAAG | 1425 | CCUACCU C UGUCGGG |
| 881 | AAGGCCU C AGUCAGU | 1429 | CCUCUGU C GGGCCAG |
| 885 | CCUCAGU C AGUGUGA | 1444 | GAGCACU C AAGGGGA |
| 933 | GUGCAGU A AUACUGG | 1455 | GGGAGGU C ACCCGCG |
| 936 | CAGUAAU A CUGGGGA | 1482 | AUGGGCU C UCCCCCC |
| 978 | UGACCAU U UACAGCU | 1484 | GUGCUCU C CCCCCGG |
| 980 | ACCAUCU A CAGCUUU | 1493 | CCCCGGU A UGAGAUU |
| 986 | UACAGCU U UCCGGCG | 1500 | AUGAGAU U GUCAUCA |
| 987 | ACAGCUU U CCGGCGC | 1503 | AGAUUGU C AUCAUCA |
| 988 | CAGCUUU C CGGCGCC | 1506 | UUGUCAU C AUCACUG |

Table II-continued

Human ICAM HH Target sequence

| nt. Position | Target Sequences | nt. Position | Target Sequences |
|---|---|---|---|
| 1005 | ACGUGAU U CUGACGA | 1509 | UCAUCAU C ACUGUGG |
| 1006 | CGUGAUU C UGACGAA | 1518 | CUGUGGU A GCAGCCG |
| 1023 | CAGAGGU C UCAGAAG | 1530 | CCGCAGU C AUAAUGG |
| 1025 | GAGGUCU C AGAAGGG | 1533 | CAGUCAU A AUGGGCA |
| 1066 | CCACCCU A GAGCCAA | 1551 | CAGGCCU C AGCACGU |
| 1092 | AUGGGGU U CCAGCCC | 1559 | AGCACGU A CCUCUAU |
| 1093 | UGGGGUU C CAGCCCA | 1563 | CGGACCU C UAUAACC |
| 1125 | CCCAGCU C CUGCUGA | 1565 | UACCUCU A UAACCGC |
| 1163 | CGCAGCU U CUCCUGC | 1567 | CCUCUAU A ACCGCCA |
| 1164 | GCAGCUU C UCCUGCU | 1584 | GGAAGAU C AAGAAAU |
| 1166 | AGCUUCU C CUGCUCU | 1592 | AAGAAAU A CAGACUA |
| 1172 | UCCUGCU C UGCAACC | 1599 | ACAGACU A CAACAGG |
| 1200 | GCCAGCU U AUACACA | 1651 | CACGCCU C CCUGAAC |
| 1201 | CCAGCUU A UACACAA | 1661 | UGAACCU A UCCCGGG |
| 1203 | AGCUUAU A CACAAGA | 1663 | AACCUAU C CCGGGAC |
| 1227 | GGGAGCU U CGUGUCC | 1678 | AGGGCCU C UUCCUCG |
| 1228 | GGAGCUU C GUGUCCU | 1680 | GGCCUCU U CCUCGGC |
| 1233 | UUCGUGU C CUGUAUG | 1681 | GCCUCUU C CUCGGCC |
| 1238 | GUCCUGU A UGGCCCC | 1684 | UCUUCCU C GGCCUUC |
| 1264 | GAGGGAU U GUCCGGG | 1690 | UCGGCCU U CCCAUAU |
| 1267 | GGAUUGU C CGGGAAA | 1691 | CGGCCUU C CCAUAUU |
| 1294 | AGAAAAU U CCCAGCA | 1696 | UUCGCAU A UUGGUGG |
| 1295 | GAAAAUU C CCAGCAG | 1698 | CCCAUAU U GGUGGCA |
| 1306 | GCAGACU C CAAUGUG | 1737 | AAGACAU A UGCCAUG |
| 1321 | CCAGGCU U GGGGGAA | 1750 | UGCAGCU A CACCUAC |
| 1334 | AACCCAU U GCCCGAG | 1756 | UACACCU A CCGGCCC |
| 1344 | CCGAGCU C AAGUGUC | 1787 | AGGGCAU U GUCCUCA |
| 1351 | CAAGUGU C UAAAGGA | 1790 | GCAUUGU C CUCAGUC |
| 1353 | AGUGUCU A AAGGAUG | 1793 | UUGUCCU C AGUCAGA |
| 1366 | UGGCACU U UCCCACU | 1797 | CCUCAGU C AGAUACA |
| 1367 | GGCACUU U CCCACUG | 1802 | GUCAGAU A CAACAGC |
| 1368 | GCAGUUU C CCACUGC | 1812 | ACAGCAU U GGGGCC |
| 1380 | UGCCCAU C GGGAAU | 1813 | CAGCAUU U GGGGCCA |
| 1388 | GGGGAAU C AGUGACU | 1825 | CCAUGGU A CCUGCAC |
| 1398 | UGACUGU C ACUCGAG | 1837 | CACACCU A AAACACU |
| 1402 | UGUCACU C GAGAUCU | 1845 | AAACACU A GGCCACG |
| 1856 | CACGCAU C UGAUCUG | 2189 | UAUUUAU U GAGUGUC |

Table II-continued

Human ICAM HH Target sequence

| nt. Position | Target Sequences | nt. Position | Target Sequences |
|---|---|---|---|
| 1861 | AUCUGAU C UGUAGUC | 2196 | UGAGUGU C UUUUAUG |
| 1865 | GAUCUGU A GUCACAU | 2198 | AGUGUCU U UUAUGUA |
| 1868 | CUGUAGU C ACAUGAC | 2199 | GUGUCUU U UAUGUAG |
| 1877 | CAUGACU A AGCCAAG | 2200 | UGUCUUU U AUGUAGG |
| 1901 | CAAGACU C AAGACAU | 2201 | GUCUUUU A UGUAGGC |
| 1912 | ACAUGAU U GAUGGAU | 2205 | UUUAUGU A GGCUAAA |
| 1922 | UGGAUGU U AAAGUCU | 2210 | GUAGGCU A AAUGAAC |
| 1923 | GGAUGUU A AAGUCUA | 2220 | UGAACAU A GGUCUCU |
| 1928 | UUAAAGU C UAGCCUG | 2224 | CAUAGGU C UCUGGCC |
| 1930 | AAAGUCU A GCCUGAU | 2226 | UAGGUCU C UGGCCUC |
| 1964 | GAGACAU A GCCCCAC | 2233 | CUGGCCU C ACGGAGC |
| 1983 | AGGACAU A CAACUGG | 2242 | CGGAGCU C CCAGUCC |
| 1996 | GGGAAAU A CUGAAAC | 2248 | UCCCAGU C CAUGUCA |
| 2005 | UGAAACU U GCUGCCU | 2254 | UCCAUGU C ACAUUCA |
| 2013 | GCUGCCU A UUGGGUA | 2259 | GUCACAU U CAAGGUC |
| 2015 | UGCCUAU U GCGUAUG | 2260 | UCACAUU C AAGGUCA |
| 2020 | AUUGGGU A UGCUGAG | 2266 | UCAAGGU C ACCAGGU |
| 2039 | ACAGACU U ACAGAAG | 2274 | ACCAGGU A CAGUUGU |
| 2040 | CAGACUU A CAGAAGA | 2279 | GUACAGU U GUACAGG |
| 2057 | UGGCCCU C CAUAGAC | 2282 | CAGUUGU A CAGGUUG |
| 2061 | CCUCCAU A GACAUGU | 2288 | UACAGGU U GUACACU |
| 2071 | CAUGUGU A GCAUCAA | 2291 | AGGUUGU A CACUGCA |
| 2076 | GUAGCAU C AAAACAC | 2321 | AAAAGAU C AAAUGGG |
| 2097 | CCACACU U CCUGACG | 2338 | UGGGACU U CUCAUUG |
| 2098 | CACACUU C CUGACGG | 2339 | GGGACUU C UCAUUGG |
| 2115 | CCCAGCU U GCGCACU | 2341 | GACUUCU C AUUGGCC |
| 2128 | CUGCUGU C UACUGAC | 2344 | UUCUCAU U GGCCAAC |
| 2130 | GCUGUCU A CUGACCC | 2358 | CCUGCCU U UCCCCAG |
| 2145 | CAACCCU U GAUGAUA | 2359 | CUGCCUU U CCCCAGA |
| 2152 | UGAUGAU A UGUAUUU | 2360 | UGCCUUU C CCCAGAA |
| 2156 | GAUAUGU A UUUAUUC | 2376 | GAGUGAU U UUUCUAU |
| 2158 | UAUGUAU U UAUUCAU | 2377 | AGUGAUU U UUCUAUC |
| 2159 | AUGUAUU U AUUCAUU | 2378 | GUGAUUU U UCUAUCG |
| 2160 | UGUAUUU A UUCAUUU | 2379 | UGAUUUU U CUAUCGG |
| 2162 | UAUUUAU U CAUUUGU | 2380 | GAUUUUU C UAUCGGC |
| 2163 | AUUUAUU C AUUUGUU | 2382 | UUUUUCU A UCGGCAC |
| 2166 | UAUUCAU U UGUUAUU | 2384 | UUUCUAU C GGCACAA |
| 2167 | AUUCAUU U GUUAUUU | 2399 | AAGCACU A UAUGGAC |

Table II-continued

Human ICAM HH Target sequence

| nt. Position | Target Sequences | nt. Position | Target Sequences |
|---|---|---|---|
| 2170 | CAUUUGU U AUUUUAC | 2401 | GCACUAU A UGGACUG |
| 2171 | AUUUGUU A UUUUACC | 2411 | GACUGGU A AUGGUUC |
| 2173 | UUGUUAU U UUACCAG | 2417 | UAAUGGU U CACAGGU |
| 2174 | UGUAUUU U UACCAGC | 2418 | AAUGGUU C ACAGGUU |
| 2175 | GUUAUUU U ACCAGCU | 2425 | CACAGCU U CAGAGAU |
| 2176 | UUAUUUU A CCAGCUA | 2426 | ACAGGUU C AGAGAUU |
| 2183 | ACCAGCU A UUUAUUG | 2433 | CAGAGAU U ACCCAGU |
| 2185 | CAGCUAU U UAUUGAG | 2434 | AGAGAUU A CCCAGUG |
| 2186 | AGCUAUU U AUUGAGU | 2448 | GAGGCCU U AUUCCUC |
| 2187 | GCUAUUU A UUGAGUG | 2449 | AGGCCUU A UUCCUCC |
| 2451 | GCCUUAU U CCUCCCU | 2750 | UAUGUGU A GACAAGC |
| 2452 | CCUUAUU C CUCCCUU | 2759 | ACAAGCU C UCGCUCU |
| 2455 | UAUUCCU C CCUUCCC | 2761 | AAGCUCU C GCUCUGU |
| 2459 | CCUCCCU U CCCCCCA | 2765 | UCUCGCU C UGUCACC |
| 2460 | CUCCCUU C CCCCCAA | 2769 | GCUCUGU C ACCCAGG |
| 2479 | GACACCU U UGUUAGC | 2797 | GUGCAAU C AUGGUUC |
| 2480 | ACACCUU U GUUAGCC | 2803 | UCAUGGU U CACUGCA |
| 2483 | CCUUUGU U AGCCACC | 2804 | CAUGGUU C ACUGCAG |
| 2484 | CUUUGUU A GCCACCU | 2813 | CUGCAGU C UUGACCU |
| 2492 | GCCACCU C CCCACCC | 2815 | CCAGUCU U GACCUUU |
| 2504 | CCCACAU A CAUUUCU | 2821 | UUGACCU U UUGGGCU |
| 2508 | CAUACAU U UCUGCCA | 2822 | UGACCUU U UGGGCUC |
| 2509 | AUACAUU U CUGCCAG | 2823 | GACCUUU U GGGCUCA |
| 2510 | UACAUUU C UGCCAGU | 2829 | UUGGGCU C AAGUGAU |
| 2520 | CCAGUGU U CACAAUG | 2837 | AAGUGAU C CUCCCAC |
| 2521 | CAGUGUU C ACAAUGA | 2840 | UGAUCCU C CCACCUC |
| 2533 | UGACACU C AGCGGUC | 2847 | CCCACCU C AGCCUCC |
| 2540 | CAGCGGU C AUGUCUG | 2853 | UCAGCCU C CUGAGUA |
| 2545 | GUCAUGU C UGGACAU | 2860 | CCUGAGU A GCUGGGA |
| 2568 | AGGGAAU A UGCCCAA | 2872 | GGACCAU A GCCUCAC |
| 2579 | CCAAGCU A UGCCUUG | 2877 | AUAGGCU C ACAACAC |
| 2585 | UAUGCCU U GUCCUCU | 2899 | GGCAAAU U GAUUUUU |
| 2588 | GCCUUGU C CUCUUGU | 2900 | GCAAAUU U GAUUUUU |
| 2591 | UUGUCCU C UUGUCCU | 2904 | AUUUGAU U UUUUUUU |
| 2593 | GUCCUCU U GUCCUGU | 2905 | UUUGAUU U UUUUUUU |
| 2596 | CUCUUGU C CUGUUUG | 2906 | UUGAUUU U UUUUUUU |
| 2601 | GUCCUGU U UGCAUUU | 2907 | UGAUUUU U UUUUUUU |

Table II-continued

Human ICAM HH Target sequence

| nt. Position | Target Sequences | nt. Position | Target Sequences |
|---|---|---|---|
| 2602 | UCCUGUU U GCAUUUC | 2908 | GAUUUUU U UUUUUUU |
| 2607 | UUUGCAU U UCACUGG | 2909 | AUUUUUU U UUUUUUU |
| 2608 | UUGCAUU U CACUGGG | 2910 | UUUUUUU U UUUUUUU |
| 2609 | UGCAUUU C ACUGGGA | 2911 | UUUUUUU U UUUUUUU |
| 2620 | GGGAGCU U GCACUAU | 2912 | UUUUUUU U UUUUUUC |
| 2626 | UUGCACU A UUGCAGC | 2913 | UUUUUUU U UUUUUCA |
| 2628 | GCACUAU U GCAGCUC | 2914 | UUUUUUU U UUUUCAG |
| 2635 | UGCAGCU C CAGUUUC | 2915 | UUUUUUU U UUUCAGA |
| 2640 | CUCCAGU U UCCUGCA | 2916 | UUUUUUU U UUCAGAG |
| 2641 | UCCAGUU U CCUGCAG | 2917 | UUUUUUU U UCAGAGA |
| 2642 | CCAGUUU C CUGCAGU | 2918 | UUUUUUU U CAGAGAC |
| 2653 | CAGUGAU C AGGGUCC | 2919 | UUUUUUU C AGAGACG |
| 2659 | UCAGGGU C CUGCAAG | 2931 | ACGGGGU C UCGCAAC |
| 2689 | CCAAGGU A UUGGAGG | 2933 | GGGGUCU C GCAACAU |
| 2691 | AAGGUAU U GCAGGAC | 2941 | GCAACAU U GCCCAGA |
| 2700 | GAGGACU C CCUCCCA | 2951 | CCAGACU U CCUUUGU |
| 2704 | ACUCCCU C CAGCUU | 2952 | CAGACUU C CUUUGUG |
| 2711 | CCCAGCU U UGGAAGG | 2955 | ACUUCCU U UGUGUUA |
| 2712 | CCAGCUU U GGAAGGG | 2956 | CUUCCUU U GUGUUAG |
| 2721 | GAAGCGU C AUCCGCG | 2961 | UUUGUGU U AGUUAAU |
| 2724 | GGGUCAU C CGCGUGU | 2962 | UUGUGUU A GUUAAUA |
| 2744 | UGUGUGU A UGUGUAG | 2965 | UGUUAGU U AAUAAAG |
| 2966 | GUUAGUU A AUAAAGC | | |
| 2969 | AGUUAAU A AAGCUUU | | |
| 2975 | UAAAGCU U UCUCAAC | | |
| 2976 | AAAGCUU U CUCAACU | | |
| 2977 | AAGCUUU C UCAACUG | | |
| 2979 | GCUUUCU C AACUGCC | | |

Table III

Mouse ICAM HH Target Sequence

| nt. Position | Target Sequence | nt. Position | Target Sequence |
|---|---|---|---|
| 11 | CCCugGU C acCGuUG | 367 | AAugGCU u CAACCcg |
| 23 | CaGuGgU u CUCUGCU | 374 | gAAgcCU U CCUgcCC |
| 26 | uGgUuCU C UGCUcCU | 375 | AAgCCUU C CUgcCCc |
| 31 | CUCUGCU c CUCcaca | 378 | CuacCaU C ACCGUCU |
| 34 | UuCUcaU a AGgGUcG | 386 | ACCGUGU A uUcGuuU |

Table III-continued

Mouse ICAM HH Target Sequence

| nt. Position | Target Sequence | nt. Position | Target Sequence |
|---|---|---|---|
| 40 | gcACAcU U GuAgCCU | 394 | CcGGACU u ucGAuCu |
| 48 | aggACCU C AGCCUgG | 420 | CACaCuU C CCCcccg |
| 54 | UggGCCU C GugAUGG | 425 | CaCCCCU C ccaGCAG |
| 58 | CaUgcCU u UaGCUCC | 427 | CagCUCU c aGCAGug |
| 64 | CAccCCU C CCAGCAG | 450 | AGgACCU c ACCCUgC |
| 96 | CucugcU C CUGGcCC | 451 | GAAaCcU u uCCUuuG |
| 102 | UgCcaGU a CUGCUgG | 456 | UUACCCU c aGCcaCu |
| 108 | cuCUGCU C cuGGCcC | 495 | CuAcCaU C ACCGUGu |
| 115 | uGGuuCU C UGcUCCu | 510 | UGCUGCU C CGUGCGG |
| 119 | GgaaUGU c aCCAGGA | 564 | CUCAGGU a uCCAuCc |
| 120 | CUCUGcU C CugGccC | 592 | GAaAGAU C ACaugGG |
| 146 | CAGuCgU C cGcuUCC | 607 | AGCCAAU U UCUCaUG |
| 152 | UCUGUGU C agCCaCu | 608 | GCCAAUU U CUCaUGC |
| 158 | UCCuguU u AAAAacC | 609 | CCAAUUU C UCaUGCC |
| 165 | CAgAAGU u gUuuUGC | 611 | AAUUUCU C aUGCCGC |
| 168 | AAGcCuU C CUGCCCC | 656 | aAGCUGU U UGAGcug |
| 185 | GGuGGgU C CGUGCaG | 657 | AGCUGUU U GAGcugA |
| 209 | gcCACuU C CUcUGgC | 668 | cgagcCU a GGCCaCC |
| 227 | CagAAGU U GUUuuGC | 677 | GaCCuCU A CCAGCcu |
| 230 | AAGUUGU U uuGCucc | 684 | uuCAGCU C CgGuCCU |
| 237 | UGuGCuU u GAGAaCu | 692 | CgGACuU U cGauCUu |
| 248 | AaCCCaU c UCCUAAA | 693 | AGgaCcU c acCCUGC |
| 253 | ccUGCCU A AggAaGA | 696 | CCUgUuU C CUGCCuc |
| 263 | AgGGuuU c uCUaCUG | 709 | gGCGgCU C CaCCuCA |
| 267 | AGggGCU C CUGCCUa | 720 | UACAACU U uUCAGCu |
| 293 | AAGcUGU u UGAgCUG | 723 | AACUUuU C AGCuCCg |
| 319 | AGgAGAU A cugAgcc | 735 | aCCaGaU C CUgGAGa |
| 335 | cUGUGCU u UgagAAC | 738 | uGGgCCU c GuGaUGG |
| 337 | GUcCaAU U CACACUG | 765 | CaGUcGU C cGcUuCC |
| 338 | aGCUgUU u gAgCUGa | 769 | GGcCUGU U uCCUGcc |
| 359 | GuGCAGU C guCcGCU | 770 | uUuUGcU C CCUGGAa |
| 785 | GGcCUGU U uCCuGcC | 1353 | AGUGggU c gAaGgUG |
| 786 | GcCUGUU u CCuGcCU | 1366 | UaaCAgU c UaCaACU |
| 792 | UggagGU C UCGGAaG | 1367 | aGCACcU c CCCACcu |
| 794 | CugGgCU u GGAGaCu | 1368 | GuACUgU a CCACUcu |
| 807 | CuCgcaU a UACCUGG | 1380 | UGCCCAU C GGGGugg |
| 833 | CAaAGcU c GAcaCCC | 1388 | GGaGAcU C AGUGgCU |
| 846 | CCcugGU C ACCguUG | 1398 | UGgCUGU C ACagaAc |

Table III-continued

Mouse ICAM HH Target Sequence

| nt. Position | Target Sequence | nt. Position | Target Sequence |
|---|---|---|---|
| 851 | GagACCU c UacCAgc | 1402 | UGUgcuU u GAGAaCU |
| 863 | AgCcACU u CCUCUgG | 1408 | gCGAGAU C ggGgaGG |
| 866 | GAagCCU U CcuGcCC | 1410 | GAGgUCU c GgaaGgg |
| 867 | AUUCgUU u cCGGagA | 1421 | ccCACCU A CuUuUGU |
| 869 | UCuUcCU C augcAAc | 1425 | aCUgcCU u gGUaGaG |
| 881 | AUGGCuU C AacCcGU | 1429 | uCUCUaU u GccCCuG |
| 885 | CCUugGu a gagGUGA | 1444 | GAaggcU C AgGaGGA |
| 933 | cUauAaU c AUuCUGG | 1455 | GGaAuGU C ACCaGga |
| 936 | UAaUCAU u CUGCuGc | 1482 | AguUGuU u UgCuCCC |
| 978 | UaACagU C UACAaCU | 1484 | cUGuUCU u CCuCauG |
| 980 | ACagUCU A CAaCUUU | 1493 | CuguGcU u UGAGAac |
| 986 | UACAaCU U UuCaGCu | 1500 | AUGAaAU c aUggUCc |
| 987 | ACAaCUU U uCaGCuC | 1503 | gGAcUaU a AUCAUuc |
| 988 | CAaCUUU u CaGCuCC | 1506 | UUaUguU u AUaACcG |
| 1005 | ACcaGAU c CUGgaGA | 1509 | cuAcCAU C ACcGUCu |
| 1006 | uGaGAgU C UGggGAA | 1518 | ucaUGGU c cCAGgCG |
| 1023 | ugGAGGU C UCgGAAG | 1530 | CuauAaU C AUucUGG |
| 1025 | GAGGUCU C gGAAGGG | 1533 | ugGUCAU u gUGGGCc |
| 1066 | CCACuCU c aAaauAA | 1551 | CAuCCCU u AGCAgcU |
| 1092 | AcuGGaU c UCACgCC | 1559 | AGCACcU c CCcaccU |
| 1093 | UGGaccU u CAGCCaA | 1563 | CuUAugU u UAUAACC |
| 1125 | CCCAaCU C uUcuUGA | 1565 | UAugUuU A UAACCGC |
| 1163 | CGaAGCU U CUuuUGC | 1567 | ugUuUAU A ACCGCCA |
| 1164 | GaAGCUU C UuuUGCU | 1584 | GaAAGAU C AgGAuAU |
| 1166 | AGCUUCU u uUGCUCU | 1592 | AgGAuAU A CAaguUA |
| 1172 | UCCUGuU u aaaAACC | 1599 | ACAaguU A CAgaAGG |
| 1200 =0 | cuCuGCU c cUcCACA | 1651 | CcCaCCU C CCUGAgC |
| 1201 | gCuGCUU u UgaACAg | 1661 | gaAACCU u UCCuuuG |
| 1203 | AcuUUuU u CACCAGu | 1663 | AACCUuU C CuuuGAa |
| 1227 | CGuAcaU a CGUGUgC | 1678 | AGGaCCU C agCCUgG |
| 1228 | GaAGCUU C uUuUgCU | 1680 | aGCCaCU U CCUCUgg |
| 1233 | UUCGUuU C CgGagaG | 1681 | GCCaCUU C CUCUggC |
| 1238 | GUgCUGU A UGGUCCu | 1684 | aCUUCCU C uGgcUgu |
| 1264 | GAaCGgU C GUgcaaG | 1690 | cCGGaCU U UCgAUcU |
| 1267 | uGAgaGU C uGGGgAA | 1691 | CGGaCUU u CgAUcUU |
| 1294 | AGgAgAU a CugAGCc | 1696 | UgCCCAU c ggGGUGG |
| 1295 | GAggggU C uCAGCAG | 1698 | CggAUAU a ccUGGag |

Table III-continued

Mouse ICAM HH Target Sequence

| nt. Position | Target Sequence | nt. Position | Target Sequence |
|---|---|---|---|
| 1306 | GCAGACU C ugAaaUG | 1737 | gAGACcU c UaCCAgc |
| 1321 | gaAGGCU c aGGaGgA | 1750 | gGCgGCU c CACCUca |
| 1334 | AACCCAU c uCCuaAa | 1756 | gAagcCU u CCuGCCC |
| 1344 | auGAGCU C gAGaGUg | 1787 | gaGaCAU U GUCCcCA |
| 1351 | ugAaUGU a UAAguuA | 1790 | GCAUUGU u CUCuaau |
| 1793 | UgGUCCU C gGcugGA | 2173 | UUagagU U UUACCAG |
| 1797 | CacCAGU C AcAUAaA | 2174 | UagagUU U UACCAGC |
| 1802 | acCAGAU c CuggAGa | 2175 | agagUUU U ACCAGCU |
| 1812 | ACuGgAU c UcaGGCC | 2176 | gagUUUU A CCAGCUA |
| 1813 | CAGCAUU U acccuCA | 2183 | ACCAGCU A UUUAUUG |
| 1825 | CCACGcU A CCUcugC | 2185 | CAGCUAU U UAUUGAG |
| 1837 | CAugcCU u uAgcuCc | 2186 | ACCUAUU U AUUGAGU |
| 1845 | cgAgcCU A GGCCACc | 2187 | GCUAUUU A UUGAGUa |
| 1856 | CggaCuU u cGAUCUu | 2189 | UAUUUAU U GAGUacC |
| 1861 | AcaUGAU a UccAGUa | 2196 | caAcUcU u cUUgAUG |
| 1865 | CAcuUGU A GcCuCAg | 2198 | gcaGcCU c UUUAUGUu |
| 1868 | CaccAGU C ACAUaAa | 2199 | GccUCUU a UgUuUAu |
| 1877 | CAUGcCU u AGCagcu | 2200 | UcUuccU c AUGcAaG |
| 1901 | uAAaACU C AAGggAc | 2201 | aagUUUU A UGCJcGGC |
| 1912 | AuAUagU a GAUcagU | 2205 | UUUAUGU c GGCcugA |
| 1922 | UGaAUGU a uAAGUua | 2210 | GgAGaCU c AgUGgcu |
| 1923 | uGAUGcU c AgGuaUc | 2220 | cuggCAU u GUUCUCU |
| 1928 | UUAgAGU u UuaCCaG | 2224 | CucAGGU a UCcauCC |
| 1930 | AgAGUUU u aCCaGcU | 2226 | UgGaUCU C aGGCCgC |
| 1964 | GAGACAU u GuCCCca | 2233 | CUGaCCU C cuGGAGg |
| 1983 | AGGAuAU A CAAgUua | 2242 | uGGAGCU a gCgGaCC |
| 1996 | aGGAgAU A CUGAgcC | 2248 | UauCcaU C CAUccCA |
| 2005 | UGgAgCU a GCgGaCc | 2254 | UCCAauU C ACAcUgA |
| 2013 | GCUauuU A UUGaGUA | 2259 | aUCACAU U CAcGGUg |
| 2015 | UGCCcAU c GGGgugG | 2260 | UCACAUU C AcGGUgc |
| 2020 | ggUGGuU c UuCUGAG | 2266 | ggAAuGU C ACCAGGa |
| 2039 | gCuGgCU a gCAGAgG | 2274 | ACCAGaU c CUGgaGa |
| 2040 | CuGACcU c CuGgAGg | 2279 | GaAggGU c GUgCAaG |
| 2057 | UGcuCCU C CAcAucC | 2282 | aAGcUGU u ugaGcUG |
| 2061 | CuaCCAU c acCgUGU | 2288 | UAuAaGU U aUggcCU |
| 2071 | CAcuUGU A GCcUCAg | 2291 | caGUgGU u CuCUGCu |
| 2076 | GUAGCcU C AgAgCua | 2321 | gAAAGAU C AcAUGGG |
| 2097 | CaACuCU U CuUGAuG | 2338 | UGaGACU c CUgccUG |

Table III-continued

Mouse ICAM HH Target Sequence

| nt. Position | Target Sequence | nt. Position | Target Sequence |
|---|---|---|---|
| 2098 | CACACUU C CcccCcG | 2339 | GaaACcU u UCcUUuG |
| 2115 | GCCAGCU c GGaggaU | 2341 | GACcUCU a ccaGcCu |
| 2128 | CaGCUaU u UAUUGAg | 2344 | UUucgAU c uuCCAgC |
| 2130 | cCUGUuU c CUGcCuC | 2358 | CCcagCU c UCagCAG |
| 2145 | CAACuCU U cuUGAUg | 2359 | CUGCuUU U gaaCAGA |
| 2152 | UauUaAU u UagAgUU | 2360 | aaCCUUU C CuuuGAA |
| 2156 | uugAUGU A UUUAUUa | 2376 | agGUGgU U cUUCUga |
| 2158 | gAUGUAU U UAUUaAU | 2377 | gGUGgUU c UUCUgag |
| 2159 | AUGUAUU U AUUaAUU | 2378 | agGgUUU c UCUAcuG |
| 2160 | UGUAUUU A UUaAUUU | 2379 | UGcUUUU c ucAUaaG |
| 2162 | UAUUUAU U aAUUUag | 2380 | aAgUUUU a UgUCGGC |
| 2163 | AUgUAUU u AUUaaUU | 2382 | aUUcUCU A UuGcCcC |
| 2166 | acUUCAU U cucUAUU | 2384 | aucCagU a GaCACAA |
| 2167 | AUgUAUU U aUUAaUU | 2399 | AAaCACU A UgUGGAC |
| 2170 | uAUUUaU U AaUUUAg | 2401 | aagCUgU u UGagCUG |
| 2171 | AgUUGUU u UgcUcCC | 2411 | UACUGGU c AgGaUgC |
| 2417 | gAAUGGU a CAuAcGU | 2691 | AAuGUcU c cGAGGcC |
| 2418 | AcUGGaU C uCAGGcc | 2700 | GAaGcCU u CCUgCCc |
| 2425 | CAugGGU c gAGgGuU | 2704 | gacCuCU a CCAGCcU |
| 2426 | AuuaaUU u AGAGuUU | 2711 | CCCAGCU c UcagcaG |
| 2433 | UAGAGuU U uaCCAGc | 2712 | gagGucU c GGAAGGG |
| 2434 | AGAGuUU u aCCAGcu | 2721 | GAAGGGU C gUgcaaG |
| 2448 | GAaGCCU U ccUgccC | 2724 | GGuaCAU a CGuGUGc |
| 2449 | AaGCCUU c cUgccCC | 2744 | gGUGgGU c cGUGcAG |
| 2451 | CCCUguU U CCUgCCU | 2750 | UAUuUaU u GAguAcC |
| 2452 | CCUguUU C CUgcCUc | 2759 | cCggaCU u UCGaUCU |
| 2455 | gAagcCU u CCUgCCC | 2761 | AgGacCU C aCcCUGc |
| 2459 | CCaCaCU U CCCCCCc | 2765 | UUUuGCU C UGcCgCu |
| 2460 | CaCaCUU C CCCCCcg | 2769 | agUCUGU C AaaCAGG |
| 2479 | GAgACCU c UacCAGC | 2797 | aUGaAAU C AUGGUcC |
| 2480 | uCACCgU U GUgAuCC | 2803 | UCAUGGU c CcagGCg |
| 2483 | CCaaUGU c AGCCACC | 2804 | ggUGGgU C cgUGCAG |
| 2484 | CUUUuUU c aCCAguc | 2813 | CUcCgGU C cUGACCc |
| 2492 | agcACCU C CCCACCu | 2815 | aCAGUCU a CAaCUUU |
| 2504 | CCCACcU A CuUUUgU | 2821 | cUGACCU c cUGGagg |
| 2508 | UAUcCAU c caUcCCA | 2822 | gGAgccU c cGGaCUu |
| 2509 | uUAgAgU U uUaCCAG | 2823 | ugcCUUU a GcuCcCA |

Table III-continued

Mouse ICAM HH Target Sequence

| nt. Position | Target Sequence | nt. Position | Target Sequence |
|---|---|---|---|
| 2510 | UAgAgUU u UaCCAGc | 2829 | cUGGaCU a UAaUCAU |
| 2520 | CuuuUGU U CcCAAUG | 2837 | AgGUGgU u CUuCuga |
| 2521 | CAGcaUU u ACccUcA | 2840 | UGAgaCU C CugcCUg |
| 2533 | UGAugCU C AGguaUC | 2847 | CCaAugU C AGCCaCC |
| 2540 | CAGCaGU C cgcUgUG | 2853 | gCAGCCU C uUauGUu |
| 2545 | GUgcUGU a UGCuCcU | 2860 | gCcaAGU A aCUGuGA |
| 2568 | guGaAgU c UGuCaAA | 2872 | GGACCuU c aGCcaAg |
| 2579 | auAAGuU A UGgCcUG | 2877 | uUccGCU a cCAuCAC |
| 2585 | cugGCaU U GUuCUCU | 2899 | cGgAcuU U cGAUcUU |
| 2588 | GCaUUGU u CUCUaaU | 2900 | uuAAuUU a GAgUUUU |
| 2591 | UgGUuCU C UgcUCCU | 2904 | AcUUCAU U cUcUaUU |
| 2593 | cUuCUuU U GcuCUGc | 2905 | cUUcAUU c UcUaUUg |
| 2596 | CUuUUGU u CccaaUG | 2906 | UUGAUgU a UUUaUUa |
| 2601 | acCgUGU a UUCgUUU | 2907 | UGuaUUU a UUaaUUU |
| 2602 | UCCaGcU a cCAUccC | 2908 | GAagcUU c UUUUgcU |
| 2607 | cUcGgAU a UacCUGG | 2909 | AgcUUcU U UUgcUcU |
| 2608 | caGCAgU c CgCUGuG | 2910 | UgUaUUU a UUaaUUU |
| 2609 | gGaAUgU C ACcaGGA | 2911 | UgUaUUU a UUaaUUU |
| 2620 | aGGAcCU c aCcCUgc | 2912 | UUgUUcU c UaaUgUC |
| 2626 | UUuCgaU c UUcCAGC | 2913 | UUUcUcU a cUggUCA |
| 2628 | GCACacU U GuAGCcu | 2914 | UgcUUUU c UcaUaAG |
| 2635 | UuCAGCU C CgGuccu | 2915 | aUUUaUU a aUUuAGA |
| 2640 | ggcCuGU U UCCUGCc | 2916 | UaUUcgU U UcCgGAG |
| 2641 | cCCAGcU c uCaGCAG | 2917 | aUUcgUU U CCgGAGA |
| 2642 | CCuGUUU C CUGCcuc | 2918 | UUcgUUU c CgGAGAg |
| 2653 | UAcUGgU C AGGaUgc | 2919 | UUcUcaU a AGgGuCG |
| 2659 | gaAGGGU C gUGCAAG | 2931 | ugGaGGU C UCGgAAg |
| 2689 | CuAAuGU c UccGAGG | 2933 | GaGGUCU C GgAAggg |
| 2941 | GagACAU U GuCCcCA | | |
| 2951 | CCAcgCU a CCUcUGc | | |
| 2952 | CAGcagU C CgcUGUG | | |
| 2955 | AgUgaCU c UGUGUCA | | |
| 2956 | uUUCCUU U GaaUCAa | | |
| 2961 | UcUGUGU c AGcCAcU | | |
| 2962 | aUGUaUU u aUUAAUu | | |
| 2965 | UuUgAaU c AAUAAAG | | |
| 2966 | GcUgGcU A gcAgAGg | | |
| 2969 | AaUcAAU A AAGuUUU | | |

Table III-continued

Mouse ICAM HH Target Sequence

| nt. Position | Target Sequence | nt. Position | Target Sequence |
|---|---|---|---|
| 2975 | UAgAGuU U UacCAgC | | |
| 2976 | gAgGgUU U CUCuACU | | |
| 2977 | AAGCUgU u UgAgCUG | | |
| 2979 | UCaUUCU C UAUUGCC | | |

TABLE IV

Human ICAM HH Ribozyme Sequences

| nt. Position | Ribozyme Sequence |
|---|---|
| 11 | CAGCGUC CUGAUGAGGCCGAAAGGCCGAA ACUGGGG |
| 23 | AGCAGAG CUGAUGAGGCCGAAAGGCCGAA AGCUCAG |
| 26 | AGUAGCA CUGAUGAGGCCGAAAGGCCGAA AGGAGCU |
| 31 | CUCUGAG CUGAUGAGGCCGAAAGGCCGAA AGCAGAG |
| 34 | CAACUCU CUGAUGAGGCCGAAAGGCCGAA AGUAGCA |
| 40 | AGGUUGC CUGAUGAGGCCGAAAGGCCGAA ACUCUGA |
| 48 | CGAGGCU CUGAUGAGGCCGAAAGGCCGAA AGGUUGC |
| 54 | CCAUAGC CUGAUGAGGCCGAAAGGCCGAA AGGCUGA |
| 58 | GGAGCCA CUGAUGAGGCCGAAAGGCCGAA AGCGAGG |
| 64 | CUGCUGG CUGAUGAGGCCGAAAGGCCGAA AGCCAUA |
| 96 | GGACCAG CUGAUGAGGCCGAAAGGCCGAA AGUGCGG |
| 102 | CGAGCAG CUGAUGAGGCCGAAAGGCCGAA ACCAGGA |
| 108 | GAGCCCC CUGAUGAGGCCGAAAGGCCGAA AGCAGGA |
| 115 | CGGAACA CUGAUGAGGCCGAAAGGCCGAA AGCCCCG |
| 119 | UCCUGGG CUGAUGAGGCCGAAAGGCCGAA ACAGAGC |
| 120 | GUCCUGG CUGAUGAGGCCGAAAGGCCGAA AACAGAG |
| 146 | GGACACA CUGAUGAGGCCGAAAGGCCGAA AUGUCUG |
| 152 | UGAGGGG CUGAUGAGGCCGAAAGGCCGAA ACACAGA |
| 158 | GACUUUU CUGAUGAGGCCGAAAGGCCGAA AGGGGGA |
| 165 | GCAGGAU CUGAUGAGGCCGAAAGGCCGAA ACUUUUG |
| 168 | GGGGCAG CUGAUGAGGCCGAAAGGCCGAA AUGACUU |
| 185 | CAGCACG CUGAUGAGGCCGAAAGGCCGAA AGCCUCC |
| 209 | GUCACAG CUGAUGAGGCCGAAAGGCCGAA AGGUGCU |
| 227 | GCCCAAC CUGAUGAGGCCGAAAGGCCGAA ACUUGGG |
| 230 | UAUGCCC CUGAUGAGGCCGAAAGGCCGAA ACAACUU |
| 237 | GGGUCUC CUGAUGAGGCCGAAAGGCCGAA AUGCCCA |
| 248 | UUUAGGC CUGAUGAGGCCGAAAGGCCGAA ACGGGGU |
| 253 | UCCUUUU CUGAUGAGGCCGAAAGGCCGAA ACGCAAC |
| 263 | CAGGAGC CUGAUGAGGCCGAAAGGCCGAA ACUCCUU |
| 267 | CAGGCAG CUGAUGAGGCCGAAAGGCCGAA AGCAACU |
| 293 | CAGUUCA CUGAUGAGGCCGAAAGGCCGAA ACACCUU |
| 319 | GGUUGGC CUGAUGAGGCCGAAAGGCCGAA AUCUUCU |
| 335 | GUUUGAA CUGAUGAGGCCGAAAGGCCGAA AGCACAU |
| 337 | CAGUUUG CUGAUGAGGCCGAAAGGCCGAA AUAGCAC |
| 338 | GCAGUUU CUGAUGAGGCCGAAAGGCCGAA AAUAGCA |
| 359 | AGCUGUU CUGAUGAGGCCGAAAGGCCGAA ACUGCCC |
| 367 | AAGGUUU CUGAUGAGGCCGAAAGGCCGAA AGCUGUU |
| 374 | GGUGAGG CUGAUGAGGCCGAAAGGCCGAA AGGUUUU |
| 375 | CGGUGAG CUGAUGAGGCCGAAAGGCCGAA AAGGUUU |
| 378 | ACACGGU CUGAUGAGGCCGAAAGGCCGAA AGGAAGG |
| 386 | AGUCCAG CUGAUGAGGCCGAAAGGCCGAA ACACGGU |
| 394 | CGUUCUG CUGAUGAGGCCGAAAGGCCGAA AGUCCAG |
| 420 | AAGAGGG CUGAUGAGGCCGAAAGGCCGAA AGGGGUG |
| 425 | CUGCCAA CUGAUGAGGCCGAAAGGCCGAA AGGGGAG |
| 427 | GGCUGCC CUGAUGAGGCCGAAAGGCCGAA AGAGGGG |
| 450 | GUAGGGU CUGAUGAGGCCGAAAGGCCGAA AGGUUCU |
| 451 | CCUAGGG CUGAUGAGGCCGAAAGGCCGAA AAGGUUC |
| 456 | GGCAGCG CUGAUGAGGCCGAAAGGCCGAA AGGGUAA |
| 495 | CCACGGU CUGAUGAGGCCGAAAGGCCGAA AGGUUGG |
| 510 | CCCCACG CUGAUGAGGCCGAAAGGCCGAA AGCAGCA |
| 564 | UGGUCGU CUGAUGAGGCCGAAAGGCCGAA ACCUCAG |
| 592 | CCAUGGU CUGAUGAGGCCGAAAGGCCGAA AUCUCUC |
| 607 | CACGAGA CUGAUGAGGCCGAAAGGCCGAA AUUGGCU |
| 608 | GCACGAG CUGAUGAGGCCGAAAGGCCGAA AAUUGGC |
| 609 | GGCACGA CUGAUGAGGCCGAAAGGCCGAA AAAUUGG |

TABLE IV-continued

Human ICAM HH Ribozyme Sequences

| nt. Position | Ribozyme Sequence |
|---|---|
| 611 | GCGGCAC CUGAUGAGGCCGAAAGGCCGAA AGAAAUU |
| 656 | GUUCUCA CUGAUGAGGCCGAAAGGCCGAA ACAGCUC |
| 657 | UGUUCUC CUGAUGAGGCCGAAAGGCCGAA AACAGCU |
| 668 | GGGGGCC CUGAUGAGGCCGAAAGGCCGAA AGGUGUU |
| 677 | GAGCUGG CUGAUGAGGCCGAAAGGCCGAA AGGGGGC |
| 684 | AGGUCUG CUGAUGAGGCCGAAAGGCCGAA AGCUGGU |
| 692 | CAGGACA CUGAUGAGGCCGAAAGGCCGAA AGGUCUG |
| 693 | GCAGGAC CUGAUGAGGCCGAAAGGCCGAA AAGGUCU |
| 696 | CUGGCAG CUGAUGAGGCCGAAAGGCCGAA ACAAAGG |
| 709 | UGUGGGG CUGAUGAGGCCGAAAGGCCGAA AGUCGCU |
| 720 | GGCUGAC CUGAUGAGGCCGAAAGGCCGAA AGUUGUG |
| 723 | GGGGGCU CUGAUGAGGCCGAAAGGCCGAA ACAAGUU |
| 735 | CCUCUAG CUGAUGAGGCCGAAAGGCCGAA ACCCGGG |
| 738 | CCACCUC CUGAUGAGGCCGAAAGGCCGAA AGGACCC |
| 765 | GGGAACA CUGAUGAGGCCGAAAGGCCGAA ACCACGG |
| 769 | UCCAGGG CUGAUGAGGCCGAAAGGCCGAA ACAGACC |
| 770 | GUCCAGG CUGAUGAGGCCGAAAGGCCGAA AACAGAC |
| 785 | GACUGGG CUGAUGAGGCCGAAAGGCCGAA ACAGCCC |
| 786 | AGACUGG CUGAUGAGGCCGAAAGGCCGAA AACAGCC |
| 792 | CCUCCGA CUGAUGAGGCCGAAAGGCCGAA ACUGGGA |
| 794 | GGCCUCC CUGAUGAGGCCGAAAGGCCGAA AGACUGG |
| 807 | CCAGGUG CUGAUGAGGCCGAAAGGCCGAA ACCUGGG |
| 833 | GGGGUUC CUGAUGAGGCCGAAAGGCCGAA ACCUCUG |
| 846 | CAUAGGU CUGAUGAGGCCGAAAGGCCGAA ACUGUGG |
| 851 | GUUGCCA CUGAUGAGGCCGAAAGGCCGAA AGGUGAC |
| 863 | CGAGAAG CUGAUGAGGCCGAAAGGCCGAA AGUGGUU |
| 866 | GGCGGAG CUGAUGAGGCCGAAAGGCCGAA AGGAGUC |
| 867 | UGGCCGA CUGAUGAGGCCGAAAGGCCGAA AAGGAGU |
| 869 | CUUGGCC CUGAUGAGGCCGAAAGGCCGAA AGAAGGA |
| 881 | ACUGACU CUGAUGAGGCCGAAAGGCCGAA AGGCCUU |
| 885 | UCACACU CUGAUGAGGCCGAAAGGCCGAA ACUGAGG |
| 933 | CCAGUAU CUGAUGAGGCCGAAAGGCCGAA ACUGCAC |
| 936 | UCCCCAG CUGAUGAGGCCGAAAGGCCGAA AUUACUG |
| 978 | AGCUGUA CUGAUGAGGCCGAAAGGCCGAA AUGGUCA |
| 980 | AAAGCUG CUGAUGAGGCCGAAAGGCCGAA AGAUGGU |
| 986 | CGCCGGA CUGAUGAGGCCGAAAGGCCGAA AGCUGUA |
| 987 | GCGCCGG CUGAUGAGGCCGAAAGGCCGAA AAGCUGU |
| 988 | GGCGCCG CUGAUGAGGCCGAAAGGCCGAA AAAGCUG |
| 1005 | UCGUCAG CUGAUGAGGCCGAAAGGCCGAA AUCACGU |
| 1006 | UUCGUCA CUGAUGAGGCCGAAAGGCCGAA AAUCACG |
| 1023 | CUUCUGA CUGAUGAGGCCGAAAGGCCGAA ACCUCUG |
| 1025 | CCCUUCU CUGAUGAGGCCGAAAGGCCGAA AGACCUC |
| 1066 | UUGGCUC CUGAUGAGGCCGAAAGGCCGAA AGGGUGG |
| 1092 | GGGCUGG CUGAUGAGGCCGAAAGGCCGAA ACCCCAU |
| 1093 | UGGGCUG CUGAUGAGGCCGAAAGGCCGAA AACCCCA |
| 1125 | UCAGCAG CUGAUGAGGCCGAAAGGCCGAA AGCUGGG |
| 1163 | CCAGGAG CUGAUGAGGCCGAAAGGCCGAA AGCUGCG |
| 1164 | AGCAGGA CUGAUGAGGCCGAAAGGCCGAA AAGCUGC |
| 1166 | AGAGCAG CUGAUGAGGCCGAAAGGCCGAA AGAAGCU |
| 1172 | GGUUGCA CUGAUGAGGCCGAAAGGCCGAA AGCAGGA |
| 1200 | UGUGUAU CUGAUGAGGCCGAAAGGCCGAA AGCUGGC |
| 1201 | UUGUGUA CUGAUGAGGCCGAAAGGCCGAA AAGCUGG |
| 1203 | UCUUGUG CUGAUGAGGCCGAAAGGCCGAA AUAAGCU |
| 1227 | GGACACG CUGAUGAGGCCGAAAGGCCGAA AGCUCCC |
| 1228 | AGGACAC CUGAUGAGGCCGAAAGGCCGAA AAGCUCC |
| 1233 | CAUACAG CUGAUGAGGCCGAAAGGCCGAA ACACGAA |
| 1238 | GGGGCCA CUGAUGAGGCCGAAAGGCCGAA ACAGGAC |
| 1264 | CCCGGAC CUGAUGAGGCCGAAAGGCCGAA AUCCCUC |
| 1267 | UUUCCCG CUGAUGAGGCCGAAAGGCCGAA ACAAUCC |
| 1294 | UGCUGGG CUGAUGAGGCCGAAAGGCCGAA AUUUUCU |
| 1295 | CUGCUGG CUGAUGAGGCCGAAAGGCCGAA AAUUUUC |
| 1306 | CACAUUG CUGAUGAGGCCGAAAGGCCGAA AGUCUGC |
| 1321 | UUCCCCC CUGAUGAGGCCGAAAGGCCGAA AGCCUGG |
| 1334 | CUCGGGC CUGAUGAGGCCGAAAGGCCGAA AUGGGUU |
| 1344 | GACACUU CUGAUGAGGCCGAAAGGCCGAA AGCUCGG |
| 1351 | UCCUUUA CUGAUGAGGCCGAAAGGCCGAA ACACUUG |
| 1353 | CAUCCUU CUGAUGAGGCCGAAAGGCCGAA AGACACU |
| 1366 | AGUGGGA CUGAUGAGGCCGAAAGGCCGAA AGUGGCA |
| 1367 | CAGUGGG CUGAUGAGGCCGAAAGGCCGAA AAGUGCC |
| 1368 | GCAGUGG CUGAUGAGGCCGAAAGGCCGAA AAAGUGC |
| 1380 | AUUCCCC CUGAUGAGGCCCAAAGGCCGAA AUGGGCA |
| 1388 | AGUCACU CUGAUGAGGCCGAAAGGCCGAA AUUCCCC |
| 1398 | CUCGAGU CUGAUGAGGCCGAAAGGCCGAA ACAGUCA |
| 1402 | AGAUCUC CUGAUGAGGCCGAAAGGCCGAA AGUGACA |

TABLE IV-continued

Human ICAM HH Ribozyme Sequences

| nt. Position | Ribozyme Sequence |
|---|---|
| 1408 | CCCUCAA CUGAUGAGGCCGAAAGGCCGAA AUCUCGA |
| 1410 | UGCCCUC CUGAUGAGGCCGAAAGGCCGAA AGAUCUC |
| 1421 | ACAGAGG CUGAUGAGGCCGAAAGGCCGAA AGGUGCC |
| 1455 | CCCGACA CUGAUGAGGCCGAAAGGCCGAA AGGUAGG |
| 1429 | CUGGCCC CUGAUGAGGCCGAAAGGCCGAA ACAGAGG |
| 1444 | UCCCCUU CUGAUGAGGCCGAAAGGCCGAA AGUGCUC |
| 1455 | CGCGGGU CUGAUGAGGCCGAAAGGCCGAA ACCUCCC |
| 1482 | GGGGGGA CUGAUGAGGCCGAAAGGCCGAA AGCACAU |
| 1484 | CCGGGGG CUGAUGAGGCCGAAAGGCCGAA AGAGCAC |
| 1493 | AAUCUCA CUGAUGAGGCCGAAAGGCCGAA ACCGGGG |
| 1500 | UGAUGAC CUGAUGAGGCCGAAAGGCCGAA AUCUCAU |
| 1503 | UGAUGAU CUGAUGAGGCCGAAAGGCCGAA ACAAUCU |
| 1506 | CAGUGAU CUGAUGAGGCCGAAAGGCCGAA AUGACAA |
| 1509 | CCACAGU CUGAUGAGGCCGAAAGGCCGAA AUGAUGA |
| 1518 | CGGCUGC CUGAUGAGGCCGAAAGGCCGAA ACCACAG |
| 1530 | CCAUUAU CUGAUGAGGCCGAAAGGCCGAA ACUGCGG |
| 1533 | UGCCCAU CUGAUGAGGCCGAAAGGCCGAA AUGACUG |
| 1551 | ACGUGCU CUGAUGAGGCCGAAAGGCCGAA AGGCCUG |
| 1559 | AUAGAGG CUGAUGAGGCCGAAAGGCCGAA ACGUGCU |
| 1563 | GGUUAUA CUGAUGAGGCCGAAAGGCCGAA AGGUACG |
| 1565 | GCGGUUA CUGAUGAGGCCGAAAGGCCGAA AGAGCUA |
| 1567 | UGGCGGU CUGAUGAGGCCGAAAGGCCGAA AUAGAGG |
| 1584 | AUUUCUU CUGAUGAGGCCGAAAGGCCGAA AUCUUCC |
| 1592 | UAGUCUG CUGAUGAGGCCGAAAGGCCGAA AUUUCUU |
| 1599 | CCUGUUG CUGAUGAGGCCGAAAGGCCGAA AGUCUGU |
| 1651 | GUUCAGG CUGAUGAGGCCGAAAGGCCGAA AGGCGUG |
| 1661 | CCCGGGA CUGAUGAGGCCGAAAGGCCGAA AGGUUCA |
| 1663 | GUCCCGG CUGAUGAGGCCGAAAGGCCGAA AUAGCUU |
| 1678 | CGAGGAA CUGAUGAGGCCGAAAGGCCGAA AGGCCCU |
| 1680 | GCCGAGG CUGAUGAGGCCGAAAGGCCGAA AGAGGCC |
| 1681 | GGCCGAG CUGAUGAGGCCGAAAGGCCGAA AAGAGGC |
| 1684 | GAAGGCC CUGAUGAGGCCGAAAGGCCGAA AGGAAGA |
| 1690 | AUAUGGG CUGAUGAGGCCGAAAGGCCGAA AGGCCGA |
| 1691 | AAUAUGG CUGAUGAGGCCGAAAGGCCGAA AAGGCCG |
| 1696 | CCACCAA CUGAUGAGGCCGAAAGGCCGAA AUGGGAA |
| 1698 | UGCCACC CUGAUGAGGCCGAAAGGCCGAA AUAUGGG |
| 1737 | CAUGGCA CUGAUGAGGCCGAAAGGCCGAA AUGUCUU |
| 1750 | GUAGGUG CUGAUGAGGCCGAAAGGCCGAA AGCUGCA |
| 1756 | GGGCCGG CUGAUGAGGCCGAAAGGCCGAA AGCUGUA |
| 1787 | UGAGGAC CUGAUGAGGCCGAAAGGCCGAA AUGCCCU |
| 1790 | GACUGAG CUGAUGAGGCCGAAAGGCCGAA ACAAUGC |
| 1793 | UCUGACU CUGAUGAGGCCGAAAGGCCGAA AGGACAA |
| 1797 | UGUAUCU CUGAUGAGGCCGAAAGGCCGAA ACUGAGG |
| 1802 | GCUGUUG CUGAUGAGGCCGAAAGGCCGAA AUCUGAC |
| 1812 | GGCCCCA CUGAUGAGGCCGAAAGGCCGAA AUGCCGU |
| 1813 | UGGCCCC CUGAUGAGGCCGAAAGGCCGAA AAUGCUG |
| 1825 | GUGCAGG CUGAUGAGGCCGAAAGGCCGAA ACCAUGG |
| 1837 | AGUCUUU CUGAUGAGGCCGAAAGGCCGAA AGGUGUG |
| 1845 | CCUGGCC CUGAUGAGGCCGAAAGGCCGAA AGUGUUU |
| 1856 | CAGAUCA CUGAUGAGGCCGAAAGGCCGAA AUGCGUG |
| 1861 | CACAACA CUGAUGAGGCCGAAAGGCCGAA AUCAGAU |
| 1865 | AUGUGAC CUGAUGAGGCCGAAAGGCCGAA ACAGAUC |
| 1868 | GUCAUGU CUGAUGAGGCCGAAAGGCCGAA ACUACAG |
| 1877 | CUUGGCU CUGAUGAGGCCGAAAGGCCGAA AGUCAUG |
| 1901 | AUGUCUU CUGAUGAGGCCGAAAGGCCGAA AGUCUUG |
| 1912 | AUCCAUC CUGAUGAGGCCGAAAGGCCGAA AUCAUGU |
| 1922 | AGACUUU CUGAUGAGGCCGAAAGGCCGAA ACAUCCA |
| 1923 | UAGACUU CUGAUGAGGCCGAAAGGCCGAA AACAUCC |
| 1928 | CAGGCUA CUGAUGAGGCCGAAAGGCCGAA ACUUUAA |
| 1930 | AUCAGGC CUGAUGAGGCCGAAAGGCCGAA AGACUUU |
| 1964 | GUGGGGC CUGAUGAGGCCGAAAGGCCGAA AUGUCUC |
| 1983 | CCAGUUG CUGAUGAGGCCGAAAGGCCGAA AUGUCCU |
| 1996 | GUUUCAG CUGAUGAGGCCGAAAGGCCGAA AUUUCCC |
| 2005 | AGGCAGC CUGAUGAGGCCGAAAGGCCGAA AGUUUCA |
| 2013 | UACCCAA CUGAUGAGGCCGAAAGGCCGAA AGGCAGC |
| 2015 | CAUACCC CUGAUGAGGCCGAAAGGCCGAA AUAGGCA |
| 2020 | CUCAGCA CUGAUGAGGCCGAAAGGCCGAA ACCGAAU |
| 2039 | CUUCUGU CUGAUGAGGCCGAAAGGCCGAA AGUCUGU |
| 2040 | UCUUCUG CUGAUGAGGCCGAAAGGCCGAA AAGUCUG |
| 2057 | GUCUAUG CUGAUGAGGCCGAAAGGCCGAA AGGGCCA |
| 2061 | ACAUGUC CUGAUGAGGCCGAAAGGCCGAA AUGGAGG |
| 2071 | UUGAUGC CUGAUGAGGCCGAAAGGCCGAA ACACAUG |
| 2076 | GUGUUUU CUGAUGAGGCCGAAAGGCCGAA AUGCUAC |
| 2097 | CGUCAGG CUGAUGAGGCCGAAAGGCCGAA AGGGUGG |

TABLE IV-continued

Human ICAM HH Ribozyme Sequences

| nt. Position | Ribozyme Sequence |
|---|---|
| 2098 | CCGUCAG CUGAUGAGGCCGAAAGGCCGAA AAGUGUG |
| 2115 | AGUGCCC CUGAUGAGGCCGAAAGGCCGAA AGCUGGC |
| 2128 | GUCAGUA CUGAUGAGGCCGAAAGGCCGAA ACAGCAG |
| 2130 | GGGUCAG CUGAUGAGGCCGAAAGGCCGAA AGACAGC |
| 2145 | UAUCAUC CUGAUGAGGCCGAAAGGCCGAA AGGGUUG |
| 2152 | AAAUACA CUGAUGAGGCCGAAAGGCCGAA AUCAUCA |
| 2156 | GAAUAAA CUGAUGAGGCCGAAAGGCCGAA ACAUAUC |
| 2158 | AUGAAUA CUGAUGAGGCCGAAAGGCCGAA AUACAUA |
| 2159 | AAUGAAU CUGAUGAGGCCGAAAGGCCGAA AAUACAU |
| 2160 | AAAUGAA CUGAUGAGGCCGAAAGGCCGAA AAAUACA |
| 2162 | ACAAAUG CUGAUGAGGCCGAAAGGCCGAA AUAAAUA |
| 2163 | AACAAAU CUGAUGAGGCCGAAAGGCCGAA AAUAAAU |
| 2166 | AAUAACA CUGAUGAGGCCGAAAGGCCGAA AUGAAUA |
| 2167 | UGCAGUG CUGAUGAGGCCGAAAGGCCGAA ACAACCU |
| 2170 | GUAAAAU CUGAUGAGGCCGAAAGGCCGAA ACAAAUG |
| 2171 | GGUAAAA CUGAUGAGGCCGAAAGGCCGAA AACAAAU |
| 2173 | CUGGUAA CUGAUGAGGCCGAAAGGCCGAA AUAACAA |
| 2174 | GCUGGUA CUGAUGAGGCCGAAAGGCCGAA AAUAACA |
| 2175 | AGCUGGU CUGAUGAGGCCGAAAGGCCGAA AAAUAAC |
| 2176 | UAGCUGG CUGAUGAGGCCGAAAGGCCGAA AAAAUAA |
| 2183 | CAAUAAA CUGAUGAGGCCGAAAGGCCGAA AGCUGGU |
| 2185 | CUCAAUA CUGAUGAGGCCGAAAGGCCGAA AUAGCUG |
| 2186 | ACUCAAU CUGAUGAGGCCGAAAGGCCGAA AAUAGCU |
| 2187 | CACUCAA CUGAUGAGGCCGAAAGGCCGAA AAAUAGC |
| 2189 | GACACUC CUGAUGAGGCCGAAAGGCCGAA AUAAAUA |
| 2196 | CAUAAAA CUGAUGAGGCCGAAAGGCCGAA ACACUCA |
| 2198 | UACAUAA CUGAUGAGGCCGAAAGGCCGAA AGACACU |
| 2199 | CUACAUA CUGAUGAGGCCGAAAGGCCGAA AAGACAC |
| 2200 | CCUACAU CUGAUGAGGCCGAAAGGCCGAA AAAGACA |
| 2201 | GCCUACA CUGAUGAGGCCGAAAGGCCGAA AAAAGAC |
| 2205 | UUUAGCC CUGAUGAGGCCGAAAGGCCGAA ACAUAAA |
| 2210 | GUUCAUU CUGAUGAGGCCGAAAGGCCGAA AGCCUAC |
| 2220 | AGAGACC CUGAUGAGGCCGAAAGGCCGAA AUGUUCA |
| 2224 | GGCCAGA CUGAUGAGGCCGAAAGGCCGAA ACCUAUG |
| 2226 | GAGGCCA CUGAUGAGGCCGAAAGGCCGAA AGACCUA |
| 2233 | GCUCCGU CUGAUGAGGCCGAAAGGCCGAA AGGCCAG |
| 2242 | GGACUGG CUGAUGAGGCCGAAAGGCCGAA AGCUCCG |
| 2248 | UGACAUG CUGAUGAGGCCGAAAGGCCGAA ACUGGGA |
| 2254 | UGAAUGU CUGAUGAGGCCGAAAGGCCGAA ACAUGGA |
| 2259 | GACCUUG CUGAUGAGGCCGAAAGGCCGAA AUGUGAC |
| 2260 | UGACCUU CUGAUGAGGCCGAAAGGCCGAA AAUGUGA |
| 2266 | ACCUGGU CUGAUGAGGCCGAAAGGCCGAA ACCUUGA |
| 2274 | ACAACUG CUGAUGAGGCCGAAAGGCCGAA ACCUGGU |
| 2279 | CCUGUAC CUGAUGAGGCCGAAAGGCCGAA ACUGUAC |
| 2282 | CAACCUG CUGAUGAGGCCGAAAGGCCGAA ACAACUG |
| 2288 | AGUGUAC CUGAUGAGGCCGAAAGGCCGAA ACCUGUA |
| 2291 | UGCAGUG CUGAUGAGGCCGAAAGGCCGAA ACAACCU |
| 2321 | CCCAUUU CUGAUGAGGCCGAAAGGCCGAA AUCUUUU |
| 2338 | CAAUGAG CUGAUGAGGCCGAAAGGCCGAA AGUCCCA |
| 2339 | CCAAUGA CUGAUGAGGCCGAAAGGCCGAA AAGUCCC |
| 2341 | GGCCAAU CUGAUGAGGCCGAAAGGCCGAA AGAAGUC |
| 2344 | GUUGGCC CUGAUGAGGCCGAAAGGCCGAA AUGAGAA |
| 2358 | CUGGGGA CUGAUGAGGCCGAAAGGCCGAA AGGCAGG |
| 2359 | UCUGGGG CUGAUGAGGCCGAAAGGCCGAA AAGGCAG |
| 2360 | UUCUGGG CUGAUGAGGCCGAAAGGCCGAA AAAGGCA |
| 2376 | AUAGAAA CUGAUGAGGCCGAAAGGCCGAA AUCACUC |
| 2377 | GAUAGAA CUGAUGAGGCCGAAAGGCCGAA AAUCACU |
| 2378 | CGAUAGA CUGAUGAGGCCGAAAGGCCGAA AAAUCAC |
| 2379 | CCGAUAG CUGAUGAGGCCGAAAGGCCGAA AAAAUCA |
| 2380 | GCCGAUA CUGAUGAGGCCGAAAGGCCGAA AAAAAUC |
| 2382 | GUGCCGA CUGAUGAGGCCGAAAGGCCGAA AGAAAAA |
| 2384 | UUGUGCC CUGAUGAGGCCGAAAGGCCGAA AUAGAAA |
| 2399 | GUCCAUA CUGAUGAGGCCGAAAGGCCGAA AGUGCUU |
| 2401 | CAGUCCA CUGAUGAGGCCGAAAGGCCGAA AUAGUGC |
| 2411 | GAACCAU CUGAUGAGGCCGAAAGGCCGAA ACCAGUC |
| 2417 | ACCUGUG CUGAUGAGGCCGAAAGGCCGAA ACCAUUA |
| 2418 | AACCUGU CUGAUGAGGCCGAAAGGCCGAA AACCAUU |
| 2425 | AUCUCUG CUGAUGAGGCCGAAAGGCCGAA ACCUGUG |
| 2426 | AAUCUCU CUGAUGAGGCCGAAAGGCCGAA AACCUGU |
| 2433 | ACUGGGU CUGAUGAGGCCGAAAGGCCGAA AUCUCUG |
| 2434 | CACUGGG CUGAUGAGGCCGAAAGGCCGAA AAUCUCU |
| 2448 | GAGGAAU CUGAUGAGGCCGAAAGGCCGAA AGGCCUC |
| 2449 | GGAGGAA CUGAUGAGGCGGAAAGGCCGAA AAGGCCU |
| 2451 | AGGGAGG CUGAUGAGGCCGAAAGGCCGAA AUAAGGC |

TABLE IV-continued

Human ICAM HH Ribozyme Sequences

| nt. Position | Ribozyme Sequence |
|---|---|
| 2452 | AAGGGAG CUGAUGAGGCCGAAAGGCCGAA AAUAAGG |
| 2455 | GGGAAGG CUGAUGAGGCCGAAAGGCCGAA AGGAAUA |
| 2459 | UGGGGGG CUGAUGAGGCCGAAAGGCCGAA AGGGAGG |
| 2460 | UUGGGGG CUGAUGAGGCCGAAAGGCCGAA AAGGGAG |
| 2479 | GCUAACA CUGAUGAGGCCGAAAGGCCGAA AGGUGUC |
| 2480 | GGCUAAC CUGAUGAGGCCGAAAGGCCGAA AAGGUGU |
| 2483 | GGUGGCU CUGAUGAGGCCGAAAGGCCGAA ACAAAGG |
| 2484 | AGGUGGC CUGAUGAGGCCGAAAGGCCGAA AACAAAG |
| 2492 | GGGUGGG CUGAUGAGGCCGAAAGGCCGAA AGGUGGC |
| 2504 | AGAAAUG CUGAUGAGGCCGAAAGGCCGAA AUGUGGG |
| 2508 | UGGCAGA CUGAUGAGGCCGAAAGGCCGAA AUGUAUG |
| 2509 | CUGGCAG CUGAUGAGGCCGAAAGGCCGAA AAUGUAU |
| 2510 | ACUGGCA CUGAUGAGGCCGAAAGGCCGAA AAAUGUA |
| 2520 | CAUUGUG CUGAUGAGGCCGAAAGGCCGAA ACACUGG |
| 2521 | UCAUUGU CUGAUGAGGCCGAAAGGCCGAA AACACUG |
| 2533 | GACCGCU CUGAUGAGGCCGAAAGGCCGAA AGUGUCA |
| 2540 | CAGACAU CUGAUGAGGCCGAAAGGCCGAA ACCGCUG |
| 2545 | AUGUCCA CUGAUGAGGCCGAAAGGCCGAA ACAUGAC |
| 2568 | UUGGGCA CUGAUGAGGCCGAAAGGCCGAA AUUCCCU |
| 2579 | CAAGCCA CUGAUGAGGCCGAAAGGCCGAA AGCUUGG |
| 2585 | AGAGGAC CUGAUGAGGCCGAAAGGCCGAA AGGGAUA |
| 2588 | ACAAGAG CUGAUGAGGCCGAAAGGCCGAA ACAAGGC |
| 2591 | AGGACAA CUGAUGAGGCCGAAAGGCCGAA AGGACAA |
| 2593 | ACAGGAC CUGAUGAGGCCGAAAGGCCGAA AGAGGAC |
| 2596 | CAAACAG CUGAUGAGGCCGAAAGGCCGAA ACAAGAG |
| 2601 | AAAUGCA CUGAUGAGGCCGAAAGGCCGAA ACAGGAC |
| 2602 | GAAAUGC CUGAUGAGGCCGAAAGGCCGAA AACAGGA |
| 2607 | CCAGUGA CUGAUGAGGCCGAAAGGCCGAA AUGCAAA |
| 2608 | CCCAGUG CUGAUGAGGCCGAAAGGCCGAA AAUGCAA |
| 2609 | UCCCAGU CUGAUGAGGCCGAAAGGCCGAA AAAUGCA |
| 2620 | AUAGUGC CUGAUGAGGCCGAAAGGCCGAA AGCUCCC |
| 2626 | GCUGCAA CUGAUGAGGCCGAAAGGCCCAA AGUGCAA |
| 2628 | GAGGUGC CUGAUGAGGCCGAAAGGCCGAA AUAGUGC |
| 2635 | GAAACUG CUGAUGAGGCCGAAAGGCGAA AGCUGCA |
| 2640 | UGCAGGA CUGAUGAGGCCGAAAGGCCGAA ACUGCAG |
| 2641 | CUGCAGG CUGAUGAGGCCGAAAGGCCGAA AACUGGA |
| 2642 | ACUGCAG CUGAUGAGGCCGAAAGGCCGAA AAACUGG |
| 2653 | GGACCCU CUGAUGAGGCCGAAAGGCCGAA AUCACUG |
| 2659 | CUUGCAG CUGAUGAGGCCGAAAGGCCGAA ACCCUGA |
| 2689 | CCUCCAA CUGAUGAGGCCGAAAGGCCGAA ACCUUGG |
| 2691 | GUCCUCC CUGAUGAGGCCGAAAGGCCGAA AUACCUU |
| 2700 | UGGGAGG CUGAUGAGGCCGAAAGGCCGAA AGUCCUC |
| 2704 | AAGCUGG CUGAUGAGGCCGAAAGGCCGAA AGGGAGU |
| 2711 | CCUUCCA CUGAUGAGGCCGAAAGGCCGAA AGCUGGG |
| 2712 | CCCUUCC CUGAUGAGGCCGAAAGGCCGAA AAGCUGG |
| 2721 | GGCGGAU CUGAUGAGGCCGAAAGGCCGAA ACCCUUC |
| 2724 | ACACGCG CUGAUGAGGCCGAAAGGCCGAA AUGACCC |
| 2744 | CUACACA CUGAUGAGGCCGAAACGCCGAA ACACACA |
| 2750 | GCUUGUC CUGAUGAGGCCGAAAGGCCGAA ACACAUA |
| 2759 | AGAGCGA CUGAUGAGGCCCAAAGGCCGAA AGCUUGU |
| 2761 | ACAGAGC CUGAUGAGGCCGAAAGGCCGAA AGAGCUU |
| 2765 | GGUGACA CUGAUGAGGCCCAAAGGCCGAA AGCGAGA |
| 2769 | CCUGGGU CUGAUGAGGCCGAAAGGCCCAA ACAGAGC |
| 2797 | GAACCAU CUGAUGAGGCCGAAAGGCCGAA AUUGCAC |
| 2803 | UGCAGUG CUGAUGAGGCCGAAAGGCCGAA ACCAUGA |
| 2804 | CUGCAGU CUGAUGAGGCCGAAAGGCCGAA AACCAUG |
| 2813 | AGGUCAA CUGAUGAGGCCGAAAGGCCGAA ACUGCAG |
| 2815 | AAAGGUC CUGAUGAGGCCGAAAGGCCGAA AGACUGC |
| 2821 | AGCCCAA CUGAUGAGGCCGAAAGGCCGAA AGGUCAA |
| 2822 | GAGCCCA CUGAUGAGGCCGAAAGGCCGAA AAGGUCA |
| 2823 | UGAGCCC CUGAUGAGGCCGAAAGGCCGAA AAAGGUC |
| 2829 | AUCACUU CUGAUGAGGCCGAAAGGCCGAA AGCCCAA |
| 2837 | GUCGGAG CUGAUGAGGCCGAAAGGCCGAA AUCACUU |
| 2840 | GAGGUGG CUGAUGAGGCCGAAAGGCCGAA AGGAUCA |
| 2847 | GGAGGCU CUGAUGAGGCCGAAAGGCCGAA AGGUGGG |
| 2853 | UACUCAG CUGAUGAGGCCGAAAGGCCGAA AGGCUGA |
| 2860 | UCCCAGC CUGAUGAGGCCGAAAGGCCGAA ACUCAGG |
| 2872 | GUGAGCC CUGAUGAGGCCGAAAGGCCGAA AUGGUCC |
| 2877 | GUGUUGU CUGAUGAGGCCGGAAGGCCGAA AGCCUAU |
| 2899 | AAAAUCA CUGAUGAGGCCGAAAGGCCGAA AUUUGCC |
| 2900 | AAAAAUC CUGAUGAGGCCGAAAGGCCGAA AAUUUGC |
| 2904 | AAAAAAA CUGAUGAGGCCGAAAGGCCGAA AUCAAAU |
| 2905 | AAAAAAA CUGAUGAGGCCGAAAGGCCGAA AAUCAAA |
| 2906 | AAAAAAA CUGAUGAGGCCGAAAGGCCGAA AAAUCAA |

TABLE IV-continued

Human ICAM HH Ribozyme Sequences

| nt. Position | Ribozyme Sequence |
|---|---|
| 2907 | AAAAAAA CUGAUGAGGCCGAAAGGCCGAA AAAAUCA |
| 2908 | AAAAAAA CUGAUGAGGCCGAAAGGCCGAA AAAAAUC |
| 2909 | AAAAAAA CUGAUGAGGCCGAAAGGCCGAA AAAAAAU |
| 2910 | AAAAAAA CUGAUGAGGCCGAAAGGCCGAA AAAAAAA |
| 2911 | AAAAAAA CUGAUGAGGCCGAAAGGCCGAA AAAAAAA |
| 2912 | GAAAAAA CUGAUGAGGCCGAAAGGCCGAA AAAAAAA |
| 2913 | UGAAAAA CUGAUGAGGCCGAAAGGCCGAA AAAAAAA |
| 2914 | CUGAAAA CUGAUGAGGCCGAAAGGCCGAA AAAAAAA |
| 2915 | UCUGAAA CUGAUGAGGCCGAAAGGCCGAA AAAAAAA |
| 2916 | CUCUGAA CUGAUGAGGCCGAAAGGCCGAA AAAAAAA |
| 2917 | UCUCUGA CUGAUGAGGCCGAAAGGCCGAA AAAAAAA |
| 2918 | GUCUCUG CUGAUGAGGCCGAAAGGCCGAA AAAAAAA |
| 2919 | CGUCUCU CUGAUGAGGCCGAAAGGCCGAA AAAAAAA |
| 2931 | GUUGCGA CUGAUGAGGCCGAAAGGCCGAA ACCCCGU |
| 2933 | AUUUUGC CUGAUGAGGCCGAAAGGCCGAA AGACCCC |
| 2941 | UCUGGGC CUGAUGAGGCCGAAAGGCCGAA AUGUUGC |
| 2951 | ACAAAGG CUGAUGAGGCCGAAAGGCCGAA AGUCUGG |
| 2952 | CACAAAG CUGAUGAGGCCGAAAGGCCGAA AAGUCUG |
| 2955 | UAACACA CUGAUGAGGCCGAAAGGCCGAA AGGAAGU |
| 2956 | CUAACAC CUGAUGAGGCCGAAAGGCCGAA AAGGAAG |
| 2961 | AUUAACU CUGAUGAGGCCGAAAGGCCGAA ACACAAA |
| 2962 | UAUUAAC CUGAUGAGGCCGAAAGGCCGAA AACACAA |
| 2965 | CUUUAUU CUGAUGAGGCCGAAAGGCCGAA ACUAACA |
| 2966 | GCUUUAU CUGAUGAGGCCGAAAGGCCGAA AACUAAC |
| 2969 | AAAGCUU CUGAUGAGGCCGAAAGGCCGAA AUUAACU |
| 2975 | GUUGAGA CUGAUGAGGCCGAAAGGCCGAA AGCAAUA |
| 2976 | AGUUGAG CUGAUGAGGCCGAAAGGCCGAA AACCUUU |
| 2977 | CAGUUGA CUGAUGAGGCCGAAAGGCCGAA AAAGCUU |
| 2979 | GGCAGUU CUGAUGAGGCCGAAAGGCCGAA AGAAAGC |

TABLE V

Mouse ICAM HH Ribozyme Sequence

| nt. Position | Ribozyme Sequence |
|---|---|
| 11 | CAACGGU CUGAUGAGGCCGAAAGGCCGAA ACCAGGG |
| 23 | AGCAGAG CUGAUGAGGCCGAAAGGCCGAA ACCACUG |
| 26 | AGGAGCA CUGAUGAGGCCGAAAGGCCGAA AGAACCA |
| 31 | UGUGGAG CUGAUGAGGCCGAAAGGCCGAA AGCAGAG |
| 34 | CGACCCU CUGAUGAGGCCGAAAGGCCGAA AUGAGAA |
| 40 | AGGCUAC CUGAUGAGGCCGAAAGGCCGAA AGUGUGC |
| 48 | CCAGGCU CUGAUGAGGCCGAAAGGCCGAA AGGUCCU |
| 54 | CCAUCAC CUGAUGAGGCCGAAAGGCCGAA AGGCCCA |
| 58 | GGAGCUA CUGAUGAGGCCGAAAGGCCGAA AGGCAUG |
| 64 | CUGCUGG CUGAUGAGGCCGAAAGGCCGAA AGGGGUG |
| 96 | GGGCCAG CUGAUGAGGCCGAAAGGCCGAA AGCAGAG |
| 102 | CCAGCAG CUGAUGAGGCCGAAAGGCCGAA ACUGGCA |
| 108 | GGGCCAG CUGAUGAGGCCGAAAGGCCGAA AGCAGAG |
| 115 | AGGAGCA CUGAUGAGGCCGAAAGGCCGAA AGAACCA |
| 119 | UCCUGGU CUGAUGAGGCCGAAAGGCCGAA ACAUUCC |
| 120 | GGGCCAG CUGAUGAGGCCGAAAGGCCGAA AGCAGAG |
| 146 | GGAAGCG CUGAUGAGGCCGAAAGGCCGAA ACGACUG |
| 152 | AGUGGCU CUGAUGAGGCCGAAAGGCCGAA ACACAGA |
| 158 | GGUUUUU CUGAUGAGGCCGAAAGGCCGAA AACAGGA |
| 165 | GCAAAAC CUGAUGAGGCCGAAAGGCCGAA ACUUCUG |
| 168 | GGGGCAG CUGAUGAGGCCGAAAGGCCGAA AAGGCUU |
| 185 | CUGCACG CUGAUGAGGCCGAAAGGCCGAA ACCCACC |
| 209 | GCCAGAG CUGAUGAGGCCGAAAGGCCGAA AGUGGC |
| 227 | GCAAAAC CUGAUGAGGCCGAAAGGCCGAA ACUUCUG |
| 230 | GGAGCAA CUGAUGAGGCCGAAAGGCCGAA ACAACUU |
| 237 | AGUUCUC CUGAUGAGGCCGAAAGGCCGAA AAGCACA |
| 248 | UUUAGGA CUGAUGAGGCCGAAAGGCCGAA AUGGGUU |
| 253 | UCUUCCU CUGAUGAGGCCGAAAGGCCGAA AGGCAGG |
| 263 | CAGUAGA CUGAUGAGGCCGAAAGGCCGAA AAACCCU |
| 267 | UAGGCAG CUGAUGAGGCCGAAAGGCCGAA AGCCCCU |
| 293 | CAGCUCA CUGAUGAGGCCGAAAGGCCGAA ACAGCUU |
| 319 | GGCUCAG CUGAUGAGGCCGAAAGGCCGAA AUCUCCU |
| 335 | GUUCUCA CUGAUGAGGCCGAAAGGCCGAA AGCACAG |
| 337 | CAGUGUG CUGAUGAGGCCGAAAGGCCGAA AUUGGAC |
| 338 | UCAGCUC CUGAUGAGGCCGAAAGGCCGAA AACAGCU |
| 359 | AGCGGAC CUGAUGAGGCCGAAAGGCCGAA ACUGCAC |
| 367 | CGGGUUG CUGAUGAGGCCGAAAGGCCGAA AGCCAUU |
| 374 | GGGCAGG CUGAUGAGGCCGAAAGGCCGAA AGGCUUC |
| 375 | GGGGCAG CUGAUGAGGCCGAAAGGCCGAA AAGGCUU |
| 378 | ACAGGGU CUGAUGAGGCCGAAAGGCCGAA AUCGGAG |

TABLE V-continued

Mouse ICAM HH Ribozyme Sequence

| nt. Position | Ribozyme Sequence |
|---|---|
| 386 | AAACGAA CUGAUGAGGCCGAAAGGCCGAA ACACGGU |
| 394 | AGAUCGA CUGAUGAGGCCGAAAGGCCGAA AGUCCGG |
| 420 | CGGGGGG CUGAUGAGGCCGAAAGGCCGAA AAGUGUG |
| 425 | CUGCUGG CUGAUGAGGCCGAAAGGCCGAA AGGGGUG |
| 427 | CACUGCU CUGAUGAGGCCGAAAGGCCGAA AGAGCUG |
| 450 | GCAGGGU CUGAUGAGGCCGAAAGGCCGAA AGGUCCU |
| 451 | CAAAGGA CUGAUGAGGCCGAAAGGCCGAA AGGUUUC |
| 456 | AGUGGCU CUGAUGAGGCCGAAAGGCCGAA AGGGUAA |
| 495 | ACACGGU CUGAUGAGGCCGAAAGGCCGAA AUGGUAG |
| 510 | CCCCACG CUGAUGAGGCCGAAAGGCCGAA AGCAGCA |
| 564 | GGAUGGA CUGAUGAGGCCGAAAGGCCGAA ACCUGAG |
| 592 | CCCAUGU CUGAUGAGGCCGAAAGGCCGAA AUCUUUC |
| 607 | CAUGAGA CUGAUGAGGCCGAAAGGCCGAA AUUGGCU |
| 608 | GCAUGAG CUGAUGAGGCCGAAAGGCCGAA AAUUGGC |
| 609 | GGCAUGA CUGAUGAGGCCGAAAGGCCGAA AAAUUGG |
| 611 | GCGGCAU CUGAUGAGGCCGAAAGGCCGAA AGAAAUU |
| 656 | CAGCUCA CUGAUGAGGCCGAAAGGCCGAA ACAGCUU |
| 657 | UCAGCUC CUGAUGAGGCCGAAAGGCCGAA AACAGCU |
| 668 | GGUGGCC CUGAUGAGGCCGAAAGGCCGAA AGGCUCG |
| 677 | AGGCUGG CUGAUGAGGCCGAAAGGCCGAA AGAGGUC |
| 684 | AGGACCG CUGAUGAGGCCGAAAGGCCGAA AGCUGAA |
| 692 | AAGAUCG CUGAUGAGGCCGAAAGGCCGAA AAGUCCG |
| 693 | GCAGGGU CUGAUGAGGCCGAAAGGCCGAA AGGUCCU |
| 696 | GAGGCAG CUGAUGAGGCCGAAAGGCCGAA AAACAGG |
| 709 | UGAGGUG CUGAUGAGGCCGAAAGGCCGAA AGCCGCC |
| 720 | AGCUGAA CUGAUGAGGCCGAAAGGCCGAA AGUUGUA |
| 723 | CGGAGCU CUGAUGAGGCCGAAAGGCCGAA AAAAGUU |
| 735 | UCUCCAG CUGAUGAGGCCGAAAGGCCGAA AUCUGGU |
| 738 | CCAUCAC CUGAUGAGGCCGAAAGGCCGAA AGGCCCA |
| 765 | GGAAGCG CUGAUGAGGCCGAAAGGCCGAA ACGACUG |
| 769 | GGCAGGA CUGAUGAGGCCGAAAGGCCGAA ACAGGCC |
| 770 | UUCCAGG CUGAUGAGGCCGAAAGGCCGAA AGCAAAA |
| 785 | GGCAGGA CUGAUGAGGCCGAAAGGCCGAA ACAGGCC |
| 786 | AGGCAGG CUGAUGAGGCCGAAAGGCCGAA AACAGGC |
| 792 | CUUCCGA CUGAUGAGGCCGAAAGGCCGAA ACCUCCA |
| 794 | AGUCUCC CUGAUGAGGCCGAAAGGCCGAA AGCCCAG |
| 807 | CCAGGUA CUGAUGAGGCCGAAAGGCCGAA AUCCGAG |
| 833 | GGGUGUC CUGAUGAGGCCGAAAGGCCGAA AGCUUUG |
| 846 | CAACGGU CUGAUGAGGCCGAAAGGCCGAA ACCAGGG |
| 851 | GCUGGUA CUGAUGAGGCCGAAAGGCCGAA AGGUCUC |
| 863 | CCAGAGG CUGAUGAGGCCGAAAGGCCGAA AGUGGCU |
| 866 | GGGCAGG CUGAUGAGGCCGAAAGGCCGAA AGGCUUC |
| 867 | UCUCCGG CUGAUGAGGCCGAAAGGCCGAA AACGAAU |
| 869 | CUUGCAU CUGAUGAGGCCGAAAGGCCGAA AGGAAGA |
| 881 | ACGGCUU CUGAUGAGGCCGAAAGGCCGAA AAGCCAU |
| 885 | UCACCUC CUGAUGAGGCCGAAAGGCCGAA ACCAAGG |
| 933 | CCAGAAU CUGAUGAGGCCGAAAGGCCGAA AUUAUAG |
| 936 | GCACCAG CUGAUGAGGCCGAAAGGCCGAA AUGAUUA |
| 978 | AGUUGUA CUGAUGAGGCCGAAAGGCCGAA ACUGUUA |
| 980 | AAAGUUG CUGAUGAGGCCGAAAGGCCGAA AGACUGU |
| 986 | AGCUGAA CUGAUGAGGCCGAAAGGCCGAA AGUUGUA |
| 987 | GAGCUGA CUGAUGAGGCCGAAAGGCCGAA AAGUUGU |
| 988 | GGAGCUG CUGAUGAGGCCGAAAGGCCGAA AAAGUUG |
| 1005 | UCUCCAG CUGAUGAGGCCGAAAGGCCGAA AUCUGGU |
| 1006 | UUCCCCA CUGAUGAGGCCGAAAGGCCGAA ACUCUCA |
| 1023 | CUUCCGA CUGAUGAGGCCGAAAGGCCGAA ACCUCCA |
| 1025 | CCCUUCC CUGAUGAGGCCGAAAGGCCGAA AGACCUC |
| 1066 | UUAUUUU CUGAUGAGGCCGAAAGGCCGAA AGAGUGG |
| 1092 | GGCCUGA CUGAUGAGGCCGAAAGGCCGAA AUCCAGU |
| 1093 | UUGGCUG CUGAUGAGGCCGAAAGGCCGAA AGCUCCA |
| 1125 | UCAAGAA CUGAUGAGGCCGAAAGGCCGAA AGUUGGG |
| 1163 | GCAAAAG CUGAUGAGGCCGAAAGGCCGAA AGCUUCG |
| 1164 | AGCAAAA CUGAUGAGGCCGAAAGGCCGAA AACCUUC |
| 1166 | AGAGCAA CUGAUGAGGCCGAAAGGCCGAA AGAAGCU |
| 1172 | GGUUUUU CUGAUGAGGCCGAAAGGCCGAA AACAGGA |
| 1200 | UGUGGAG CUGAUGAGGCCGAAAGGCCGAA AGCAGAG |
| 1201 | CUCUUCA CUGAUGAGGCCGAAAGGCCGAA AAGCAGC |
| 1203 | ACUGGUG CUGAUGAGGCCGAAAGGCCGAA AAAAAGU |
| 1227 | GCACACG CUGAUGAGGCCGAAAGGCCGAA AUGUACC |
| 1228 | AGCAAAA CUGAUGAGGCCGAAAGGCCGAA AAGCUUC |
| 1233 | CUCUCCG CUGAUGAGGCCGAAAGGCCGAA AAACGAA |
| 1238 | AGGACCA CUGAUGAGGCCGAAAGGCCGAA ACAGCAC |
| 1264 | CUUGCAC CUGAUGAGGCCGAAAGGCCGAA ACCCUUC |
| 1267 | UUCCCCA CUGAUGAGGCCGAAAGGCCGAA ACUCUCA |

TABLE V-continued

Mouse ICAM HH Ribozyme Sequence

| nt. Position | Ribozyme Sequence |
|---|---|
| 1294 | GGCUCAG CUGAUGAGGCCGAAAGGCCGAA AUCUCCU |
| 1295 | CUGCUGA CUGAUGAGGCCGAAAGGCCGAA ACCCCUC |
| 1306 | CAUUUCA CUGAUGAGGCCGAAAGGCCGAA AGUCUGC |
| 1321 | UCCUCCU CUGAUGAGGCCGAAAGGCCGAA AGCCUUC |
| 1334 | UUUAGGA CUGAUGAGGCCGAAAGGCCGAA AUGGGUU |
| 1344 | CACUCUC CUGAUGAGGCCGAAAGGCCGAA AGCUCAU |
| 1351 | UAACUUA CUGAUGAGGCCGAAAGGCCGAA ACAUUCA |
| 1353 | CACCUUC CUGAUGAGGCCGAAAGGCCGAA ACCCACU |
| 1366 | ACUUGUA CUGAUGAGGCCGAAAGGCCGAA ACUGUUA |
| 1367 | AGGUGGG CUGAUGAGGCCGAAAGGCCGAA AGGUGCU |
| 1368 | AGAGUGG CUGAUGAGGCCGAAAGGCCGAA ACAGUAC |
| 1380 | CCACCCC CUGAUGAGGCCGAAAGGCCGAA AUGGGCA |
| 1388 | AGCCACU CUGAUGAGGCCGAAAGGCCGAA AGUCUCC |
| 1398 | CUUCUGU CUGAUGAGGCCGAAAGGCCGAA ACAGCCA |
| 1402 | ACUUCUC CUGAUGAGGCCGAAAGGCCGAA AAGCACA |
| 1408 | CCUCCCC CUGAUGAGGCCGAAAGGCCGAA AUCUCGC |
| 1410 | CCCUUCC CUGAUGAGGCCGAAAGGCCGAA AGACCUC |
| 1421 | ACAAAAG CUGAUGAGGCCGAAAGGCCGAA AGGUGGG |
| 1425 | CUCUACC CUGAUGAGGCCGAAAGGCCGAA AGGCAGU |
| 1429 | CAGGGGC CUGAUGAGGCCGAAAGGCCGAA AUAGAGA |
| 1444 | UCCUCCU CUGAUGAGGCCGAAAGGCCGAA AGCCUUC |
| 1455 | UCCUGGU CUGAUGAGGCCGAAAGGCCGAA ACAUUCC |
| 1482 | GGGAGCA CUGAUGAGGCCGAAAGGCCGAA AACAACU |
| 1484 | CAUGAGG CUGAUGAGGCCGAAAGGCCGAA AGAACAG |
| 1493 | GUUCUCA CUGAUGAGGCCGAAAGGCCGAA AGCACAG |
| 1500 | GGACCAU CUGAUGAGGCCGAAAGGCCGAA AUUUCAU |
| 1503 | GAAUGAU CUGAUGAGGCCGAAAGGCCGAA AUAGUCC |
| 1506 | CGGUUAU CUGAUGAGGCCGAAAGGCCGAA AACAUAA |
| 1509 | ACACGGU CUGAUGAGGCCGAAAGGCCGAA AUGGUAG |
| 1518 | CGCCUGG CUGAUGAGGCCGAAAGGCCGAA ACCAUGA |
| 1530 | CCAGAAU CUGAUGAGGCCGAAAGGCCGAA AUUAUAG |
| 1533 | GGCCCAC CUGAUGAGGCCGAAAGGCCGAA AUGACCA |
| 1551 | AGCUGCU CUGAUGAGGCCGAAAGGCCGAA AGGCAUG |
| 1559 | AGGUGGG CUGAUGAGGCCGAAAGGCCGAA AGGUGCU |
| 1563 | GGUUAUA CUGAUGAGGCCGAAAGGCCGAA ACAUAAG |
| 1565 | GCGGUUA CUGAUGAGGCCGAAAGGCCGAA AAACAUA |
| 1567 | UGGCGGU CUGAUGAGGCCGAAAGGCCGAA AUAAACA |
| 1584 | AUAUCCU CUGAUGAGGCCGAAAGGCCGAA AUCUUUC |
| 1592 | UAACUUG CUGAUGAGGCCGAAAGGCCGAA AUAUCCU |
| 1599 | CCUUCUG CUGAUGAGGCCGAAAGGCCGAA AACUUGU |
| 1651 | GCUCAGG CUGAUGAGGCCGAAAGGCCGAA AGGUGGG |
| 1661 | CAAAGGA CUGAUGAGGCCGAAAGGCCGAA AGGUUUC |
| 1663 | UUCAAAG CUGAUGAGGCCGAAAGGCCGAA AAAGGUU |
| 1678 | CCAGGCU CUGAUGAGGCCGAAAGGCCGAA AGGUCCU |
| 1680 | CCAGAGG CUGAUGAGGCCGAAAGGCCGAA AGUGGCU |
| 1681 | GCCAGAG CUGAUGAGGCCGAAAGGCCGAA AAGUGGC |
| 1684 | ACAGCCA CUGAUGAGGCCGAAAGGCCGAA AGGAAGU |
| 1690 | AGAUCGA CUGAUGAGGCCGAAAGGCCGAA AGUCCGG |
| 1691 | AAGAUCG CUGAUGAGGCCGAAAGGCCGAA AAGUCCG |
| 1696 | CCACCCC CUGAUGAGGCCGAAAGGCCGAA AUGGGCA |
| 1698 | CUCCAGG CUGAUGAGGCCGAAAGGCCGAA AUAUCCG |
| 1737 | GCUGGUA CUGAUGAGGCCGAAAGGCCGAA AGGUCUC |
| 1750 | UGAGGUG CUGAUGAGGCCGAAAGGCCGAA AGCCGCC |
| 1756 | GGGCAGG CUGAUGAGGCCGAAAGGCCGAA AGGCUUC |
| 1787 | UGGGGAC CUGAUGAGGCCGAAAGGCCGAA AUGUCUC |
| 1790 | AUUAGAG CUGAUGAGGCCGAAAGGCCGAA ACAAUGC |
| 1793 | UCCAGCC CUGAUGAGGCCGAAAGGCCGAA AGGACCA |
| 1797 | UUUAUGU CUGAUGAGGCCGAAAGGCCGAA ACUGGUG |
| 1802 | UCUCCAG CUGAUGAGGCCGAAAGGCCGAA AUCUGGU |
| 1812 | GGCCUGA CUGAUGAGGCCGAAAGGCCGAA AUCCAGU |
| 1813 | UGAGGGU CUGAUGAGGCCGAAAGGCCGAA AAUGCUG |
| 1825 | GCAGAGG CUGAUGAGGCCGAAAGGCCGAA AGCGUGG |
| 1837 | GGAGCCA CUGAUGAGGCCGAAAGGCCGAA AGGCAUG |
| 1845 | GGUGGCC CUGAUGAGGCCGAAAGGCCGAA AGGCUCG |
| 1856 | AAGAUCG CUGAUGAGGCCGAAAGGCCGAA AAGUCCG |
| 1861 | UACUGGA CUGAUGAGGCCGAAAGGCCGAA AUCAUGU |
| 1865 | CUGAGGC CUGAUGAGGCCGAAAGGCCGAA ACAAGUG |
| 1868 | UUUAUGU CUGAUGAGGCCGAAAGGCCGAA ACUGGUG |
| 1877 | AGCUGCU CUGAUGAGGCCGAAAGGCCGAA AGGCAUG |
| 1901 | GUCCCUU CUGAUGAGGCCGAAAGGCCGAA AGUUUUA |
| 1912 | ACUGAUC CUGAUGAGGCCGAAAGGCCGAA ACUAUAU |
| 1922 | UAACUUA CUGAUGAGGCCGAAAGGCCGAA ACAUUCA |
| 1923 | GAUACCU CUGAUGAGGCCGAAAGGCCGAA AGCAUCA |
| 1928 | CUGGUAA CUGAUGAGGCCGAAAGGCCGAA ACUCUAA |

TABLE V-continued

Mouse ICAM HH Ribozyme Sequence

| nt. Position | Ribozyme Sequence |
|---|---|
| 1930 | AGCUGGU CUGAUGAGGCCGAAAGGCCGAA AAACUCU |
| 1964 | UGGGGAC CUGAUGAGGCCGAAAGGCCGAA AUGUCUC |
| 1983 | UAACUUG CUGAUGAGGCCGAAAGGCCGAA AUAUCCU |
| 1996 | GGCUCAG CUGAUGAGGCCGAAAGGCCGAA AUCUCCU |
| 2005 | GGUCCGC CUGAUGAGGCCGAAAGGCCGAA AGCUCCA |
| 2013 | UACUCAA CUGAUGAGGCCGAAAGGCCGAA AAAUAGC |
| 2015 | CCACCCC CUGAUGAGGCCGAAAGGCCGAA AUGGGCA |
| 2020 | CUCAGAA CUGAUGAGGCCGAAAGGCCGAA AACCACC |
| 2039 | CCUCUGC CUGAUGAGGCCGAAAGGCCGAA AGCCAGC |
| 2040 | CCUCCAG CUGAUGAGGCCGAAAGGCCGAA AGGUCAG |
| 2057 | GGAUGUG CUGAUGAGGCCGAAAGGCCGAA AGGAGCA |
| 2061 | ACACGGU CUGAUGAGGCCGAAAGGCCGAA AUGGUAG |
| 2071 | CUGAGGC CUGAUGAGGCCGAAAGGCCGAA ACAAGUG |
| 2076 | UAGCUCU CUGAUGAGGCCGAAAGGCCGAA AGGCUAC |
| 2097 | CAUCAAG CUGAUGAGGCCGAAAGGCCGAA AGAGUUG |
| 2098 | CGGGGGG CUGAUGAGGCCGAAAGGCCGAA AAGUGUG |
| 2115 | AUCCUCC CUGAUGAGGCCGAAAGGCCGAA AGCUGGC |
| 2128 | CUCAAUA CUGAUGAGGCCGAAAGGCCGAA AUAGCUG |
| 2130 | GAGGCAG CUGAUGAGGCCGAAAGGCCGAA AAACAGG |
| 2145 | CAUCAAG CUGAUGAGGCCGAAAGGCCGAA AGAGUUG |
| 2152 | AACUCUA CUGAUGAGGCCGAAAGGCCGAA AUUAAUA |
| 2156 | UAAUAAA CUGAUGAGGCCGAAAGGCCGAA ACAUCAA |
| 2158 | AUUAAUA CUGAUGAGGCCGAAAGGCCGAA AUACAUC |
| 2159 | AAUUAAU CUGAUGAGGCCGAAAGGCCGAA AAUACAU |
| 2160 | AAAUUAA CUGAUGAGGCCGAAAGGCCGAA AAAUACA |
| 2162 | CUAAAUU CUGAUGAGGCCGAAAGGCCGAA AUAAAUA |
| 2163 | AAUUAAU CUGAUGAGGCCGAAAGGCCGAA AAUACAU |
| 2166 | AAUAGAG CUGAUGAGGCCGAAAGGCCGAA AUGAAGU |
| 2167 | AAUUAAU CUGAUGAGGCCGAAAGGCCGAA AAUACAU |
| 2170 | CUAAAUU CUGAUGAGGCCGAAAGGCCGAA AUAAAUA |
| 2171 | GGCAGCA CUGAUGAGGCCGAAAGGCCGAA AACAACU |
| 2173 | CUGGUAA CUGAUGAGGCCGAAAGGCCGAA ACUCUAA |
| 2174 | GCUGGUA CUGAUGAGGCCGAAAGGCCGAA AACUCUA |
| 2175 | AGCUGGU CUGAUGAGGCCGAAAGGCCGAA AAACUCU |
| 2176 | UAGCUGG CUGAUGAGGCCGAAAGGCCGAA AAAACUC |
| 2183 | CAAUAAA CUGAUGAGGCCGAAAGGCCGAA AGCUGGU |
| 2185 | CUCAAUA CUGAUGAGGCCGAAAGGCCGAA AUAGCUG |
| 2186 | ACUCAAU CUGAUGAGGCCGAAAGGCCGAA AAUAGCU |
| 2187 | UACUCAA CUGAUGAGGCCGAAAGGCCGAA AAAUAGC |
| 2189 | GGUACUC CUGAUGAGGCCGAAAGGCCGAA AUAAAUA |
| 2196 | CAUCAAG CUGAUGAGGCCGAAAGGCCGAA AGAGUUG |
| 2198 | AACAUAA CUGAUGAGGCCGAAAGGCCGAA AGCCUGC |
| 2199 | AUAAACA CUGAUGAGGCCGAAAGGCCGAA AAGAGGC |
| 2200 | GUUGCAU CUGAUGAGGCCGAAAGGCCGAA AGGAAGA |
| 2201 | GCCGACA CUGAUGAGGCCGAAAGGCCGAA AAAACUU |
| 2205 | UCAGGCC CUGAUGAGGCCGAAAGGCCGAA ACAUAAA |
| 2210 | AGCCACU CUGAUGAGGCCGAAAGGCCGAA AGUCUCC |
| 2220 | AGAGAAC CUGAUGAGGCCGAAAGGCCGAA AUGCCAG |
| 2224 | GGAUGGA CUGAUGAGGCCGAAAGGCCGAA ACCUGAG |
| 2226 | GCGGCCU CUGAUGAGGCCGAAAGGCCGAA AGAUCCA |
| 2233 | CCUCCAG CUGAUGAGGCCGAAAGGCCGAA AGGUCAG |
| 2242 | GGUCCGC CUGAUGAGGCCGAAAGGCCGAA AGCUCCA |
| 2248 | UGGGAUG CUGAUGAGGCCGAAAGGCCGAA AUGGAUA |
| 2254 | UCAGUGU CUGAUGAGGCCGAAAGGCCGAA AAUUGGA |
| 2259 | CACCGUG CUGAUGAGGCCGAAAGGCCGAA AUGUGAU |
| 2260 | GCACCGU CUGAUGAGGCCGAAAGGCCGAA AAUGUGA |
| 2266 | UCCUGGU CUGAUGAGGCCGAAAGGCCGAA ACAUUCC |
| 2274 | UCUCCAG CUGAUGAGGCCGAAAGGCCGAA AUCUGGU |
| 2279 | CUUGCAC CUGAUGAGGCCGAAAGGCCGAA ACCCUUC |
| 2282 | CAGCUCA CUGAUGAGGCCGAAAGGCCGAA ACAGCUU |
| 2288 | AGGCCAU CUGAUGAGGCCGAAAGGCCGAA ACUUAUA |
| 2291 | AGCAGAG CUGAUGAGGCCGAAAGGCCGAA ACCACUG |
| 2321 | CCCAUGU CUGAUGAGGCCGAAAGGCCGAA AUCUUUC |
| 2338 | CAGGCAG CUGAUGAGGCCGAAAGGCCGAA AGUCUCA |
| 2339 | CAAAGGA CUGAUGAGGCCGAAAGGCCGAA ACGUUUC |
| 2341 | AGGCUGG CUGAUGAGGCCGAAAGGCCGAA AGAGGUC |
| 2344 | GCUGGAA CUGAUGAGGCCGAAAGGCCGAA AUCGAAA |
| 2358 | CUGCUGA CUGAUGAGGCCGAAAGGCCGAA AGCUGGG |
| 2359 | UCUGUUC CUGAUGAGGCCGAAAGGCCGAA AAAGCAG |
| 2360 | UUCAAAG CUGAUGAGGCCGAAAGGCCGAA AAAGGUU |
| 2376 | UCAGAAG CUGAUGAGGCCGAAAGGCCGAA ACCACCU |
| 2377 | CUCAGAA CUGAUGAGGCCGAAAGGCCGAA AACCACC |
| 2378 | CAGUAGA CUGAUGAGGCCGAAAGGCCGAA AAACCCU |
| 2379 | CUUAUGA CUGAUGAGGCCGAAAGGCCGAA AAAAGCA |

TABLE V-continued

Mouse ICAM HH Ribozyme Sequence

| nt. Position | Ribozyme Sequence |
|---|---|
| 2380 | GCCGACA CUGAUGAGGCCGAAAGGCCGAA AAAACUU |
| 2382 | GGGGCAA CUGAUGAGGCCGAAAGGCCGAA AGAGAAU |
| 2384 | UUGUGUC CUGAUGAGGCCGAAAGGCCGAA ACUGGAU |
| 2399 | GUCCACA CUGAUGAGGCCGAAAGGCCGAA AGUGUUU |
| 2401 | CAGCUCA CUGAUGAGGCCGAAAGGCCGAA ACAGCUU |
| 2411 | GCAUCCU CUGAUGAGGCCGAAAGGCCGAA ACCAGUA |
| 2417 | ACGUAUG CUGAUGAGGCCGAAAGGCCGAA ACCAUUC |
| 2418 | GGCCUGA CUGAUGAGGCCGAAAGGCCGAA AUCCAGU |
| 2425 | AACCCUC CUGAUGAGGCCGAAAGGCCGAA ACCCAUG |
| 2426 | AAACUCU CUGAUGAGGCCGAAAGGCCGAA AAUUAAU |
| 2433 | GCUGGUA CUGAUGAGGCCGAAAGGCCGAA AACUCUA |
| 2434 | AGCUGGU CUGAUGAGGCCGAAAGGCCGAA AAACUCU |
| 2448 | GGGCAGG CUGAUGAGGCCGAAAGGCCGAA AGGCCUC |
| 2449 | GGGGCAG CUGAUGAGGCCGAAAGGCCGAA AAGGCUU |
| 2451 | AGGCAGG CUGAUGAGGCCGAAAGGCCGAA AACAGGC |
| 2452 | GAGGCAG CUGAUGAGGCCGAAAGGCCGAA AAACAGG |
| 2455 | GGGCAGG CUGAUGAGGCCGAAAGGCCGAA AGGCGUC |
| 2459 | GGGGGGG CUGAUGAGGCCGAAAGGCCGAA AGUGUGG |
| 2460 | CGGGGGG CUGAUGAGGCCGAAAGGCCGAA AAGUGUG |
| 2479 | GCUGGUA CUGAUGAGGCCGAAAGGCCGAA AGGUCUC |
| 2480 | GGAUCAC CUGAUGAGGCCGAAAGGCCGAA ACGGUGA |
| 2483 | GGUGGCU CUGAUGAGGCCGAAAGGCCGAA ACAUUGG |
| 2484 | GACUGGU CUGAUGAGGCCGAAAGGCCGAA AAAAAAG |
| 2492 | AGGUGGG CUGAUGAGGCCGAAAGGCCGAA AGGUGCU |
| 2504 | ACAAAAG CUGAUGAGGCCGAAAGGCCGAA AGGUGGG |
| 2508 | UGGGAUG CUGAUGAGGCCGAAAGGCCGAA AUGGAUA |
| 2509 | CUGGUAA CUGAUGAGGCCGAAAGGCCGAA ACUCUAA |
| 2510 | GCUGGUA CUGAUGAGGCCGAAAGGCCGAA AACUCUA |
| 2520 | CAUUGGG CUGAUGAGGCCGAAAGGCCGAA ACAAAAG |
| 2521 | UGAGGGU CUGAUGAGGCCGAAAGGCCGAA AAUGCUG |
| 2533 | GAUACCU CUGAUGAGGCCGAAAGGCCGAA AGCAUCA |
| 2540 | CACAGCG CUGAUGAGGCCGAAAGGCCGAA ACUGCUG |
| 2545 | AGGACCA CUGAUGAGGCCGAAAGGCCGAA ACAGCAC |
| 2568 | UUUGACA CUGAUGAGGCCGAAAGGCCGAA ACUUCAC |
| 2579 | CAGGCCA CUGAUGAGGCCGAAAGGCCGAA AACUUAU |
| 2585 | AGAGAAC CUGAUGAGGCCGAAAGGCCGAA AUGCCAG |
| 2588 | AUUAGAG CUGAUGAGGCCGAAAGGCCGAA ACAAUGC |
| 2591 | AGGAGCA CUGAUGAGGCCGAAAGGCCGAA AGAACCA |
| 2593 | GCAGAGC CUGAUGAGGCCGAAAGGCCGAA AAAGAAG |
| 2596 | CAUUGGG CUGAUGAGGCCGAAAGGCCGAA ACAAAAG |
| 2601 | AAACGAA CUGAUGAGGCCGAAAGGCCGAA ACACGGU |
| 2602 | GGGAUGG CUGAUGAGGCCGAAAGGCCGAA AGCUGGA |
| 2607 | CCAGGUA CUGAUGAGGCCGAAAGGCCGAA AUCCGAG |
| 2608 | CACAGCG CUGAUGAGGCCGAAAGGCCGAA ACUGCUG |
| 2609 | UCCUGGU CUGAUGAGGCCGAAAGGCCGAA ACAUUCC |
| 2620 | GCAGGGU CUGAUGAGGCCGAAAGGCCGAA AGGUCCU |
| 2626 | GCUGGAA CUGAUGAGGCCGAAAGGCCGAA AUCGAAA |
| 2628 | AGGCUAC CUGAUGAGGCCGAAAGGCCGAA AGUGUGC |
| 2635 | AGGACCG CUGAUGAGGCCGAAAGGCCGAA AGCUGAA |
| 2640 | GGCAGGA CUGAUGAGGCCGAAAGGCCGAA ACAGGCC |
| 2641 | CUGCUGA CUGAUGAGGCCGAAAGGCCGAA AGCUGGG |
| 2642 | GAGGCAG CUGAUGAGGCCGAAAGGCCGAA AAACAGG |
| 2653 | GCAUCCU CUGAUGAGGCCGAAAGGCCGAA ACCAGUA |
| 2659 | CUUGCAC CUGAUGAGGCCGAAAGGCCGAA ACCCUUC |
| 2689 | CCUCGGA CUGAUGAGGCCGAAAGGCCGAA ACAUUAG |
| 2691 | GGCCUCG CUGAUGAGGCCGAAAGGCCGAA AGACAUU |
| 2700 | GGGCAGG CUGAUGAGGCCGAAAGGCCGAA AGGCUUC |
| 2704 | AGGCUGG CUGAUGAGGCCGAAAGGCCGAA AGAGGUC |
| 2711 | CUGCUGA CUGAUGAGGCCGAAAGGCCGAA AGCUGGG |
| 2712 | CCCUUCC CUGAUGAGGCCGAAAGGCCGAA AGACCUC |
| 2721 | CUUGCAC CUGAUGAGGCCGAAAGGCCGAA ACCCUUC |
| 2724 | GCACACG CUGAUGAGGCCGAAAGGCCGAA AUGUACC |
| 2744 | CUGCACG CUGAUGAGGCCGAAAGGCCGAA ACCCACC |
| 2750 | GGUACUC CUGAUGAGGCCGAAAGGCCGAA AUAAAUA |
| 2759 | AGAUCGA CUGAUGAGGCCGAAAGGCCGAA AGUCCGG |
| 2761 | GCAGGGU CUGAUGAGGCCGAAAGGCCGAA AGGUCCU |
| 2765 | AGCGGCA CUGAUGAGGCCGAAAGGCCGAA AGCAAAA |
| 2769 | CCUGUUU CUGAUGAGGCCGAAAGGCCGAA ACAGACU |
| 2797 | GGACCAU CUGAUGAGGCCGAAAGGCCGAA AUUUCAU |
| 2803 | CGCCUGG CUGAUGAGGCCGAAAGGCCGAA ACCAUGA |
| 2804 | CUGCACG CUGAUGAGGCCGAAAGGCCGAA ACCCACC |
| 2813 | GGGUCAG CUGAUGAGGCCGAAAGGCCGAA ACCGGAG |
| 2815 | AAAGUUG CUGAUGAGGCCGAAAGGCCGAA AGACUGU |
| 2821 | CCUCCAG CUGAUGAGGCCGAAAGGCCGAA AGGUCAG |

TABLE V-continued

Mouse ICAM HH Ribozyme Sequence

| nt. Position | Ribozyme Sequence |
|---|---|
| 2822 | AAGUCCG CUGAUGAGGCCGAAAGGCCGAA AGGCUCC |
| 2823 | UGGGAGC CUGAUGAGGCCGAAAGGCCGAA AAAGGCA |
| 2829 | AUGAUUA CUGAUGAGGCCGAAAGGCCGAA AGUCCAG |
| 2837 | UCAGAAG CUGAUGAGGCCGAAAGGCCGAA ACCACCU |
| 2840 | CAGGCAG CUGAUGAGGCCGAAAGGCCGAA AGUCUCA |
| 2847 | GGUGGCU CUGAUGAGGCCGAAAGGCCGAA ACAUUGG |
| 2853 | AACAUAA CUGAUGAGGCCGAAAGGCCGAA AGGCUGC |
| 2860 | UCACAGU CUGAUGAGGCCGAAAGGCCGAA ACUUGGC |
| 2872 | CUUGGCU CUGAUGAGGCCGAAAGGCCGAA AAGGUCC |
| 2877 | GUGAUGG CUGAUGAGGCCGAAAGGCCGAA AGCGGAA |
| 2899 | AAGAUCG CUGAUGAGGCCGAAAGGCCGAA AAGUCCG |
| 2900 | AAAACUC CUGAUGAGGCCGAAAGGCCGAA AAAUUAA |
| 2904 | AAUAGAG CUGAUGAGGCCGAAAGGCCGAA AUGAAGU |
| 2905 | CAAUAGA CUGAUGAGGCCGAAAGGCCGAA AAUGAAG |
| 2906 | UAAUAAA CUGAUGAGGCCGAAAGGCCGAA ACAUCAA |
| 2907 | AAAUUAA CUGAUGAGGCCGAAAGGCCGAA AAAUACA |
| 2908 | AGCAAAA CUGAUGAGGCCGAAAGGCCGAA AAGCUUC |
| 2909 | AGAGCAA CUGAUGAGGCCGAAAGGCCGAA AGAAGCU |
| 2910 | AAAUUAA CUGAUGAGGCCGAAAGGCCGAA AAAUACA |
| 2911 | AAAUUAA CUGAUGAGGCCGAAAGGCCGAA AAAUACA |
| 2912 | GACAUUA CUGAUGAGGCCGAAAGGCCGAA AGAACAA |
| 2913 | UGACCAG CUGAUGAGGCCGAAAGGCCGAA AGAGAAA |
| 2914 | CUUAUGA CUGAUGAGGCCGAAAGGCCGAA AAAAGCA |
| 2915 | UCUAAAU CUGAUGAGGCCGAAAGGCCGAA AAUAAAU |
| 2916 | CUCGGGA CUGAUGAGGCCGAAAGGCCGAA ACGAAUA |
| 2917 | UCUCCGG CUGAUGAGGCCGAAAGGCCGAA AACGAAU |
| 2918 | CUCUCCG CUGAUGAGGCCGAAAGGCCGAA AAACGAA |
| 2919 | CGACCCU CUGAUGAGGCCGAAAGGCCGAA AUGAGAA |
| 2931 | CUUCCGA CUGAUGAGGCCGAAAGGCCGAA ACCUCCA |
| 2933 | CCCCUCC CUGAUGAGGCCGAAAGGCCGAA AGACCUC |
| 2941 | UGGGGAC CUGAUGAGGCCGAAAGGCCGAA AUGUCUC |
| 2951 | GCAGAGG CUGAUGAGGCCGAAAGGCCGAA AGCGUGG |
| 2952 | CACAGCG CUGAUGAGGCCGAAAGGCCGAA ACUGCUG |
| 2955 | UGACACA CUGAUGAGGCCGAAAGGCCGAA AGUCACU |
| 2956 | UUGAUUC CUGAUGAGGCCGAAAGGCCGAA AAGGAAA |
| 2961 | AGUGGCU CUGAUGAGGCCGAAAGGCCGAA ACACAGA |
| 2962 | AAUUAAU CUGAUGAGGCCGAAAGGCCGAA AAUACAU |
| 2965 | CUUUAUU CUGAUGAGGCCGAAAGGCCGAA AUUGAAA |
| 2966 | CCUCUGC CUGAUGAGGCCGAAAGGCCGAA AGCCAGC |
| 2969 | AAAACUU CUGAUGAGGCCGAAAGGCCGAA AUUGAUU |
| 2975 | GCUGGUA CUGAUGAGGCCGAAAGGCCGAA AACUCUA |
| 2976 | AGUAGAG CUGAUGAGGCCGAAAGGCCGAA AACCCUC |
| 2977 | CAGCUCA CUGAUGAGGCCGAAAGGCCGAA ACAGCUU |
| 2979 | GGCAAUA CUGAUGAGGCCGAAAGGCCGAA AGAAUGA |

TABLE VI

Human ICAM Hairpin Ribozyme/Substrate Sequences

| nt. Position | Hairpin Ribozyme Sequence | Substrate |
|---|---|---|
| 70 | GGGCCGGG AGAA GCUG ACCAGAGAAACACACGUUGUGGUACAUUACCUGGUA | CAGCA GCC CCCGGCCC |
| 86 | GGAGUGCG AGAA GCGC ACCAGAGAAACACACGUUGUGGUACAUUACCUGGUA | GCGCU GCC CGCACUCC |
| 343 | CCCAUCAG AGAA GUUU ACCAGAGAAACACACGUUGUGGUACAUUACCUGGUA | AAACU GCC CUGAUGGG |
| 635 | GCCCUUGG AGAA GCAG ACCAGAGAAACACACGUUGUGGUACAUUACCUGGUA | CUGCG GCC CAAGGGC |
| 653 | UGUUCUCA AGAA GCUC ACCAGAGAAACACACGUUGUGGUACAUUACCUGGUA | GAGCU GUU UGAGAACA |
| 782 | AGACUGGG AGAA GCCC ACCAGAGAAACACACGUUGUGGUACAUUACCUGGUA | GGGCU GUU CCCAGUCU |
| 920 | CUGCACAC AGAA GCCG ACCAGAGAAACACACGUUGUGGUACAUUACCUGGUA | CGGCU GAC GUGUGCAG |

TABLE VI-continued

Human ICAM Hairpin Ribozyme/Substrate Sequences

| nt. Position | Hairpin Ribozyme Sequence | Substrate |
|---|---|---|
| 1301 | ACAUUGGA AGAA GCUG ACCAGAGAAACACACGUUGUGGUACAUUACCUGGUA | CAGCA GAC UCCAAUGU |
| 1373 | CCCCGAUG AGAA GUGG ACCAGAGAAACACACGUUGUGGUACAUUACCUGGUA | CCACU GCC CAUCGGGG |
| 1521 | AUGACUGC ACAA GCUA ACCAGAGAAACACACGUUGUGGUACAUUACCUGGUA | UAGCA GCC GCAGUCAU |
| 1594 | CUGUUGUA AGAA GUAU ACCAGAGAAACACACGUUGUGGUACAUUACCUGGUA | AUACA GAC UACAACAG |
| 2008 | ACCCAAUA AGAA GCAA ACCAGAGAAACACACGUUGUGGUACAUUACCUGGUA | UUGCU GCC UAUUCCCU |
| 2034 | UUCUGUAA AGAA GUGG ACCAGAGAAACACACGUUGUGGUACAUUACCUGGUA | CCACA GAC UUACAGAA |
| 2125 | GGUCAGUA AGAA GCAG ACCAGAGAAACACACGUUGUGGUACAUUACCUGGUA | CUGCU GUC UACUGACC |
| 2132 | GGGUUGGG AGAA GUAG ACCAGAGAAACACACGUUGUGGUACAUUACCUGGUA | CUACU GAC CCCAACCC |
| 2276 | ACCUGUAC AGAA GUAC ACCAGAGAAACACACGUUGUGGUACAUUACCUGGUA | GUACA GUU GUACAGGU |
| 2810 | AAGGUCAA AGAA GCAG ACCAGAGAAACACACGUUGUGGUACAUUACCUGGUA | CUGCA GUC UUGACCUU |

TABLE VII

Mouse ICAM Hairpin Ribozyme/Substrate Sequences

| nt. Position | Hairpin Ribozyme Sequence | Substrate |
|---|---|---|
| 76 | GGGAUCAC AGAA GUGA ACCAGAGAAACACACGUUGUGGUACAUUACCUGGUA | UCACC GUU GUGAUCCC |
| 164 | UGAGGAAG AGAA GUUC ACCAGAGAAACACACGUUGUGGUACAUUACCUGGUA | GAACA GUU CUUCCUCA |
| 252 | UCAGCUCA AGAA GCUU ACCAGAGAAACACACGUUGUGGUACAUUACCUGGUA | AAGCU GUU UGAGCUGA |
| 284 | GCACAGCG AGAA GCUG ACCAGAGAAACACACGUUGUGGUACAUUACCUGGUA | CAGCA GUC CGCUGUGC |
| 318 | AAGCGGAC AGAA GCAC ACCAGAGAAACACACGUUGUGGUACAUUACCUGGUA | GUGCA GUC GUCCGCUU |
| 447 | AGAGCUGG AGAA GCGG ACCAGAGAAACACACGUUGUGGUACAUUACCUGGUA | CCGCG GAC CCAGCUGU |
| 804 | UCUCCUGG AGAA GCAU ACCAGAGAAACACACGUUGUGGUACAUUACCUGGUA | AUGCC GAC CCAGGAGA |
| 847 | UCUACCAA AGAA GUGG ACCAGAGAAACACACGUUGUGGUACAUUACCUGGUA | CCACU GCC UUGGUAGA |
| 913 | AGGAUCUG AGAA GCUA ACCAGAGAAACACACGUUGUGGUACAUUACCUGGUA | UAGCG GAC CAGAUCCU |
| 946 | AAGUUGUA AGAA GUUA ACCAGAGAAACACACGUUGUGGUACAUUACCUGGUA | UAACA GUC UACAACUU |
| 1234 | CCCAAGCA AGAA GUCU ACCAGAGAAACACACGUUGUGGUACAUUACCUGGUA | AGACG GAC UGCUUGGG |
| 1275 | AUUUCAGA AGAA GCUG ACCAGAGAAACACACGUUGUGGUACAUUACCUGGUA | CAGCA GAC UCUGAAAU |
| 1325 | UGCCUUCC AGAA GCAG ACCAGAGAAACACACGUUGUGGUACAUUACCUGGUA | CUGCA GAC GGAAGGCA |
| 1350 | CCCCGAUG AGAA GCAG ACCAGAGAAACACACGUUGUGGUACAUUACCUGGUA | CUGCU GCC CAUCGGGG |
| 1534 | ACAUAAGA AGAA GCCA ACCAGAGAAACACACGUUGUGGUACAUUACCUGGUA | UGGCA GCC UCUUAUGU |

TABLE VII-continued

Mouse ICAM Hairpin Ribozyme/Substrate Sequences

| nt. Position | Hairpin Ribozyme Sequence | Substrate |
|---|---|---|
| 1851 | GUCCACCG AGAA GUAG ACCAGAGAAACACACGUUGUGGUACAUUACCUGGUA CUACA GCC | CGGUGGAC |
| 1880 | AGAAUGAA AGAA GCGU ACCAGAGAAACACACGUUGUGGUACAUUACCUGGUA ACGCU GAC | UUCAUUCU |

TABLE VIII

Rat ICAM Hairpin Ribozyme/Substrate Sequences

| nt. Position | Hairpin Ribozyme Sequence | Substrate |
|---|---|---|
| 5 | AAAGUGCA AGAA GCAG ACCAGAGAAACACACGUUGUGGUACAUUACCUGGUA CUGCU GCC | UGCACUUU |
| 59 | GGAGCAGA AGAA GCAU ACCAGAGAAACACACGUUGUGGUACAUUACCUGGUA AUGCU GCC | UCUGCUGG |
| 84 | GGGAUCAC AGAA GCGA ACCAGAGAAACACACGUUGUGGUACAUUACCUGGUA UCGCC GUU | GUGAUCCC |
| 295 | GCACAGUG AGAA GCUG ACCAGAGAAACACACGUUGUGGUACAUUACCUGGUA CAGCA GAC | CACUGUGC |
| 329 | AAGCCGAG AGAA GCGU ACCAGAGAAACACACGUUGUGGUACAUUACCUGGUA ACGCA GUC | CUCGGCUU |
| 433 | UUCCACCA AGAA GCGC ACCAGAGAAACACACGUUGUGGUACAUUACCUGGUA GCGCU GCC | UGGUGGAA |
| 626 | CAUUCUUG AGAA GUGA ACCAGAGAAACACACGUUGUGGUACAUUACCUGGUA UCACU GUU | CAAGAAUG |
| 806 | UCUCCAGG AGAA GCAU ACCAGAGAAACACACGUUGUGGUACAUUACCUGGUA AUGCU GAC | CCUGGAGA |
| 849 | UCCACUGA AGAA GUGG ACCAGAGAAACACACGUUGUGGUACAUUACCUGGUA CCACU GCC | UCAGUGGA |
| 915 | AGGGUCUG AGAA GCCA ACCAGAGAAACACACGUUGUGGUACAUUACCUGGUA UGGCG GAC | CAGACCCU |
| 1182 | ACCUCCAA AGAA GCAG ACCAGAGAAACACACGUUGUGGUACAUUACCUGGUA CUGCG GCC | UUGGAGGU |
| 1307 | AUGUAAGA AGAA GCUG ACCAGAGAAACACACGUUGUGGUACAUUACCUGGUA CAGCA GAC | UCUUACAU |
| 1357 | UGCUUUCC AGAA GCAG ACCAGAGAAACACACGUUGUGGUACAUUACCUGGUA CUGCA GCC | GGAAAGCA |
| 1382 | UCCCGAUA AGAA GCGG ACCAGAGAAACACACGUUGUGGUACAUUACCUGGUA CCGCU GCC | UAUCGGGA |
| 1858 | GCCCACCA AGAA GUAG ACCAGAGAAACACACGUUGUGGUACAUUACCUGGUA CUACA GCC | UGGUGGGC |
| 1887 | AGAAGGAA AGAA GCCU ACCAGAGAAACACACGUUGUGGUACAUUACCUGGUA AGGCU GAC | UUCCUUCU |
| 2012 | GAGUUGGG AGAA GUGU ACCAGAGAAACACACGUUGUGGUACAUUACCUGGUA ACACU GUC | CCCAACUC |
| 2303 | AGACUCCA AGAA GUGG ACCAGAGAAACACACGUUGUGGUACAUUACCUGGUA CCACA GCC | UGGAGUCU |
| 2539 | CCUCCCAC AGAA GCUU ACCAGAGAAACACACGUUGUGGUACAUUACCUGGUA AAGCU GUU | GUGGGAGG |

TABLE IX

Rat ICAM HH Ribozyme Target Sequence

| nt. Position | HH Target sequence | nt. Position | HH Target sequence | nt. Position | HH Target sequence | nt. Position | HH Target sequence |
|---|---|---|---|---|---|---|---|
| 11 | GAUCCAAU U CACACUGA | 394 | GUGGUGCU U CUGAACAG | 31 | CCUCUGCU C CUGGUCCU | 427 | UCCUGUU U AAAAACCA |
| 23 | GCUGACUU C CUUCUCUA | 420 | GCACCCCU C CCAGCGCA | 34 | CUGAAGCU C AGAUAUAC | 450 | AAGAACCU C AUCCGCG |
| 26 | GAACUGCU C UUCCUCUU | 425 | CCUCGGCU U CUGCCACC | 40 | CUCAAGGU A CAAUCCCC | 451 | GGGUACUU C CCCAGGC |

TABLE IX-continued

Rat ICAM HH Ribozyme Target Sequence

| nt. Position | HH Target sequence | nt. Position | HH Target sequence |
|---|---|---|---|
| 48 | GAGAACCU C GGCCUGGG | 456 | CUCGGCUU C UGCCACCA |
| 54 | CCCCGCCU C CCUGAGCC | 495 | GCCACCAU U ACUGUGUA |
| 58 | CCGUGCCU U UAGCUCCC | 510 | GUGCUGCU C CGUGGGAA |
| 64 | CAAUGGCU U CAACCCGU | 564 | GAAAAUGU U CCAACCAC |
| 96 | CCUCUGCU C CUGGUCCU | 592 | GGGAGUAU C ACCAGGGA |
| 102 | CUCCUGGU C CUGGUCGC | 607 | GAGCCAAU U UCUCAUGC |
| 108 | GGACUGCU U GGGGAACU | 608 | AGCCAAUU U CUCAUGCU |
| 115 | UCCUACCU U UGUUCCCA | 609 | GCCAAUUU C UCAUGCUU |
| 119 | GACACUGU C CCCAACUC | 611 | CAAUUUCU C AUGCUUCA |
| 120 | GUUGUGAU C CCCGGGCC | 656 | GUCACUGU U CAAGAAUG |
| 146 | CCAGACCU U GGAACUCC | 657 | UCACUGUU C AAGAAUGU |
| 152 | ACCCGGCU C CACCUCAA | 668 | GAACUGCU C UUCCUCUU |
| 158 | AUUUCUUU C ACGAGUCA | 677 | GCACCCCU C CCAGCGCA |
| 165 | UGAACAGU A CUUCCCCC | 684 | AGGCAGCU C CGGACUUU |
| 168 | GAAGCCUU C CUGCCUCG | 692 | CCAGACCU U GGAACUCC |
| 185 | GGGUGGAU C CGUGCAGG | 693 | CGGACUUU C GAUCUUCC |
| 209 | CAGCCCCU A AUCUGACC | 696 | GCCUGUUU C CUGCCUGU |
| 227 | GACCAAGU A ACUGUGAA | 709 | CAGCAUUU A CCCCUCAC |
| 230 | CAAGCUGU U GUGGGAGG | 720 | CUACAACU U UUCAGCUC |
| 237 | CUGAAGCU C GACACCCC | 723 | CAACUUUU C AGCUCCCA |
| 248 | GGCCCCCU A CCUUAGGA | 735 | CUCCUGGU C CUGGUCGC |
| 253 | CACUGCCU C AGUGGAGG | 738 | UCCUGCCU C GGGGUGGA |
| 263 | GAGCCAAU U UCUCAUGC | 765 | ACUGUGCU U UGAGAACU |
| 267 | GAAGCCUU C CUGCCUCG | 769 | UCUUGUGU U CCCUGGAA |
| 293 | GAAGCUCU U CAAGCUGA | 770 | CUUGUGUU C CCUGGAAG |
| 319 | CGGAGGAU C ACAAACGA | 785 | AGGCCUGU U UCCUGCCU |
| 335 | ACUGUGCU U UGAGAACU | 786 | GGCCUGUU U CCUGCCUC |
| 337 | UGUGCUAU A UGGUCCUC | 792 | CUCCUGGU C CUGGUCGC |
| 338 | AAGCUCUU C AAGCUGAG | 794 | UCCUGCCU C UGAAGCUC |
| 359 | CACGCAGU C CUCGGCUU | 807 | GCUCAGAU A UACCUGGA |
| 367 | CAAUGGCU U CAACCCGU | 833 | CCUGGGGU U GGAGACUA |
| 374 | UUACCCCU C ACCCACCU | 846 | CUGACAGU U AUUUAUUG |
| 375 | AGAAGCCU U CCUGCCUC | 851 | GCUCACCU U UAGCAGCU |
| 378 | ACCCACCU C ACAGGGUA | 863 | CAAUGGCU U CAACCCGU |
| 386 | CGCUGUGU U UUGGAGCU | 866 | CCAUGCUU C UCUGACA |
| 867 | GACCACCU C CCCACCUA | 1421 | GGGUACUU C CCCCAGGC |
| 869 | CUCUUCCU C UUGCGAAC | 1425 | ACCCACCU C CUCUGGCU |
| 881 | AAUGGCUU C AACCCGUG | 1429 | AUACUUGU A GCCUCAGG |
| 885 | GACCAAGU A ACUGUGAA | 1444 | AGAAGGCU C AGGAGGAG |
| 933 | UGUGUAUU C GUUCCCAG | 1455 | GGGAGUAU C ACCAGGGA |
| 936 | GCAGAGAU U UGUGUCA | 1482 | AGGGUACU U CCCCCAGG |
| 978 | UUGAGAAU C UACAACUU | 1484 | ACUGUCUCU U CCUCUUGC |
| 980 | GAGAAUCU A CAACUUUU | 1493 | CCUGGGGU U GGAGACUA |
| 986 | CUACAACU U UUCAGCUC | 1500 | CGUGAAAU U AUGGUCAA |
| 987 | UACAACUU U CAGCUCC | 1503 | GAAAAUGU U CCAACCAC |
| 988 | ACAACUUU U CAGCUCCC | 1506 | UGGGUCAU A AUUGUUGG |
| 1005 | UUCGUGAU C GUGGCGUC | 1509 | GCCACCAU U ACUGUGUA |
| 1006 | GUGGGAGU A UCACCAGG | 1518 | GUCCUGGU C GCCGUUGU |
| 1023 | CCGGAGGU U UCAGAAGG | 1530 | ACCUGGGU C AUAAUUGU |
| 1025 | GGAGGUCU C AGAAGGGG | 1533 | CUGAUCAU U GCGGGCUU |
| 1066 | CCUACCUU C GUUCCCAA | 1551 | GUGGCCCU C UGCUCGUA |
| 1092 | AGAGGGGU C UCAGCAGA | 1559 | UGGGAAGU C CCUGUUUA |
| 1093 | AGGGGAAU C CAGCCCCU | 1563 | UCCUACCU U UGUUCCCA |
| 1125 | CCCCAACU C UUGUUGAU | 1565 | UUACACCU A UUACCGCC |
| 1163 | ACGACGCU U CUUUUGCU | 1567 | ACACCUAU U ACCGCCAG |
| 1164 | CGACGCUU C UUUUGCUC | 1584 | AGGAAGAU C AGGAUAUA |
| 1166 | ACGCUUCU U UUGCUCUG | 1592 | CAGGAUAU A CAAGUUAC |
| 1172 | CUUUUGCU C UGCGGCCU | 1599 | UACAAGUU A CAGAAGGC |
| 1200 | AUCCAAUU C ACACUGAA | 1651 | CCCCGCCU C CUGAGCC |
| 1201 | UUGGGCUU C UCCACAGG | 1661 | CUGCACUU U GCCCUGGU |
| 1203 | GGGCUUCU C CACAGGUC | 1663 | GAACAGAU C AAUGGACA |
| 1227 | UUGGAACU C CAUGUGCU | 1678 | GAGAACCU C GGCCUGGG |
| 1228 | GCGGGCUU C GUGAUCGU | 1680 | GGGCUUCU C CACAGGUC |
| 1233 | CUCCUGGU C CUGGUCGC | 1681 | GGCUGUUU U CCUGCCUC |
| 1238 | UGUGCUAU A UGGUCCUC | 1684 | CUGCUCGU A GACCUCUC |
| 1264 | GGAAAGAU C AUACGGGU | 1690 | CCCCACCU A CAUACAUU |
| 1267 | GUCACUGU U CAAGAAUG | 1691 | CCGGACUU U CGAUCUUC |
| 1294 | CAGAGAUU U GUGUCAG | 1696 | CUCCUGGU C CUGGUCGC |
| 1295 | AGAGGGGU C UCAGCAGA | 1698 | UCAGAUAU A CCUGGAGA |
| 1306 | AGCAGACU C UUACAUGC | 1737 | GAUCACAU U CACGGUGC |
| 1321 | AACAGAGU C UGGGGAAA | 1750 | GUCCAUUU A CACCUAUU |
| 1334 | GUAUUCGU U CCCAGAGC | 1756 | CCUCUGCU C CUGGUCCU |

TABLE IX-continued

Rat ICAM HH Ribozyme Target Sequence

| nt. Position | HH Target sequence | nt. Position | HH Target sequence |
|---|---|---|---|
| 1344 | UCGGUGCU C AGGUAUCC | 1787 | GAGAACCU C GGCCUGGG |
| 1351 | UCAGGCCU A AGAGGACU | 1790 | GACACUGU C CCCAACUC |
| 1353 | UAGCAGCU C AACAAUGG | 1793 | AUGGUCCU C ACCUGGAC |
| 1366 | AGGGUACU U CCCCCAGG | 1797 | UCCCUGUU U AAAAACCA |
| 1367 | GGGUACUU C CCCCAGGC | 1802 | GCUCAGAU A UACCUGGA |
| 1368 | GAUGGUGU C CCGCUGCC | 1812 | AACAGAGU C UGGGGAAA |
| 1380 | CUGCCUAU C GGGAUGGU | 1813 | GCGGGCUU C GUGAUCGU |
| 1388 | UGGAGACU A ACUGGAUG | 1825 | GCCACCAU C ACUGUGUA |
| 1398 | CUGGCUGU C ACAGGACA | 1837 | ACCCACCU C ACAGGGUA |
| 1402 | CUGUGCUU U GAGAACUG | 1845 | AGAGGACU C GGAGGGGC |
| 1408 | UUCGUGAU C GUGGCGUC | 1856 | CCCCUAAU C UGACCUGC |
| 1410 | CGAACUAU C GAGUGGAC | 1861 | CAUGUGCU A UAUGGUCC |
| 1865 | UAUCCGGU A GACACAAG | 2198 | GAAUGUCU C CGAGGUCA |
| 1868 | UCACGACU C AUAUAAAU | 2199 | AGACUCUA C CAUGCCAG |
| 1877 | ACAGUACU U CCCCCAGG | 2200 | GGGUACUU C CCCCAGGC |
| 1901 | CUAAAACU C AAGGUACA | 2201 | GGCUUCU C CACAGGUC |
| 1912 | GAACAGAU C AAUGGACA | 2205 | UUUUGUGU C AGCCACUG |
| 1922 | AUGUAAGU U AUUGCCUA | 2210 | UGGAGACU A ACUGGAUG |
| 1923 | UGGACGCU C ACCUUUAG | 2220 | GAGAACCU C GGCCUGGG |
| 1928 | GCUCAGAU A UACCUGGA | 2224 | ACAUACAU U CCUACCUU |
| 1930 | UGGAGACU A ACUGGAUG | 2226 | CUGGACCU C AGGCCACA |
| 1964 | AGAGAUUU U GUGUCAGC | 2233 | UCAUGCUU C ACAGAACU |
| 1983 | GAGAACCU C GGCCUGGG | 2242 | ACACAGCU C UCAGUAGU |
| 1996 | UGGAAGCU C UUCAAGCU | 2248 | CUCCUGGU C CUGGUCGC |
| 2005 | AUGUAAGU U AUUGCCUA | 2254 | AUCCAAUU C ACACUGAA |
| 2013 | CGCUGCCU A UCGGGAUG | 2259 | GAUCACAU U CACGGUGC |
| 2015 | CUGCCUAU C GGGAUGGU | 2260 | AUCACAUU C ACGGUGCU |
| 2020 | UAUUGAGU A CCCUGUAC | 2266 | AUCAGGAU A UACAAGUU |
| 2039 | CGGAGGAU C ACAAACGA | 2274 | GAGCAGGU U AACAUGUA |
| 2040 | CCUGACCU C CUGGAGGU | 2279 | GGAAAGAU C AUACGGGU |
| 2057 | CUGGUCCU C CAAUGGCU | 2282 | ACAGUUAU U UAUUGAGU |
| 2061 | GCGUCCAU U UACACCUA | 2288 | GCCCUGGU C CUCCAAUG |
| 2071 | AUACUUGU A GCCUCAGG | 2291 | CAGGAUAU A CAAGUUAC |
| 2076 | UGUAGCCU C AGGCCUAA | 2321 | GGAAAGAU C AUACGGGU |
| 2097 | CCAACUCU U GUUGAUGU | 2338 | UUGGGCUU C UCCACAGG |
| 2098 | CCUGACCU C CUGGAGGU | 2339 | GGGUACUU C CCCCAGGC |
| 2115 | UUCCGACU A GGGUCCUG | 2341 | GGGCCUGU C GGUGCUCA |
| 2128 | AGUGCUGU A CCAUGAUC | 2344 | CUGCUCGU A GACCUCUC |
| 2130 | GCCUGUUU C CUGCUCU | 2358 | CCCUGCCU C CUCCCACA |
| 2145 | CCAACUCU U GUUGAUGU | 2359 | CCAUCCAU C CCACAGAA |
| 2152 | UUGAGAAU C UACAACUU | 2360 | CUUGUGUU C CCUGGAAG |
| 2156 | UGACAGUU A UUUAUUGA | 2376 | GAACUGCU C UUCCUCUU |
| 2158 | UGAUGUAU U AUUAAUU | 2377 | GACUUCCU U CUCUAUUA |
| 2159 | GAUGUAUU U AUUAAUUC | 2378 | GCUGAUUU C UUUCACGA |
| 2160 | AUGUAUUA U UAAUUCA | 2379 | CUGCUCUU C CUCUUGCG |
| 2162 | ACAUUCCU A CCUUUGUU | 2380 | UGAUUCU U UCACGAGU |
| 2163 | UAUUUAUU A AUUCAGAG | 2382 | AUUUCUUU C ACGAGUCA |
| 2166 | UGAUGUAU U AUUAAUU | 2384 | UAUCCGGU A GACACAAG |
| 2167 | GAUGUAUU U AUUAAUUC | 2399 | UAAAUACU A UGUGGACG |
| 2170 | GUAUUAU U AAUUCAGA | 2401 | UGUGCUAU A UGGUCCUC |
| 2171 | CAGUUAUU U AUUGAGUA | 2411 | CAAUUUCU C AUGCUUCA |
| 2173 | UGUGCUAU A UGGUCCUC | 2417 | AUCAGGAU A UACAAGUU |
| 2174 | UCUCUAUU A CCCUGCU | 2418 | UCAUGCUU C ACAGAACU |
| 2175 | AUUUCUUU C ACGAGUCA | 2425 | UUAUUAAU U CAGAGUUC |
| 2176 | GAAAAUGU U CCAACCAC | 2426 | CCUGGGGU U GGAGACUA |
| 2183 | UGACAGUU A UUUAUUGA | 2433 | UCAGAGUU C UGACAGUU |
| 2185 | ACAGUUAU U UAUUGAGU | 2434 | CGGAGGAU C ACAAACGA |
| 2186 | CAGUUAUU U AUUGAGUA | 2448 | UGAACAGU A CUUCCCCC |
| 2187 | AGUUAUUU A UUGAGUAC | 2449 | GAAGCCUU C CUGCCUCG |
| 218 | UUAUUUAU U GAGUACCC | 2451 | GGCCUGUU U CCUGCCUC |
| 2196 | CUGACAGU U AUUUAUUG | 2452 | GCCUGUUU C CUGCCUCU |
| 2455 | ACAUUCCU A CCUUUGUU | 2761 | CGGACUUU C GAUCUUCC |
| 2459 | CCCUGCCU C CUCCCACA | 2765 | CUUUUGCU C UGCGGCCU |
| 2460 | CCUACCUU U CUUCCCAA | 2769 | UUCUCUAU U ACCCCUGC |
| 2479 | UUACACCU A UUACCGCC | 2797 | CGUGAAAU U AUGGUCAA |
| 2480 | GUCGCCGU U GUGAUCCC | 2803 | CUCAUGCU U CACAGAAC |
| 2483 | ACCUUUGU U CCCAAUGU | 2804 | UCAUGCUU C ACAGAACU |
| 2484 | CCUUUGUU C CAAUGUC | 2813 | GCUCCCAU C CUGACCCU |
| 2492 | GACCACCU C CCCACCUA | 2815 | CGGACUUU C GAUCUUCC |
| 2504 | ACCUACAU A CAUUCCUA | 2821 | CCUGACCU C CUGGACCU |
| 2508 | ACAUACAU U CCUACCUU | 2822 | UACAACUU U CAGCUCC |
| 2509 | CAUACAUU C CUACCUUU | 2823 | CAACUUUU C AGCUCCCA |

TABLE IX-continued

Rat ICAM HH Ribozyme Target Sequence

| nt. Position | HH Target sequence | nt. Position | HH Target sequence |
|---|---|---|---|
| 2510 | GUCCAUUU A CACCUAUU | 2829 | UCGGUGCU C AGGUAUCC |
| 2520 | ACCUUUGU U CCCAAUGU | 2837 | CACAGGGU A CUUCCCCC |
| 2521 | CCUUUGUU C CCAAUGUC | 2840 | GCACCCCU C CCAGCGCA |
| 2533 | ACAGCAUU U ACCCCUCA | 2847 | UUACCCCU C ACCCACCU |
| 2540 | UCGGUGCU C AGGUAUCC | 2853 | UUCGAUCU U CCGACUAG |
| 2545 | AGGCAGCU C CGGACUUU | 2860 | UCUUGUGU U CCCUGGAA |
| 2568 | CAGAGAUU U UGUGUCAG | 2872 | GGGCCUGU C GGUGCUCA |
| 2579 | CCUGCACU U UGCCCUGG | 2877 | UGGAGUCU C CCAGCACC |
| 2585 | CUGCUCGU A GACCUCUC | 2899 | AGGCAGCU C CGGACUUU |
| 2588 | UGCCUCCU C CCACAGCC | 2900 | GGCUGACU U CCUUCUCU |
| 2591 | CUCUUCCU C UUGCGAAG | 2904 | GAACUGCU C UUCCUCUU |
| 2593 | UCUCUAUU A CCCCUGCU | 2905 | GGCUGACU U CCUUCUCU |
| 2596 | CUCCUGGU C CUGGUCGC | 2906 | GUUGAUGU A UUUAUUAA |
| 2601 | UGUGCUAU A UGGUCCUC | 2907 | CUGCUCUU C CUCUUGCG |
| 2602 | GUCCUGGU C GCCGUUGU | 2908 | UGAUGUAU U UAUUAAUU |
| 2607 | GUGGGAGU A UCACCUGG | 2909 | GAACUGCU C CUUCUCUU |
| 2608 | CUUUAGCU C CCGUGGGA | 2910 | ACUUCCUU C UCUAUUAC |
| 2609 | UGGAGACU A ACUGGAUG | 2911 | UUCCUUCU C UAUUACCC |
| 2620 | UCAGAGUU C UGACAGUU | 2912 | AUGUAUUU A UUAAUUCA |
| 2626 | CUCUCAGU A GUGCGCGU | 2913 | UGUGUAUU C GUUCCCAG |
| 2628 | UACAACUU U UCAGCUCC | 2914 | GUAUUUAU U AAUUCAGA |
| 2635 | UCACAGAU C CAAUUCAC | 2915 | UAUUUAUU A AUUCAGAG |
| 2640 | GCUCAGGU A UCCAUCCA | 2916 | CUCUUCCU C UUGCGAAG |
| 2641 | CCCCACCU A CAUACAUU | 2917 | CUUCCUCU U GCGAAGAC |
| 2642 | GCCUGUUU C CUGCCUCU | 2918 | AUUUCUUU C ACGAGUCA |
| 2653 | CCACAGGU C AGGGUGCU | 2919 | UUUUGUGU C AGCCACUG |
| 2659 | AGAAGGGU C CUGCAAGC | 2931 | GAUGGUGU C CCGCUGCC |
| 2689 | ACUAGGGU C CUGAAGCU | 2933 | UGGAGUCU C CCAGCACC |
| 2691 | UCAGGCCU A AGAGGACU | 2941 | CAGUACUU C CCCCAGGC |
| 2700 | AGGGUACU U CCCCCAGG | 2951 | ACCAUGCU U CCUCUGAC |
| 2704 | GACCACCU C CCCACCUA | 2952 | CCGGACUU U CGAUCUUC |
| 2711 | CCCUACCU U AGGAAGGU | 2955 | UGCUUCCU C UGACAUGG |
| 2712 | CCUACCUU A GGAAGGUG | 2956 | CUUUCCUU U GAAUCAAU |
| 2721 | GGAAAGAU C AUACGGGU | 2961 | UUUUGUGU A AGCCACUG |
| 2724 | AAGAUCAU A CGGGUUUG | 2962 | UGUGUAUU C GUUCCCAG |
| 2744 | GGGUGGAU C CGUGCAGG | 2965 | CUUUGAAU C AAUAAAGU |
| 2750 | GUCCCUGU U UAAAAACC | 2966 | UGGAAGCU C UUCAAGCU |
| 2759 | GACGAACU A UCGAGUGG | 2969 | GAAUCAAU A AAGUUUUA |
| 2975 | UGGAAGCU C UUCAAGCU | | |
| 2976 | UAUAUGGU C CUCACCUG | | |
| 2977 | GAAGCUCU U CAAGCUGA | | |

TABLE X

Rat ICAM HH Ribozyme Sequences

| nt. Position | Rat HH Ribozyme Sequence |
|---|---|
| 11 | UCAGUGUG CUGAUGAGGCCGAAAGGCCGAA AUUGGAUC |
| 23 | UAGAGAAG CUGAUGAGGCCGAAAGGCCGAA AAGUCAGC |
| 26 | AAGAGGAA CUGAUGAGGCCGAAAGGCCGAA AGCAGUUC |
| 31 | AGGACCAG CUGAUGAGGCCGAAAGGCCGAA AGCAGAGG |
| 34 | GUAUAUCU CUGAUGAGGCCGAAAGGCCGAA AGCUUCAG |
| 40 | GGGGCUUG CUGAUGAGGCCGAAAGGCCGAA ACCUUGAG |
| 48 | CCCAGGCC CUGAUGAGGCCGAAAGGCCGAA AGGUUCUC |
| 54 | GGCUCAGG CUGAUGAGGCCGAAAGGCCGAA AGGCGGGG |
| 58 | GGGAGCUA CUGAUGAGGCCGAAAGGCCGAA AGGCACGG |
| 64 | ACGGGUUG CUGAUGAGGCCGAAAGGCCGAA AGCCAUUG |
| 96 | AGGACCAG CUGAUGAGGCCGAAAGGCCGAA AGCAGAGG |
| 102 | GCGACCAG CUGAUGAGGCCGAAAGGCCGAA ACCAGGAG |
| 108 | AGUUCCCC CUGAUGAGGCCGAAAGGCCGAA AGCAGUCC |
| 115 | UGGGAACA CUGAUGAGGCCGAAAGGCCGAA AGGUAGGA |
| 119 | GAGUUGGG CUGAUGAGGCCGAAAGGCCGAA ACAGUGUC |
| 120 | GGCCCGGG CUGAUGAGGCCGAAAGGCCGAA AUCACAAC |
| 146 | GGAGUUCC CUGAUGAGGCCGAAAGGCCGAA AGGUCUGG |
| 152 | UUGAGGUG CUGAUGAGGCCGAAAGGCCGAA AGCCGGGU |
| 158 | UGACUCGU CUGAUGAGGCCGAAAGGCCGAA AAAGAAAU |
| 165 | GGGGGAAG CUGAUGAGGCCGAAAGGCCGAA ACUGUUCA |
| 168 | CGAGGCAG CUGAUGAGGCCGAAAGGCCGAA AAGGCUUC |
| 185 | CCUGCACG CUGAUGAGGCCGAAAGGCCGAA AUCCACCC |
| 209 | GGUCAGAU CUGAUGAGGCCGAAAGGCCGAA AGGGGCUG |
| 227 | UUCACAGU CUGAUGAGGCCGAAAGGCCGAA ACUGGUC |
| 230 | CCUCCCAC CUGAUGAGGCCGAAAGGCCGAA ACAGCUUG |
| 237 | GGGGUGUC CUGAUGAGGCCGAAAGGCCGAA AGCUUCAG |

TABLE X-continued

Rat ICAM HH Ribozyme Sequences

| nt. Position | Rat HH Ribozyme Sequence |
|---|---|
| 248 | UCCUAAGG CUGAUGAGGCCGAAAGGCCGAA AGGGGGCC |
| 253 | CCUCCACU CUGAUGAGGCCGAAAGGCCGAA AGGCAGUG |
| 263 | GCAUGAGA CUGAUGAGGCCGAAAGGCCGAA AUUGGCUC |
| 267 | CGAGGCAG CUGAUGAGGCCGAAAGGCCGAA AAGGCUUC |
| 293 | UCAGCUUG CUGAUGAGGCCGAAAGGCCGAA AGAGCUUC |
| 319 | UCGUUUGU CUGAUGAGGCCGAAAGGCCGAA AUCCUCCG |
| 335 | AGUUCUCA CUGAUGAGGCCGAAAGGCCGAA AGCACAGU |
| 337 | GAGGACCA CUGAUGAGGCCGAAAGGCCGAA AUAGCACA |
| 338 | CUCAGCUU CUGAUGAGGCCGAAAGGCCGAA AAGAGCUU |
| 359 | AAGCCGAG CUGAUGAGGCCGAAAGGCCGAA ACUGCGUG |
| 367 | ACGGUUG CUGAUGAGGCCGAAAGGCCGAA AGCCAUUG |
| 374 | AGGUGGGU CUGAUGAGGCCGAAAGGCCGAA AGGGGUAA |
| 375 | GAGGCAGG CUGAUGAGGCCGAAAGGCCGAA AGGCUUCU |
| 378 | UACCCUGU CUGAUGAGGCCGAAAGGCCGAA AGGUGGGU |
| 386 | AGCUCCAA CUGAUGAGGCCGAAAGGCCGAA ACACAGCG |
| 394 | CUGUUCAG CUGAUGAGGCCGAAAGGCCGAA AGCACCAC |
| 420 | UGCGCUGG CUGAUGAGGCCGAAAGGCCGAA AGGGGUGC |
| 425 | GGUGGCAG CUGAUGAGGCCGAAAGGCCGAA AGCCGAGG |
| 427 | UGGUUUUU CUGAUGAGGCCGAAAGGCCGAA AACAGGGA |
| 450 | CGCAGGAU CUGAUGAGGCCGAAAGGCCGAA AGGUUCUU |
| 451 | GCCYGGGG CUGAUGAGGCCGAAAGGCCGAA AAGUACCC |
| 456 | UGGUGGCA CUGAUGAGGCCGAAAGGCCGAA AAGCCGAG |
| 495 | UACACAGU CUGAUGAGGCCGAAAGGCCGAA AUGGUGGC |
| 510 | UUCCCACG CUGAUGAGGCCGAAAGGCCGAA AGCAGCAC |
| 564 | GUGGUUGG CUGAUGAGGCCGAAAGGCCGAA ACAUUUUC |
| 592 | UCCCUGGU CUGAUGAGGCCGAAAGGCCGAA AUACUCCC |
| 607 | GCAUGAGA CUGAUGAGGCCGAAAGGCCGAA AUUGGCUC |
| 608 | AGCAUGAG CUGAUGAGGCCGAAAGGCCGAA AAUUGGCU |
| 609 | AAGCAUGA CUGAUGAGGCCGAAAGGCCGAA AAAUUGGC |
| 611 | UGAAGCAU CUGAUGAGGCCGAAAGGCCGAA AGAAAUUG |
| 656 | CAUUCUUG CUGAUGAGGCCGAAAGGCCGAA ACAGUGAC |
| 657 | ACAUUCUU CUGAUGAGGCCGAAAGGCCGAA AACAGUGA |
| 668 | AAGAGGAA CUGAUGAGGCCGAAAGGCCGAA AGCAGUUC |
| 677 | UGCGCUGG CUGAUGAGGCCGAAAGGCCGAA AGGGGUGC |
| 684 | AAAGUCCG CUGAUGAGGCCGAAAGGCCGAA AGCUGCCU |
| 692 | GGAGUUCC CUGAUGAGGCCGAAAGGCCGAA AGGUCUGG |
| 693 | GGAAGAUC CUGAUGAGGCCGAAAGGCCGAA AAAGUCCG |
| 696 | AGAGGCAG CUGAUGAGGCCGAAAGGCCGAA AAACAGGC |
| 709 | GUGAGGGG CUGAUGAGGCCGAAAGGCCGAA AAAUGCUG |
| 720 | GAGCUGAA CUGAUGAGGCCGAAAGGCCGAA AGUUGUAG |
| 723 | UGGGAGCU CUGAUGAGGCCGAAAGGCCGAA AAAAGUUG |
| 735 | GCGACCAG CUGAUGAGGCCGAAAGGCCGAA ACCAGGAG |
| 738 | UCCACCCC CUGAUGAGGCCGAAAGGCCGAA AGGCAGGA |
| 765 | AGUUCUCA CUGAUGAGGCCGAAAGGCCGAA AGCACAGU |
| 769 | UUCCAGGG CUGAUGAGGCCGAAAGGCCGAA ACACAAGA |
| 770 | CUUCCAGG CUGAUGAGGCCGAAAGGCCGAA AACACAAG |
| 785 | AGGCAGGA CUGAUGAGGCCGAAAGGCCGAA ACAGGCCU |
| 786 | GAGGCAGG CUGAUGAGGCCGAAAGGCCGAA AACAGGCC |
| 792 | GCGACCAG CUGAUGAGGCCGAAAGGCCGAA ACCAGGAG |
| 794 | GAGCUUCA CUGAUGAGGCCGAAAGGCCGAA AGGCAGGA |
| 807 | UCCAGGUA CUGAUGAGGCCGAAAGGCCGAA AUCUGAGC |
| 833 | UAGUCUCC CUGAUGAGGCCGAAAGGCCGAA ACCCCAGG |
| 846 | CAAUAAAU CUGAUGAGGCCGAAAGGCCGAA ACUGUCAG |
| 851 | AGCUGCUA CUGAUGAGGCCGAAAGGCCGAA AGGUGAGC |
| 863 | ACGGGUUG CUGAUGAGGCCGAAAGGCCGAA AGCCAUUG |
| 866 | UGUCAGAG CUGAUGAGGCCGAAAGGCCGAA AAGCAUGG |
| 867 | UAGGUGGG CUGAUGAGGCCGAAAGGCCGAA AGGUGGUC |
| 869 | CUUCGCAA CUGAUGAGGCCGAAAGGCCGAA AGGAAGAG |
| 881 | CACGGGUU CUGAUGAGGCCGAAAGGCCGAA AAGCCAUU |
| 885 | UUCACAGU CUGAUGAGGCCGAAAGGCCGAA ACUUGGUC |
| 933 | CUGGGAAC CUGAUGAGGCCGAAAGGCCGAA AAUACACA |
| 936 | UGACACAA CUGAUGAGGCCGAAAGGCCGAA AUCUCUGC |
| 978 | AAGUUGUA CUGAUGAGGCCGAAAGGCCGAA AUUCUCAA |
| 980 | AAAAGUUG CUGAUGAGGCCGAAAGGCCGAA AGAUUCUC |
| 986 | GAGCUGAA CUGAUGAGGCCGAAAGGCCGAA AGUUGUAG |
| 987 | GGAGCUGA CUGAUGAGGCCGAAAGGCCGAA AAGUUGUA |
| 988 | GGGAGCUG CUGAUGAGGCCGAAAGGCCGAA AAAGUUGU |
| 1005 | GACGCCAC CUGAUGAGGCCGAAAGGCCGAA AUCACGAA |
| 1006 | CCUGGUGA CUGAUGAGGCCGAAAGGCCGAA ACUCCCAC |
| 1023 | CCUUCUGA CUGAUGAGGCCGAAAGGCCGAA ACCUCCGG |
| 1025 | CCCCUUCU CUGAUGAGGCCGAAAGGCCGAA AGACCUCC |
| 1066 | UUGGGAAC CUGAUGAGGCCGAAAGGCCGAA AAGGUAGG |
| 1092 | UCUGCUGA CUGAUGAGGCCGAAAGGCCGAA ACCCCUCU |
| 1093 | AGGGGCUG CUGAUGAGGCCGAAAGGCCGAA AUUCCCCU |

TABLE X-continued

Rat ICAM HH Ribozyme Sequences

| nt. Position | Rat HH Ribozyme Sequence |
|---|---|
| 1125 | AUCAACAA CUGAUGAGGCCGAAAGGCCGAA AGUUGGGG |
| 1163 | AGCAAAAG CUGAUGAGGCCGAAAGGCCGAA AGCGUCGU |
| 1164 | GAGCAAAA CUGAUGAGGCCGAAAGGCCGAA AAGCGUCG |
| 1166 | CAGAGCAA CUGAUGAGGCCGAAAGGCCGAA AGAAGCGU |
| 1172 | AGGCCGCA CUGAUGAGGCCGAAAGGCCGAA AGCAAAAG |
| 1200 | UUCAGUGU CUGAUGAGGCCGAAAGGCCGAA AAUUGGAU |
| 1201 | CCUGUGGA CUGAUGAGGCCGAAAGGCCGAA AAGCCCAA |
| 1203 | GACCUGUG CUGAUGAGGCCGAAAGGCCGAA AGAAGCCC |
| 1227 | AGCACAUG CUGAUGAGGCCGAAAGGCCGAA AGUUCCAA |
| 1228 | ACGAUCAC CUGAUGAGGCCGAAAGGCCGAA AAGCCCGC |
| 1233 | GCGACCAG CUGAUGAGGCCGAAAGGCCGAA ACCAGGAG |
| 1238 | GAGGACCA CUGAUGAGGCCGAAAGGCCGAA AUAGCACA |
| 1264 | ACCCGUAU CUGAUGAGGCCGAAAGGCCGAA AUCUUUCC |
| 1267 | CAUUCUUG CUGAUGAGGCCGAAAGGCCGAA ACAGUGAC |
| 1294 | CUGACACA CUGAUGAGGCCGAAAGGCCGAA AAUCUCUG |
| 1295 | UCUGCUGA CUGAUGAGGCCGAAAGGCCGAA ACCCCUCU |
| 1306 | GCAUGUAA CUGAUGAGGCCGAAAGGCCGAA AGUCUGCU |
| 1321 | UUUCCCCA CUGAUGAGGCCGAAAGGCCGAA ACUCUGUU |
| 1334 | GGUCUGGG CUGAUGAGGCCGAAAGGCCGAA ACGAAUAC |
| 1344 | GGAUACCU CUGAUGAGGCCGAAAGGCCGAA AGCACCGA |
| 1351 | AGUCUCU CUGAUGAGGCCGAAAGGCCGAA AGGCCUGA |
| 1353 | CCAUUGUU CUGAUGAGGCCGAAAGGCCGAA AGCUGCUA |
| 1366 | CCUGGGGG CUGAUGAGGCCGAAAGGCCGAA AGUACCCU |
| 1367 | GCCUGGGG CUGAUGAGGCCGAAAGGCCGAA AAGUACCC |
| 1368 | GGCAGCGG CUGAUGAGGCCGAAAGGCCGAA ACACCAUC |
| 1380 | ACCAUCCC CUGAUGAGGCCGAAAGGCCGAA AUAGGCAG |
| 1388 | CAUCCAGU CUGAUGAGGCCGAAAGGCCGAA AGUCUCCA |
| 1398 | UGUCCUGU CUGAUGAGGCCGAAAGGCCGAA ACAGCCAG |
| 1402 | CAGUUCUC CUGAUGAGGCCGAAAGGCCGAA AAGCACAG |
| 1408 | GACGCCAC CUGAUGAGGCCGAAAGGCCGAA AUCACGAA |
| 1410 | GUCCACUC CUGAUGAGGCCGAAAGGCCGAA AUAGUUCG |
| 1421 | GCCUGGGG CUGAUGAGGCCGAAAGGCCGAA AAGUACCC |
| 1425 | AGCCAGAG CUGAUGAGGCCGAAAGGCCGAA AGGUGGGU |
| 1429 | CCUGAGGC CUGAUGAGGCCGAAAGGCCGAA ACAAGUAU |
| 1444 | CUCCUCCU CUGAUGAGGCCGAAAGGCCGAA AGCCUUCU |
| 1455 | UCCCUGGU CUGAUGAGGCCGAAAGGCCGAA AUACUCCC |
| 1482 | CCUGGGGG CUGAUGAGGCCGAAAGGCCGAA AGUACCCU |
| 1484 | GCAAGAGG CUGAUGAGGCCGAAAGGCCGAA AGAGCAGU |
| 1493 | UAGUCUCC CUGAUGAGGCCGAAAGGCCGAA ACCCCAGG |
| 1500 | UUGACCAU CUGAUGAGGCCGAAAGGCCGAA AUUUCACG |
| 1503 | GUGGUUGG CUGAUGAGGCCGAAAGGCCGAA ACAUUUUC |
| 1506 | CCAACAAU CUGAUGAGGCCGAAAGGCCGAA AUGACCCA |
| 1509 | UACACAGU CUGAUGAGGCCGAAAGGCCGAA AUGGUGGC |
| 1518 | ACAACGGC CUGAUGAGGCCGAAAGGCCGAA ACCAGGAC |
| 1530 | ACAAUUAU CUGAUGAGGCCGAAAGGCCGAA ACCCAGGU |
| 1533 | AAGCCCGC CUGAUGAGGCCGAAAGGCCGAA AUGAUCAG |
| 1551 | UACGAGCA CUGAUGAGGCCGAAAGGCCGAA AGGGCCAC |
| 1559 | UAAACAGG CUGAUGAGGCCGAAAGGCCGAA ACUUCCCA |
| 1563 | UGGGAACA CUGAUGAGGCCGAAAGGCCGAA AGGUAGGA |
| 1565 | GGCGGUAA CUGAUGAGGCCGAAAGGCCGAA AGGUGUAA |
| 1567 | CUGGCGGU CUGAUGAGGCCGAAAGGCCGAA AUAGGUGU |
| 1584 | UAUAUCCU CUGAUGAGGCCGAAAGGCCGAA AUCUUCCU |
| 1592 | GUAACUUG CUGAUGAGGCCGAAAGGCCGAA AUAUCCUG |
| 1599 | GCCUUCUG CUGAUGAGGCCGAAAGGCCGAA AACUUGUA |
| 1651 | GGCUCAGG CUGAUGAGGCCGAAAGGCCGAA AGGCGGGG |
| 1661 | ACCAGGGC CUGAUGAGGCCGAAAGGCCGAA AAGUGCAG |
| 1663 | UGUCCAUU CUGAUGAGGCCGAAAGGCCGAA AUCUGUUC |
| 1678 | CCCAGGCC CUGAUGAGGCCGAAAGGCCGAA AGGUUCUC |
| 1680 | GACCUGUG CUGAUGAGGCCGAAAGGCCGAA AGAAGCCC |
| 1681 | GAGGCAGG CUGAUGAGGCCGAAAGGCCGAA AACAGGCC |
| 1684 | GAGAGGUC CUGAUGAGGCCGAAAGGCCGAA ACGAGCAG |
| 1690 | AAUGUAUG CUGAUGAGGCCGAAAGGCCGAA AGGUGGGG |
| 1691 | GAAGAUCG CUGAUGAGGCCGAAAGGCCGAA AAGUCCGG |
| 1696 | GCGACCAG CUGAUGAGGCCGAAAGGCCGAA ACCAGGAG |
| 1698 | UCUCCAGG CUGAUGAGGCCGAAAGGCCGAA AUAUCUGA |
| 1737 | GCACCGUG CUGAUGAGGCCGAAAGGCCGAA AUGUGAUC |
| 1750 | AAUAGGUG CUGAUGAGGCCGAAAGGCCGAA AAAUGGAC |
| 1756 | AGGACCAG CUGAUGAGGCCGAAAGGCCGAA AGCAGAGG |
| 1787 | CCCAGGCC CUGAUGAGGCCGAAAGGCCGAA AGGUUCUC |
| 1790 | GAGUUGGG CUGAUGAGGCCGAAAGGCCGAA ACAGUGUC |
| 1793 | GUCCAGGU CUGAUGAGGCCGAAAGGCCGAA AGGACCAU |
| 1797 | UGGUUUUU CUGAUGAGGCCGAAAGGCCGAA AACAGGGA |
| 1802 | UCCAGGUA CUGAUGAGGCCGAAAGGCCGAA AUCUGAGC |
| 1812 | UUUCCCCA CUGAUGAGGCCGAAAGGCCGAA ACUCUGUU |

TABLE X-continued

Rat ICAM HH Ribozyme Sequences

| nt. Position | Rat HH Ribozyme Sequence |
|---|---|
| 1813 | ACGAUCAC CUGAUGAGGCCGAAAGGCCGAA AAGCCCGC |
| 1825 | UACACAGU CUGAUGAGGCCGAAAGGCCGAA AUGGUGGC |
| 1837 | UACCCUGU CUGAUGAGGCCGAAAGGCCGAA AGGUGGGU |
| 1845 | GCCCCUCC CUGAUGAGGCCGAAAGGCCGAA AGUCCUCU |
| 1856 | GCAGGUCA CUGAUGAGGCCGAAAGGCCGAA AUUAGGGG |
| 1861 | GGACCAUA CUGAUGAGGCCGAAAGGCCGAA AGCACAUG |
| 1865 | CUUGUGUC CUGAUGAGGCCGAAAGGCCGAA ACCGGAUA |
| 1868 | AUUUAUAU CUGAUGAGGCCGAAAGGCCGAA ACUCGUGA |
| 1877 | CCUGGGGG CUGAUGAGGCCGAAAGGCCGAA AGUACUGU |
| 1901 | UGUACCUU CUGAUGAGGCCGAAAGGCCGAA AGUUUUAG |
| 1912 | UGUCCAUU CUGAUGAGGCCGAAAGGCCGAA AUCUGUUC |
| 1922 | UAGGCAAU CUGAUGAGGCCGAAAGGCCGAA ACUUACAU |
| 1923 | CUAAAGGU CUGAUGAGGCCGAAAGGCCGAA AGCGUCCA |
| 1928 | UCCAGGUA CUGAUGAGGCCGAAAGGCCGAA AUCUGAGC |
| 1930 | CAUCCAGU CUGAUGAGGCCGAAAGGCCGAA AGUCCCA |
| 1964 | GCUGACAC CUGAUGAGGCCGAAAGGCCGAA AAAUCUCU |
| 1983 | CCCAGGCC CUGAUGAGGCCGAAAGGCCGAA AGGUUCUC |
| 1996 | AGCUUGAA CUGAUGAGGCCGAAAGGCCGAA AGCUUCCA |
| 2005 | UAGGCAAU CUGAUGAGGCCGAAAGGCCGAA ACUUACAU |
| 2013 | CAUCCCGA CUGAUGAGGCCGAAAGGCCGAA AGGCAGCG |
| 2015 | ACCAUCCC CUGAUGAGGCCGAAAGGCCGAA AUAGGCAG |
| 2020 | GUACAGGG CUGAUGAGGCCGAAAGGCCGAA ACUCAAUA |
| 2039 | UCGUUUGU CUGAUGAGGCCGAAAGGCCGAA AUCCUCCG |
| 2040 | ACCUCCAG CUGAUGAGGCCGAAAGGCCGAA AGGUCAGG |
| 2057 | AGCCAUUG CUGAUGAGGCCGAAAGGCCGAA AGGACCAG |
| 2061 | UAGGUGUA CUGAUGAGGCCGAAAGGCCGAA AUGGACGC |
| 2071 | CCUGAGGC CUGAUGAGGCCGAAAGGCCGAA ACAAGUAU |
| 2076 | UUAGGCCU CUGAUGAGGCCGAAAGGCCGAA AGGCUACA |
| 2097 | ACAUCAAC CUGAUGAGGCCGAAAGGCCGAA AGAGUUGG |
| 2098 | ACCUCCAG CUGAUGAGGCCGAAAGGCCGAA AGGUCAGG |
| 2115 | CAGGACCC CUGAUGAGGCCGAAAGGCCGAA AGUCGGAA |
| 2128 | GAUCAUGG CUGAUGAGGCCGAAAGGCCGAA ACAGCACU |
| 2130 | AGAGGCAG CUGAUGAGGCCGAAAGGCCGAA AAACAGGC |
| 2145 | ACAUCAAC CUGAUGAGGCCGAAAGGCCGAA AGAGUUGG |
| 2152 | AAGUUGUA CUGAUGAGGCCGAAAGGCCGAA AUUCUCAA |
| 2156 | UCAAUAAA CUGAUGAGGCCGAAAGGCCGAA AACUGUCA |
| 2158 | AAUUAAUA CUGAUGAGGCCGAAAGGCCGAA AUACAUCA |
| 2159 | GAAUUAAU CUGAUGAGGCCGAAAGGCCGAA AAUACAUC |
| 2160 | UGAAUUAA CUGAUGAGGCCGAAAGGCCGAA AAAUACAU |
| 2162 | AACAAAGG CUGAUGAGGCCGAAAGGCCGAA AGGAAUGU |
| 2163 | CUCUGAAU CUGAUGAGGCCGAAAGGCCGAA AAUAAAUA |
| 2166 | AAUUAAUA CUGAUGAGGCCGAAAGGCCGAA AUACAUCA |
| 2167 | GAAUUAAU CUGAUGAGGCCGAAAGGCCGAA AAUACAUC |
| 2170 | UCUGAAUU CUGAUGAGGCCGAAAGGCCGAA AUAAAUAC |
| 2171 | UACUCAAU CUGAUGAGGCCGAAAGGCCGAA AAUAACUG |
| 2173 | GAGGACCA CUGAUGAGGCCGAAAGGCCGAA AUAGCACA |
| 2174 | AGCAGGGG CUGAUGAGGCCGAAAGGCCGAA AAUAGAGA |
| 2175 | UGACUCGU CUGAUGAGGCCGAAAGGCCGAA AAAGAAAU |
| 2176 | GUGGUUGG CUGAUGAGGCCGAAAGGCCGAA ACAUUUUC |
| 2183 | UCAAUAAA CUGAUGAGGCCGAAAGGCCGAA AACUGUCA |
| 2185 | ACUCAAUA CUGAUGAGGCCGAAAGGCCGAA AUAACUGU |
| 2186 | UACUCAAU CUGAUGAGGCCGAAAGGCCGAA AAUAACUG |
| 2187 | GUACUCAA CUGAUGAGGCCGAAAGGCCGAA AAAUAACU |
| 2189 | GGGUACUC CUGAUGAGGCCGAAAGGCCGAA AUAAAUAA |
| 2196 | CAAUAAAU CUGAUGAGGCCGAAAGGCCGAA ACUGUCAG |
| 2198 | UGACCUCG CUGAUGAGGCCGAAAGGCCGAA AGACAUUC |
| 2199 | CUGGCAUG CUGAUGAGGCCGAAAGGCCGAA AAGAGUCU |
| 2200 | GCCUGGGG CUGAUGAGGCCGAAAGGCCGAA AAGUACCC |
| 2201 | GACCUGUG CUGAUGAGGCCGAAAGGCCGAA AGAAGCCC |
| 2205 | CAGUGGCU CUGAUGAGGCCGAAAGGCCGAA ACACAAAA |
| 2210 | CAUCCAGU CUGAUGAGGCCGAAAGGCCGAA AGUCUCCA |
| 2220 | CCCAGGCC CUGAUGAGGCCGAAAGGCCGAA AGGUUCUC |
| 2224 | AAGGUAGG CUGAUGAGGCCGAAAGGCCGAA AUGUAUGU |
| 2226 | UGUGGCCU CUGAUGAGGCCGAAAGGCCGAA AGGUCCAG |
| 2233 | AGUUCUGU CUGAUGAGGCCGAAAGGCCGAA AAGCAUGA |
| 2242 | ACUACUGA CUGAUGAGGCCGAAAGGCCGAA AGCUGUGU |
| 2248 | GCGACCAG CUGAUGAGGCCGAAAGGCCGAA ACCAGGAG |
| 2254 | UUCAGUGU CUGAUGAGGCCGAAAGGCCGAA AAUUGGAU |
| 2259 | GCACCGUG CUGAUGAGGCCGAAAGGCCGAA AUGUGAUC |
| 2260 | AGCACCGU CUGAUGAGGCCGAAAGGCCGAA AAUGUGAU |
| 2266 | AACUUGUA CUGAUGAGGCCGAAAGGCCGAA AUCCUGAU |
| 2274 | UACAUGUU CUGAUGAGGCCGAAAGGCCGAA ACCUGCUC |
| 2279 | ACCCGUAU CUGAUGAGGCCGAAAGGCCGAA AUCUUUCC |
| 2282 | ACUCAAUA CUGAUGAGGCCGAAAGGCCGAA AUAACUGU |

TABLE X-continued

Rat ICAM HH Ribozyme Sequences

| nt. Position | Rat HH Ribozyme Sequence |
|---|---|
| 2288 | CAUUGGAG CUGAUGAGGCCGAAAGGCCGAA ACCAGGGC |
| 2291 | GUAACUUG CUGAUGAGGCCGAAAGGCCGAA AUAUCCUG |
| 2321 | ACCCGUAU CUGAUGAGGCCGAAAGGCCGAA AUCUUUCC |
| 2338 | CCUGUGGA CUGAUGAGGCCGAAAGGCCGAA AAGCCCAA |
| 2339 | GCCUGGGG CUGAUGAGGCCGAAAGGCCGAA AAGUACCC |
| 2341 | UGAGCACC CUGAUGAGGCCGAAAGGCCGAA ACAGGCCC |
| 2344 | GAGAGGUC CUGAUGAGGCCGAAAGGCCGAA ACGAGCAG |
| 2358 | UGUGGGAG CUGAUGAGGCCGAAAGGCCGAA AGGCAGGG |
| 2359 | UUCUGUGG CUGAUGAGGCCGAAAGGCCGAA AUGGAUGG |
| 2360 | CUUCCAGG CUGAUGAGGCCGAAAGGCCGAA AACACAAG |
| 2376 | AAGAGGAA CUGAUGAGGCCGAAAGGCCGAA AGCAGUUC |
| 2377 | UAAUAGAG CUGAUGAGGCCGAAAGGCCGAA AGGAAGUC |
| 2378 | UCGUGAAA CUGAUGAGGCCGAAAGGCCGAA AAAUCAGC |
| 2379 | CGCAAGAG CUGAUGAGGCCGAAAGGCCGAA AAGAGCAG |
| 2380 | ACUCGUGA CUGAUGAGGCCGAAAGGCCGAA AGAAAUCA |
| 2382 | UGACUCGU CUGAUGAGGCCGAAAGGCCGAA AAAGAAAU |
| 2384 | CUUGUGUC CUGAUGAGGCCGAAAGGCCGAA ACCGGAUA |
| 2399 | CGUCCACA CUGAUGAGGCCGAAAGGCCGAA AGUAUUUA |
| 2401 | GAGGACCA CUGAUGAGGCCGAAAGGCCGAA AUAGCACA |
| 2411 | UGAAGCAU CUGAUGAGGCCGAAAGGCCGAA AGAAAUUG |
| 2417 | AACUUGUA CUGAUGAGGCCGAAAGGCCGAA AUCCUGAU |
| 2418 | AGUUCUGU CUGAUGAGGCCGAAAGGCCGAA AAGCAUGA |
| 2425 | GAACUCUG CUGAUGAGGCCGAAAGGCCGAA AUUAAUAA |
| 2426 | UAGUCUCC CUGAUGAGGCCGAAAGGCCGAA ACCCCAGG |
| 2433 | AACUGUCA CUGAUGAGGCCGAAAGGCCGAA AACUCUGA |
| 2434 | UCGUUUGU CUGAUGAGGCCGAAAGGCCGAA AUCCUCCG |
| 2448 | GGGGGAAG CUGAUGAGGCCGAAAGGCCGAA ACUGUUCA |
| 2449 | CGAGGCAG CUGAUGAGGCCGAAAGGCCGAA AAGGCUUC |
| 2451 | GAGGCAGG CUGAUGAGGCCGAAAGGCCGAA AACAGGCC |
| 2452 | AGAGGCAG CUGAUGAGGCCGAAAGGCCGAA AAACAGGC |
| 2455 | AACAAAGG CUGAUGAGGCCGAAAGGCCGAA AGGAAUGU |
| 2459 | UGUGGGAG CUGAUGAGGCCGAAAGGCCGAA AGGCAGGG |
| 2460 | UUGGGAAC CUGAUGAGGCCGAAAGGCCGAA AAGGUAGG |
| 2479 | GGCGGUAA CUGAUGAGGCCGAAAGGCCGAA AGGUGUAA |
| 2480 | GGGAUCAC CUGAUGAGGCCGAAAGGCCGAA ACGGCGAC |
| 2483 | ACAUUGGG CUGAUGAGGCCGAAAGGCCGAA ACAAAGGU |
| 2484 | GACAUUGG CUGAUGAGGCCGAAAGGCCGAA AACAAAGG |
| 2492 | UAGGUGGG CUGAUGAGGCCGAAAGGCCGAA AGGUGGUC |
| 2504 | UAGGAAUG CUGAUGAGGCCGAAAGGCCGAA AUGUAGGU |
| 2508 | AAGGUAGG CUGAUGAGGCCGAAAGGCCGAA AUGUAUGU |
| 2509 | AAAGGUAG CUGAUGAGGCCGAAAGGCCGAA AAUGUAUG |
| 2510 | AAUAGGUG CUGAUGAGGCCGAAAGGCCGAA AAAUGGAC |
| 2520 | ACAUUGGG CUGAUGAGGCCGAAAGGCCGAA ACAAAGGU |
| 2521 | GACAUUGG CUGAUGAGGCCGAAAGGCCGAA AACAAAGG |
| 2533 | UGAGGGGU CUGAUGAGGCCGAAAGGCCGAA AAUGCUGU |
| 2540 | GGAUACCU CUGAUGAGGCCGAAAGGCCGAA AGCACCGA |
| 2545 | AAAGUCCG CUGAUGAGGCCGAAAGGCCGAA AGCUGCCU |
| 2568 | CUGACACA CUGAUGAGGCCGAAAGGCCGAA AAUCUCUG |
| 2579 | CCAGGGCA CUGAUGAGGCCGAAAGGCCGAA AGUGCAGG |
| 2585 | GAGAGGUC CUGAUGAGGCCGAAAGGCCGAA ACGAGCAG |
| 2588 | GGCUGUGG CUGAUGAGGCCGAAAGGCCGAA AGGAGGCA |
| 2591 | CUUCGCAA CUGAUGAGGCCGAAAGGCCGAA AGGAAGAG |
| 2593 | AGCAGGGG CUGAUGAGGCCGAAAGGCCGAA AAUAGAGA |
| 2596 | GCGACCAG CUGAUGAGGCCGAAAGGCCGAA ACCAGGAG |
| 2601 | GAGGACCA CUGAUGAGGCCGAAAGGCCGAA AUAGCACA |
| 2602 | ACAACGGC CUGAUGAGGCCGAAAGGCCGAA ACCAGGAC |
| 2607 | CCUGGUGA CUGAUGAGGCCGAAAGGCCGAA ACUCCCAC |
| 2608 | UCCCACGG CUGAUGAGGCCGAAAGGCCGAA AGCUAAAG |
| 2609 | CAUCCAGU CUGAUGAGGCCGAAAGGCCGAA AGUCUCCA |
| 2620 | AACUGUCA CUGAUGAGGCCGAAAGGCCGAA AACUCUGA |
| 2626 | AGCAGCAC CUGAUGAGGCCGAAAGGCCGAA ACUGAGAG |
| 2628 | GGAGCUGA CUGAUGAGGCCGAAAGGCCGAA AAGUUGUA |
| 2635 | GUGAAUUG CUGAUGAGGCCGAAAGGCCGAA AUCUGUGA |
| 2640 | UGGAUGGA CUGAUGAGGCCGAAAGGCCGAA ACCUGAGC |
| 2641 | AAUGUAUG CUGAUGAGGCCGAAAGGCCGAA AGGUGGGG |
| 2642 | AGAGGCAG CUGAUGAGGCCGAAAGGCCGAA AAACAGGC |
| 2653 | AGCACCCU CUGAUGAGGCCGAAAGGCCGAA ACCUGUGG |
| 2659 | GCUUGCAG CUGAUGAGGCCGAAAGGCCGAA ACCCUUCU |
| 2689 | AGCUUCAG CUGAUGAGGCCGAAAGGCCGAA ACCCUAGU |
| 2691 | AGUCCUCU CUGAUGAGGCCGAAAGGCCGAA AGGCCUGA |
| 2700 | CCUGGGGG CUGAUGAGGCCGAAAGGCCGAA AGUACCCU |
| 2704 | UAGGUGGG CUGAUGAGGCCGAAAGGCCGAA AGGUGGUC |
| 2711 | ACCUUCCU CUGAUGAGGCCGAAAGGCCGAA AGGUAGGG |
| 2712 | CACCUUCC CUGAUGAGGCCGAAAGGCCGAA AAGGUAGG |

TABLE X-continued

Rat ICAM HH Ribozyme Sequences

| nt. Position | Rat HH Ribozyme Sequence |
|---|---|
| 2721 | ACCCGUAU CUGAUGAGGCCGAAAGGCCGAA AUCUUUCC |
| 2724 | CAAACCCG CUGAUGAGGCCGAAAGGCCGAA AUGAUCUU |
| 2744 | CCUGCACG CUGAUGAGGCCGAAAGGCCGAA AUCCACCC |
| 2750 | GGUUUUUA CUGAUGAGGCCGAAAGGCCGAA ACAGGGAC |
| 2759 | CCACUCGA CUGAUGAGGCCGAAAGGCCGAA AGUUCGUC |
| 2761 | GGAAGAUC CUGAUGAGGCCGAAAGGCCGAA AAAGUCCG |
| 2765 | AGGCCGCA CUGAUGAGGCCGAAAGGCCGAA AGCAAAAG |
| 2769 | GCAGGGGU CUGAUGAGGCCGAAAGGCCGAA AUAGAGAA |
| 2797 | UUGACCAU CUGAUGAGGCCGAAAGGCCGAA AUUUCACG |
| 2803 | GUUCUGUG CUGAUGAGGCCGAAAGGCCGAA AGCAUGAG |
| 2804 | AGUUCUGU CUGAUGAGGCCGAAAGGCCGAA AAGCAUGA |
| 2813 | AGGGUCAG CUGAUGAGGCCGAAAGGCCGAA AUGGGAGC |
| 2815 | GGAAGAUC CUGAUGAGGCCGAAAGGCCGAA AAAGUCCG |
| 2821 | ACCUCCAG CUGAUGAGGCCGAAAGGCCGAA AGGUCAGG |
| 2822 | GGAGCUGA CUGAUGAGGCCGAAAGGCCGAA AAGUUGUA |
| 2823 | UGGGAGCU CUGAUGAGGCCGAAAGGCCGAA AAAAGUUG |
| 2829 | GGAUACCU CUGAUGAGGCCGAAAGGCCGAA AGCACCGA |
| 2837 | GGGGGAAG CUGAUGAGGCCGAAAGGCCGAA ACCCUGUG |
| 2840 | UGCGCUGG CUGAUGAGGCCGAAAGGCCGAA AGGGGUGC |
| 2847 | AGGUGGGU CUGAUGAGGCCGAAAGGCCGAA AGGGGUAA |
| 2853 | CUAGUCGG CUGAUGAGGCCGAAAGGCCGAA AGAUCGAA |
| 2860 | UUCCAGGG CUGAUGAGGCCGAAAGGCCGAA ACACAAGA |
| 2872 | UGAGCACC CUGAUGAGGCCGAAAGGCCGAA ACAGGCCC |
| 2877 | GGUGCUGG CUGAUGAGGCCGAAAGGCCGAA AGACUCCA |
| 2899 | AAAGUCCG CUGAUGAGGCCGAAAGGCCGAA AGCUGCCU |
| 2900 | AGAGAAGG CUGAUGAGGCCGAAAGGCCGAA AGUCAGCC |
| 2904 | AAGAGGAA CUGAUGAGGCCGAAAGGCCGAA AGCAGUUC |
| 2905 | AGAGAAGG CUGAUGAGGCCGAAAGGCCGAA AGUCAGCC |
| 2906 | UUAAUAAA CUGAUGAGGCCGAAAGGCCGAA ACAUCAAC |
| 2907 | CGCAAGAG CUGAUGAGGCCGAAAGGCCGAA AAGAGCAG |
| 2908 | AAUUAAUA CUGAUGAGGCCGAAAGGCCGAA AUACAUCA |
| 2909 | AAGAGGAA CUGAUGAGGCCGAAAGGCCGAA AGCAGUUC |
| 2910 | GUAAUAGA CUGAUGAGGCCGAAAGGCCGAA AAGGAAGU |
| 2911 | GGGUAAUA CUGAUGAGGCCGAAAGGCCGAA AGAAGGAA |
| 2912 | UGAAUUAA CUGAUGAGGCCGAAAGGCCGAA AAAUACAU |
| 2913 | CUGGGAAC CUGAUGAGGCCGAAAGGCCGAA AAUACACA |
| 2914 | UCUGAAUU CUGAUGAGGCCGAAAGGCCGAA AUAAAUAC |
| 2915 | CUCUGAAU CUGAUGAGGCCGAAAGGCCGAA AAUAAAUA |
| 2916 | CUUCGCAA CUGAUGAGGCCGAAAGGCCGAA AGGAAGAG |
| 2917 | GUCUUCGC CUGAUGAGGCCGAAAGGCCGAA AGAGGAAG |
| 2918 | UGACUCGU CUGAUGAGGCCGAAAGGCCGAA AAAGAAAU |
| 2919 | CAGUGGCU CUGAUGAGGCCGAAAGGCCGAA ACACAAAA |
| 2931 | GGCAGCGG CUGAUGAGGCCGAAAGGCCGAA ACACCAUC |
| 2933 | GGUGCUGG CUGAUGAGGCCGAAAGGCCGAA AGACUCCA |
| 2941 | GCCUGGGG CUGAUGAGGCCGAAAGGCCGAA AAGUACUG |
| 2951 | GUCAGAGG CUGAUGAGGCCGAAAGGCCGAA AGCAUGGU |
| 2952 | GAAGAUCG CUGAUGAGGCCGAAAGGCCGAA AAGUCCGG |
| 2955 | CCAUGUCA CUGAUGAGGCCGAAAGGCCGAA AGGAAGCA |
| 2956 | AUUGAUUC CUGAUGAGGCCGAAAGGCCGAA AAGGAAAG |
| 2961 | CAGUGGCU CUGAUGAGGCCGAAAGGCCGAA ACACAAAA |
| 2962 | CUGGGAAC CUGAUGAGGCCGAAAGGCCGAA AAUACACA |
| 2965 | ACUUUAUU CUGAUGAGGCCGAAAGGCCGAA AUUCAAAG |
| 2966 | AGCUUGAA CUGAUGAGGCCGAAAGGCCGAA AGCUUCCA |
| 2969 | UAAAACUU CUGAUGAGGCCGAAAGGCCGAA AUUGAUUC |
| 2975 | AGCUUGAA CUGAUGAGGCCGAAAGGCCGAA AGCUUCCA |
| 2976 | CAGGUGAG CUGAUGAGGCCGAAAGGCCGAA ACCAUAUA |
| 2977 | UCAGCUUG CUGAUGAGGCCGAAAGGCCGAA AGAGCUUC |

What is claimed is:

1. An enzymatic nucleic acid molecule which specifically cleaves RNA encoded by ICAM-1 gene, wherein said enzymatic nucleic acid molecule comprises a substrate binding site and a nucleotide sequence within or surrounding said substrate binding site wherein said nucleotide sequence imparts to said enzymatic nucleic acid molecule activity for the cleavage of said RNA encoded by the ICAM-1 gene.

2. The enzymatic nucleic acid molecule of claim 1, wherein said substrate binding site is complementary to said RNA encoded by the ICAM-1 gene.

3. The enzymatic nucleic acid molecule of claim 1, wherein said enzymatic nucleic acid molecule is in a hammerhead motif.

4. The enzymatic nucleic acid molecule of claim 1, wherein said substrate binding site comprises between 12 and 100 nucleotides complementary to said RNA encoded by the ICAM-1 gene.

5. The enzymatic nucleic acid molecule of claim 1, wherein said substrate binding site comprises between 14 and 24 nucleotides complementary to said RNA encoded by the ICAM-1 gene.

6. The enzymatic nucleic acid molecule of claim 1, wherein said enzymatic nucleic acid molecule is chemically synthesized.

7. The enzymatic nucleic acid molecule of claim 1, wherein said enzymatic nucleic acid molecule is in a purified form.

8. The enzymatic nucleic acid molecule of claim 1, wherein said enzymatic nucleic acid molecule is active in the presence of divalent metal ions.

9. The enzymatic nucleic acid molecule of claim 8, wherein said divalent metal ion is magnesium.

10. The enzymatic nucleic acid molecule of claim 1, wherein said enzymatic nucleic acid molecule comprises a sugar modification.

11. The enzymatic nucleic acid molecule of claim 1, wherein said enzymatic nucleic acid molecule comprises a 5'-cap.

12. The enzymatic nucleic acid molecule of claim 1, wherein said enzymatic nucleic acid molecule comprises a 3'-cap.

13. The enzymatic RNA molecule of claim 1, wherein said enzymatic nucleic acid molecule comprises a 3'-polyA tail.

14. The enzymatic nucleic acid molecule of claim 1, wherein said enzymatic RNA molecule is capable of inhibiting proliferation of a mammalian cell.

15. The enzymatic nucleic acid molecule of claim 14, wherein said enzymatic nucleic acid molecule is in a hammerhead motif.

16. A method of cleaving RNA encoded by the ICAM-1 gene comprising the step of contacting said RNA in vitro with the enzymatic nucleic acid molecule of claim 1 under conditions suitable for the cleavage of said RNA.

17. An expression vector comprising nucleic acid sequence encoding one or more enzymatic nucleic acid molecule of claim 1 in a manner which allows expression of said enzymatic nucleic acid molecules.

18. The expression vector of claim 1, wherein said expression vector is a viral vector.

19. The expression vector of claim 18, wherein said viral vector is a retrovirus vector.

20. The expression vector of claim 1, wherein said nucleic acid sequence encoding said enzymatic nucleic acid molecule is under the control of a mammalian transcription promoter.

21. The expression vector of claim 20, wherein said mammalian transcription promoter is a cytomegalovirus promoter.

22. The expression vector of claim 20, wherein said mammalian transcription promoter is a U6 small nuclear RNA promoter.

23. A mammalian cell in culture comprising the enzymatic nucleic acid molecule of claim 1.

24. The mammalian cell of claim 23, wherein said mammalian cell is a human cell.

* * * * *

SEQUENCE LISTING (1) GENERAL INFORMATION:

(iii) NUMBER OF SEQUENCES:           2390

(2) INFORMATION FOR SEQ ID NO: 1:

(i) SEQUENCE CHARACTERISTICS:
       (A) LENGTH:            11
       (B) TYPE:              nucleic acid
       (C) STRANDEDNESS:      single
       (D) TOPOLOGY:          linear (ix) FEATURE:
       (D) OTHER INFORMATION: The letter "N" stands for
           any base. "H" represents
           nucleotide C, A, or U.

(xi) SEQUENCE DESCRIPTION: SEQ ID NO: 1:

NNNNUHNNNN N                                                         11

(2) INFORMATION FOR SEQ ID NO: 2:

(i) SEQUENCE CHARACTERISTICS:
       (A) LENGTH:            32
       (B) TYPE:              nucleic acid
       (C) STRANDEDNESS:      single
       (D) TOPOLOGY:          linear (ix) FEATURE:
       (D) OTHER INFORMATION: The letter "N" stands for
           any base.

(xi) SEQUENCE DESCRIPTION: SEQ ID NO: 2:

NNNNNCUGAN GAGNNNNNNN NNNCGAAANN NN                                  32

(2) INFORMATION FOR SEQ ID NO: 3:

(i) SEQUENCE CHARACTERISTICS:
       (A) LENGTH:            14
       (B) TYPE:              nucleic acid
       (C) STRANDEDNESS:      single
       (D) TOPOLOGY:          linear (ix) FEATURE:
       (D) OTHER INFORMATION: The letter "N" stands for
           any base.

(xi) SEQUENCE DESCRIPTION: SEQ ID NO: 3:

NNNNNGUCNN NNNN                                                      14

(2) INFORMATION FOR SEQ ID NO: 4:

(i) SEQUENCE CHARACTERISTICS:
       (A) LENGTH:            50
       (B) TYPE:              nucleic acid
       (C) STRANDEDNESS:      single
       (D) TOPOLOGY:          linear (ix) FEATURE:
       (D) OTHER INFORMATION: The letter "N" stands for
           any base.

(xi) SEQUENCE DESCRIPTION: SEQ ID NO: 4:

NNNNNNAGAA NNNNACCAGA GAAACACACG UUGUGGUAUA UUACCUGGUA                50

(2) INFORMATION FOR SEQ ID NO: 5:

```
      (i) SEQUENCE CHARACTERISTICS:
           (A) LENGTH:              85
           (B) TYPE:                nucleic acid
           (C) STRANDEDNESS:        single
           (D) TOPOLOGY:            linear (xi) SEQUENCE DESCRIPTION: SEQ ID NO: 5:

UGGCCGGCAU GGUCCCAGCC UCCUCGCUGG CGCCGGCUGG GCAACAUUCC GAGGGGACCG      60

UCCCCUCGGU AAUGGCGAAU GGGAC                                            85

(2) INFORMATION FOR SEQ ID NO:   6:

(i) SEQUENCE CHARACTERISTICS:
           (A) LENGTH:              176
           (B) TYPE:                nucleic acid
           (C) STRANDEDNESS:        single
           (D) TOPOLOGY:            linear (xi) SEQUENCE DESCRIPTION: SEQ ID NO: 6:

GGGAAAGCUU GCGAAGGGCG UCGUCGCCCC GAGCGGUAGU AAGCAGGGAA CUCACCUCCA      60

AUUUCAGUAC UGAAAUUGUC GUAGCAGUUG ACUACUGUUA UGUGAUUGGU AGAGGCUAAG     120

UGACGGUAUU GGCGUAAGUC AGUAUUGCAG CACAGCACAA GCCCGCUUGC GAGAAU         176

(2) INFORMATION FOR SEQ ID NO:   7:

(i) SEQUENCE CHARACTERISTICS:
           (A) LENGTH:              15 base pairs
           (B) TYPE:                nucleic acid
           (C) STRANDEDNESS:        single
           (D) TOPOLOGY:            linear (xi) SEQUENCE DESCRIPTION: SEQ ID NO: 7:

CCCCAGUCGA CGCUG                                                       15

(2) INFORMATION FOR SEQ ID NO:   8:

(i) SEQUENCE CHARACTERISTICS:
           (A) LENGTH:              15 base pairs
           (B) TYPE:                nucleic acid
           (C) STRANDEDNESS:        single
           (D) TOPOLOGY:            linear (xi) SEQUENCE DESCRIPTION: SEQ ID NO: 8:

CUGAGCUCCU CUGCU                                                       15

(2) INFORMATION FOR SEQ ID NO:   9:

(i) SEQUENCE CHARACTERISTICS:
           (A) LENGTH:              15 base pairs
           (B) TYPE:                nucleic acid
           (C) STRANDEDNESS:        single
           (D) TOPOLOGY:            linear (xi) SEQUENCE DESCRIPTION: SEQ ID NO: 9:

AGCUCCUCUG CUACU                                                       15

(2) INFORMATION FOR SEQ ID NO:  10:

(i) SEQUENCE CHARACTERISTICS:
           (A) LENGTH:              15 base pairs
           (B) TYPE:                nucleic acid
           (C) STRANDEDNESS:        single
           (D) TOPOLOGY:            linear (xi) SEQUENCE DESCRIPTION: SEQ ID NO: 10:
```

```
CUCUGCUACU CAGAG                                                          15

(2) INFORMATION FOR SEQ ID NO: 11:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 11:

UGCUACUCAG AGUUG                                                          15

(2) INFORMATION FOR SEQ ID NO: 12:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 12:

UCAGAGUUGC AACCU                                                          15

(2) INFORMATION FOR SEQ ID NO: 13:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 13:

GCAACCUCAG CCUCG                                                          15

(2) INFORMATION FOR SEQ ID NO: 14:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 14:

UCAGCCUCGC UAUGG                                                          15

(2) INFORMATION FOR SEQ ID NO: 15:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 15:

CCUCGCUAUG GCUCC                                                          15

(2) INFORMATION FOR SEQ ID NO: 16:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 16:

UAUGGCUCCC AGCAG                                                          15
```

(2) INFORMATION FOR SEQ ID NO: 17:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 17:

CCGCACUCCU GGUCC                                              15

(2) INFORMATION FOR SEQ ID NO: 18:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 18:

UCCUGGUCCU GCUCG                                              15

(2) INFORMATION FOR SEQ ID NO: 19:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 19:

UCCUGCUCGG GGCUC                                              15

(2) INFORMATION FOR SEQ ID NO: 20:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 20:

CGGGGCUCUG UUCCC                                              15

(2) INFORMATION FOR SEQ ID NO: 21:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 21:

GCUCUGUUCC CAGGA                                              15

(2) INFORMATION FOR SEQ ID NO: 22:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 22:

CUCUGUUCCC AGGAC                                              15

(2) INFORMATION FOR SEQ ID NO: 23:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 23:

CAGACAUCUG UGUCC                                              15

(2) INFORMATION FOR SEQ ID NO: 24:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 24:

UCUGUGUCCC CCUCA                                              15

(2) INFORMATION FOR SEQ ID NO: 25:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 25:

UCCCCCUCAA AAGUC                                            15

(2) INFORMATION FOR SEQ ID NO: 26:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 26:

CAAAAGUCAU CCUGC                                            15

(2) INFORMATION FOR SEQ ID NO: 27:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 27:

AAGUCAUCCU GCCCC                                            15

(2) INFORMATION FOR SEQ ID NO: 28:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 28:

GGAGGCUCCG UGCUG                                            15

```
(2) INFORMATION FOR SEQ ID NO: 29:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 29:

AGCACCUCCU GUGAC                                                        15

(2) INFORMATION FOR SEQ ID NO: 30:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 30:

CCCAAGUUGU UGGGC                                                        15

(2) INFORMATION FOR SEQ ID NO: 31:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 31:

AAGUUGUUGG GCAUA                                                        15

(2) INFORMATION FOR SEQ ID NO: 32:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 32:

UGGGCAUAGA GACCC                                                        15

(2) INFORMATION FOR SEQ ID NO: 33:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 33:

ACCCCGUUGC CUAAA                                                        15

(2) INFORMATION FOR SEQ ID NO: 34:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 34:

GUUGCCUAAA AAGGA                                                        15

(2) INFORMATION FOR SEQ ID NO: 35:
```

```
    (i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 35:

AAGGAGUUGC UCCUG                                                 15

(2) INFORMATION FOR SEQ ID NO: 36:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 36:

AGUUGCUCCU GCCUG                                                 15

(2) INFORMATION FOR SEQ ID NO: 37:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 37:

AAGGUGUAUG AACUG                                                 15

(2) INFORMATION FOR SEQ ID NO: 38:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 38:

AGAAGAUAGC CAACC                                                 15

(2) INFORMATION FOR SEQ ID NO: 39:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 39:

AUGUGCUAUU CAAAC                                                 15

(2) INFORMATION FOR SEQ ID NO: 40:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 40:

GUGCUAUUCA AACUG                                                 15

(2) INFORMATION FOR SEQ ID NO: 41:
```

```
    (i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 41:

UGCUAUUCAA ACUGC                                                    15

(2) INFORMATION FOR SEQ ID NO: 42:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 42:

GGGCAGUCAA CAGCU                                                    15

(2) INFORMATION FOR SEQ ID NO: 43:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 43:

AACAGCUAAA ACCUU                                                    15

(2) INFORMATION FOR SEQ ID NO: 44:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 44:

AAAACCUUCC UCACC                                                    15

(2) INFORMATION FOR SEQ ID NO: 45:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 45:

AAACCUUCCU CACCG                                                    15

(2) INFORMATION FOR SEQ ID NO: 46:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 46:

CCUUCCUCAC CGUGU                                                    15

(2) INFORMATION FOR SEQ ID NO: 47:

(i) SEQUENCE CHARACTERISTICS:
```

```
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 47:

ACCGUGUACU GGACU                                                     15

(2) INFORMATION FOR SEQ ID NO: 48:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 48:

CUGGACUCCA GAACG                                                     15

(2) INFORMATION FOR SEQ ID NO: 49:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 49:

CACCCCUCCC CUCUU                                                     15

(2) INFORMATION FOR SEQ ID NO: 50:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 50:

CUCCCCUCUU GGCAG                                                     15

(2) INFORMATION FOR SEQ ID NO: 51:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 51:

CCCCUCUUGG CAGCC                                                     15

(2) INFORMATION FOR SEQ ID NO: 52:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 52:

AGAACCUUAC CCUAC                                                     15

(2) INFORMATION FOR SEQ ID NO: 53:

(i) SEQUENCE CHARACTERISTICS:
            (A) LENGTH:            15 base pairs
```

```
            (B) TYPE:                nucleic acid
            (C) STRANDEDNESS:        single
            (D) TOPOLOGY:            linear (xi) SEQUENCE DESCRIPTION: SEQ ID NO: 53:

GAACCUUACC CUACG                                                          15

(2) INFORMATION FOR SEQ ID NO: 54:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 54:

UUACCCUACG CUGCC                                                          15

(2) INFORMATION FOR SEQ ID NO: 55:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 55:

CCAACCUCAC CGUGG                                                          15

(2) INFORMATION FOR SEQ ID NO: 56:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 56:

UGCUGCUCCG UGGGG                                                          15

(2) INFORMATION FOR SEQ ID NO: 57:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 57:

CUGAGGUCAC GACCA                                                          15

(2) INFORMATION FOR SEQ ID NO: 58:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 58:

GAGAGAUCAC CAUGG                                                          15

(2) INFORMATION FOR SEQ ID NO: 59:

(i) SEQUENCE CHARACTERISTICS:
            (A) LENGTH:              15 base pairs
            (B) TYPE:                nucleic acid
```

```
            (C) STRANDEDNESS:          single
            (D) TOPOLOGY:              linear (xi) SEQUENCE DESCRIPTION: SEQ ID NO: 59:

AGCCAAUUUC UCGUG                                                       15

(2) INFORMATION FOR SEQ ID NO: 60:

(i) SEQUENCE CHARACTERISTICS:
            (A) LENGTH:                15 base pairs
            (B) TYPE:                  nucleic acid
            (C) STRANDEDNESS:          single
            (D) TOPOLOGY:              linear (xi) SEQUENCE DESCRIPTION: SEQ ID NO: 60:

GCCAAUUUCU CGUGC                                                       15

(2) INFORMATION FOR SEQ ID NO: 61:

(i) SEQUENCE CHARACTERISTICS:
            (A) LENGTH:                15 base pairs
            (B) TYPE:                  nucleic acid
            (C) STRANDEDNESS:          single
            (D) TOPOLOGY:              linear (xi) SEQUENCE DESCRIPTION: SEQ ID NO: 61:

CCAAUUUCUC GUGCC                                                       15

(2) INFORMATION FOR SEQ ID NO: 62:

(i) SEQUENCE CHARACTERISTICS:
            (A) LENGTH:                15 base pairs
            (B) TYPE:                  nucleic acid
            (C) STRANDEDNESS:          single
            (D) TOPOLOGY:              linear (xi) SEQUENCE DESCRIPTION: SEQ ID NO: 62:

AAUUUCUCGU GCCGC                                                       15

(2) INFORMATION FOR SEQ ID NO: 63:

(i) SEQUENCE CHARACTERISTICS:
            (A) LENGTH:                15 base pairs
            (B) TYPE:                  nucleic acid
            (C) STRANDEDNESS:          single
            (D) TOPOLOGY:              linear (xi) SEQUENCE DESCRIPTION: SEQ ID NO: 63:

GAGCUGUUUG AGAAC                                                       15

(2) INFORMATION FOR SEQ ID NO: 64:

(i) SEQUENCE CHARACTERISTICS:
            (A) LENGTH:                15 base pairs
            (B) TYPE:                  nucleic acid
            (C) STRANDEDNESS:          single
            (D) TOPOLOGY:              linear (xi) SEQUENCE DESCRIPTION: SEQ ID NO: 64:

AGCUGUUUGA GAACA                                                       15

(2) INFORMATION FOR SEQ ID NO: 65:

(i) SEQUENCE CHARACTERISTICS:
            (A) LENGTH:                15 base pairs
            (B) TYPE:                  nucleic acid
```

```
          (C) STRANDEDNESS:        single
          (D) TOPOLOGY:            linear (xi) SEQUENCE DESCRIPTION: SEQ ID NO: 65:

AACACCUCGG CCCCC                                                       15

(2) INFORMATION FOR SEQ ID NO: 66:

(i) SEQUENCE CHARACTERISTICS:
          (A) LENGTH:              15 base pairs
          (B) TYPE:                nucleic acid
          (C) STRANDEDNESS:        single
          (D) TOPOLOGY:            linear (xi) SEQUENCE DESCRIPTION: SEQ ID NO: 66:

GCCCCCUACC AGCUC                                                       15

(2) INFORMATION FOR SEQ ID NO: 67:

(i) SEQUENCE CHARACTERISTICS:
          (A) LENGTH:              15 base pairs
          (B) TYPE:                nucleic acid
          (C) STRANDEDNESS:        single
          (D) TOPOLOGY:            linear (xi) SEQUENCE DESCRIPTION: SEQ ID NO: 67:

ACCAGCUCCA GACCU                                                       15

(2) INFORMATION FOR SEQ ID NO: 68:

(i) SEQUENCE CHARACTERISTICS:
          (A) LENGTH:              15 base pairs
          (B) TYPE:                nucleic acid
          (C) STRANDEDNESS:        single
          (D) TOPOLOGY:            linear (xi) SEQUENCE DESCRIPTION: SEQ ID NO: 68:

CAGACCUUUG UCCUG                                                       15

(2) INFORMATION FOR SEQ ID NO: 69:

(i) SEQUENCE CHARACTERISTICS:
          (A) LENGTH:              15 base pairs
          (B) TYPE:                nucleic acid
          (C) STRANDEDNESS:        single
          (D) TOPOLOGY:            linear (xi) SEQUENCE DESCRIPTION: SEQ ID NO: 69:

AGACCUUUGU CCUGC                                                       15

(2) INFORMATION FOR SEQ ID NO: 70:

(i) SEQUENCE CHARACTERISTICS:
          (A) LENGTH:              15 base pairs
          (B) TYPE:                nucleic acid
          (C) STRANDEDNESS:        single
          (D) TOPOLOGY:            linear (xi) SEQUENCE DESCRIPTION: SEQ ID NO: 70:

CCUUUGUCCU GCCAG                                                       15

(2) INFORMATION FOR SEQ ID NO: 71:

(i) SEQUENCE CHARACTERISTICS:
          (A) LENGTH:              15 base pairs
          (B) TYPE:                nucleic acid
          (C) STRANDEDNESS:        single
```

```
       (D) TOPOLOGY:           linear (xi) SEQUENCE DESCRIPTION: SEQ ID NO: 71:

AGCGACUCCC CCACA                                               15

(2) INFORMATION FOR SEQ ID NO: 72:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 72:

CACAACUUGU CAGCC                                               15

(2) INFORMATION FOR SEQ ID NO: 73:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 73:

AACUUGUCAG CCCCC                                               15

(2) INFORMATION FOR SEQ ID NO: 74:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 74:

CCCGGGUCCU AGAGG                                               15

(2) INFORMATION FOR SEQ ID NO: 75:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 75:

GGGUCCUAGA GGUGG                                               15

(2) INFORMATION FOR SEQ ID NO: 76:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 76:

CCGUGGUCUG UUCCC                                               15

(2) INFORMATION FOR SEQ ID NO: 77:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear
```

(xi) SEQUENCE DESCRIPTION: SEQ ID NO: 77:

GGUCUGUUCC CUGGA                                                    15

(2) INFORMATION FOR SEQ ID NO: 78:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 78:

GUCUGUUCCC UGGAC                                                    15

(2) INFORMATION FOR SEQ ID NO: 79:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 79:

GGGCUGUUCC CAGUC                                                    15

(2) INFORMATION FOR SEQ ID NO: 80:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 80:

GGCUGUUCCC AGUCU                                                    15

(2) INFORMATION FOR SEQ ID NO: 81:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 81:

UCCCAGUCUC GGAGG                                                    15

(2) INFORMATION FOR SEQ ID NO: 82:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 82:

CCAGUCUCGG AGGCC                                                    15

(2) INFORMATION FOR SEQ ID NO: 83:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 83:

CCCAGGUCCA CCUGG                                                        15

(2) INFORMATION FOR SEQ ID NO: 84:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 84:

CAGAGGUUGA ACCCC                                                        15

(2) INFORMATION FOR SEQ ID NO: 85:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 85:

CCACAGUCAC CUAUG                                                        15

(2) INFORMATION FOR SEQ ID NO: 86:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 86:

GUCACCUAUG GCAAC                                                        15

(2) INFORMATION FOR SEQ ID NO: 87:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 87:

AACGACUCCU UCUCG                                                        15

(2) INFORMATION FOR SEQ ID NO: 88:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 88:

GACUCCUUCU CGGCC                                                        15

(2) INFORMATION FOR SEQ ID NO: 89:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 89:

ACUCCUUCUC GGCCA                                                        15

(2) INFORMATION FOR SEQ ID NO: 90:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 90:

UCCUUCUCGG CCAAG                                                        15

(2) INFORMATION FOR SEQ ID NO: 91:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 91:

AAGGCCUCAG UCAGU                                                        15

(2) INFORMATION FOR SEQ ID NO: 92:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 92:

CCUCAGUCAG UGUGA                                                        15

(2) INFORMATION FOR SEQ ID NO: 93:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 93:

GUGCAGUAAU ACUGG                                                        15

(2) INFORMATION FOR SEQ ID NO: 94:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 94:

CAGUAAUACU GGGGA                                                        15

(2) INFORMATION FOR SEQ ID NO: 95:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 95:

```
UGACCAUCUA CAGCU                                                              15

(2) INFORMATION FOR SEQ ID NO: 96:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 96:

ACCAUCUACA GCUUU                                                              15

(2) INFORMATION FOR SEQ ID NO: 97:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 97:

UACAGCUUUC CGGCG                                                              15

(2) INFORMATION FOR SEQ ID NO: 98:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 98:

ACAGCUUUCC GGCGC                                                              15

(2) INFORMATION FOR SEQ ID NO: 99:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 99:

CAGCUUUCCG GCGCC                                                              15

(2) INFORMATION FOR SEQ ID NO: 100:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 100:

ACGUGAUUCU GACGA                                                              15

(2) INFORMATION FOR SEQ ID NO: 101:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 101:

CGUGAUUCUG ACGAA                                                              15
```

(2) INFORMATION FOR SEQ ID NO: 102:

(i) SEQUENCE CHARACTERISTICS:
        (A) LENGTH:          15 base pairs
        (B) TYPE:            nucleic acid
        (C) STRANDEDNESS:   single
        (D) TOPOLOGY:      linear (xi) SEQUENCE DESCRIPTION: SEQ ID NO: 102:

CAGAGGUCUC AGAAG                                       15

(2) INFORMATION FOR SEQ ID NO: 103:

(i) SEQUENCE CHARACTERISTICS:
        (A) LENGTH:          15 base pairs
        (B) TYPE:            nucleic acid
        (C) STRANDEDNESS:   single
        (D) TOPOLOGY:      linear (xi) SEQUENCE DESCRIPTION: SEQ ID NO: 103:

GAGGUCUCAG AAGGG                                       15

(2) INFORMATION FOR SEQ ID NO: 104:

(i) SEQUENCE CHARACTERISTICS:
        (A) LENGTH:          15 base pairs
        (B) TYPE:            nucleic acid
        (C) STRANDEDNESS:   single
        (D) TOPOLOGY:      linear (xi) SEQUENCE DESCRIPTION: SEQ ID NO: 104:

CCACCCUAGA GCCAA                                       15

(2) INFORMATION FOR SEQ ID NO: 105:

(i) SEQUENCE CHARACTERISTICS:
        (A) LENGTH:          15 base pairs
        (B) TYPE:            nucleic acid
        (C) STRANDEDNESS:   single
        (D) TOPOLOGY:      linear (xi) SEQUENCE DESCRIPTION: SEQ ID NO: 105:

AUGGGGUUCC AGCCC                                       15

(2) INFORMATION FOR SEQ ID NO: 106:

(i) SEQUENCE CHARACTERISTICS:
        (A) LENGTH:          15 base pairs
        (B) TYPE:            nucleic acid
        (C) STRANDEDNESS:   single
        (D) TOPOLOGY:      linear (xi) SEQUENCE DESCRIPTION: SEQ ID NO: 106:

UGGGGUUCCA GCCCA                                       15

(2) INFORMATION FOR SEQ ID NO: 107:

(i) SEQUENCE CHARACTERISTICS:
        (A) LENGTH:          15 base pairs
        (B) TYPE:            nucleic acid
        (C) STRANDEDNESS:   single
        (D) TOPOLOGY:      linear (xi) SEQUENCE DESCRIPTION: SEQ ID NO: 107:

CCCAGCUCCU GCUGA                                       15

(2) INFORMATION FOR SEQ ID NO: 108:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 108:

CGCAGCUUCU CCUGC                                                    15

(2) INFORMATION FOR SEQ ID NO: 109:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 109:

GCAGCUUCUC CUGCU                                                    15

(2) INFORMATION FOR SEQ ID NO: 110:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 110:

AGCUUCUCCU GCUCU                                                    15

(2) INFORMATION FOR SEQ ID NO: 111:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 111:

UCCUGCUCUG CAACC                                                    15

(2) INFORMATION FOR SEQ ID NO: 112:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 112:

GCCAGCUUAU ACACA                                                    15

(2) INFORMATION FOR SEQ ID NO: 113:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 113:

CCAGCUUAUA CACAA                                                    15

(2) INFORMATION FOR SEQ ID NO: 114:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 114:

AGCUUAUACA CAAGA                                                   15

(2) INFORMATION FOR SEQ ID NO: 115:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 115:

GGGAGCUUCG UGUCC                                                   15

(2) INFORMATION FOR SEQ ID NO: 116:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 116:

GGAGCUUCGU GUCCU                                                   15

(2) INFORMATION FOR SEQ ID NO: 117:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 117:

UUCGUGUCCU GUAUG                                                   15

(2) INFORMATION FOR SEQ ID NO: 118:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 118:

GUCCUGUAUG GCCCC                                                   15

(2) INFORMATION FOR SEQ ID NO: 119:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 119:

GAGGGAUUGU CCGGG                                                   15

(2) INFORMATION FOR SEQ ID NO: 120:

```
    (i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 120:

GGAUUGUCCG GGAAA                                                          15

(2) INFORMATION FOR SEQ ID NO: 121:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 121:

AGAAAAUUCC CAGCA                                                          15

(2) INFORMATION FOR SEQ ID NO: 122:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 122:

GAAAAUUCCC AGCAG                                                          15

(2) INFORMATION FOR SEQ ID NO: 123:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 123:

GCAGACUCCA AUGUG                                                          15

(2) INFORMATION FOR SEQ ID NO: 124:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 124:

CCAGGCUUGG GGGAA                                                          15

(2) INFORMATION FOR SEQ ID NO: 125:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 125:

AACCCAUUGC CCGAG                                                          15

(2) INFORMATION FOR SEQ ID NO: 126:
```

```
        (i) SEQUENCE CHARACTERISTICS:
             (A) LENGTH:              15 base pairs
             (B) TYPE:                nucleic acid
             (C) STRANDEDNESS:        single
             (D) TOPOLOGY:            linear (xi) SEQUENCE DESCRIPTION: SEQ ID NO: 126:

CCGAGCUCAA GUGUC                                                          15

(2) INFORMATION FOR SEQ ID NO: 127:

(i) SEQUENCE CHARACTERISTICS:
             (A) LENGTH:              15 base pairs
             (B) TYPE:                nucleic acid
             (C) STRANDEDNESS:        single
             (D) TOPOLOGY:            linear (xi) SEQUENCE DESCRIPTION: SEQ ID NO: 127:

CAAGUGUCUA AAGGA                                                          15

(2) INFORMATION FOR SEQ ID NO: 128:

(i) SEQUENCE CHARACTERISTICS:
             (A) LENGTH:              15 base pairs
             (B) TYPE:                nucleic acid
             (C) STRANDEDNESS:        single
             (D) TOPOLOGY:            linear (xi) SEQUENCE DESCRIPTION: SEQ ID NO: 128:

AGUGUCUAAA GGAUG                                                          15

(2) INFORMATION FOR SEQ ID NO: 129:

(i) SEQUENCE CHARACTERISTICS:
             (A) LENGTH:              15 base pairs
             (B) TYPE:                nucleic acid
             (C) STRANDEDNESS:        single
             (D) TOPOLOGY:            linear (xi) SEQUENCE DESCRIPTION: SEQ ID NO: 129:

UGGCACUUUC CCACU                                                          15

(2) INFORMATION FOR SEQ ID NO: 130:

(i) SEQUENCE CHARACTERISTICS:
             (A) LENGTH:              15 base pairs
             (B) TYPE:                nucleic acid
             (C) STRANDEDNESS:        single
             (D) TOPOLOGY:            linear (xi) SEQUENCE DESCRIPTION: SEQ ID NO: 130:

GGCACUUUCC CACUG                                                          15

(2) INFORMATION FOR SEQ ID NO: 131:

(i) SEQUENCE CHARACTERISTICS:
             (A) LENGTH:              15 base pairs
             (B) TYPE:                nucleic acid
             (C) STRANDEDNESS:        single
             (D) TOPOLOGY:            linear (xi) SEQUENCE DESCRIPTION: SEQ ID NO: 131:

GCACUUUCCC ACUGC                                                          15

(2) INFORMATION FOR SEQ ID NO: 132:

(i) SEQUENCE CHARACTERISTICS:
```

```
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO: 132:

UGCCCAUCGG GGAAU                                                    15

(2) INFORMATION FOR SEQ ID NO: 133:

(i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO: 133:

GGGGAAUCAG UGACU                                                    15

(2) INFORMATION FOR SEQ ID NO: 134:

(i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO: 134:

UGACUGUCAC UCGAG                                                    15

(2) INFORMATION FOR SEQ ID NO: 135:

(i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO: 135:

UGUCACUCGA GAUCU                                                    15

(2) INFORMATION FOR SEQ ID NO: 136:

(i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO: 136:

UCGAGAUCUU GAGGG                                                    15

(2) INFORMATION FOR SEQ ID NO: 137:

(i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO: 137:

GAGAUCUUGA GGGCA                                                    15

(2) INFORMATION FOR SEQ ID NO: 138:

(i) SEQUENCE CHARACTERISTICS:
            (A) LENGTH:           15 base pairs
```

```
            (B) TYPE:                nucleic acid
            (C) STRANDEDNESS:        single
            (D) TOPOLOGY:            linear (xi) SEQUENCE DESCRIPTION: SEQ ID NO: 138:

GGCACCUACC UCUGU                                                          15

(2) INFORMATION FOR SEQ ID NO: 139:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 139:

CCUACCUCUG UCGGG                                                          15

(2) INFORMATION FOR SEQ ID NO: 140:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 140:

CCUCUGUCGG GCCAG                                                          15

(2) INFORMATION FOR SEQ ID NO: 141:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 141:

GAGCACUCAA GGGGA                                                          15

(2) INFORMATION FOR SEQ ID NO: 142:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 142:

GGGAGGUCAC CCGCG                                                          15

(2) INFORMATION FOR SEQ ID NO: 143:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 143:

AUGUGCUCUC CCCCC                                                          15

(2) INFORMATION FOR SEQ ID NO: 144:

(i) SEQUENCE CHARACTERISTICS:
            (A) LENGTH:              15 base pairs
            (B) TYPE:                nucleic acid
```

```
        (C) STRANDEDNESS:         single
        (D) TOPOLOGY:             linear (xi) SEQUENCE DESCRIPTION: SEQ ID NO: 144:

GUGCUCUCCC CCCGG                                                        15

(2) INFORMATION FOR SEQ ID NO: 145:

(i) SEQUENCE CHARACTERISTICS:
        (A) LENGTH:               15 base pairs
        (B) TYPE:                 nucleic acid
        (C) STRANDEDNESS:         single
        (D) TOPOLOGY:             linear (xi) SEQUENCE DESCRIPTION: SEQ ID NO: 145:

CCCCGGUAUG AGAUU                                                        15

(2) INFORMATION FOR SEQ ID NO: 146:

(i) SEQUENCE CHARACTERISTICS:
        (A) LENGTH:               15 base pairs
        (B) TYPE:                 nucleic acid
        (C) STRANDEDNESS:         single
        (D) TOPOLOGY:             linear (xi) SEQUENCE DESCRIPTION: SEQ ID NO: 146:

AUGAGAUUGU CAUCA                                                        15

(2) INFORMATION FOR SEQ ID NO: 147:

(i) SEQUENCE CHARACTERISTICS:
        (A) LENGTH:               15 base pairs
        (B) TYPE:                 nucleic acid
        (C) STRANDEDNESS:         single
        (D) TOPOLOGY:             linear (xi) SEQUENCE DESCRIPTION: SEQ ID NO: 147:

AGAUUGUCAU CAUCA                                                        15

(2) INFORMATION FOR SEQ ID NO: 148:

(i) SEQUENCE CHARACTERISTICS:
        (A) LENGTH:               15 base pairs
        (B) TYPE:                 nucleic acid
        (C) STRANDEDNESS:         single
        (D) TOPOLOGY:             linear (xi) SEQUENCE DESCRIPTION: SEQ ID NO: 148:

UUGUCAUCAU CACUG                                                        15

(2) INFORMATION FOR SEQ ID NO: 149:

(i) SEQUENCE CHARACTERISTICS:
        (A) LENGTH:               15 base pairs
        (B) TYPE:                 nucleic acid
        (C) STRANDEDNESS:         single
        (D) TOPOLOGY:             linear (xi) SEQUENCE DESCRIPTION: SEQ ID NO: 149:

UCAUCAUCAC UGUGG                                                        15

(2) INFORMATION FOR SEQ ID NO: 150:

(i) SEQUENCE CHARACTERISTICS:
        (A) LENGTH:               15 base pairs
        (B) TYPE:                 nucleic acid
        (C) STRANDEDNESS:         single
```

(D) TOPOLOGY:           linear (xi) SEQUENCE DESCRIPTION: SEQ ID NO: 150:

CUGUGGUAGC AGCCG                                                        15

(2) INFORMATION FOR SEQ ID NO: 151:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 151:

CCGCAGUCAU AAUGG                                                        15

(2) INFORMATION FOR SEQ ID NO: 152:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 152:

CAGUCAUAAU GGGCA                                                        15

(2) INFORMATION FOR SEQ ID NO: 153:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 153:

CAGGCCUCAG CACGU                                                        15

(2) INFORMATION FOR SEQ ID NO: 154:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 154:

AGCACGUACC UCUAU                                                        15

(2) INFORMATION FOR SEQ ID NO: 155:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 155:

CGUACCUCUA UAACC                                                        15

(2) INFORMATION FOR SEQ ID NO: 156:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 156:

UACCUCUAUA ACCGC                    15

(2) INFORMATION FOR SEQ ID NO: 157:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 157:

CCUCUAUAAC CGCCA                    15

(2) INFORMATION FOR SEQ ID NO: 158:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 158:

GGAAGAUCAA GAAAU                    15

(2) INFORMATION FOR SEQ ID NO: 159:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 159:

AAGAAAUACA GACUA                    15

(2) INFORMATION FOR SEQ ID NO: 160:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 160:

ACAGACUACA ACAGG                    15

(2) INFORMATION FOR SEQ ID NO: 161:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 161:

CACGCCUCCC UGAAC                    15

(2) INFORMATION FOR SEQ ID NO: 162:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 162:

UGAACCUAUC CCGGG                                                        15

(2) INFORMATION FOR SEQ ID NO: 163:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 163:

AACCUAUCCC GGGAC                                                        15

(2) INFORMATION FOR SEQ ID NO: 164:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 164:

AGGGCCUCUU CCUCG                                                        15

(2) INFORMATION FOR SEQ ID NO: 165:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 165:

GGCCUCUUCC UCGGC                                                        15

(2) INFORMATION FOR SEQ ID NO: 166:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 166:

GCCUCUUCCU CGGCC                                                        15

(2) INFORMATION FOR SEQ ID NO: 167:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 167:

UCUUCCUCGG CCUUC                                                        15

(2) INFORMATION FOR SEQ ID NO: 168:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 168:

UCGGCCUUCC CAUAU                     15

(2) INFORMATION FOR SEQ ID NO: 169:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 169:

CGGCCUUCCC AUAUU                     15

(2) INFORMATION FOR SEQ ID NO: 170:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 170:

UUCCCAUAUU GGUGG                     15

(2) INFORMATION FOR SEQ ID NO: 171:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 171:

CCCAUAUUGG UGGCA                     15

(2) INFORMATION FOR SEQ ID NO: 172:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 172:

AAGACAUAUG CCAUG                     15

(2) INFORMATION FOR SEQ ID NO: 173:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 173:

UGCAGCUACA CCUAC                     15

(2) INFORMATION FOR SEQ ID NO: 174:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 174:

UACACCUACC GGCCC											15

(2) INFORMATION FOR SEQ ID NO: 175:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 175:

AGGGCAUUGU CCUCA											15

(2) INFORMATION FOR SEQ ID NO: 176:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 176:

GCAUUGUCCU CAGUC											15

(2) INFORMATION FOR SEQ ID NO: 177:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 177:

UUGUCCUCAG UCAGA											15

(2) INFORMATION FOR SEQ ID NO: 178:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 178:

CCUCAGUCAG AUACA											15

(2) INFORMATION FOR SEQ ID NO: 179:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 179:

GUCAGAUACA ACAGC											15

(2) INFORMATION FOR SEQ ID NO: 180:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 180:

ACAGCAUUUG GGGCC											15

(2) INFORMATION FOR SEQ ID NO: 181:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 181:

CAGCAUUUGG GGCCA                                                            15

(2) INFORMATION FOR SEQ ID NO: 182:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 182:

CCAUGGUACC UGCAC                                                            15

(2) INFORMATION FOR SEQ ID NO: 183:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 183:

CACACCUAAA ACACU                                                            15

(2) INFORMATION FOR SEQ ID NO: 184:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 184:

AAACACUAGG CCACG                                                            15

(2) INFORMATION FOR SEQ ID NO: 185:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 185:

CACGCAUCUG AUCUG                                                            15

(2) INFORMATION FOR SEQ ID NO: 186:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 186:

AUCUGAUCUG UAGUC                                                            15

(2) INFORMATION FOR SEQ ID NO: 187:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 187:

GAUCUGUAGU CACAU                                        15

(2) INFORMATION FOR SEQ ID NO: 188:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 188:

CUGUAGUCAC AUGAC                                        15

(2) INFORMATION FOR SEQ ID NO: 189:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 189:

CAUGACUAAG CCAAG                                        15

(2) INFORMATION FOR SEQ ID NO: 190:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 190:

CAAGACUCAA GACAU                                        15

(2) INFORMATION FOR SEQ ID NO: 191:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 191:

ACAUGAUUGA UGGAU                                        15

(2) INFORMATION FOR SEQ ID NO: 192:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 192:

UGGAUGUUAA AGUCU                                        15

(2) INFORMATION FOR SEQ ID NO: 193:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 193:

GGAUGUUAAA GUCUA                                    15

(2) INFORMATION FOR SEQ ID NO: 194:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 194:

UUAAAGUCUA GCCUG                                    15

(2) INFORMATION FOR SEQ ID NO: 195:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 195:

AAAGUCUAGC CUGAU                                    15

(2) INFORMATION FOR SEQ ID NO: 196:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 196:

GAGACAUAGC CCCAC                                    15

(2) INFORMATION FOR SEQ ID NO: 197:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 197:

AGGACAUACA ACUGG                                    15

(2) INFORMATION FOR SEQ ID NO: 198:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 198:

GGGAAAUACU GAAAC                                    15

(2) INFORMATION FOR SEQ ID NO: 199:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 199:

UGAAACUUGC UGCCU                                                          15

(2) INFORMATION FOR SEQ ID NO: 200:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 200:

GCUGCCUAUU GGGUA                                                          15

(2) INFORMATION FOR SEQ ID NO: 201:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 201:

UGCCUAUUGG GUAUG                                                          15

(2) INFORMATION FOR SEQ ID NO: 202:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 202:

AUUGGGUAUG CUGAG                                                          15

(2) INFORMATION FOR SEQ ID NO: 203:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 203:

ACAGACUUAC AGAAG                                                          15

(2) INFORMATION FOR SEQ ID NO: 204:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 204:

CAGACUUACA GAAGA                                                          15

(2) INFORMATION FOR SEQ ID NO: 205:

```
        (i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 205:

UGGCCCUCCA UAGAC                                                          15

(2) INFORMATION FOR SEQ ID NO: 206:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 206:

CCUCCAUAGA CAUGU                                                          15

(2) INFORMATION FOR SEQ ID NO: 207:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 207:

CAUGUGUAGC AUCAA                                                          15

(2) INFORMATION FOR SEQ ID NO: 208:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 208:

GUAGCAUCAA AACAC                                                          15

(2) INFORMATION FOR SEQ ID NO: 209:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 209:

CCACACUUCC UGACG                                                          15

(2) INFORMATION FOR SEQ ID NO: 210:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 210:

CACACUUCCU GACGG                                                          15

(2) INFORMATION FOR SEQ ID NO: 211:

(i) SEQUENCE CHARACTERISTICS:
```

```
        (A) LENGTH:            15 base pairs
        (B) TYPE:               nucleic acid
        (C) STRANDEDNESS:       single
        (D) TOPOLOGY:           linear (xi) SEQUENCE DESCRIPTION: SEQ ID NO: 211:

GCCAGCUUGG GCACU                                                    15

(2) INFORMATION FOR SEQ ID NO: 212:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 212:

CUGCUGUCUA CUGAC                                                    15

(2) INFORMATION FOR SEQ ID NO: 213:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 213:

GCUGUCUACU GACCC                                                    15

(2) INFORMATION FOR SEQ ID NO: 214:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 214:

CAACCCUUGA UGAUA                                                    15

(2) INFORMATION FOR SEQ ID NO: 215:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 215:

UGAUGAUAUG UAUUU                                                    15

(2) INFORMATION FOR SEQ ID NO: 216:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 216:

GAUAUGUAUU UAUUC                                                    15

(2) INFORMATION FOR SEQ ID NO: 217:

(i) SEQUENCE CHARACTERISTICS:
        (A) LENGTH:             15 base pairs
```

```
        (B) TYPE:               nucleic acid
        (C) STRANDEDNESS:       single
        (D) TOPOLOGY:           linear (xi) SEQUENCE DESCRIPTION: SEQ ID NO: 217:

UAUGUAUUUA UUCAU                                                    15

(2) INFORMATION FOR SEQ ID NO: 218:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 218:

AUGUAUUUAU UCAUU                                                    15

(2) INFORMATION FOR SEQ ID NO: 219:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 219:

UGUAUUUAUU CAUUU                                                    15

(2) INFORMATION FOR SEQ ID NO: 220:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 220:

UAUUUAUUCA UUUGU                                                    15

(2) INFORMATION FOR SEQ ID NO: 221:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 221:

AUUUAUUCAU UUGUU                                                    15

(2) INFORMATION FOR SEQ ID NO: 222:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 222:

UAUUCAUUUG UUAUU                                                    15

(2) INFORMATION FOR SEQ ID NO: 223:

(i) SEQUENCE CHARACTERISTICS:
        (A) LENGTH:             15 base pairs
        (B) TYPE:               nucleic acid
```

```
            (C) STRANDEDNESS:        single
            (D) TOPOLOGY:            linear (xi) SEQUENCE DESCRIPTION: SEQ ID NO: 223:

AUUCAUUUGU UAUUU                                                            15

(2) INFORMATION FOR SEQ ID NO: 224:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 224:

CAUUUGUUAU UUUAC                                                            15

(2) INFORMATION FOR SEQ ID NO: 225:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 225:

AUUUGUUAUU UUACC                                                            15

(2) INFORMATION FOR SEQ ID NO: 226:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 226:

UUGUUAUUUU ACCAG                                                            15

(2) INFORMATION FOR SEQ ID NO: 227:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 227:

UGUUAUUUUA CCAGC                                                            15

(2) INFORMATION FOR SEQ ID NO: 228:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 228:

GUUAUUUUAC CAGCU                                                            15

(2) INFORMATION FOR SEQ ID NO: 229:

(i) SEQUENCE CHARACTERISTICS:
            (A) LENGTH:              15 base pairs
            (B) TYPE:                nucleic acid
            (C) STRANDEDNESS:        single
```

(D) TOPOLOGY:            linear (xi) SEQUENCE DESCRIPTION: SEQ ID NO: 229:

UUAUUUUACC AGCUA                                                    15

(2) INFORMATION FOR SEQ ID NO: 230:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 230:

ACCAGCUAUU UAUUG                                                    15

(2) INFORMATION FOR SEQ ID NO: 231:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 231:

CAGCUAUUUA UUGAG                                                    15

(2) INFORMATION FOR SEQ ID NO: 232:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 232:

AGCUAUUUAU UGAGU                                                    15

(2) INFORMATION FOR SEQ ID NO: 233:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 233:

GCUAUUUAUU GAGUG                                                    15

(2) INFORMATION FOR SEQ ID NO: 234:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 234:

UAUUUAUUGA GUGUC                                                    15

(2) INFORMATION FOR SEQ ID NO: 235:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 235:

UGAGUGUCUU UUAUG                                                15

(2) INFORMATION FOR SEQ ID NO: 236:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 236:

AGUGUCUUUU AUGUA                                                15

(2) INFORMATION FOR SEQ ID NO: 237:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 237:

GUGUCUUUUA UGUAG                                                15

(2) INFORMATION FOR SEQ ID NO: 238:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 238:

UGUCUUUUAU GUAGG                                                15

(2) INFORMATION FOR SEQ ID NO: 239:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 239:

GUCUUUUAUG UAGGC                                                15

(2) INFORMATION FOR SEQ ID NO: 240:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 240:

UUUAUGUAGG CUAAA                                                15

(2) INFORMATION FOR SEQ ID NO: 241:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 241:

GUAGGCUAAA UGAAC                                                15

(2) INFORMATION FOR SEQ ID NO: 242:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 242:

UGAACAUAGG UCUCU                                                15

(2) INFORMATION FOR SEQ ID NO: 243:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 243:

CAUAGGUCUC UGGCC                                                15

(2) INFORMATION FOR SEQ ID NO: 244:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 244:

UAGGUCUCUG GCCUC                                                15

(2) INFORMATION FOR SEQ ID NO: 245:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 245:

CUGGCCUCAC GGAGC                                                15

(2) INFORMATION FOR SEQ ID NO: 246:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 246:

CGGAGCUCCC AGUCC                                                15

(2) INFORMATION FOR SEQ ID NO: 247:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 247:

UCCCAGUCCA UGUCA                                                                15

(2) INFORMATION FOR SEQ ID NO: 248:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 248:

UCCAUGUCAC AUUCA                                                                15

(2) INFORMATION FOR SEQ ID NO: 249:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 249:

GUCACAUUCA AGGUC                                                                15

(2) INFORMATION FOR SEQ ID NO: 250:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 250:

UCACAUUCAA GGUCA                                                                15

(2) INFORMATION FOR SEQ ID NO: 251:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 251:

UCAAGGUCAC CAGGU                                                                15

(2) INFORMATION FOR SEQ ID NO: 252:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 252:

ACCAGGUACA GUUGU                                                                15

(2) INFORMATION FOR SEQ ID NO: 253:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 253:

```
GUACAGUUGU ACAGG                                                          15

(2) INFORMATION FOR SEQ ID NO: 254:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO: 254:

CAGUUGUACA GGUUG                                                          15

(2) INFORMATION FOR SEQ ID NO: 255:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO: 255:

UACAGGUUGU ACACU                                                          15

(2) INFORMATION FOR SEQ ID NO: 256:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO: 256:

AGGUUGUACA CUGCA                                                          15

(2) INFORMATION FOR SEQ ID NO: 257:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO: 257:

AAAAGAUCAA AUGGG                                                          15

(2) INFORMATION FOR SEQ ID NO: 258:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO: 258:

UGGGACUUCU CAUUG                                                          15

(2) INFORMATION FOR SEQ ID NO: 259:

(i) SEQUENCE CHARACTERISTICS:
         (A) LENGTH:         15 base pairs
         (B) TYPE:           nucleic acid
         (C) STRANDEDNESS:   single
         (D) TOPOLOGY:       linear (xi) SEQUENCE DESCRIPTION: SEQ ID NO: 259:

GGGACUUCUC AUUGG                                                          15
```

(2) INFORMATION FOR SEQ ID NO: 260:

(i) SEQUENCE CHARACTERISTICS:
        (A) LENGTH:        15 base pairs
        (B) TYPE:          nucleic acid
        (C) STRANDEDNESS:   single
        (D) TOPOLOGY:      linear (xi) SEQUENCE DESCRIPTION: SEQ ID NO: 260:

GACUUCUCAU UGGCC                                        15

(2) INFORMATION FOR SEQ ID NO: 261:

(i) SEQUENCE CHARACTERISTICS:
        (A) LENGTH:        15 base pairs
        (B) TYPE:          nucleic acid
        (C) STRANDEDNESS:   single
        (D) TOPOLOGY:      linear (xi) SEQUENCE DESCRIPTION: SEQ ID NO: 261:

UUCUCAUUGG CCAAC                                        15

(2) INFORMATION FOR SEQ ID NO: 262:

(i) SEQUENCE CHARACTERISTICS:
        (A) LENGTH:        15 base pairs
        (B) TYPE:          nucleic acid
        (C) STRANDEDNESS:   single
        (D) TOPOLOGY:      linear (xi) SEQUENCE DESCRIPTION: SEQ ID NO: 262:

CCUGCCUUUC CCCAG                                        15

(2) INFORMATION FOR SEQ ID NO: 263:

(i) SEQUENCE CHARACTERISTICS:
        (A) LENGTH:        15 base pairs
        (B) TYPE:          nucleic acid
        (C) STRANDEDNESS:   single
        (D) TOPOLOGY:      linear (xi) SEQUENCE DESCRIPTION: SEQ ID NO: 263:

CUGCCUUUCC CCAGA                                        15

(2) INFORMATION FOR SEQ ID NO: 264:

(i) SEQUENCE CHARACTERISTICS:
        (A) LENGTH:        15 base pairs
        (B) TYPE:          nucleic acid
        (C) STRANDEDNESS:   single
        (D) TOPOLOGY:      linear (xi) SEQUENCE DESCRIPTION: SEQ ID NO: 264:

UGCCUUUCCC CAGAA                                        15

(2) INFORMATION FOR SEQ ID NO: 265:

(i) SEQUENCE CHARACTERISTICS:
        (A) LENGTH:        15 base pairs
        (B) TYPE:          nucleic acid
        (C) STRANDEDNESS:   single
        (D) TOPOLOGY:      linear (xi) SEQUENCE DESCRIPTION: SEQ ID NO: 265:

GAGUGAUUUU UCUAU                                        15

(2) INFORMATION FOR SEQ ID NO: 266:

(i) SEQUENCE CHARACTERISTICS:
        (A) LENGTH:          15 base pairs
        (B) TYPE:            nucleic acid
        (C) STRANDEDNESS:   single
        (D) TOPOLOGY:      linear (xi) SEQUENCE DESCRIPTION: SEQ ID NO: 266:

AGUGAUUUUU CUAUC                                            15

(2) INFORMATION FOR SEQ ID NO: 267:

(i) SEQUENCE CHARACTERISTICS:
        (A) LENGTH:          15 base pairs
        (B) TYPE:            nucleic acid
        (C) STRANDEDNESS:   single
        (D) TOPOLOGY:      linear (xi) SEQUENCE DESCRIPTION: SEQ ID NO: 267:

GUGAUUUUUC UAUCG                                            15

(2) INFORMATION FOR SEQ ID NO: 268:

(i) SEQUENCE CHARACTERISTICS:
        (A) LENGTH:          15 base pairs
        (B) TYPE:            nucleic acid
        (C) STRANDEDNESS:   single
        (D) TOPOLOGY:      linear (xi) SEQUENCE DESCRIPTION: SEQ ID NO: 268:

UGAUUUUUCU AUCGG                                            15

(2) INFORMATION FOR SEQ ID NO: 269:

(i) SEQUENCE CHARACTERISTICS:
        (A) LENGTH:          15 base pairs
        (B) TYPE:            nucleic acid
        (C) STRANDEDNESS:   single
        (D) TOPOLOGY:      linear (xi) SEQUENCE DESCRIPTION: SEQ ID NO: 269:

GAUUUUUCUA UCGGC                                            15

(2) INFORMATION FOR SEQ ID NO: 270:

(i) SEQUENCE CHARACTERISTICS:
        (A) LENGTH:          15 base pairs
        (B) TYPE:            nucleic acid
        (C) STRANDEDNESS:   single
        (D) TOPOLOGY:      linear (xi) SEQUENCE DESCRIPTION: SEQ ID NO: 270:

UUUUUCUAUC GGCAC                                            15

(2) INFORMATION FOR SEQ ID NO: 271:

(i) SEQUENCE CHARACTERISTICS:
        (A) LENGTH:          15 base pairs
        (B) TYPE:            nucleic acid
        (C) STRANDEDNESS:   single
        (D) TOPOLOGY:      linear (xi) SEQUENCE DESCRIPTION: SEQ ID NO: 271:

UUUCUAUCGG CACAA                                            15

(2) INFORMATION FOR SEQ ID NO: 272:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 272:

AAGCACUAUA UGGAC                                                    15

(2) INFORMATION FOR SEQ ID NO: 273:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 273:

GCACUAUAUG GACUG                                                    15

(2) INFORMATION FOR SEQ ID NO: 274:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 274:

GACUGGUAAU GGUUC                                                    15

(2) INFORMATION FOR SEQ ID NO: 275:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 275:

UAAUGGUUCA CAGGU                                                    15

(2) INFORMATION FOR SEQ ID NO: 276:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 276:

AAUGGUUCAC AGGUU                                                    15

(2) INFORMATION FOR SEQ ID NO: 277:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 277:

CACAGGUUCA GAGAU                                                    15

(2) INFORMATION FOR SEQ ID NO: 278:

```
        (i) SEQUENCE CHARACTERISTICS:
              (A) LENGTH:           15 base pairs
              (B) TYPE:             nucleic acid
              (C) STRANDEDNESS:     single
              (D) TOPOLOGY:         linear (xi) SEQUENCE DESCRIPTION: SEQ ID NO: 278:

ACAGGUUCAG AGAUU                                                   15

(2) INFORMATION FOR SEQ ID NO: 279:

(i) SEQUENCE CHARACTERISTICS:
              (A) LENGTH:           15 base pairs
              (B) TYPE:             nucleic acid
              (C) STRANDEDNESS:     single
              (D) TOPOLOGY:         linear (xi) SEQUENCE DESCRIPTION: SEQ ID NO: 279:

CAGAGAUUAC CCAGU                                                   15

(2) INFORMATION FOR SEQ ID NO: 280:

(i) SEQUENCE CHARACTERISTICS:
              (A) LENGTH:           15 base pairs
              (B) TYPE:             nucleic acid
              (C) STRANDEDNESS:     single
              (D) TOPOLOGY:         linear (xi) SEQUENCE DESCRIPTION: SEQ ID NO: 280:

AGAGAUUACC CAGUG                                                   15

(2) INFORMATION FOR SEQ ID NO: 281:

(i) SEQUENCE CHARACTERISTICS:
              (A) LENGTH:           15 base pairs
              (B) TYPE:             nucleic acid
              (C) STRANDEDNESS:     single
              (D) TOPOLOGY:         linear (xi) SEQUENCE DESCRIPTION: SEQ ID NO: 281:

GAGGCCUUAU UCCUC                                                   15

(2) INFORMATION FOR SEQ ID NO: 282:

(i) SEQUENCE CHARACTERISTICS:
              (A) LENGTH:           15 base pairs
              (B) TYPE:             nucleic acid
              (C) STRANDEDNESS:     single
              (D) TOPOLOGY:         linear (xi) SEQUENCE DESCRIPTION: SEQ ID NO: 282:

AGGCCUUAUU CCUCC                                                   15

(2) INFORMATION FOR SEQ ID NO: 283:

(i) SEQUENCE CHARACTERISTICS:
              (A) LENGTH:           15 base pairs
              (B) TYPE:             nucleic acid
              (C) STRANDEDNESS:     single
              (D) TOPOLOGY:         linear (xi) SEQUENCE DESCRIPTION: SEQ ID NO: 283:

GCCUUAUUCC UCCCU                                                   15

(2) INFORMATION FOR SEQ ID NO: 284:
```

```
    (i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 284:

CCUUAUUCCU CCCUU                                                             15

(2) INFORMATION FOR SEQ ID NO: 285:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 285:

UAUUCCUCCC UUCCC                                                             15

(2) INFORMATION FOR SEQ ID NO: 286:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 286:

CCUCCCUUCC CCCCA                                                             15

(2) INFORMATION FOR SEQ ID NO: 287:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 287:

CUCCCUUCCC CCCAA                                                             15

(2) INFORMATION FOR SEQ ID NO: 288:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 288:

GACACCUUUG UUAGC                                                             15

(2) INFORMATION FOR SEQ ID NO: 289:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 289:

ACACCUUUGU UAGCC                                                             15

(2) INFORMATION FOR SEQ ID NO: 290:

(i) SEQUENCE CHARACTERISTICS:
```

```
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 290:

CCUUUGUUAG CCACC                                                        15

(2) INFORMATION FOR SEQ ID NO: 291:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 291:

CUUUGUUAGC CACCU                                                        15

(2) INFORMATION FOR SEQ ID NO: 292:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 292:

GCCACCUCCC CACCC                                                        15

(2) INFORMATION FOR SEQ ID NO: 293:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 293:

CCCACAUACA UUUCU                                                        15

(2) INFORMATION FOR SEQ ID NO: 294:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 294:

CAUACAUUUC UGCCA                                                        15

(2) INFORMATION FOR SEQ ID NO: 295:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 295:

AUACAUUUCU GCCAG                                                        15

(2) INFORMATION FOR SEQ ID NO: 296:

(i) SEQUENCE CHARACTERISTICS:
            (A) LENGTH:              15 base pairs
```

```
            (B) TYPE:              nucleic acid
            (C) STRANDEDNESS:      single
            (D) TOPOLOGY:          linear (xi) SEQUENCE DESCRIPTION: SEQ ID NO: 296:

UACAUUUCUG CCAGU                                                    15

(2) INFORMATION FOR SEQ ID NO: 297:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 297:

CCAGUGUUCA CAAUG                                                    15

(2) INFORMATION FOR SEQ ID NO: 298:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 298:

CAGUGUUCAC AAUGA                                                    15

(2) INFORMATION FOR SEQ ID NO: 299:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 299:

UGACACUCAG CGGUC                                                    15

(2) INFORMATION FOR SEQ ID NO: 300:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 300:

CAGCGGUCAU GUCUG                                                    15

(2) INFORMATION FOR SEQ ID NO: 301:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 301:

GUCAUGUCUG GACAU                                                    15

(2) INFORMATION FOR SEQ ID NO: 302:

(i) SEQUENCE CHARACTERISTICS:
            (A) LENGTH:            15 base pairs
            (B) TYPE:              nucleic acid
```

```
            (C) STRANDEDNESS:          single
            (D) TOPOLOGY:              linear (xi) SEQUENCE DESCRIPTION: SEQ ID NO: 302:

AGGGAAUAUG CCCAA                                                    15

(2) INFORMATION FOR SEQ ID NO: 303:

(i) SEQUENCE CHARACTERISTICS:
            (A) LENGTH:                15 base pairs
            (B) TYPE:                  nucleic acid
            (C) STRANDEDNESS:          single
            (D) TOPOLOGY:              linear (xi) SEQUENCE DESCRIPTION: SEQ ID NO: 303:

CCAAGCUAUG CCUUG                                                    15

(2) INFORMATION FOR SEQ ID NO: 304:

(i) SEQUENCE CHARACTERISTICS:
            (A) LENGTH:                15 base pairs
            (B) TYPE:                  nucleic acid
            (C) STRANDEDNESS:          single
            (D) TOPOLOGY:              linear (xi) SEQUENCE DESCRIPTION: SEQ ID NO: 304:

UAUGCCUUGU CCUCU                                                    15

(2) INFORMATION FOR SEQ ID NO: 305:

(i) SEQUENCE CHARACTERISTICS:
            (A) LENGTH:                15 base pairs
            (B) TYPE:                  nucleic acid
            (C) STRANDEDNESS:          single
            (D) TOPOLOGY:              linear (xi) SEQUENCE DESCRIPTION: SEQ ID NO: 305:

GCCUUGUCCU CUUGU                                                    15

(2) INFORMATION FOR SEQ ID NO: 306:

(i) SEQUENCE CHARACTERISTICS:
            (A) LENGTH:                15 base pairs
            (B) TYPE:                  nucleic acid
            (C) STRANDEDNESS:          single
            (D) TOPOLOGY:              linear (xi) SEQUENCE DESCRIPTION: SEQ ID NO: 306:

UUGUCCUCUU GUCCU                                                    15

(2) INFORMATION FOR SEQ ID NO: 307:

(i) SEQUENCE CHARACTERISTICS:
            (A) LENGTH:                15 base pairs
            (B) TYPE:                  nucleic acid
            (C) STRANDEDNESS:          single
            (D) TOPOLOGY:              linear (xi) SEQUENCE DESCRIPTION: SEQ ID NO: 307:

GUCCUCUUGU CCUGU                                                    15

(2) INFORMATION FOR SEQ ID NO: 308:

(i) SEQUENCE CHARACTERISTICS:
            (A) LENGTH:                15 base pairs
            (B) TYPE:                  nucleic acid
            (C) STRANDEDNESS:          single
```

(D) TOPOLOGY:          linear (xi) SEQUENCE DESCRIPTION: SEQ ID NO: 308:

CUCUUGUCCU GUUUG                                                          15

(2) INFORMATION FOR SEQ ID NO: 309:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 309:

GUCCUGUUUG CAUUU                                                          15

(2) INFORMATION FOR SEQ ID NO: 310:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 310:

UCCUGUUUGC AUUUC                                                          15

(2) INFORMATION FOR SEQ ID NO: 311:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 311:

UUUGCAUUUC ACUGG                                                          15

(2) INFORMATION FOR SEQ ID NO: 312:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 312:

UUGCAUUUCA CUGGG                                                          15

(2) INFORMATION FOR SEQ ID NO: 313:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 313:

UGCAUUUCAC UGGGA                                                          15

(2) INFORMATION FOR SEQ ID NO: 314:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 314:

GGGAGCUUGC ACUAU                                                              15

(2) INFORMATION FOR SEQ ID NO: 315:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 315:

UUGCACUAUU GCAGC                                                              15

(2) INFORMATION FOR SEQ ID NO: 316:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 316:

GCACUAUUGC AGCUC                                                              15

(2) INFORMATION FOR SEQ ID NO: 317:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 317:

UGCAGCUCCA GUUUC                                                              15

(2) INFORMATION FOR SEQ ID NO: 318:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 318:

CUCCAGUUUC CUGCA                                                              15

(2) INFORMATION FOR SEQ ID NO: 319:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 319:

UCCAGUUUCC UGCAG                                                              15

(2) INFORMATION FOR SEQ ID NO: 320:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 320:

CCAGUUUCCU GCAGU                                                15

(2) INFORMATION FOR SEQ ID NO: 321:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 321:

CAGUGAUCAG GGUCC                                                15

(2) INFORMATION FOR SEQ ID NO: 322:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 322:

UCAGGGUCCU GCAAG                                                15

(2) INFORMATION FOR SEQ ID NO: 323:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 323:

CCAAGGUAUU GGAGG                                                15

(2) INFORMATION FOR SEQ ID NO: 324:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 324:

AAGGUAUUGG AGGAC                                                15

(2) INFORMATION FOR SEQ ID NO: 325:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 325:

GAGGACUCCC UCCCA                                                15

(2) INFORMATION FOR SEQ ID NO: 326:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 326:

ACUCCCUCCC AGCUU                          15

(2) INFORMATION FOR SEQ ID NO: 327:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 327:

CCCAGCUUUG GAAGG                          15

(2) INFORMATION FOR SEQ ID NO: 328:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 328:

CCAGCUUUGG AAGGG                          15

(2) INFORMATION FOR SEQ ID NO: 329:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 329:

GAAGGGUCAU CCGCG                          15

(2) INFORMATION FOR SEQ ID NO: 330:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 330:

GGGUCAUCCG CGUGU                          15

(2) INFORMATION FOR SEQ ID NO: 331:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 331:

UGUGUGUAUG UGUAG                          15

(2) INFORMATION FOR SEQ ID NO: 332:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 332:

UAUGUGUAGA CAAGC                                                    15

(2) INFORMATION FOR SEQ ID NO: 333:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 333:

ACAAGCUCUC GCUCU                                                    15

(2) INFORMATION FOR SEQ ID NO: 334:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 334:

AAGCUCUCGC UCUGU                                                    15

(2) INFORMATION FOR SEQ ID NO: 335:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 335:

UCUCGCUCUG UCACC                                                    15

(2) INFORMATION FOR SEQ ID NO: 336:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 336:

GCUCUGUCAC CCAGG                                                    15

(2) INFORMATION FOR SEQ ID NO: 337:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 337:

GUGCAAUCAU GGUUC                                                    15

(2) INFORMATION FOR SEQ ID NO: 338:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 338:

UCAUGGUUCA CUGCA                                                    15

(2) INFORMATION FOR SEQ ID NO: 339:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 339:

CAUGGUUCAC UGCAG                                        15

(2) INFORMATION FOR SEQ ID NO: 340:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 340:

CUGCAGUCUU GACCU                                        15

(2) INFORMATION FOR SEQ ID NO: 341:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 341:

GCAGUCUUGA CCUUU                                        15

(2) INFORMATION FOR SEQ ID NO: 342:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 342:

UUGACCUUUU GGGCU                                        15

(2) INFORMATION FOR SEQ ID NO: 343:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 343:

UGACCUUUUG GGCUC                                        15

(2) INFORMATION FOR SEQ ID NO: 344:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 344:

GACCUUUUGG GCUCA                                        15

(2) INFORMATION FOR SEQ ID NO: 345:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 345:

UUGGGCUCAA GUGAU                                                  15

(2) INFORMATION FOR SEQ ID NO: 346:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 346:

AAGUGAUCCU CCCAC                                                  15

(2) INFORMATION FOR SEQ ID NO: 347:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 347:

UGAUCCUCCC ACCUC                                                  15

(2) INFORMATION FOR SEQ ID NO: 348:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 348:

CCCACCUCAG CCUCC                                                  15

(2) INFORMATION FOR SEQ ID NO: 349:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 349:

UCAGCCUCCU GAGUA                                                  15

(2) INFORMATION FOR SEQ ID NO: 350:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 350:

CCUGAGUAGC UGGGA                                                  15

(2) INFORMATION FOR SEQ ID NO: 351:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 351:

GGACCAUAGG CUCAC                                                15

(2) INFORMATION FOR SEQ ID NO: 352:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 352:

AUAGGCUCAC AACAC                                                15

(2) INFORMATION FOR SEQ ID NO: 353:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 353:

GGCAAAUUUG AUUUU                                                15

(2) INFORMATION FOR SEQ ID NO: 354:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 354:

GCAAAUUUGA UUUUU                                                15

(2) INFORMATION FOR SEQ ID NO: 355:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 355:

AUUUGAUUUU UUUUU                                                15

(2) INFORMATION FOR SEQ ID NO: 356:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 356:

UUUGAUUUUU UUUUU                                                15

(2) INFORMATION FOR SEQ ID NO: 357:

(i) SEQUENCE CHARACTERISTICS:
    (A) LENGTH:           15 base pairs
    (B) TYPE:             nucleic acid
    (C) STRANDEDNESS:     single
    (D) TOPOLOGY:         linear (xi) SEQUENCE DESCRIPTION: SEQ ID NO: 357:

UUGAUUUUUU UUUUU                                                15

(2) INFORMATION FOR SEQ ID NO: 358:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 358:

UGAUUUUUUU UUUUU                                                15

(2) INFORMATION FOR SEQ ID NO: 359:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 359:

GAUUUUUUUU UUUUU                                                15

(2) INFORMATION FOR SEQ ID NO: 360:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 360:

AUUUUUUUUU UUUUU                                                15

(2) INFORMATION FOR SEQ ID NO: 361:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 361:

UUUUUUUUUU UUUUU                                                15

(2) INFORMATION FOR SEQ ID NO: 362:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 362:

UUUUUUUUUU UUUUU                                                15

(2) INFORMATION FOR SEQ ID NO: 363:

```
        (i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO: 363:

UUUUUUUUUU UUUUC                                                         15

(2) INFORMATION FOR SEQ ID NO: 364:

(i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO: 364:

UUUUUUUUUU UUUCA                                                         15

(2) INFORMATION FOR SEQ ID NO: 365:

(i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO: 365:

UUUUUUUUUU UUCAG                                                         15

(2) INFORMATION FOR SEQ ID NO: 366:

(i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO: 366:

UUUUUUUUUU UCAGA                                                         15

(2) INFORMATION FOR SEQ ID NO: 367:

(i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO: 367:

UUUUUUUUUU CAGAG                                                         15

(2) INFORMATION FOR SEQ ID NO: 368:

(i) SEQUENCE CHARACTERISTICS:
            (A) LENGTH:           15 base pairs
            (B) TYPE:             nucleic acid
            (C) STRANDEDNESS:     single
            (D) TOPOLOGY:         linear (xi) SEQUENCE DESCRIPTION: SEQ ID NO: 368:

UUUUUUUUUC AGAGA                                                         15

(2) INFORMATION FOR SEQ ID NO: 369:

(i) SEQUENCE CHARACTERISTICS:
```

```
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 369:

UUUUUUUUCA GAGAC                                                     15

(2) INFORMATION FOR SEQ ID NO: 370:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 370:

UUUUUUUCAG AGACG                                                     15

(2) INFORMATION FOR SEQ ID NO: 371:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 371:

ACGGGGUCUC GCAAC                                                     15

(2) INFORMATION FOR SEQ ID NO: 372:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 372:

GGGGUCUCGC AACAU                                                     15

(2) INFORMATION FOR SEQ ID NO: 373:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 373:

GCAACAUUGC CCAGA                                                     15

(2) INFORMATION FOR SEQ ID NO: 374:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 374:

CCAGACUUCC UUUGU                                                     15

(2) INFORMATION FOR SEQ ID NO: 375:

(i) SEQUENCE CHARACTERISTICS:
            (A) LENGTH:              15 base pairs
```

```
            (B) TYPE:               nucleic acid
            (C) STRANDEDNESS:       single
            (D) TOPOLOGY:           linear (xi) SEQUENCE DESCRIPTION: SEQ ID NO: 375:

CAGACUUCCU UUGUG                                                        15

(2) INFORMATION FOR SEQ ID NO: 376:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 376:

ACUUCCUUUG UGUUA                                                        15

(2) INFORMATION FOR SEQ ID NO: 377:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 377:

CUUCCUUUGU GUUAG                                                        15

(2) INFORMATION FOR SEQ ID NO: 378:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 378:

UUUGUGUUAG UUAAU                                                        15

(2) INFORMATION FOR SEQ ID NO: 379:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 379:

UUGUGUUAGU UAAUA                                                        15

(2) INFORMATION FOR SEQ ID NO: 380:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 380:

UGUUAGUUAA UAAAG                                                        15

(2) INFORMATION FOR SEQ ID NO: 381:

(i) SEQUENCE CHARACTERISTICS:
            (A) LENGTH:             15 base pairs
            (B) TYPE:               nucleic acid
```

```
            (C) STRANDEDNESS:        single
            (D) TOPOLOGY:            linear (xi) SEQUENCE DESCRIPTION: SEQ ID NO: 381:

GUUAGUUAAU AAAGC                                                    15

(2) INFORMATION FOR SEQ ID NO: 382:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 382:

AGUUAAUAAA GCUUU                                                    15

(2) INFORMATION FOR SEQ ID NO: 383:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 383:

UAAAGCUUUC UCAAC                                                    15

(2) INFORMATION FOR SEQ ID NO: 384:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 384:

AAAGCUUUCU CAACU                                                    15

(2) INFORMATION FOR SEQ ID NO: 385:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 385:

AAGCUUUCUC AACUG                                                    15

(2) INFORMATION FOR SEQ ID NO: 386:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 386:

GCUUUCUCAA CUGCC                                                    15

(2) INFORMATION FOR SEQ ID NO: 387:

(i) SEQUENCE CHARACTERISTICS:
            (A) LENGTH:              15 base pairs
            (B) TYPE:                nucleic acid
            (C) STRANDEDNESS:        single
```

```
        (D) TOPOLOGY:           linear (xi) SEQUENCE DESCRIPTION: SEQ ID NO: 387:

CCCUGGUCAC CGUUG                                                    15

(2) INFORMATION FOR SEQ ID NO: 388:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 388:

CAGUGGUUCU CUGCU                                                    15

(2) INFORMATION FOR SEQ ID NO: 389:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 389:

UGGUUCUCUG CUCCU                                                    15

(2) INFORMATION FOR SEQ ID NO: 390:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 390:

CUCUGCUCCU CCACA                                                    15

(2) INFORMATION FOR SEQ ID NO: 391:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 391:

UUCUCAUAAG GGUCG                                                    15

(2) INFORMATION FOR SEQ ID NO: 392:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 392:

GCACACUUGU AGCCU                                                    15

(2) INFORMATION FOR SEQ ID NO: 393:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear
```

(xi) SEQUENCE DESCRIPTION: SEQ ID NO: 393:

AGGACCUCAG CCUGG                                                          15

(2) INFORMATION FOR SEQ ID NO: 394:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 394:

UGGGCCUCGU GAUGG                                                          15

(2) INFORMATION FOR SEQ ID NO: 395:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 395:

CAUGCCUUUA GCUCC                                                          15

(2) INFORMATION FOR SEQ ID NO: 396:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 396:

CACCCCUCCC AGCAG                                                          15

(2) INFORMATION FOR SEQ ID NO: 397:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 397:

CUCUGCUCCU GGCCC                                                          15

(2) INFORMATION FOR SEQ ID NO: 398:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 398:

UGCCAGUACU GCUGG                                                          15

(2) INFORMATION FOR SEQ ID NO: 399:

(i) SEQUENCE CHARACTERISTICS:
        (A) LENGTH:           15 base pairs
        (B) TYPE:             nucleic acid
        (C) STRANDEDNESS:     single
        (D) TOPOLOGY:         linear (xi) SEQUENCE DESCRIPTION: SEQ ID NO: 399:

CUCUGCUCCU GGCCC                                                     15

(2) INFORMATION FOR SEQ ID NO: 400:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 400:

UGGUUCUCUG CUCCU                                                     15

(2) INFORMATION FOR SEQ ID NO: 401:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 401:

GGAAUGUCAC CAGGA                                                     15

(2) INFORMATION FOR SEQ ID NO: 402:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 402:

CUCUGCUCCU GGCCC                                                     15

(2) INFORMATION FOR SEQ ID NO: 403:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 403:

CAGUCGUCCG CUUCC                                                     15

(2) INFORMATION FOR SEQ ID NO: 404:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 404:

UCUGUGUCAG CCACU                                                     15

(2) INFORMATION FOR SEQ ID NO: 405:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 405:

UCCUGUUUAA AAACC 15

(2) INFORMATION FOR SEQ ID NO: 406:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 406:

CAGAAGUUGU UUUGC 15

(2) INFORMATION FOR SEQ ID NO: 407:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 407:

AAGCCUUCCU GCCCC 15

(2) INFORMATION FOR SEQ ID NO: 408:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 408:

GGUGGGUCCG UGCAG 15

(2) INFORMATION FOR SEQ ID NO: 409:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 409:

GCCACUUCCU CUGGC 15

(2) INFORMATION FOR SEQ ID NO: 410:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 410:

CAGAAGUUGU UUUGC 15

(2) INFORMATION FOR SEQ ID NO: 411:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 411:

```
AAGUUGUUUU GCUCC                                                             15

(2) INFORMATION FOR SEQ ID NO: 412:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO: 412:

UGUGCUUUGA GAACU                                                             15

(2) INFORMATION FOR SEQ ID NO: 413:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO: 413:

AACCCAUCUC CUAAA                                                             15

(2) INFORMATION FOR SEQ ID NO: 414:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO: 414:

CCUGCCUAAG GAAGA                                                             15

(2) INFORMATION FOR SEQ ID NO: 415:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO: 415:

AGGGUUUCUC UACUG                                                             15

(2) INFORMATION FOR SEQ ID NO: 416:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO: 416:

AGGGGCUCCU GCCUA                                                             15

(2) INFORMATION FOR SEQ ID NO: 417:

(i) SEQUENCE CHARACTERISTICS:
          (A) LENGTH:          15 base pairs
          (B) TYPE:            nucleic acid
          (C) STRANDEDNESS:    single
          (D) TOPOLOGY:        linear (xi) SEQUENCE DESCRIPTION: SEQ ID NO: 417:

AAGCUGUUUG AGCUG                                                             15
```

(2) INFORMATION FOR SEQ ID NO: 418:

(i) SEQUENCE CHARACTERISTICS:
        (A) LENGTH:          15 base pairs
        (B) TYPE:            nucleic acid
        (C) STRANDEDNESS:   single
        (D) TOPOLOGY:       linear (xi) SEQUENCE DESCRIPTION: SEQ ID NO: 418:

AGGAGAUACU GAGCC                                          15

(2) INFORMATION FOR SEQ ID NO: 419:

(i) SEQUENCE CHARACTERISTICS:
        (A) LENGTH:          15 base pairs
        (B) TYPE:            nucleic acid
        (C) STRANDEDNESS:   single
        (D) TOPOLOGY:       linear (xi) SEQUENCE DESCRIPTION: SEQ ID NO: 419:

CUGUGCUUUG AGAAC                                          15

(2) INFORMATION FOR SEQ ID NO: 420:

(i) SEQUENCE CHARACTERISTICS:
        (A) LENGTH:          15 base pairs
        (B) TYPE:            nucleic acid
        (C) STRANDEDNESS:   single
        (D) TOPOLOGY:       linear (xi) SEQUENCE DESCRIPTION: SEQ ID NO: 420:

GUCCAAUUCA CACUG                                          15

(2) INFORMATION FOR SEQ ID NO: 421:

(i) SEQUENCE CHARACTERISTICS:
        (A) LENGTH:          15 base pairs
        (B) TYPE:            nucleic acid
        (C) STRANDEDNESS:   single
        (D) TOPOLOGY:       linear (xi) SEQUENCE DESCRIPTION: SEQ ID NO: 421:

AGCUGUUUGA GCUGA                                          15

(2) INFORMATION FOR SEQ ID NO: 422:

(i) SEQUENCE CHARACTERISTICS:
        (A) LENGTH:          15 base pairs
        (B) TYPE:            nucleic acid
        (C) STRANDEDNESS:   single
        (D) TOPOLOGY:       linear (xi) SEQUENCE DESCRIPTION: SEQ ID NO: 422:

GUGCAGUCGU CCGCU                                          15

(2) INFORMATION FOR SEQ ID NO: 423:

(i) SEQUENCE CHARACTERISTICS:
        (A) LENGTH:          15 base pairs
        (B) TYPE:            nucleic acid
        (C) STRANDEDNESS:   single
        (D) TOPOLOGY:       linear (xi) SEQUENCE DESCRIPTION: SEQ ID NO: 423:

GGCCUGUUUC CUGCC                                          15

(2) INFORMATION FOR SEQ ID NO: 424:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 424:

GCCUGUUUCC UGCCU                                              15

(2) INFORMATION FOR SEQ ID NO: 425:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 425:

UGGAGGUCUC GGAAG                                              15

(2) INFORMATION FOR SEQ ID NO: 426:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 426:

CUGGGCUUGG AGACU                                              15

(2) INFORMATION FOR SEQ ID NO: 427:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 427:

CUCGGAUAUA CCUGG                                              15

(2) INFORMATION FOR SEQ ID NO: 428:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 428:

CAAAGCUCGA CACCC                                              15

(2) INFORMATION FOR SEQ ID NO: 429:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 429:

CCCUGGUCAC CGUUG                                              15

(2) INFORMATION FOR SEQ ID NO: 430:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 430:

GAGACCUCUA CCAGC                                    15

(2) INFORMATION FOR SEQ ID NO: 431:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 431:

AGCCACUUCC UCUGG                                    15

(2) INFORMATION FOR SEQ ID NO: 432:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 432:

GAAGCCUUCC UGCCC                                    15

(2) INFORMATION FOR SEQ ID NO: 433:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 433:

AUUCGUUUCC GGAGA                                    15

(2) INFORMATION FOR SEQ ID NO: 434:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 434:

UCUUCCUCAU GCAAG                                    15

(2) INFORMATION FOR SEQ ID NO: 435:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 435:

AUGGCUUCAA CCCGU                                    15

(2) INFORMATION FOR SEQ ID NO: 436:

```
    (i) SEQUENCE CHARACTERISTICS:
         (A) LENGTH:            15 base pairs
         (B) TYPE:              nucleic acid
         (C) STRANDEDNESS:      single
         (D) TOPOLOGY:          linear (xi) SEQUENCE DESCRIPTION: SEQ ID NO: 436:

CCUUGGUAGA GGUGA                                                        15

(2) INFORMATION FOR SEQ ID NO: 437:

(i) SEQUENCE CHARACTERISTICS:
         (A) LENGTH:            15 base pairs
         (B) TYPE:              nucleic acid
         (C) STRANDEDNESS:      single
         (D) TOPOLOGY:          linear (xi) SEQUENCE DESCRIPTION: SEQ ID NO: 437:

CUAUAAUCAU UCUGG                                                        15

(2) INFORMATION FOR SEQ ID NO: 438:

(i) SEQUENCE CHARACTERISTICS:
         (A) LENGTH:            15 base pairs
         (B) TYPE:              nucleic acid
         (C) STRANDEDNESS:      single
         (D) TOPOLOGY:          linear (xi) SEQUENCE DESCRIPTION: SEQ ID NO: 438:

UAAUCAUUCU GGUGC                                                        15

(2) INFORMATION FOR SEQ ID NO: 439:

(i) SEQUENCE CHARACTERISTICS:
         (A) LENGTH:            15 base pairs
         (B) TYPE:              nucleic acid
         (C) STRANDEDNESS:      single
         (D) TOPOLOGY:          linear (xi) SEQUENCE DESCRIPTION: SEQ ID NO: 439:

UAACAGUCUA CAACU                                                        15

(2) INFORMATION FOR SEQ ID NO: 440:

(i) SEQUENCE CHARACTERISTICS:
         (A) LENGTH:            15 base pairs
         (B) TYPE:              nucleic acid
         (C) STRANDEDNESS:      single
         (D) TOPOLOGY:          linear (xi) SEQUENCE DESCRIPTION: SEQ ID NO: 440:

ACAGUCUACA ACUUU                                                        15

(2) INFORMATION FOR SEQ ID NO: 441:

(i) SEQUENCE CHARACTERISTICS:
         (A) LENGTH:            15 base pairs
         (B) TYPE:              nucleic acid
         (C) STRANDEDNESS:      single
         (D) TOPOLOGY:          linear (xi) SEQUENCE DESCRIPTION: SEQ ID NO: 441:

UACAACUUUU CAGCU                                                        15

(2) INFORMATION FOR SEQ ID NO: 442:
```

```
    (i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 442:

ACAACUUUUC AGCUC                                               15

(2) INFORMATION FOR SEQ ID NO: 443:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 443:

CAACUUUUCA GCUCC                                               15

(2) INFORMATION FOR SEQ ID NO: 444:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 444:

ACCAGAUCCU GGAGA                                               15

(2) INFORMATION FOR SEQ ID NO: 445:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 445:

UGAGAGUCUG GGGAA                                               15

(2) INFORMATION FOR SEQ ID NO: 446:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 446:

UGGAGGUCUC GGAAG                                               15

(2) INFORMATION FOR SEQ ID NO: 447:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 447:

GAGGUCUCGG AAGGG                                               15

(2) INFORMATION FOR SEQ ID NO: 448:

(i) SEQUENCE CHARACTERISTICS:
```

```
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 448:

CCACUCUCAA AAUAA                                                15

(2) INFORMATION FOR SEQ ID NO: 449:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 449:

ACUGGAUCUC AGGCC                                                15

(2) INFORMATION FOR SEQ ID NO: 450:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 450:

UGGACCUUCA GCCAA                                                15

(2) INFORMATION FOR SEQ ID NO: 451:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 451:

CCCAACUCUU CUUGA                                                15

(2) INFORMATION FOR SEQ ID NO: 452:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 452:

CGAAGCUUCU UUUGC                                                15

(2) INFORMATION FOR SEQ ID NO: 453:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 453:

GAAGCUUCUU UUGCU                                                15

(2) INFORMATION FOR SEQ ID NO: 454:

(i) SEQUENCE CHARACTERISTICS:
            (A) LENGTH:             15 base pairs
```

```
        (B) TYPE:               nucleic acid
        (C) STRANDEDNESS:       single
        (D) TOPOLOGY:           linear (xi) SEQUENCE DESCRIPTION: SEQ ID NO: 454:

AGCUUCUUUU GCUCU                                                15

(2) INFORMATION FOR SEQ ID NO: 455:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 455:

UCCUGUUUAA AAACC                                                15

(2) INFORMATION FOR SEQ ID NO: 456:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 456:

CUCUGCUCCU CCACA                                                15

(2) INFORMATION FOR SEQ ID NO: 457:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 457:

GCUGCUUUUG AACAG                                                15

(2) INFORMATION FOR SEQ ID NO: 458:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 458:

ACUUUUUUCA CCAGU                                                15

(2) INFORMATION FOR SEQ ID NO: 459:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 459:

GGUACAUACG UGUGC                                                15

(2) INFORMATION FOR SEQ ID NO: 460:

(i) SEQUENCE CHARACTERISTICS:
        (A) LENGTH:             15 base pairs
        (B) TYPE:               nucleic acid
```

```
            (C) STRANDEDNESS:         single
            (D) TOPOLOGY:             linear (xi) SEQUENCE DESCRIPTION: SEQ ID NO: 460:

GAAGCUUCUU UUGCU                                                              15

(2) INFORMATION FOR SEQ ID NO: 461:

(i) SEQUENCE CHARACTERISTICS:
            (A) LENGTH:               15 base pairs
            (B) TYPE:                 nucleic acid
            (C) STRANDEDNESS:         single
            (D) TOPOLOGY:             linear (xi) SEQUENCE DESCRIPTION: SEQ ID NO: 461:

UUCGUUUCCG GAGAG                                                              15

(2) INFORMATION FOR SEQ ID NO: 462:

(i) SEQUENCE CHARACTERISTICS:
            (A) LENGTH:               15 base pairs
            (B) TYPE:                 nucleic acid
            (C) STRANDEDNESS:         single
            (D) TOPOLOGY:             linear (xi) SEQUENCE DESCRIPTION: SEQ ID NO: 462:

GUGCUGUAUG GUCCU                                                              15

(2) INFORMATION FOR SEQ ID NO: 463:

(i) SEQUENCE CHARACTERISTICS:
            (A) LENGTH:               15 base pairs
            (B) TYPE:                 nucleic acid
            (C) STRANDEDNESS:         single
            (D) TOPOLOGY:             linear (xi) SEQUENCE DESCRIPTION: SEQ ID NO: 463:

GAAGGGUCGU GCAAG                                                              15

(2) INFORMATION FOR SEQ ID NO: 464:

(i) SEQUENCE CHARACTERISTICS:
            (A) LENGTH:               15 base pairs
            (B) TYPE:                 nucleic acid
            (C) STRANDEDNESS:         single
            (D) TOPOLOGY:             linear (xi) SEQUENCE DESCRIPTION: SEQ ID NO: 464:

UGAGAGUCUG GGGAA                                                              15

(2) INFORMATION FOR SEQ ID NO: 465:

(i) SEQUENCE CHARACTERISTICS:
            (A) LENGTH:               15 base pairs
            (B) TYPE:                 nucleic acid
            (C) STRANDEDNESS:         single
            (D) TOPOLOGY:             linear (xi) SEQUENCE DESCRIPTION: SEQ ID NO: 465:

AGGAGAUACU GAGCC                                                              15

(2) INFORMATION FOR SEQ ID NO: 466:

(i) SEQUENCE CHARACTERISTICS:
            (A) LENGTH:               15 base pairs
            (B) TYPE:                 nucleic acid
            (C) STRANDEDNESS:         single
```

```
            (D) TOPOLOGY:           linear (xi) SEQUENCE DESCRIPTION: SEQ ID NO: 466:

GAGGGGUCUC AGCAG                                                    15

(2) INFORMATION FOR SEQ ID NO: 467:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 467:

GCAGACUCUG AAAUG                                                    15

(2) INFORMATION FOR SEQ ID NO: 468:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 468:

GAAGGCUCAG GAGGA                                                    15

(2) INFORMATION FOR SEQ ID NO: 469:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 469:

AACCCAUCUC CUAAA                                                    15

(2) INFORMATION FOR SEQ ID NO: 470:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 470:

AUGAGCUCGA GAGUG                                                    15

(2) INFORMATION FOR SEQ ID NO: 471:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 471:

UGAAUGUAUA AGUUA                                                    15

(2) INFORMATION FOR SEQ ID NO: 472:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear
```

(xi) SEQUENCE DESCRIPTION: SEQ ID NO: 472:

UGGUCCUCGG CUGGA                                                15

(2) INFORMATION FOR SEQ ID NO: 473:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 473:

CACCAGUCAC AUAAA                                                15

(2) INFORMATION FOR SEQ ID NO: 474:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 474:

ACCAGAUCCU GGAGA                                                15

(2) INFORMATION FOR SEQ ID NO: 475:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 475:

ACUGGAUCUC AGGCC                                                15

(2) INFORMATION FOR SEQ ID NO: 476:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 476:

CAGCAUUUAC CCUCA                                                15

(2) INFORMATION FOR SEQ ID NO: 477:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 477:

CCACGCUACC UCUGC                                                15

(2) INFORMATION FOR SEQ ID NO: 478:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 478:

CAUGCCUUUA GCUCC                                                    15

(2) INFORMATION FOR SEQ ID NO: 479:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 479:

CGAGCCUAGG CCACC                                                    15

(2) INFORMATION FOR SEQ ID NO: 480:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 480:

CGGACUUUCG AUCUU                                                    15

(2) INFORMATION FOR SEQ ID NO: 481:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 481:

ACAUGAUAUC CAGUA                                                    15

(2) INFORMATION FOR SEQ ID NO: 482:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 482:

CACUUGUAGC CUCAG                                                    15

(2) INFORMATION FOR SEQ ID NO: 483:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 483:

CACCAGUCAC AUAAA                                                    15

(2) INFORMATION FOR SEQ ID NO: 484:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 484:

```
CAUGCCUUAG CAGCU                                                          15

(2) INFORMATION FOR SEQ ID NO: 485:

(i) SEQUENCE CHARACTERISTICS:
          (A) LENGTH:           15 base pairs
          (B) TYPE:             nucleic acid
          (C) STRANDEDNESS:     single
          (D) TOPOLOGY:         linear (xi) SEQUENCE DESCRIPTION: SEQ ID NO: 485:

UAAAACUCAA GGGAC                                                          15

(2) INFORMATION FOR SEQ ID NO: 486:

(i) SEQUENCE CHARACTERISTICS:
          (A) LENGTH:           15 base pairs
          (B) TYPE:             nucleic acid
          (C) STRANDEDNESS:     single
          (D) TOPOLOGY:         linear (xi) SEQUENCE DESCRIPTION: SEQ ID NO: 486:

AUAUAGUAGA UCAGU                                                          15

(2) INFORMATION FOR SEQ ID NO: 487:

(i) SEQUENCE CHARACTERISTICS:
          (A) LENGTH:           15 base pairs
          (B) TYPE:             nucleic acid
          (C) STRANDEDNESS:     single
          (D) TOPOLOGY:         linear (xi) SEQUENCE DESCRIPTION: SEQ ID NO: 487:

UGAAUGUAUA AGUUA                                                          15

(2) INFORMATION FOR SEQ ID NO: 488:

(i) SEQUENCE CHARACTERISTICS:
          (A) LENGTH:           15 base pairs
          (B) TYPE:             nucleic acid
          (C) STRANDEDNESS:     single
          (D) TOPOLOGY:         linear (xi) SEQUENCE DESCRIPTION: SEQ ID NO: 488:

UGAUGCUCAG GUAUC                                                          15

(2) INFORMATION FOR SEQ ID NO: 489:

(i) SEQUENCE CHARACTERISTICS:
          (A) LENGTH:           15 base pairs
          (B) TYPE:             nucleic acid
          (C) STRANDEDNESS:     single
          (D) TOPOLOGY:         linear (xi) SEQUENCE DESCRIPTION: SEQ ID NO: 489:

UUAGAGUUUU ACCAG                                                          15

(2) INFORMATION FOR SEQ ID NO: 490:

(i) SEQUENCE CHARACTERISTICS:
          (A) LENGTH:           15 base pairs
          (B) TYPE:             nucleic acid
          (C) STRANDEDNESS:     single
          (D) TOPOLOGY:         linear (xi) SEQUENCE DESCRIPTION: SEQ ID NO: 490:
```

```
AGAGUUUUAC CAGCU                                                15

(2) INFORMATION FOR SEQ ID NO: 491:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 491:

GAGACAUUGU CCCCA                                                15

(2) INFORMATION FOR SEQ ID NO: 492:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 492:

AGGAUAUACA AGUUA                                                15

(2) INFORMATION FOR SEQ ID NO: 493:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 493:

AGGAGAUACU GAGCC                                                15

(2) INFORMATION FOR SEQ ID NO: 494:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 494:

UGGAGCUAGC GGACC                                                15

(2) INFORMATION FOR SEQ ID NO: 495:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 495:

GCUAUUUAUU GAGUA                                                15

(2) INFORMATION FOR SEQ ID NO: 496:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 496:

UGCCCAUCGG GGUGG                                                15
```

(2) INFORMATION FOR SEQ ID NO: 497:

(i) SEQUENCE CHARACTERISTICS:
        (A) LENGTH:            15 base pairs
        (B) TYPE:              nucleic acid
        (C) STRANDEDNESS:     single
        (D) TOPOLOGY:          linear (xi) SEQUENCE DESCRIPTION: SEQ ID NO: 497:

GGUGGUUCUU CUGAG                                                15

(2) INFORMATION FOR SEQ ID NO: 498:

(i) SEQUENCE CHARACTERISTICS:
        (A) LENGTH:            15 base pairs
        (B) TYPE:              nucleic acid
        (C) STRANDEDNESS:     single
        (D) TOPOLOGY:          linear (xi) SEQUENCE DESCRIPTION: SEQ ID NO: 498:

GCUGGCUAGC AGAGG                                                15

(2) INFORMATION FOR SEQ ID NO: 499:

(i) SEQUENCE CHARACTERISTICS:
        (A) LENGTH:            15 base pairs
        (B) TYPE:              nucleic acid
        (C) STRANDEDNESS:     single
        (D) TOPOLOGY:          linear (xi) SEQUENCE DESCRIPTION: SEQ ID NO: 499:

CUGACCUCCU GGAGG                                                15

(2) INFORMATION FOR SEQ ID NO: 500:

(i) SEQUENCE CHARACTERISTICS:
        (A) LENGTH:            15 base pairs
        (B) TYPE:              nucleic acid
        (C) STRANDEDNESS:     single
        (D) TOPOLOGY:          linear (xi) SEQUENCE DESCRIPTION: SEQ ID NO: 500:

UGCUCCUCCA CAUCC                                                15

(2) INFORMATION FOR SEQ ID NO: 501:

(i) SEQUENCE CHARACTERISTICS:
        (A) LENGTH:            15 base pairs
        (B) TYPE:              nucleic acid
        (C) STRANDEDNESS:     single
        (D) TOPOLOGY:          linear (xi) SEQUENCE DESCRIPTION: SEQ ID NO: 501:

CUACCAUCAC CGUGU                                                15

(2) INFORMATION FOR SEQ ID NO: 502:

(i) SEQUENCE CHARACTERISTICS:
        (A) LENGTH:            15 base pairs
        (B) TYPE:              nucleic acid
        (C) STRANDEDNESS:     single
        (D) TOPOLOGY:          linear (xi) SEQUENCE DESCRIPTION: SEQ ID NO: 502:

CACUUGUAGC CUCAG                                                15

(2) INFORMATION FOR SEQ ID NO: 503:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 503:

GUAGCCUCAG AGCUA 15

(2) INFORMATION FOR SEQ ID NO: 504:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 504:

CAACUCUUCU UGAUG 15

(2) INFORMATION FOR SEQ ID NO: 505:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 505:

CACACUUCCC CCCCG 15

(2) INFORMATION FOR SEQ ID NO: 506:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 506:

GCCAGCUCGG AGGAU 15

(2) INFORMATION FOR SEQ ID NO: 507:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 507:

CAGCUAUUUA UUGAG 15

(2) INFORMATION FOR SEQ ID NO: 508:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 508:

CCUGUUUCCU GCCUC 15

(2) INFORMATION FOR SEQ ID NO: 509:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 509:

CAACUCUUCU UGAUG                                     15

(2) INFORMATION FOR SEQ ID NO: 510:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 510:

UAUUAAUUUA GAGUU                                     15

(2) INFORMATION FOR SEQ ID NO: 511:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 511:

UUGAUGUAUU UAUUA                                     15

(2) INFORMATION FOR SEQ ID NO: 512:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 512:

GAUGUAUUUA UUAAU                                     15

(2) INFORMATION FOR SEQ ID NO: 513:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 513:

AUGUAUUUAU UAAUU                                     15

(2) INFORMATION FOR SEQ ID NO: 514:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 514:

UGUAUUUAUU AAUUU                                     15

(2) INFORMATION FOR SEQ ID NO: 515:

(i) SEQUENCE CHARACTERISTICS:
    (A) LENGTH:         15 base pairs
    (B) TYPE:           nucleic acid
    (C) STRANDEDNESS:   single
    (D) TOPOLOGY:       linear (xi) SEQUENCE DESCRIPTION: SEQ ID NO: 515:

UAUUUAUUAA UUUAG                                             15

(2) INFORMATION FOR SEQ ID NO: 516:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 516:

AUGUAUUUAU UAAUU                                             15

(2) INFORMATION FOR SEQ ID NO: 517:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 517:

ACUUCAUUCU CUAUU                                             15

(2) INFORMATION FOR SEQ ID NO: 518:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 518:

AUGUAUUUAU UAAUU                                             15

(2) INFORMATION FOR SEQ ID NO: 519:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 519:

UAUUUAUUAA UUUAG                                             15

(2) INFORMATION FOR SEQ ID NO: 520:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 520:

AGUUGUUUUG CUCCC                                             15

(2) INFORMATION FOR SEQ ID NO: 521:

-continued

```
    (i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 521:

GAAUGGUACA UACGU                                                        15

(2) INFORMATION FOR SEQ ID NO: 522:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 522:

ACUGGAUCUC AGGCC                                                        15

(2) INFORMATION FOR SEQ ID NO: 523:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 523:

CAUGGGUCGA GGGUU                                                        15

(2) INFORMATION FOR SEQ ID NO: 524:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 524:

AUUAAUUUAG AGUUU                                                        15

(2) INFORMATION FOR SEQ ID NO: 525:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 525:

UAGAGUUUUA CCAGC                                                        15

(2) INFORMATION FOR SEQ ID NO: 526:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (xi) SEQUENCE DESCRIPTION: SEQ ID NO: 526:

AGAGUUUUAC CAGCU                                                        15

(2) INFORMATION FOR SEQ ID NO: 527:

(i) SEQUENCE CHARACTERISTICS:
```

```
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 527:

GAAGCCUUCC UGCCC                                                         15

(2) INFORMATION FOR SEQ ID NO: 528:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 528:

AAGCCUUCCU GCCCC                                                         15

(2) INFORMATION FOR SEQ ID NO: 529:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 529:

GCCUGUUUCC UGCCU                                                         15

(2) INFORMATION FOR SEQ ID NO: 530:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 530:

CCUGUUUCCU GCCUC                                                         15

(2) INFORMATION FOR SEQ ID NO: 531:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 531:

GAAGCCUUCC UGCCC                                                         15

(2) INFORMATION FOR SEQ ID NO: 532:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 532:

CCACACUUCC CCCCC                                                         15

(2) INFORMATION FOR SEQ ID NO: 533:

(i) SEQUENCE CHARACTERISTICS:
            (A) LENGTH:            15 base pairs
```

```
            (B) TYPE:              nucleic acid
            (C) STRANDEDNESS:      single
            (D) TOPOLOGY:          linear (xi) SEQUENCE DESCRIPTION: SEQ ID NO: 533:

CACACUUCCC CCCCG                                                          15

(2) INFORMATION FOR SEQ ID NO: 534:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 534:

GAGACCUCUA CCAGC                                                          15

(2) INFORMATION FOR SEQ ID NO: 535:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 535:

UCACCGUUGU GAUCC                                                          15

(2) INFORMATION FOR SEQ ID NO: 536:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 536:

CCAAUGUCAG CCACC                                                          15

(2) INFORMATION FOR SEQ ID NO: 537:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 537:

CUUUUUUCAC CAGUC                                                          15

(2) INFORMATION FOR SEQ ID NO: 538:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 538:

AGCACCUCCC CACCU                                                          15

(2) INFORMATION FOR SEQ ID NO: 539:

(i) SEQUENCE CHARACTERISTICS:
            (A) LENGTH:            15 base pairs
            (B) TYPE:              nucleic acid
```

```
        (C) STRANDEDNESS:       single
        (D) TOPOLOGY:           linear (xi) SEQUENCE DESCRIPTION: SEQ ID NO: 539:

CCCACCUACU UUUGU                                                    15

(2) INFORMATION FOR SEQ ID NO: 540:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 540:

UAUCCAUCCA UCCCA                                                    15

(2) INFORMATION FOR SEQ ID NO: 541:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 541:

UUAGAGUUUU ACCAG                                                    15

(2) INFORMATION FOR SEQ ID NO: 542:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 542:

UAGAGUUUUA CCAGC                                                    15

(2) INFORMATION FOR SEQ ID NO: 543:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 543:

CUUUUGUUCC CAAUG                                                    15

(2) INFORMATION FOR SEQ ID NO: 544:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 544:

CAGCAUUUAC CCUCA                                                    15

(2) INFORMATION FOR SEQ ID NO: 545:

(i) SEQUENCE CHARACTERISTICS:
        (A) LENGTH:             15 base pairs
        (B) TYPE:               nucleic acid
        (C) STRANDEDNESS:       single
```

```
          (D) TOPOLOGY:           linear (xi) SEQUENCE DESCRIPTION: SEQ ID NO: 545:

UGAUGCUCAG GUAUC                                              15

(2) INFORMATION FOR SEQ ID NO: 546:

(i) SEQUENCE CHARACTERISTICS:
          (A) LENGTH:             15 base pairs
          (B) TYPE:               nucleic acid
          (C) STRANDEDNESS:       single
          (D) TOPOLOGY:           linear (xi) SEQUENCE DESCRIPTION: SEQ ID NO: 546:

CAGCAGUCCG CUGUG                                              15

(2) INFORMATION FOR SEQ ID NO: 547:

(i) SEQUENCE CHARACTERISTICS:
          (A) LENGTH:             15 base pairs
          (B) TYPE:               nucleic acid
          (C) STRANDEDNESS:       single
          (D) TOPOLOGY:           linear (xi) SEQUENCE DESCRIPTION: SEQ ID NO: 547:

GUGCUGUAUG GUCCU                                              15

(2) INFORMATION FOR SEQ ID NO: 548:

(i) SEQUENCE CHARACTERISTICS:
          (A) LENGTH:             15 base pairs
          (B) TYPE:               nucleic acid
          (C) STRANDEDNESS:       single
          (D) TOPOLOGY:           linear (xi) SEQUENCE DESCRIPTION: SEQ ID NO: 548:

GUGAAGUCUG UCAAA                                              15

(2) INFORMATION FOR SEQ ID NO: 549:

(i) SEQUENCE CHARACTERISTICS:
          (A) LENGTH:             15 base pairs
          (B) TYPE:               nucleic acid
          (C) STRANDEDNESS:       single
          (D) TOPOLOGY:           linear (xi) SEQUENCE DESCRIPTION: SEQ ID NO: 549:

AUAAGUUAUG GCCUG                                              15

(2) INFORMATION FOR SEQ ID NO: 550:

(i) SEQUENCE CHARACTERISTICS:
          (A) LENGTH:             15 base pairs
          (B) TYPE:               nucleic acid
          (C) STRANDEDNESS:       single
          (D) TOPOLOGY:           linear (xi) SEQUENCE DESCRIPTION: SEQ ID NO: 550:

CUGGCAUUGU UCUCU                                              15

(2) INFORMATION FOR SEQ ID NO: 551:

(i) SEQUENCE CHARACTERISTICS:
          (A) LENGTH:             15 base pairs
          (B) TYPE:               nucleic acid
          (C) STRANDEDNESS:       single
          (D) TOPOLOGY:           linear
```

(xi) SEQUENCE DESCRIPTION: SEQ ID NO: 551:

GCAUUGUUCU CUAAU                                                     15

(2) INFORMATION FOR SEQ ID NO: 552:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 552:

UGGUUCUCUG CUCCU                                                     15

(2) INFORMATION FOR SEQ ID NO: 553:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 553:

CUUCUUUUGC UCUGC                                                     15

(2) INFORMATION FOR SEQ ID NO: 554:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 554:

CUUUUGUUCC CAAUG                                                     15

(2) INFORMATION FOR SEQ ID NO: 555:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 555:

ACCGUGUAUU CGUUU                                                     15

(2) INFORMATION FOR SEQ ID NO: 556:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 556:

UCCAGCUACC AUCCC                                                     15

(2) INFORMATION FOR SEQ ID NO: 557:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 557:

CUCGGAUAUA CCUGG                                                      15

(2) INFORMATION FOR SEQ ID NO: 558:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 558:

CAGCAGUCCG CUGUG                                                      15

(2) INFORMATION FOR SEQ ID NO: 559:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 559:

GGAAUGUCAC CAGGA                                                      15

(2) INFORMATION FOR SEQ ID NO: 560:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 560:

AGGACCUCAC CCUGC                                                      15

(2) INFORMATION FOR SEQ ID NO: 561:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 561:

UUUCGAUCUU CCAGC                                                      15

(2) INFORMATION FOR SEQ ID NO: 562:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 562:

GCACACUUGU AGCCU                                                      15

(2) INFORMATION FOR SEQ ID NO: 563:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 563:

UUCAGCUCCG GUCCU                                                              15

(2) INFORMATION FOR SEQ ID NO: 564:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 564:

GGCCUGUUUC CUGCC                                                              15

(2) INFORMATION FOR SEQ ID NO: 565:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 565:

CCCAGCUCUC AGCAG                                                              15

(2) INFORMATION FOR SEQ ID NO: 566:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 566:

CCUGUUUCCU GCCUC                                                              15

(2) INFORMATION FOR SEQ ID NO: 567:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 567:

UACUGGUCAG GAUGC                                                              15

(2) INFORMATION FOR SEQ ID NO: 568:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 568:

GAAGGGUCGU GCAAG                                                              15

(2) INFORMATION FOR SEQ ID NO: 569:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 569:

```
CUAAUGUCUC CGAGG                                                    15

(2) INFORMATION FOR SEQ ID NO: 570:

(i) SEQUENCE CHARACTERISTICS:
         (A) LENGTH:           15 base pairs
         (B) TYPE:             nucleic acid
         (C) STRANDEDNESS:     single
         (D) TOPOLOGY:         linear (xi) SEQUENCE DESCRIPTION: SEQ ID NO: 570:

GAGACAUUGU CCCCA                                                    15

(2) INFORMATION FOR SEQ ID NO: 571:

(i) SEQUENCE CHARACTERISTICS:
         (A) LENGTH:           15 base pairs
         (B) TYPE:             nucleic acid
         (C) STRANDEDNESS:     single
         (D) TOPOLOGY:         linear (xi) SEQUENCE DESCRIPTION: SEQ ID NO: 571:

CCACGCUACC UCUGC                                                    15

(2) INFORMATION FOR SEQ ID NO: 572:

(i) SEQUENCE CHARACTERISTICS:
         (A) LENGTH:           15 base pairs
         (B) TYPE:             nucleic acid
         (C) STRANDEDNESS:     single
         (D) TOPOLOGY:         linear (xi) SEQUENCE DESCRIPTION: SEQ ID NO: 572:

CAGCAGUCCG CUGUG                                                    15

(2) INFORMATION FOR SEQ ID NO: 573:

(i) SEQUENCE CHARACTERISTICS:
         (A) LENGTH:           15 base pairs
         (B) TYPE:             nucleic acid
         (C) STRANDEDNESS:     single
         (D) TOPOLOGY:         linear (xi) SEQUENCE DESCRIPTION: SEQ ID NO: 573:

AGUGACUCUG UGUCA                                                    15

(2) INFORMATION FOR SEQ ID NO: 574:

(i) SEQUENCE CHARACTERISTICS:
         (A) LENGTH:           15 base pairs
         (B) TYPE:             nucleic acid
         (C) STRANDEDNESS:     single
         (D) TOPOLOGY:         linear (xi) SEQUENCE DESCRIPTION: SEQ ID NO: 574:

UUUCCUUUGA AUCAA                                                    15

(2) INFORMATION FOR SEQ ID NO: 575:

(i) SEQUENCE CHARACTERISTICS:
         (A) LENGTH:           15 base pairs
         (B) TYPE:             nucleic acid
         (C) STRANDEDNESS:     single
         (D) TOPOLOGY:         linear (xi) SEQUENCE DESCRIPTION: SEQ ID NO: 575:

UCUGUGUCAG CCACU                                                    15
```

(2) INFORMATION FOR SEQ ID NO: 576:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 576:

AUGUAUUUAU UAAUU                                    15

(2) INFORMATION FOR SEQ ID NO: 577:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 577:

UUUGAAUCAA UAAAG                                    15

(2) INFORMATION FOR SEQ ID NO: 578:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 578:

GCUGGCUAGC AGAGG                                    15

(2) INFORMATION FOR SEQ ID NO: 579:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 579:

AAUCAAUAAA GUUUU                                    15

(2) INFORMATION FOR SEQ ID NO: 580:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 580:

UAGAGUUUUA CCAGC                                    15

(2) INFORMATION FOR SEQ ID NO: 581:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 581:

GAGGGUUUCU CUACU                                    15

(2) INFORMATION FOR SEQ ID NO: 582:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 582:

AAGCUGUUUG AGCUG                                              15

(2) INFORMATION FOR SEQ ID NO: 583:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 583:

UCAUUCUCUA UUGCC                                              15

(2) INFORMATION FOR SEQ ID NO: 584:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 584:

AAUGGCUUCA ACCCG                                              15

(2) INFORMATION FOR SEQ ID NO: 585:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 585:

GAAGCCUUCC UGCCC                                              15

(2) INFORMATION FOR SEQ ID NO: 586:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 586:

AAGCCUUCCU GCCCC                                              15

(2) INFORMATION FOR SEQ ID NO: 587:

(i) SEQUENCE CHARACTERISTICS:
        (A) LENGTH:        15 base pairs
        (B) TYPE:          nucleic acid
        (C) STRANDEDNESS:  single
        (D) TOPOLOGY:      linear (xi) SEQUENCE DESCRIPTION: SEQ ID NO: 587:

CUACCAUCAC CGUGU                                              15

(2) INFORMATION FOR SEQ ID NO: 588:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 588:

ACCGUGUAUU CGUUU                                                15

(2) INFORMATION FOR SEQ ID NO: 589:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 589:

CCGGACUUUC GAUCU                                                15

(2) INFORMATION FOR SEQ ID NO: 590:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 590:

CACACUUCCC CCCCG                                                15

(2) INFORMATION FOR SEQ ID NO: 591:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 591:

CACCCCUCCC AGCAG                                                15

(2) INFORMATION FOR SEQ ID NO: 592:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 592:

CAGCUCUCAG CAGUG                                               15

(2) INFORMATION FOR SEQ ID NO: 593:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 593:

AGGACCUCAC CCUGC                                               15

(2) INFORMATION FOR SEQ ID NO: 594:

```
      (i) SEQUENCE CHARACTERISTICS:
          (A) LENGTH:              15 base pairs
          (B) TYPE:                nucleic acid
          (C) STRANDEDNESS:        single
          (D) TOPOLOGY:            linear (xi) SEQUENCE DESCRIPTION: SEQ ID NO: 594:

GAAACCUUUC CUUUG                                                           15

(2) INFORMATION FOR SEQ ID NO: 595:

(i) SEQUENCE CHARACTERISTICS:
          (A) LENGTH:              15 base pairs
          (B) TYPE:                nucleic acid
          (C) STRANDEDNESS:        single
          (D) TOPOLOGY:            linear (xi) SEQUENCE DESCRIPTION: SEQ ID NO: 595:

UUACCCUCAG CCACU                                                           15

(2) INFORMATION FOR SEQ ID NO: 596:

(i) SEQUENCE CHARACTERISTICS:
          (A) LENGTH:              15 base pairs
          (B) TYPE:                nucleic acid
          (C) STRANDEDNESS:        single
          (D) TOPOLOGY:            linear (xi) SEQUENCE DESCRIPTION: SEQ ID NO: 596:

CUACCAUCAC CGUGU                                                           15

(2) INFORMATION FOR SEQ ID NO: 597:

(i) SEQUENCE CHARACTERISTICS:
          (A) LENGTH:              15 base pairs
          (B) TYPE:                nucleic acid
          (C) STRANDEDNESS:        single
          (D) TOPOLOGY:            linear (xi) SEQUENCE DESCRIPTION: SEQ ID NO: 597:

UGCUGCUCCG UGGGG                                                           15

(2) INFORMATION FOR SEQ ID NO: 598:

(i) SEQUENCE CHARACTERISTICS:
          (A) LENGTH:              15 base pairs
          (B) TYPE:                nucleic acid
          (C) STRANDEDNESS:        single
          (D) TOPOLOGY:            linear (xi) SEQUENCE DESCRIPTION: SEQ ID NO: 598:

CUCAGGUAUC CAUCC                                                           15

(2) INFORMATION FOR SEQ ID NO: 599:

(i) SEQUENCE CHARACTERISTICS:
          (A) LENGTH:              15 base pairs
          (B) TYPE:                nucleic acid
          (C) STRANDEDNESS:        single
          (D) TOPOLOGY:            linear (xi) SEQUENCE DESCRIPTION: SEQ ID NO: 599:

GAAAGAUCAC AUGGG                                                           15

(2) INFORMATION FOR SEQ ID NO: 600:
```

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 600:

AGCCAAUUUC UCAUG                                                        15

(2) INFORMATION FOR SEQ ID NO: 601:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 601:

GCCAAUUUCU CAUGC                                                        15

(2) INFORMATION FOR SEQ ID NO: 602:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 602:

CCAAUUUCUC AUGCC                                                        15

(2) INFORMATION FOR SEQ ID NO: 603:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 603:

AAUUUCUCAU GCCGC                                                        15

(2) INFORMATION FOR SEQ ID NO: 604:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 604:

AAGCUGUUUG AGCUG                                                        15

(2) INFORMATION FOR SEQ ID NO: 605:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 605:

AGCUGUUUGA GCUGA                                                        15

(2) INFORMATION FOR SEQ ID NO: 606:

(i) SEQUENCE CHARACTERISTICS:

(A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 606:

CGAGCCUAGG CCACC                                                      15

(2) INFORMATION FOR SEQ ID NO: 607:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 607:

GACCUCUACC AGCCU                                                      15

(2) INFORMATION FOR SEQ ID NO: 608:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 608:

UUCAGCUCCG GUCCU                                                      15

(2) INFORMATION FOR SEQ ID NO: 609:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 609:

CGGACUUUCG AUCUU                                                      15

(2) INFORMATION FOR SEQ ID NO: 610:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 610:

AGGACCUCAC CCUGC                                                      15

(2) INFORMATION FOR SEQ ID NO: 611:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 611:

CCUGUUUCCU GCCUC                                                      15

(2) INFORMATION FOR SEQ ID NO: 612:

(i) SEQUENCE CHARACTERISTICS:
            (A) LENGTH:              15 base pairs

```
            (B) TYPE:              nucleic acid
            (C) STRANDEDNESS:      single
            (D) TOPOLOGY:          linear (xi) SEQUENCE DESCRIPTION: SEQ ID NO: 612:

GGCGGCUCCA CCUCA                                               15

(2) INFORMATION FOR SEQ ID NO: 613:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 613:

UACAACUUUU CAGCU                                               15

(2) INFORMATION FOR SEQ ID NO: 614:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 614:

AACUUUUCAG CUCCG                                               15

(2) INFORMATION FOR SEQ ID NO: 615:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 615:

ACCAGAUCCU GGAGA                                               15

(2) INFORMATION FOR SEQ ID NO: 616:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 616:

UGGGCCUCGU GAUGG                                               15

(2) INFORMATION FOR SEQ ID NO: 617:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 617:

CAGUCGUCCG CUUCC                                               15

(2) INFORMATION FOR SEQ ID NO: 618:

(i) SEQUENCE CHARACTERISTICS:
            (A) LENGTH:            15 base pairs
            (B) TYPE:              nucleic acid
```

```
          (C) STRANDEDNESS:         single
          (D) TOPOLOGY:             linear (xi) SEQUENCE DESCRIPTION: SEQ ID NO: 618:

GGCCUGUUUC CUGCC                                                        15

(2) INFORMATION FOR SEQ ID NO: 619:

(i) SEQUENCE CHARACTERISTICS:
          (A) LENGTH:               15 base pairs
          (B) TYPE:                 nucleic acid
          (C) STRANDEDNESS:         single
          (D) TOPOLOGY:             linear (xi) SEQUENCE DESCRIPTION: SEQ ID NO: 619:

UUUUGCUCCC UGGAA                                                        15

(2) INFORMATION FOR SEQ ID NO: 620:

(i) SEQUENCE CHARACTERISTICS:
          (A) LENGTH:               15 base pairs
          (B) TYPE:                 nucleic acid
          (C) STRANDEDNESS:         single
          (D) TOPOLOGY:             linear (xi) SEQUENCE DESCRIPTION: SEQ ID NO: 620:

AGUGGGUCGA AGGUG                                                        15

(2) INFORMATION FOR SEQ ID NO: 621:

(i) SEQUENCE CHARACTERISTICS:
          (A) LENGTH:               15 base pairs
          (B) TYPE:                 nucleic acid
          (C) STRANDEDNESS:         single
          (D) TOPOLOGY:             linear (xi) SEQUENCE DESCRIPTION: SEQ ID NO: 621:

UAACAGUCUA CAACU                                                        15

(2) INFORMATION FOR SEQ ID NO: 622:

(i) SEQUENCE CHARACTERISTICS:
          (A) LENGTH:               15 base pairs
          (B) TYPE:                 nucleic acid
          (C) STRANDEDNESS:         single
          (D) TOPOLOGY:             linear (xi) SEQUENCE DESCRIPTION: SEQ ID NO: 622:

AGCACCUCCC CACCU                                                        15

(2) INFORMATION FOR SEQ ID NO: 623:

(i) SEQUENCE CHARACTERISTICS:
          (A) LENGTH:               15 base pairs
          (B) TYPE:                 nucleic acid
          (C) STRANDEDNESS:         single
          (D) TOPOLOGY:             linear (xi) SEQUENCE DESCRIPTION: SEQ ID NO: 623:

GUACUGUACC ACUCU                                                        15

(2) INFORMATION FOR SEQ ID NO: 624:

(i) SEQUENCE CHARACTERISTICS:
          (A) LENGTH:               15 base pairs
          (B) TYPE:                 nucleic acid
          (C) STRANDEDNESS:         single
```

(D) TOPOLOGY:           linear (xi) SEQUENCE DESCRIPTION: SEQ ID NO: 624:

UGCCCAUCGG GGUGG                                                          15

(2) INFORMATION FOR SEQ ID NO: 625:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 625:

GGAGACUCAG UGGCU                                                          15

(2) INFORMATION FOR SEQ ID NO: 626:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 626:

UGGCUGUCAC AGAAC                                                          15

(2) INFORMATION FOR SEQ ID NO: 627:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 627:

UGUGCUUUGA GAACU                                                          15

(2) INFORMATION FOR SEQ ID NO: 628:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 628:

GCGAGAUCGG GGAGG                                                          15

(2) INFORMATION FOR SEQ ID NO: 629:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 629:

GAGGUCUCGG AAGGG                                                          15

(2) INFORMATION FOR SEQ ID NO: 630:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 630:

CCCACCUACU UUUGU                                                15

(2) INFORMATION FOR SEQ ID NO: 631:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 631:

ACUGCCUUGG UAGAG                                                15

(2) INFORMATION FOR SEQ ID NO: 632:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 632:

UCUCUAUUGC CCCUG                                                15

(2) INFORMATION FOR SEQ ID NO: 633:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 633:

GAAGGCUCAG GAGGA                                                15

(2) INFORMATION FOR SEQ ID NO: 634:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 634:

GGAAUGUCAC CAGGA                                                15

(2) INFORMATION FOR SEQ ID NO: 635:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 635:

AGUUGUUUUG CUCCC                                                15

(2) INFORMATION FOR SEQ ID NO: 636:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 636:

CUGUUCUUCC UCAUG                                                15

(2) INFORMATION FOR SEQ ID NO: 637:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 637:

CUGUGCUUUG AGAAC                                                15

(2) INFORMATION FOR SEQ ID NO: 638:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 638:

AUGAAAUCAU GGUCC                                                15

(2) INFORMATION FOR SEQ ID NO: 639:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 639:

GGACUAUAAU CAUUC                                                15

(2) INFORMATION FOR SEQ ID NO: 640:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 640:

UUAUGUUUAU AACCG                                                15

(2) INFORMATION FOR SEQ ID NO: 641:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 641:

CUACCAUCAC CGUGU                                                15

(2) INFORMATION FOR SEQ ID NO: 642:

(i) SEQUENCE CHARACTERISTICS:
        (A) LENGTH:         15 base pairs
        (B) TYPE:           nucleic acid
        (C) STRANDEDNESS:   single
        (D) TOPOLOGY:       linear (xi) SEQUENCE DESCRIPTION: SEQ ID NO: 642:

```
UCAUGGUCCC AGGCG                                                    15

(2) INFORMATION FOR SEQ ID NO: 643:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 643:

CUAUAAUCAU UCUGG                                                    15

(2) INFORMATION FOR SEQ ID NO: 644:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 644:

UGGUCAUUGU GGGCC                                                    15

(2) INFORMATION FOR SEQ ID NO: 645:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 645:

CAUGCCUUAG CAGCU                                                    15

(2) INFORMATION FOR SEQ ID NO: 646:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 646:

AGCACCUCCC CACCU                                                    15

(2) INFORMATION FOR SEQ ID NO: 647:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 647:

CUUAUGUUUA UAACC                                                    15

(2) INFORMATION FOR SEQ ID NO: 648:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 648:
```

```
UAUGUUUAUA ACCGC                                                              15

(2) INFORMATION FOR SEQ ID NO: 649:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 649:

UGUUUAUAAC CGCCA                                                              15

(2) INFORMATION FOR SEQ ID NO: 650:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 650:

GAAAGAUCAG GAUAU                                                              15

(2) INFORMATION FOR SEQ ID NO: 651:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 651:

AGGAUAUACA AGUUA                                                              15

(2) INFORMATION FOR SEQ ID NO: 652:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 652:

ACAAGUUACA GAAGG                                                              15

(2) INFORMATION FOR SEQ ID NO: 653:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 653:

CCCACCUCCC UGAGC                                                              15

(2) INFORMATION FOR SEQ ID NO: 654:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 654:

GAAACCUUUC CUUUG                                                              15
```

(2) INFORMATION FOR SEQ ID NO: 655:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 655:

AACCUUCCU UUGAA                                               15

(2) INFORMATION FOR SEQ ID NO: 656:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 656:

AGGACCUCAG CCUGG                                               15

(2) INFORMATION FOR SEQ ID NO: 657:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 657:

AGCCACUUCC UCUGG                                               15

(2) INFORMATION FOR SEQ ID NO: 658:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 658:

GCCACUUCCU CUGGC                                               15

(2) INFORMATION FOR SEQ ID NO: 659:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 659:

ACUUCCUCUG GCUGU                                               15

(2) INFORMATION FOR SEQ ID NO: 660:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 660:

CCGGACUUUC GAUCU                                               15

(2) INFORMATION FOR SEQ ID NO: 661:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 661:

CGGACUUUCG AUCUU                                                       15

(2) INFORMATION FOR SEQ ID NO: 662:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 662:

UGCCCAUCGG GGUGG                                                       15

(2) INFORMATION FOR SEQ ID NO: 663:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 663:

CGGAUAUACC UGGAG                                                       15

(2) INFORMATION FOR SEQ ID NO: 664:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 664:

GAGACCUCUA CCAGC                                                       15

(2) INFORMATION FOR SEQ ID NO: 665:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 665:

GGCGGCUCCA CCUCA                                                       15

(2) INFORMATION FOR SEQ ID NO: 666:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 666:

GAAGCCUUCC UGCCC                                                       15

(2) INFORMATION FOR SEQ ID NO: 667:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 667:

GAGACAUUGU CCCCA                                                      15

(2) INFORMATION FOR SEQ ID NO: 668:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 668:

GCAUUGUUCU CUAAU                                                      15

(2) INFORMATION FOR SEQ ID NO: 669:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 669:

UUAGAGUUUU ACCAG                                                      15

(2) INFORMATION FOR SEQ ID NO: 670:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 670:

UAGAGUUUUA CCAGC                                                      15

(2) INFORMATION FOR SEQ ID NO: 671:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 671:

AGAGUUUUAC CAGCU                                                      15

(2) INFORMATION FOR SEQ ID NO: 672:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 672:

GAGUUUUACC AGCUA                                                      15

(2) INFORMATION FOR SEQ ID NO: 673:

```
        (i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 673:

ACCAGCUAUU UAUUG                                                      15

(2) INFORMATION FOR SEQ ID NO: 674:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 674:

CAGCUAUUUA UUGAG                                                      15

(2) INFORMATION FOR SEQ ID NO: 675:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 675:

AGCUAUUUAU UGAGU                                                      15

(2) INFORMATION FOR SEQ ID NO: 676:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 676:

GCUAUUUAUU GAGUA                                                      15

(2) INFORMATION FOR SEQ ID NO: 677:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 677:

UAUUUAUUGA GUACC                                                      15

(2) INFORMATION FOR SEQ ID NO: 678:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 678:

CAACUCUUCU UGAUG                                                      15

(2) INFORMATION FOR SEQ ID NO: 679:
```

```
    (i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 679:

GCAGCCUCUU AUGUU                                                          15

(2) INFORMATION FOR SEQ ID NO: 680:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 680:

GCCUCUUAUG UUUAU                                                          15

(2) INFORMATION FOR SEQ ID NO: 681:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 681:

UCUUCCUCAU GCAAG                                                          15

(2) INFORMATION FOR SEQ ID NO: 682:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 682:

AAGUUUUAUG UCGGC                                                          15

(2) INFORMATION FOR SEQ ID NO: 683:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 683:

UUUAUGUCGG CCUGA                                                          15

(2) INFORMATION FOR SEQ ID NO: 684:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 684:

GGAGACUCAG UGGCU                                                          15

(2) INFORMATION FOR SEQ ID NO: 685:

(i) SEQUENCE CHARACTERISTICS:
```

```
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 685:

CUGGCAUUGU UCUCU                                                       15

(2) INFORMATION FOR SEQ ID NO: 686:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 686:

CUCAGGUAUC CAUCC                                                       15

(2) INFORMATION FOR SEQ ID NO: 687:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 687:

UGGAUCUCAG GCCGC                                                       15

(2) INFORMATION FOR SEQ ID NO: 688:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 688:

CUGACCUCCU GGAGG                                                       15

(2) INFORMATION FOR SEQ ID NO: 689:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 689:

UGGAGCUAGC GGACC                                                       15

(2) INFORMATION FOR SEQ ID NO: 690:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (xi) SEQUENCE DESCRIPTION: SEQ ID NO: 690:

UAUCCAUCCA UCCCA                                                       15

(2) INFORMATION FOR SEQ ID NO: 691:

(i) SEQUENCE CHARACTERISTICS:
            (A) LENGTH:            15 base pairs
```

```
        (B) TYPE:               nucleic acid
        (C) STRANDEDNESS:       single
        (D) TOPOLOGY:           linear (xi) SEQUENCE DESCRIPTION: SEQ ID NO: 691:

UCCAAUUCAC ACUGA                                                15

(2) INFORMATION FOR SEQ ID NO: 692:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 692:

AUCACAUUCA CGGUG                                                15

(2) INFORMATION FOR SEQ ID NO: 693:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 693:

UCACAUUCAC GGUGC                                                15

(2) INFORMATION FOR SEQ ID NO: 694:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 694:

GGAAUGUCAC CAGGA                                                15

(2) INFORMATION FOR SEQ ID NO: 695:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 695:

ACCAGAUCCU GGAGA                                                15

(2) INFORMATION FOR SEQ ID NO: 696:

(i) SEQUENCE CHARACTERISTICS:
        (A) LENGTH:             15 base pairs
        (B) TYPE:               nucleic acid
        (C) STRANDEDNESS:       single
        (D) TOPOLOGY:           linear (xi) SEQUENCE DESCRIPTION: SEQ ID NO: 696:

GAAGGGUCGU GCAAG                                                15

(2) INFORMATION FOR SEQ ID NO: 697:

(i) SEQUENCE CHARACTERISTICS:
        (A) LENGTH:             15 base pairs
        (B) TYPE:               nucleic acid
```

```
        (C) STRANDEDNESS:         single
        (D) TOPOLOGY:             linear (xi) SEQUENCE DESCRIPTION: SEQ ID NO: 697:

AAGCUGUUUG AGCUG                                                     15

(2) INFORMATION FOR SEQ ID NO: 698:

(i) SEQUENCE CHARACTERISTICS:
        (A) LENGTH:               15 base pairs
        (B) TYPE:                 nucleic acid
        (C) STRANDEDNESS:         single
        (D) TOPOLOGY:             linear (xi) SEQUENCE DESCRIPTION: SEQ ID NO: 698:

UAUAAGUUAU GGCCU                                                     15

(2) INFORMATION FOR SEQ ID NO: 699:

(i) SEQUENCE CHARACTERISTICS:
        (A) LENGTH:               15 base pairs
        (B) TYPE:                 nucleic acid
        (C) STRANDEDNESS:         single
        (D) TOPOLOGY:             linear (xi) SEQUENCE DESCRIPTION: SEQ ID NO: 699:

CAGUGGUUCU CUGCU                                                     15

(2) INFORMATION FOR SEQ ID NO: 700:

(i) SEQUENCE CHARACTERISTICS:
        (A) LENGTH:               15 base pairs
        (B) TYPE:                 nucleic acid
        (C) STRANDEDNESS:         single
        (D) TOPOLOGY:             linear (xi) SEQUENCE DESCRIPTION: SEQ ID NO: 700:

GAAAGAUCAC AUGGG                                                     15

(2) INFORMATION FOR SEQ ID NO: 701:

(i) SEQUENCE CHARACTERISTICS:
        (A) LENGTH:               15 base pairs
        (B) TYPE:                 nucleic acid
        (C) STRANDEDNESS:         single
        (D) TOPOLOGY:             linear (xi) SEQUENCE DESCRIPTION: SEQ ID NO: 701:

UGAGACUCCU GCCUG                                                     15

(2) INFORMATION FOR SEQ ID NO: 702:

(i) SEQUENCE CHARACTERISTICS:
        (A) LENGTH:               15 base pairs
        (B) TYPE:                 nucleic acid
        (C) STRANDEDNESS:         single
        (D) TOPOLOGY:             linear (xi) SEQUENCE DESCRIPTION: SEQ ID NO: 702:

GAAACCUUUC CUUUG                                                     15

(2) INFORMATION FOR SEQ ID NO: 703:

(i) SEQUENCE CHARACTERISTICS:
        (A) LENGTH:               15 base pairs
        (B) TYPE:                 nucleic acid
        (C) STRANDEDNESS:         single
```

(D) TOPOLOGY:            linear (xi) SEQUENCE DESCRIPTION: SEQ ID NO: 703:

GACCUCUACC AGCCU                                                    15

(2) INFORMATION FOR SEQ ID NO: 704:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 704:

UUUCGAUCUU CCAGC                                                    15

(2) INFORMATION FOR SEQ ID NO: 705:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 705:

CCCAGCUCUC AGCAG                                                    15

(2) INFORMATION FOR SEQ ID NO: 706:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 706:

CUGCUUUUGA ACAGA                                                    15

(2) INFORMATION FOR SEQ ID NO: 707:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 707:

AACCUUUCCU UUGAA                                                    15

(2) INFORMATION FOR SEQ ID NO: 708:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 708:

AGGUGGUUCU UCUGA                                                    15

(2) INFORMATION FOR SEQ ID NO: 709:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 709:

GGUGGUUCUU CUGAG                                                            15

(2) INFORMATION FOR SEQ ID NO: 710:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 710:

AGGGUUUCUC UACUG                                                            15

(2) INFORMATION FOR SEQ ID NO: 711:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 711:

UGCUUUUCUC AUAAG                                                            15

(2) INFORMATION FOR SEQ ID NO: 712:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 712:

AAGUUUUAUG UCGGC                                                            15

(2) INFORMATION FOR SEQ ID NO: 713:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 713:

AUUCUCUAUU GCCCC                                                            15

(2) INFORMATION FOR SEQ ID NO: 714:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 714:

AUCCAGUAGA CACAA                                                            15

(2) INFORMATION FOR SEQ ID NO: 715:

(i) SEQUENCE CHARACTERISTICS:
            (A) LENGTH:             15 base pairs
            (B) TYPE:               nucleic acid
            (C) STRANDEDNESS:       single
            (D) TOPOLOGY:           linear (xi) SEQUENCE DESCRIPTION: SEQ ID NO: 715:

AAACACUAUG UGGAC                                                             15

(2) INFORMATION FOR SEQ ID NO: 716:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 716:

AAGCUGUUUG AGCUG                                                             15

(2) INFORMATION FOR SEQ ID NO: 717:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 717:

UACUGGUCAG GAUGC                                                             15

(2) INFORMATION FOR SEQ ID NO: 718:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 718:

AAUGUCUCCG AGGCC                                                             15

(2) INFORMATION FOR SEQ ID NO: 719:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 719:

GAAGCCUUCC UGCCC                                                             15

(2) INFORMATION FOR SEQ ID NO: 720:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 720:

GACCUCUACC AGCCU                                                             15

(2) INFORMATION FOR SEQ ID NO: 721:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 721:

```
CCCAGCUCUC AGCAG                                                15
```

(2) INFORMATION FOR SEQ ID NO: 722:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 722:

```
GAGGUCUCGG AAGGG                                                15
```

(2) INFORMATION FOR SEQ ID NO: 723:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 723:

```
GAAGGUCGU GCAAG                                                 15
```

(2) INFORMATION FOR SEQ ID NO: 724:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 724:

```
GGUACAUACG UGUGC                                                15
```

(2) INFORMATION FOR SEQ ID NO: 725:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 725:

```
GGUGGGUCCG UGCAG                                                15
```

(2) INFORMATION FOR SEQ ID NO: 726:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 726:

```
UAUUUAUUGA GUACC                                                15
```

(2) INFORMATION FOR SEQ ID NO: 727:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 727:

```
CCGGACUUUC GAUCU                                                          15

(2) INFORMATION FOR SEQ ID NO: 728:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 728:

AGGACCUCAC CCUGC                                                          15

(2) INFORMATION FOR SEQ ID NO: 729:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 729:

UUUUGCUCUG CCGCU                                                          15

(2) INFORMATION FOR SEQ ID NO: 730:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 730:

AGUCUGUCAA ACAGG                                                          15

(2) INFORMATION FOR SEQ ID NO: 731:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 731:

AUGAAAUCAU GGUCC                                                          15

(2) INFORMATION FOR SEQ ID NO: 732:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 732:

UCAUGGUCCC AGGCG                                                          15

(2) INFORMATION FOR SEQ ID NO: 733:

(i) SEQUENCE CHARACTERISTICS:
        (A) LENGTH:          15 base pairs
        (B) TYPE:            nucleic acid
        (C) STRANDEDNESS:    single
        (D) TOPOLOGY:        linear (xi) SEQUENCE DESCRIPTION: SEQ ID NO: 733:

GGUGGGUCCG UGCAG                                                          15
```

(2) INFORMATION FOR SEQ ID NO: 734:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 734:

CUCCGGUCCU GACCC                                    15

(2) INFORMATION FOR SEQ ID NO: 735:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 735:

ACAGUCUACA ACUUU                                    15

(2) INFORMATION FOR SEQ ID NO: 736:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 736:

CUGACCUCCU GGAGG                                    15

(2) INFORMATION FOR SEQ ID NO: 737:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 737:

GGAGCCUCCG GACUU                                    15

(2) INFORMATION FOR SEQ ID NO: 738:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 738:

UGCCUUUAGC UCCCA                                    15

(2) INFORMATION FOR SEQ ID NO: 739:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 739:

CUGGACUAUA AUCAU                                    15

(2) INFORMATION FOR SEQ ID NO: 740:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 740:

AGGUGGUUCU UCUGA                                          15

(2) INFORMATION FOR SEQ ID NO: 741:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 741:

UGAGACUCCU GCCUG                                          15

(2) INFORMATION FOR SEQ ID NO: 742:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 742:

CCAAUGUCAG CCACC                                          15

(2) INFORMATION FOR SEQ ID NO: 743:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 743:

GCAGCCUCUU AUGUU                                          15

(2) INFORMATION FOR SEQ ID NO: 744:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 744:

GCCAAGUAAC UGUGA                                          15

(2) INFORMATION FOR SEQ ID NO: 745:

(i) SEQUENCE CHARACTERISTICS:
        (A) LENGTH:        15 base pairs
        (B) TYPE:          nucleic acid
        (C) STRANDEDNESS:  single
        (D) TOPOLOGY:     linear (xi) SEQUENCE DESCRIPTION: SEQ ID NO: 745:

GGACCUUCAG CCAAG                                          15

(2) INFORMATION FOR SEQ ID NO: 746:

(i) SEQUENCE CHARACTERISTICS:
        (A) LENGTH:            15 base pairs
        (B) TYPE:              nucleic acid
        (C) STRANDEDNESS:     single
        (D) TOPOLOGY:          linear (xi) SEQUENCE DESCRIPTION: SEQ ID NO: 746:

UUCCGCUACC AUCAC                                                      15

(2) INFORMATION FOR SEQ ID NO: 747:

(i) SEQUENCE CHARACTERISTICS:
        (A) LENGTH:            15 base pairs
        (B) TYPE:              nucleic acid
        (C) STRANDEDNESS:     single
        (D) TOPOLOGY:          linear (xi) SEQUENCE DESCRIPTION: SEQ ID NO: 747:

CGGACUUUCG AUCUU                                                      15

(2) INFORMATION FOR SEQ ID NO: 748:

(i) SEQUENCE CHARACTERISTICS:
        (A) LENGTH:            15 base pairs
        (B) TYPE:              nucleic acid
        (C) STRANDEDNESS:     single
        (D) TOPOLOGY:          linear (xi) SEQUENCE DESCRIPTION: SEQ ID NO: 748:

UUAAUUUAGA GUUUU                                                      15

(2) INFORMATION FOR SEQ ID NO: 749:

(i) SEQUENCE CHARACTERISTICS:
        (A) LENGTH:            15 base pairs
        (B) TYPE:              nucleic acid
        (C) STRANDEDNESS:     single
        (D) TOPOLOGY:          linear (xi) SEQUENCE DESCRIPTION: SEQ ID NO: 749:

ACUUCAUUCU CUAUU                                                      15

(2) INFORMATION FOR SEQ ID NO: 750:

(i) SEQUENCE CHARACTERISTICS:
        (A) LENGTH:            15 base pairs
        (B) TYPE:              nucleic acid
        (C) STRANDEDNESS:     single
        (D) TOPOLOGY:          linear (xi) SEQUENCE DESCRIPTION: SEQ ID NO: 750:

CUUCAUUCUC UAUUG                                                      15

(2) INFORMATION FOR SEQ ID NO: 751:

(i) SEQUENCE CHARACTERISTICS:
        (A) LENGTH:            15 base pairs
        (B) TYPE:              nucleic acid
        (C) STRANDEDNESS:     single
        (D) TOPOLOGY:          linear (xi) SEQUENCE DESCRIPTION: SEQ ID NO: 751:

UUGAUGUAUU UAUUA                                                      15

(2) INFORMATION FOR SEQ ID NO: 752:

```
        (i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 752:

UGUAUUUAUU AAUUU                                                          15

(2) INFORMATION FOR SEQ ID NO: 753:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 753:

GAAGCUUCUU UUGCU                                                          15

(2) INFORMATION FOR SEQ ID NO: 754:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 754:

AGCUUCUUUU GCUCU                                                          15

(2) INFORMATION FOR SEQ ID NO: 755:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 755:

UGUAUUUAUU AAUUU                                                          15

(2) INFORMATION FOR SEQ ID NO: 756:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 756:

UGUAUUUAUU AAUUU                                                          15

(2) INFORMATION FOR SEQ ID NO: 757:

(i) SEQUENCE CHARACTERISTICS:
              (A) LENGTH:              15 base pairs
              (B) TYPE:                nucleic acid
              (C) STRANDEDNESS:        single
              (D) TOPOLOGY:            linear (xi) SEQUENCE DESCRIPTION: SEQ ID NO: 757:

UUGUUCUCUA AUGUC                                                          15

(2) INFORMATION FOR SEQ ID NO: 758:
```

```
    (i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 758:

UUUCUCUACU GGUCA                                                             15

(2) INFORMATION FOR SEQ ID NO: 759:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 759:

UGCUUUUCUC AUAAG                                                             15

(2) INFORMATION FOR SEQ ID NO: 760:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 760:

AUUUAUUAAU UUAGA                                                             15

(2) INFORMATION FOR SEQ ID NO: 761:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 761:

UAUUCGUUUC CGGAG                                                             15

(2) INFORMATION FOR SEQ ID NO: 762:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 762:

AUUCGUUUCC GGAGA                                                             15

(2) INFORMATION FOR SEQ ID NO: 763:

(i) SEQUENCE CHARACTERISTICS:
        (A) LENGTH:              15 base pairs
        (B) TYPE:                nucleic acid
        (C) STRANDEDNESS:        single
        (D) TOPOLOGY:            linear (xi) SEQUENCE DESCRIPTION: SEQ ID NO: 763:

UUCGUUUCCG GAGAG                                                             15

(2) INFORMATION FOR SEQ ID NO: 764:

(i) SEQUENCE CHARACTERISTICS:
```

```
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 764:

UUCUCAUAAG GGUCG                                                          15

(2) INFORMATION FOR SEQ ID NO: 765:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 765:

UGGAGGUCUC GGAAG                                                          15

(2) INFORMATION FOR SEQ ID NO: 766:

(i) SEQUENCE CHARACTERISTICS:
            (A) LENGTH:              15 base pairs
            (B) TYPE:                nucleic acid
            (C) STRANDEDNESS:        single
            (D) TOPOLOGY:            linear (xi) SEQUENCE DESCRIPTION: SEQ ID NO: 766:

GAGGUCUCGG AAGGG                                                          15

(2) INFORMATION FOR SEQ ID NO: 767:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 767:

CAGCGUCCUG AUGAGGCCGA AAGGCCGAAA CUGGGG                                   36

(2) INFORMATION FOR SEQ ID NO: 768:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 768:

AGCAGAGCUG AUGAGGCCGA AAGGCCGAAA GCUCAG                                   36

(2) INFORMATION FOR SEQ ID NO: 769:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 769:

AGUAGCACUG AUGAGGCCGA AAGGCCGAAA GGAGCU                                   36

(2) INFORMATION FOR SEQ ID NO: 770:

(i) SEQUENCE CHARACTERISTICS:
            (A) LENGTH:              36 base pairs
```

```
            (B) TYPE:              nucleic acid
            (C) STRANDEDNESS:      single
            (D) TOPOLOGY:          linear (xi) SEQUENCE DESCRIPTION: SEQ ID NO: 770:

CUCUGAGCUG AUGAGGCCGA AAGGCCGAAA GCAGAG                               36

(2) INFORMATION FOR SEQ ID NO: 771:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 771:

CAACUCUCUG AUGAGGCCGA AAGGCCGAAA GUAGCA                               36

(2) INFORMATION FOR SEQ ID NO: 772:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 772:

AGGUUGCCUG AUGAGGCCGA AAGGCCGAAA CUCUGA                               36

(2) INFORMATION FOR SEQ ID NO: 773:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 773:

CGAGGCUCUG AUGAGGCCGA AAGGCCGAAA GGUUGC                               36

(2) INFORMATION FOR SEQ ID NO: 774:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 774:

CCAUAGCCUG AUGAGGCCGA AAGGCCGAAA GGCUGA                               36

(2) INFORMATION FOR SEQ ID NO: 775:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 775:

GGAGCCACUG AUGAGGCCGA AAGGCCGAAA GCGAGG                               36

(2) INFORMATION FOR SEQ ID NO: 776:

(i) SEQUENCE CHARACTERISTICS:
            (A) LENGTH:            36 base pairs
            (B) TYPE:              nucleic acid
```

```
        (C) STRANDEDNESS:        single
        (D) TOPOLOGY:            linear (xi) SEQUENCE DESCRIPTION: SEQ ID NO: 776:

CUGCUGGCUG AUGAGGCCGA AAGGCCGAAA GCCAUA                              36

(2) INFORMATION FOR SEQ ID NO: 777:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 777:

GGACCAGCUG AUGAGGCCGA AAGGCCGAAA GUGCGG                              36

(2) INFORMATION FOR SEQ ID NO: 778:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 778:

CGAGCAGCUG AUGAGGCCGA AAGGCCGAAA CCAGGA                              36

(2) INFORMATION FOR SEQ ID NO: 779:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 779:

GAGCCCCCUG AUGAGGCCGA AAGGCCGAAA GCAGGA                              36

(2) INFORMATION FOR SEQ ID NO: 780:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 780:

GGGAACACUG AUGAGGCCGA AAGGCCGAAA GCCCCG                              36

(2) INFORMATION FOR SEQ ID NO: 781:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 781:

UCCUGGGCUG AUGAGGCCGA AAGGCCGAAA CAGAGC                              36

(2) INFORMATION FOR SEQ ID NO: 782:

(i) SEQUENCE CHARACTERISTICS:
        (A) LENGTH:              36 base pairs
        (B) TYPE:                nucleic acid
        (C) STRANDEDNESS:        single
```

(D) TOPOLOGY:          linear (xi) SEQUENCE DESCRIPTION: SEQ ID NO: 782:

GUCCUGGCUG AUGAGGCCGA AAGGCCGAAA ACAGAG                                36

(2) INFORMATION FOR SEQ ID NO: 783:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 783:

GGACACACUG AUGAGGCCGA AAGGCCGAAA UGUCUG                                36

(2) INFORMATION FOR SEQ ID NO: 784:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 784:

UGAGGGGCUG AUGAGGCCGA AAGGCCGAAA CACAGA                                36

(2) INFORMATION FOR SEQ ID NO: 785:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 785:

GACUUUCUG AUGAGGCCGA AAGGCCGAAA GGGGGA                                 36

(2) INFORMATION FOR SEQ ID NO: 786:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 786:

GCAGGAUCUG AUGAGGCCGA AAGGCCGAAA CUUUUG                                36

(2) INFORMATION FOR SEQ ID NO: 787:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 787:

GGGGCAGCUG AUGAGGCCGA AAGGCCGAAA UGACUU                                36

(2) INFORMATION FOR SEQ ID NO: 788:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 788:

CAGCACGCUG AUGAGGCCGA AAGGCCGAAA GCCUCC                                    36

(2) INFORMATION FOR SEQ ID NO: 789:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 789:

GUCACAGCUG AUGAGGCCGA AAGGCCGAAA GGUGCU                                    36

(2) INFORMATION FOR SEQ ID NO: 790:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 790:

GCCCAACCUG AUGAGGCCGA AAGGCCGAAA CUUGGG                                    36

(2) INFORMATION FOR SEQ ID NO: 791:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 791:

UAUGCCCCUG AUGAGGCCGA AAGGCCGAAA CAACUU                                    36

(2) INFORMATION FOR SEQ ID NO: 792:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 792:

GGGUCUCCUG AUGAGGCCGA AAGGCCGAAA UGCCCA                                    36

(2) INFORMATION FOR SEQ ID NO: 793:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 793:

UUUAGGCCUG AUGAGGCCGA AAGGCCGAAA CGGGGU                                    36

(2) INFORMATION FOR SEQ ID NO: 794:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 794:

UCCUUUUCUG AUGAGGCCGA AAGGCCGAAA GGCAAC                                    36

(2) INFORMATION FOR SEQ ID NO: 795:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 795:

CAGGAGCCUG AUGAGGCCGA AAGGCCGAAA CUCCUU                                    36

(2) INFORMATION FOR SEQ ID NO: 796:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 796:

CAGGCAGCUG AUGAGGCCGA AAGGCCGAAA GCAACU                                    36

(2) INFORMATION FOR SEQ ID NO: 797:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 797:

CAGUUCACUG AUGAGGCCGA AAGGCCGAAA CACCUU                                    36

(2) INFORMATION FOR SEQ ID NO: 798:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 798:

GGUUGGCCUG AUGAGGCCGA AAGGCCGAAA UCUUCU                                    36

(2) INFORMATION FOR SEQ ID NO: 799:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 799:

GUUUGAACUG AUGAGGCCGA AAGGCCGAAA GCACAU                                    36

(2) INFORMATION FOR SEQ ID NO: 800:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 800:

CAGUUUGCUG AUGAGGCCGA AAGGCCGAAA UAGCAC                                      36

(2) INFORMATION FOR SEQ ID NO: 801:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 801:

GCAGUUUCUG AUGAGGCCGA AAGGCCGAAA AUAGCA                                      36

(2) INFORMATION FOR SEQ ID NO: 802:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 802:

AGCUGUUCUG AUGAGGCCGA AAGGCCGAAA CUGCCC                                      36

(2) INFORMATION FOR SEQ ID NO: 803:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 803:

AAGGUUUCUG AUGAGGCCGA AAGGCCGAAA GCUGUU                                      36

(2) INFORMATION FOR SEQ ID NO: 804:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 804:

GGUGAGGCUG AUGAGGCCGA AAGGCCGAAA GGUUUU                                      36

(2) INFORMATION FOR SEQ ID NO: 805:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 805:

CGGUGAGCUG AUGAGGCCGA AAGGCCGAAA AGGUUU                                      36

(2) INFORMATION FOR SEQ ID NO: 806:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 806:

```
ACACGGUCUG AUGAGGCCGA AAGGCCGAAA GGAAGG                                         36

(2) INFORMATION FOR SEQ ID NO: 807:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 807:

AGUCCAGCUG AUGAGGCCGA AAGGCCGAAA CACGGU                                         36

(2) INFORMATION FOR SEQ ID NO: 808:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 808:

CGUUCUGCUG AUGAGGCCGA AAGGCCGAAA GUCCAG                                         36

(2) INFORMATION FOR SEQ ID NO: 809:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 809:

AAGAGGGCUG AUGAGGCCGA AAGGCCGAAA GGGGUG                                         36

(2) INFORMATION FOR SEQ ID NO: 810:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 810:

CUGCCAACUG AUGAGGCCGA AAGGCCGAAA GGGGAG                                         36

(2) INFORMATION FOR SEQ ID NO: 811:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 811:

GGCUGCCCUG AUGAGGCCGA AAGGCCGAAA GAGGGG                                         36

(2) INFORMATION FOR SEQ ID NO: 812:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 812:

GUAGGGUCUG AUGAGGCCGA AAGGCCGAAA GGUUCU                                         36
```

(2) INFORMATION FOR SEQ ID NO: 813:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 813:

CGUAGGGCUG AUGAGGCCGA AAGGCCGAAA AGGUUC                           36

(2) INFORMATION FOR SEQ ID NO: 814:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 814:

GGCAGCGCUG AUGAGGCCGA AAGGCCGAAA GGGUAA                           36

(2) INFORMATION FOR SEQ ID NO: 815:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 815:

CCACGGUCUG AUGAGGCCGA AAGGCCGAAA GGUUGG                           36

(2) INFORMATION FOR SEQ ID NO: 816:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 816:

CCCCACGCUG AUGAGGCCGA AAGGCCGAAA GCAGCA                           36

(2) INFORMATION FOR SEQ ID NO: 817:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 817:

UGGUCGUCUG AUGAGGCCGA AAGGCCGAAA CCUCAG                           36

(2) INFORMATION FOR SEQ ID NO: 818:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 818:

CCAUGGUCUG AUGAGGCCGA AAGGCCGAAA UCUCUC                           36

```
(2) INFORMATION FOR SEQ ID NO: 819:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 819:

CACGAGACUG AUGAGGCCGA AAGGCCGAAA UUGGCU                              36

(2) INFORMATION FOR SEQ ID NO: 820:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 820:

GCACGAGCUG AUGAGGCCGA AAGGCCGAAA AUUGGC                              36

(2) INFORMATION FOR SEQ ID NO: 821:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 821:

GGCACGACUG AUGAGGCCGA AAGGCCGAAA AAUUGG                              36

(2) INFORMATION FOR SEQ ID NO: 822:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 822:

GCGGCACCUG AUGAGGCCGA AAGGCCGAAA GAAAUU                              36

(2) INFORMATION FOR SEQ ID NO: 823:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 823:

GUUCUCACUG AUGAGGCCGA AAGGCCGAAA CAGCUC                              36

(2) INFORMATION FOR SEQ ID NO: 824:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 824:

UGUUCUCCUG AUGAGGCCGA AAGGCCGAAA ACAGCU                              36
```

```
(2) INFORMATION FOR SEQ ID NO: 825:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 825:

GGGGGCCCUG AUGAGGCCGA AAGGCCGAAA GGUGUU                              36

(2) INFORMATION FOR SEQ ID NO: 826:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 826:

GAGCUGGCUG AUGAGGCCGA AAGGCCGAAA GGGGGC                              36

(2) INFORMATION FOR SEQ ID NO: 827:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 827:

AGGUCUGCUG AUGAGGCCGA AAGGCCGAAA GCUGGU                              36

(2) INFORMATION FOR SEQ ID NO: 828:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 828:

CAGGACACUG AUGAGGCCGA AAGGCCGAAA GGUCUG                              36

(2) INFORMATION FOR SEQ ID NO: 829:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 829:

GCAGGACCUG AUGAGGCCGA AAGGCCGAAA AGGUCU                              36

(2) INFORMATION FOR SEQ ID NO: 830:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 830:

CUGGCAGCUG AUGAGGCCGA AAGGCCGAAA CAAAGG                              36

(2) INFORMATION FOR SEQ ID NO: 831:
```

(i) SEQUENCE CHARACTERISTICS:
              (A) LENGTH:            36 base pairs
              (B) TYPE:              nucleic acid
              (C) STRANDEDNESS:      single
              (D) TOPOLOGY:          linear (xi) SEQUENCE DESCRIPTION: SEQ ID NO: 831:

UGUGGGCUG AUGAGGCCGA AAGGCCGAAA GUCGCU                              36

(2) INFORMATION FOR SEQ ID NO: 832:

(i) SEQUENCE CHARACTERISTICS:
              (A) LENGTH:            36 base pairs
              (B) TYPE:              nucleic acid
              (C) STRANDEDNESS:      single
              (D) TOPOLOGY:          linear (xi) SEQUENCE DESCRIPTION: SEQ ID NO: 832:

GGCUGACCUG AUGAGGCCGA AAGGCCGAAA GUUGUG                             36

(2) INFORMATION FOR SEQ ID NO: 833:

(i) SEQUENCE CHARACTERISTICS:
              (A) LENGTH:            36 base pairs
              (B) TYPE:              nucleic acid
              (C) STRANDEDNESS:      single
              (D) TOPOLOGY:          linear (xi) SEQUENCE DESCRIPTION: SEQ ID NO: 833:

GGGGGCUCUG AUGAGGCCGA AAGGCCGAAA CAAGUU                             36

(2) INFORMATION FOR SEQ ID NO: 834:

(i) SEQUENCE CHARACTERISTICS:
              (A) LENGTH:            36 base pairs
              (B) TYPE:              nucleic acid
              (C) STRANDEDNESS:      single
              (D) TOPOLOGY:          linear (xi) SEQUENCE DESCRIPTION: SEQ ID NO: 834:

CCUCUAGCUG AUGAGGCCGA AAGGCCGAAA CCCGGG                             36

(2) INFORMATION FOR SEQ ID NO: 835:

(i) SEQUENCE CHARACTERISTICS:
              (A) LENGTH:            36 base pairs
              (B) TYPE:              nucleic acid
              (C) STRANDEDNESS:      single
              (D) TOPOLOGY:          linear (xi) SEQUENCE DESCRIPTION: SEQ ID NO: 835:

CCACCUCCUG AUGAGGCCGA AAGGCCGAAA GGACCC                             36

(2) INFORMATION FOR SEQ ID NO: 836:

(i) SEQUENCE CHARACTERISTICS:
              (A) LENGTH:            36 base pairs
              (B) TYPE:              nucleic acid
              (C) STRANDEDNESS:      single
              (D) TOPOLOGY:          linear (xi) SEQUENCE DESCRIPTION: SEQ ID NO: 836:

GGGAACACUG AUGAGGCCGA AAGGCCGAAA CCACGG                             36

(2) INFORMATION FOR SEQ ID NO: 837:

```
    (i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 837:

UCCAGGGCUG AUGAGGCCGA AAGGCCGAAA CAGACC                          36

(2) INFORMATION FOR SEQ ID NO: 838:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 838:

GUCCAGGCUG AUGAGGCCGA AAGGCCGAAA ACAGAC                          36

(2) INFORMATION FOR SEQ ID NO: 839:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 839:

GACUGGGCUG AUGAGGCCGA AAGGCCGAAA CAGCCC                          36

(2) INFORMATION FOR SEQ ID NO: 840:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 840:

AGACUGGCUG AUGAGGCCGA AAGGCCGAAA ACAGCC                          36

(2) INFORMATION FOR SEQ ID NO: 841:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 841:

CCUCCGACUG AUGAGGCCGA AAGGCCGAAA CUGGGA                          36

(2) INFORMATION FOR SEQ ID NO: 842:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 842:

GGCCUCCCUG AUGAGGCCGA AAGGCCGAAA GACUGG                          36

(2) INFORMATION FOR SEQ ID NO: 843:

(i) SEQUENCE CHARACTERISTICS:
```

```
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 843:

CCAGGUGCUG AUGAGGCCGA AAGGCCGAAA CCUGGG                           36

(2) INFORMATION FOR SEQ ID NO: 844:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 844:

GGGGUUCCUG AUGAGGCCGA AAGGCCGAAA CCUCUG                           36

(2) INFORMATION FOR SEQ ID NO: 845:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 845:

CAUAGGUCUG AUGAGGCCGA AAGGCCGAAA CUGUGG                           36

(2) INFORMATION FOR SEQ ID NO: 846:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 846:

GUUGCCACUG AUGAGGCCGA AAGGCCGAAA GGUGAC                           36

(2) INFORMATION FOR SEQ ID NO: 847:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 847:

CGAGAAGCUG AUGAGGCCGA AAGGCCGAAA GUCGUU                           36

(2) INFORMATION FOR SEQ ID NO: 848:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 848:

GGCCGAGCUG AUGAGGCCGA AAGGCCGAAA GGAGUC                           36

(2) INFORMATION FOR SEQ ID NO: 849:

(i) SEQUENCE CHARACTERISTICS:
            (A) LENGTH:           36 base pairs
```

```
        (B) TYPE:               nucleic acid
        (C) STRANDEDNESS:       single
        (D) TOPOLOGY:           linear (xi) SEQUENCE DESCRIPTION: SEQ ID NO: 849:

UGGCCGACUG AUGAGGCCGA AAGGCCGAAA AGGAGU                            36

(2) INFORMATION FOR SEQ ID NO: 850:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 850:

CUUGGCCCUG AUGAGGCCGA AAGGCCGAAA GAAGGA                            36

(2) INFORMATION FOR SEQ ID NO: 851:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 851:

ACUGACUCUG AUGAGGCCGA AAGGCCGAAA GGCCUU                            36

(2) INFORMATION FOR SEQ ID NO: 852:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 852:

UCACACUCUG AUGAGGCCGA AAGGCCGAAA CUGAGG                            36

(2) INFORMATION FOR SEQ ID NO: 853:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 853:

CCAGUAUCUG AUGAGGCCGA AAGGCCGAAA CUGCAC                            36

(2) INFORMATION FOR SEQ ID NO: 854:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 854:

UCCCCAGCUG AUGAGGCCGA AAGGCCGAAA UUACUG                            36

(2) INFORMATION FOR SEQ ID NO: 855:

(i) SEQUENCE CHARACTERISTICS:
        (A) LENGTH:             36 base pairs
        (B) TYPE:               nucleic acid
```

```
            (C) STRANDEDNESS:        single
            (D) TOPOLOGY:            linear (xi) SEQUENCE DESCRIPTION: SEQ ID NO: 855:

AGCUGUACUG AUGAGGCCGA AAGGCCGAAA UGGUCA                                36

(2) INFORMATION FOR SEQ ID NO: 856:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 856:

AAAGCUGCUG AUGAGGCCGA AAGGCCGAAA GAUGGU                                36

(2) INFORMATION FOR SEQ ID NO: 857:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 857:

CGCCGGACUG AUGAGGCCGA AAGGCCGAAA GCUGUA                                36

(2) INFORMATION FOR SEQ ID NO: 858:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 858:

GCGCCGGCUG AUGAGGCCGA AAGGCCGAAA AGCUGU                                36

(2) INFORMATION FOR SEQ ID NO: 859:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 859:

GGCGCCGCUG AUGAGGCCGA AAGGCCGAAA AAGCUG                                36

(2) INFORMATION FOR SEQ ID NO: 860:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 860:

UCGUCAGCUG AUGAGGCCGA AAGGCCGAAA UCACGU                                36

(2) INFORMATION FOR SEQ ID NO: 861:

(i) SEQUENCE CHARACTERISTICS:
            (A) LENGTH:              36 base pairs
            (B) TYPE:                nucleic acid
            (C) STRANDEDNESS:        single
```

(D) TOPOLOGY:          linear (xi) SEQUENCE DESCRIPTION: SEQ ID NO: 861:

UUCGUCACUG AUGAGGCCGA AAGGCCGAAA AUCACG                        36

(2) INFORMATION FOR SEQ ID NO: 862:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 862:

CUUCUGACUG AUGAGGCCGA AAGGCCGAAA CCUCUG                        36

(2) INFORMATION FOR SEQ ID NO: 863:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 863:

CCCUUCUCUG AUGAGGCCGA AAGGCCGAAA GACCUC                        36

(2) INFORMATION FOR SEQ ID NO: 864:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 864:

UUGGCUCCUG AUGAGGCCGA AAGGCCGAAA GGGUGG                        36

(2) INFORMATION FOR SEQ ID NO: 865:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 865:

GGGCUGGCUG AUGAGGCCGA AAGGCCGAAA CCCCAU                        36

(2) INFORMATION FOR SEQ ID NO: 866:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 866:

UGGGCUGCUG AUGAGGCCGA AAGGCCGAAA ACCCCA                        36

(2) INFORMATION FOR SEQ ID NO: 867:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 867:

UCAGCAGCUG AUGAGGCCGA AAGGCCGAAA GCUGGG     36

(2) INFORMATION FOR SEQ ID NO: 868:

(i) SEQUENCE CHARACTERISTICS:
      (A) LENGTH:        36 base pairs
      (B) TYPE:          nucleic acid
      (C) STRANDEDNESS:  single
      (D) TOPOLOGY:      linear (xi) SEQUENCE DESCRIPTION: SEQ ID NO: 868:

GCAGGAGCUG AUGAGGCCGA AAGGCCGAAA GCUGCG     36

(2) INFORMATION FOR SEQ ID NO: 869:

(i) SEQUENCE CHARACTERISTICS:
      (A) LENGTH:        36 base pairs
      (B) TYPE:          nucleic acid
      (C) STRANDEDNESS:  single
      (D) TOPOLOGY:      linear (xi) SEQUENCE DESCRIPTION: SEQ ID NO: 869:

AGCAGGACUG AUGAGGCCGA AAGGCCGAAA AGCUGC     36

(2) INFORMATION FOR SEQ ID NO: 870:

(i) SEQUENCE CHARACTERISTICS:
      (A) LENGTH:        36 base pairs
      (B) TYPE:          nucleic acid
      (C) STRANDEDNESS:  single
      (D) TOPOLOGY:      linear (xi) SEQUENCE DESCRIPTION: SEQ ID NO: 870:

AGAGCAGCUG AUGAGGCCGA AAGGCCGAAA GAAGCU     36

(2) INFORMATION FOR SEQ ID NO: 871:

(i) SEQUENCE CHARACTERISTICS:
      (A) LENGTH:        36 base pairs
      (B) TYPE:          nucleic acid
      (C) STRANDEDNESS:  single
      (D) TOPOLOGY:      linear (xi) SEQUENCE DESCRIPTION: SEQ ID NO: 871:

GGUUGCACUG AUGAGGCCGA AAGGCCGAAA GCAGGA     36

(2) INFORMATION FOR SEQ ID NO: 872:

(i) SEQUENCE CHARACTERISTICS:
      (A) LENGTH:        36 base pairs
      (B) TYPE:          nucleic acid
      (C) STRANDEDNESS:  single
      (D) TOPOLOGY:      linear (xi) SEQUENCE DESCRIPTION: SEQ ID NO: 872:

UGUGUAUCUG AUGAGGCCGA AAGGCCGAAA GCUGGC     36

(2) INFORMATION FOR SEQ ID NO: 873:

(i) SEQUENCE CHARACTERISTICS:
      (A) LENGTH:        36 base pairs
      (B) TYPE:          nucleic acid
      (C) STRANDEDNESS:  single
      (D) TOPOLOGY:      linear (xi) SEQUENCE DESCRIPTION: SEQ ID NO: 873:

UUGUGUACUG AUGAGGCCGA AAGGCCGAAA AGCUGG     36

(2) INFORMATION FOR SEQ ID NO: 874:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 874:

UCUUGUGCUG AUGAGGCCGA AAGGCCGAAA UAAGCU     36

(2) INFORMATION FOR SEQ ID NO: 875:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 875:

GGACACGCUG AUGAGGCCGA AAGGCCGAAA GCUCCC     36

(2) INFORMATION FOR SEQ ID NO: 876:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 876:

AGGACACCUG AUGAGGCCGA AAGGCCGAAA AGCUCC     36

(2) INFORMATION FOR SEQ ID NO: 877:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 877:

CAUACAGCUG AUGAGGCCGA AAGGCCGAAA CACGAA     36

(2) INFORMATION FOR SEQ ID NO: 878:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 878:

GGGGCCACUG AUGAGGCCGA AAGGCCGAAA CAGGAC     36

(2) INFORMATION FOR SEQ ID NO: 879:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 879:

CCCGGACCUG AUGAGGCCGA AAGGCCGAAA UCCCUC                                      36

(2) INFORMATION FOR SEQ ID NO: 880:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 880:

UUUCCCGCUG AUGAGGCCGA AAGGCCGAAA CAAUCC                                      36

(2) INFORMATION FOR SEQ ID NO: 881:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 881:

UGCUGGGCUG AUGAGGCCGA AAGGCCGAAA UUUUCU                                      36

(2) INFORMATION FOR SEQ ID NO: 882:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 882:

CUGCUGGCUG AUGAGGCCGA AAGGCCGAAA AUUUUC                                      36

(2) INFORMATION FOR SEQ ID NO: 883:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 883:

CACAUUGCUG AUGAGGCCGA AAGGCCGAAA GUCUGC                                      36

(2) INFORMATION FOR SEQ ID NO: 884:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 884:

UUCCCCCCUG AUGAGGCCGA AAGGCCGAAA GCCUGG                                      36

(2) INFORMATION FOR SEQ ID NO: 885:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 885:

```
CUCGGGCCUG AUGAGGCCGA AAGGCCGAAA UGGGUU                                    36
```

(2) INFORMATION FOR SEQ ID NO: 886:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 886:

```
GACACUUCUG AUGAGGCCGA AAGGCCGAAA GCUCGG                                    36
```

(2) INFORMATION FOR SEQ ID NO: 887:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 887:

```
UCCUUUACUG AUGAGGCCGA AAGGCCGAAA CACUUG                                    36
```

(2) INFORMATION FOR SEQ ID NO: 888:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 888:

```
CAUCCUUCUG AUGAGGCCGA AAGGCCGAAA GACACU                                    36
```

(2) INFORMATION FOR SEQ ID NO: 889:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 889:

```
AGUGGGACUG AUGAGGCCGA AAGGCCGAAA GUGCCA                                    36
```

(2) INFORMATION FOR SEQ ID NO: 890:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 890:

```
CAGUGGGCUG AUGAGGCCGA AAGGCCGAAA AGUGCC                                    36
```

(2) INFORMATION FOR SEQ ID NO: 891:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 891:

```
GCAGUGGCUG AUGAGGCCGA AAGGCCGAAA AAGUGC                                    36
```

(2) INFORMATION FOR SEQ ID NO: 892:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 892:

AUUCCCCUG AUGAGGCCGA AAGGCCGAAA UGGGCA                                36

(2) INFORMATION FOR SEQ ID NO: 893:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 893:

AGUCACUCUG AUGAGGCCGA AAGGCCGAAA UUCCCC                               36

(2) INFORMATION FOR SEQ ID NO: 894:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 894:

CUCGAGUCUG AUGAGGCCGA AAGGCCGAAA CAGUCA                               36

(2) INFORMATION FOR SEQ ID NO: 895:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 895:

AGAUCUCCUG AUGAGGCCGA AAGGCCGAAA GUGACA                               36

(2) INFORMATION FOR SEQ ID NO: 896:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 896:

CCCUCAACUG AUGAGGCCGA AAGGCCGAAA UCUCGA                               36

(2) INFORMATION FOR SEQ ID NO: 897:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 897:

UGCCCUCCUG AUGAGGCCGA AAGGCCGAAA GAUCUC                               36

(2) INFORMATION FOR SEQ ID NO: 898:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 898:

ACAGAGGCUG AUGAGGCCGA AAGGCCGAAA GGUGCC                    36

(2) INFORMATION FOR SEQ ID NO: 899:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 899:

CCCGACACUG AUGAGGCCGA AAGGCCGAAA GGUAGG                    36

(2) INFORMATION FOR SEQ ID NO: 900:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 900:

CUGGCCCCUG AUGAGGCCGA AAGGCCGAAA CAGAGG                    36

(2) INFORMATION FOR SEQ ID NO: 901:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 901:

UCCCCUUCUG AUGAGGCCGA AAGGCCGAAA GUGCUC                    36

(2) INFORMATION FOR SEQ ID NO: 902:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 902:

CGCGGGUCUG AUGAGGCCGA AAGGCCGAAA CCUCCC                    36

(2) INFORMATION FOR SEQ ID NO: 903:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 903:

GGGGGGACUG AUGAGGCCGA AAGGCCGAAA GCACAU                    36

```
(2) INFORMATION FOR SEQ ID NO:  904:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO:  904:

CCGGGGCUG AUGAGGCCGA AAGGCCGAAA GAGCAC                              36

(2) INFORMATION FOR SEQ ID NO:  905:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO:  905:

AAUCUCACUG AUGAGGCCGA AAGGCCGAAA CCGGGG                              36

(2) INFORMATION FOR SEQ ID NO:  906:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO:  906:

UGAUGACCUG AUGAGGCCGA AAGGCCGAAA UCUCAU                              36

(2) INFORMATION FOR SEQ ID NO:  907:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO:  907:

UGAUGAUCUG AUGAGGCCGA AAGGCCGAAA CAAUCU                              36

(2) INFORMATION FOR SEQ ID NO:  908:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO:  908:

CAGUGAUCUG AUGAGGCCGA AAGGCCGAAA UGACAA                              36

(2) INFORMATION FOR SEQ ID NO:  909:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO:  909:

CCACAGUCUG AUGAGGCCGA AAGGCCGAAA UGAUGA                              36

(2) INFORMATION FOR SEQ ID NO:  910:
```

```
    (i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 910:

CGGCUGCCUG AUGAGGCCGA AAGGCCGAAA CCACAG                                  36

(2) INFORMATION FOR SEQ ID NO: 911:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 911:

CCAUUAUCUG AUGAGGCCGA AAGGCCGAAA CUGCGG                                  36

(2) INFORMATION FOR SEQ ID NO: 912:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 912:

UGCCCAUCUG AUGAGGCCGA AAGGCCGAAA UGACUG                                  36

(2) INFORMATION FOR SEQ ID NO: 913:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 913:

ACGUGCUCUG AUGAGGCCGA AAGGCCGAAA GGCCUG                                  36

(2) INFORMATION FOR SEQ ID NO: 914:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 914:

AUAGAGGCUG AUGAGGCCGA AAGGCCGAAA CGUGCU                                  36

(2) INFORMATION FOR SEQ ID NO: 915:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 915:

GGUUAUACUG AUGAGGCCGA AAGGCCGAAA GGUACG                                  36

(2) INFORMATION FOR SEQ ID NO: 916:
```

```
    (i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 916:

GCGGUUACUG AUGAGGCCGA AAGGCCGAAA GAGGUA                              36

(2) INFORMATION FOR SEQ ID NO: 917:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 917:

UGGCGGUCUG AUGAGGCCGA AAGGCCGAAA UAGAGG                              36

(2) INFORMATION FOR SEQ ID NO: 918:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 918:

AUUUCUUCUG AUGAGGCCGA AAGGCCGAAA UCUUCC                              36

(2) INFORMATION FOR SEQ ID NO: 919:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 919:

UAGUCUGCUG AUGAGGCCGA AAGGCCGAAA UUUCUU                              36

(2) INFORMATION FOR SEQ ID NO: 920:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 920:

CCUGUUGCUG AUGAGGCCGA AAGGCCGAAA GUCUGU                              36

(2) INFORMATION FOR SEQ ID NO: 921:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 921:

GUUCAGGCUG AUGAGGCCGA AAGGCCGAAA GGCGUG                              36

(2) INFORMATION FOR SEQ ID NO: 922:

(i) SEQUENCE CHARACTERISTICS:
```

(A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO: 922:

CCCGGGACUG AUGAGGCCGA AAGGCCGAAA GGUUCA                         36

(2) INFORMATION FOR SEQ ID NO: 923:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO: 923:

GUCCCGGCUG AUGAGGCCGA AAGGCCGAAA UAGGUU                         36

(2) INFORMATION FOR SEQ ID NO: 924:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO: 924:

CGAGGAACUG AUGAGGCCGA AAGGCCGAAA GGCCCU                         36

(2) INFORMATION FOR SEQ ID NO: 925:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO: 925:

GCCGAGGCUG AUGAGGCCGA AAGGCCGAAA GAGGCC                         36

(2) INFORMATION FOR SEQ ID NO: 926:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO: 926:

GGCCGAGCUG AUGAGGCCGA AAGGCCGAAA AGAGGC                         36

(2) INFORMATION FOR SEQ ID NO: 927:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO: 927:

GAAGGCCCUG AUGAGGCCGA AAGGCCGAAA GGAAGA                         36

(2) INFORMATION FOR SEQ ID NO: 928:

(i) SEQUENCE CHARACTERISTICS:
            (A) LENGTH:          36 base pairs

```
            (B) TYPE:                nucleic acid
            (C) STRANDEDNESS:        single
            (D) TOPOLOGY:            linear (xi) SEQUENCE DESCRIPTION: SEQ ID NO: 928:

AUAUGGGCUG AUGAGGCCGA AAGGCCGAAA GGCCGA                         36

(2) INFORMATION FOR SEQ ID NO: 929:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 929:

AAUAUGGCUG AUGAGGCCGA AAGGCCGAAA AGGCCG                         36

(2) INFORMATION FOR SEQ ID NO: 930:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 930:

CCACCAACUG AUGAGGCCGA AAGGCCGAAA UGGGAA                         36

(2) INFORMATION FOR SEQ ID NO: 931:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 931:

UGCCACCCUG AUGAGGCCGA AAGGCCGAAA UAUGGG                         36

(2) INFORMATION FOR SEQ ID NO: 932:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 932:

CAUGGCACUG AUGAGGCCGA AAGGCCGAAA UGUCUU                         36

(2) INFORMATION FOR SEQ ID NO: 933:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 933:

GUAGGUGCUG AUGAGGCCGA AAGGCCGAAA GCUGCA                         36

(2) INFORMATION FOR SEQ ID NO: 934:

(i) SEQUENCE CHARACTERISTICS:
            (A) LENGTH:              36 base pairs
            (B) TYPE:                nucleic acid
```

```
            (C) STRANDEDNESS:        single
            (D) TOPOLOGY:            linear (xi) SEQUENCE DESCRIPTION: SEQ ID NO:  934:

GGGCCGGCUG AUGAGGCCGA AAGGCCGAAA GGUGUA                              36

(2) INFORMATION FOR SEQ ID NO: 935:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO:  935:

UGAGGACCUG AUGAGGCCGA AAGGCCGAAA UGCCCU                              36

(2) INFORMATION FOR SEQ ID NO: 936:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO:  936:

GACUGAGCUG AUGAGGCCGA AAGGCCGAAA CAAUGC                              36

(2) INFORMATION FOR SEQ ID NO: 937:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO:  937:

UCUGACUCUG AUGAGGCCGA AAGGCCGAAA GGACAA                              36

(2) INFORMATION FOR SEQ ID NO: 938:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO:  938:

UGUAUCUCUG AUGAGGCCGA AAGGCCGAAA CUGAGG                              36

(2) INFORMATION FOR SEQ ID NO: 939:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO:  939:

GCUGUUGCUG AUGAGGCCGA AAGGCCGAAA UCUGAC                              36

(2) INFORMATION FOR SEQ ID NO: 940:

(i) SEQUENCE CHARACTERISTICS:
            (A) LENGTH:             36 base pairs
            (B) TYPE:               nucleic acid
            (C) STRANDEDNESS:       single
```

```
            (D) TOPOLOGY:          linear (xi) SEQUENCE DESCRIPTION: SEQ ID NO: 940:

GGCCCCACUG AUGAGGCCGA AAGGCCGAAA UGCUGU                              36

(2) INFORMATION FOR SEQ ID NO: 941:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 941:

UGGCCCCCUG AUGAGGCCGA AAGGCCGAAA AUGCUG                              36

(2) INFORMATION FOR SEQ ID NO: 942:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 942:

GUGCAGGCUG AUGAGGCCGA AAGGCCGAAA CCAUGG                              36

(2) INFORMATION FOR SEQ ID NO: 943:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 943:

AGUGUUUCUG AUGAGGCCGA AAGGCCGAAA GGUGUG                              36

(2) INFORMATION FOR SEQ ID NO: 944:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 944:

CGUGGCCCUG AUGAGGCCGA AAGGCCGAAA GUGUUU                              36

(2) INFORMATION FOR SEQ ID NO: 945:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 945:

CAGAUCACUG AUGAGGCCGA AAGGCCGAAA UGCGUG                              36

(2) INFORMATION FOR SEQ ID NO: 946:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear
```

(xi) SEQUENCE DESCRIPTION: SEQ ID NO: 946:

GACUACACUG AUGAGGCCGA AAGGCCGAAA UCAGAU                    36

(2) INFORMATION FOR SEQ ID NO: 947:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 947:

AUGUGACCUG AUGAGGCCGA AAGGCCGAAA CAGAUC                    36

(2) INFORMATION FOR SEQ ID NO: 948:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 948:

GUCAUGUCUG AUGAGGCCGA AAGGCCGAAA CUACAG                    36

(2) INFORMATION FOR SEQ ID NO: 949:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 949:

CUUGGCUCUG AUGAGGCCGA AAGGCCGAAA GUCAUG                    36

(2) INFORMATION FOR SEQ ID NO: 950:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 950:

AUGUCUUCUG AUGAGGCCGA AAGGCCGAAA GUCUUG                    36

(2) INFORMATION FOR SEQ ID NO: 951:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 951:

AUCCAUCCUG AUGAGGCCGA AAGGCCGAAA UCAUGU                    36

(2) INFORMATION FOR SEQ ID NO: 952:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 952:

AGACUUCUG AUGAGGCCGA AAGGCCGAAA CAUCCA                    36

(2) INFORMATION FOR SEQ ID NO: 953:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 953:

UAGACUUCUG AUGAGGCCGA AAGGCCGAAA ACAUCC                    36

(2) INFORMATION FOR SEQ ID NO: 954:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 954:

CAGGCUACUG AUGAGGCCGA AAGGCCGAAA CUUUAA                    36

(2) INFORMATION FOR SEQ ID NO: 955:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 955:

AUCAGGCCUG AUGAGGCCGA AAGGCCGAAA GACUUU                    36

(2) INFORMATION FOR SEQ ID NO: 956:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 956:

GUGGGGCCUG AUGAGGCCGA AAGGCCGAAA UGUCUC                    36

(2) INFORMATION FOR SEQ ID NO: 957:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 957:

CCAGUUGCUG AUGAGGCCGA AAGGCCGAAA UGUCCU                    36

(2) INFORMATION FOR SEQ ID NO: 958:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 958:

GUUUCAGCUG AUGAGGCCGA AAGGCCGAAA UUUCCC 36

(2) INFORMATION FOR SEQ ID NO: 959:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 959:

AGGCAGCCUG AUGAGGCCGA AAGGCCGAAA GUUUCA 36

(2) INFORMATION FOR SEQ ID NO: 960:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 960:

UACCCAACUG AUGAGGCCGA AAGGCCGAAA GGCAGC 36

(2) INFORMATION FOR SEQ ID NO: 961:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 961:

CAUACCCCUG AUGAGGCCGA AAGGCCGAAA UAGGCA 36

(2) INFORMATION FOR SEQ ID NO: 962:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 962:

CUCAGCACUG AUGAGGCCGA AAGGCCGAAA CCCAAU 36

(2) INFORMATION FOR SEQ ID NO: 963:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 963:

CUUCUGUCUG AUGAGGCCGA AAGGCCGAAA GUCUGU 36

(2) INFORMATION FOR SEQ ID NO: 964:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 964:

```
UCUUCUGCUG AUGAGGCCGA AAGGCCGAAA AGUCUG                                              36

(2) INFORMATION FOR SEQ ID NO: 965:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 965:

GUCUAUGCUG AUGAGGCCGA AAGGCCGAAA GGGCCA                                              36

(2) INFORMATION FOR SEQ ID NO: 966:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 966:

ACAUGUCCUG AUGAGGCCGA AAGGCCGAAA UGGAGG                                              36

(2) INFORMATION FOR SEQ ID NO: 967:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 967:

UUGAUGCCUG AUGAGGCCGA AAGGCCGAAA CACAUG                                              36

(2) INFORMATION FOR SEQ ID NO: 968:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 968:

GUGUUUUCUG AUGAGGCCGA AAGGCCGAAA UGCUAC                                              36

(2) INFORMATION FOR SEQ ID NO: 969:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 969:

CGUCAGGCUG AUGAGGCCGA AAGGCCGAAA GUGUGG                                              36

(2) INFORMATION FOR SEQ ID NO: 970:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 970:

CCGUCAGCUG AUGAGGCCGA AAGGCCGAAA AGUGUG                                              36
```

(2) INFORMATION FOR SEQ ID NO: 971:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 971:

AGUGCCCCUG AUGAGGCCGA AAGGCCGAAA GCUGGC                    36

(2) INFORMATION FOR SEQ ID NO: 972:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 972:

GUCAGUACUG AUGAGGCCGA AAGGCCGAAA CAGCAG                    36

(2) INFORMATION FOR SEQ ID NO: 973:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 973:

GGGUCAGCUG AUGAGGCCGA AAGGCCGAAA GACAGC                    36

(2) INFORMATION FOR SEQ ID NO: 974:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 974:

UAUCAUCCUG AUGAGGCCGA AAGGCCGAAA GGGUUG                    36

(2) INFORMATION FOR SEQ ID NO: 975:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 975:

AAAUACACUG AUGAGGCCGA AAGGCCGAAA UCAUCA                    36

(2) INFORMATION FOR SEQ ID NO: 976:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 976:

GAAUAAACUG AUGAGGCCGA AAGGCCGAAA CAUAUC                    36

(2) INFORMATION FOR SEQ ID NO: 977:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 977:

AUGAAUACUG AUGAGGCCGA AAGGCCGAAA UACAUA                        36

(2) INFORMATION FOR SEQ ID NO: 978:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 978:

AAUGAAUCUG AUGAGGCCGA AAGGCCGAAA AUACAU                        36

(2) INFORMATION FOR SEQ ID NO: 979:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 979:

AAAUGAACUG AUGAGGCCGA AAGGCCGAAA AAUACA                        36

(2) INFORMATION FOR SEQ ID NO: 980:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 980:

ACAAAUGCUG AUGAGGCCGA AAGGCCGAAA UAAAUA                        36

(2) INFORMATION FOR SEQ ID NO: 981:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 981:

AACAAAUCUG AUGAGGCCGA AAGGCCGAAA AUAAAU                        36

(2) INFORMATION FOR SEQ ID NO: 982:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 982:

AAUAACACUG AUGAGGCCGA AAGGCCGAAA UGAAUA                        36

(2) INFORMATION FOR SEQ ID NO: 983:

(i) SEQUENCE CHARACTERISTICS:
      (A) LENGTH:         36 base pairs
      (B) TYPE:           nucleic acid
      (C) STRANDEDNESS:   single
      (D) TOPOLOGY:      linear (xi) SEQUENCE DESCRIPTION: SEQ ID NO: 983:

AAAUAACCUG AUGAGGCCGA AAGGCCGAAA AUGAAU                             36

(2) INFORMATION FOR SEQ ID NO: 984:

(i) SEQUENCE CHARACTERISTICS:
      (A) LENGTH:         36 base pairs
      (B) TYPE:           nucleic acid
      (C) STRANDEDNESS:   single
      (D) TOPOLOGY:      linear (xi) SEQUENCE DESCRIPTION: SEQ ID NO: 984:

GUAAAAUCUG AUGAGGCCGA AAGGCCGAAA CAAAUG                             36

(2) INFORMATION FOR SEQ ID NO: 985:

(i) SEQUENCE CHARACTERISTICS:
      (A) LENGTH:         36 base pairs
      (B) TYPE:           nucleic acid
      (C) STRANDEDNESS:   single
      (D) TOPOLOGY:      linear (xi) SEQUENCE DESCRIPTION: SEQ ID NO: 985:

GGUAAAACUG AUGAGGCCGA AAGGCCGAAA ACAAAU                             36

(2) INFORMATION FOR SEQ ID NO: 986:

(i) SEQUENCE CHARACTERISTICS:
      (A) LENGTH:         36 base pairs
      (B) TYPE:           nucleic acid
      (C) STRANDEDNESS:   single
      (D) TOPOLOGY:      linear (xi) SEQUENCE DESCRIPTION: SEQ ID NO: 986:

CUGGUAACUG AUGAGGCCGA AAGGCCGAAA UAACAA                             36

(2) INFORMATION FOR SEQ ID NO: 987:

(i) SEQUENCE CHARACTERISTICS:
      (A) LENGTH:         36 base pairs
      (B) TYPE:           nucleic acid
      (C) STRANDEDNESS:   single
      (D) TOPOLOGY:      linear (xi) SEQUENCE DESCRIPTION: SEQ ID NO: 987:

GCUGGUACUG AUGAGGCCGA AAGGCCGAAA AUAACA                             36

(2) INFORMATION FOR SEQ ID NO: 988:

(i) SEQUENCE CHARACTERISTICS:
      (A) LENGTH:         36 base pairs
      (B) TYPE:           nucleic acid
      (C) STRANDEDNESS:   single
      (D) TOPOLOGY:      linear (xi) SEQUENCE DESCRIPTION: SEQ ID NO: 988:

AGCUGGUCUG AUGAGGCCGA AAGGCCGAAA AAUAAC                             36

(2) INFORMATION FOR SEQ ID NO: 989:

```
      (i) SEQUENCE CHARACTERISTICS:
           (A) LENGTH:            36 base pairs
           (B) TYPE:              nucleic acid
           (C) STRANDEDNESS:      single
           (D) TOPOLOGY:          linear (xi) SEQUENCE DESCRIPTION: SEQ ID NO: 989:

UAGCUGGCUG AUGAGGCCGA AAGGCCGAAA AAAUAA                                    36

(2) INFORMATION FOR SEQ ID NO: 990:

(i) SEQUENCE CHARACTERISTICS:
           (A) LENGTH:            36 base pairs
           (B) TYPE:              nucleic acid
           (C) STRANDEDNESS:      single
           (D) TOPOLOGY:          linear (xi) SEQUENCE DESCRIPTION: SEQ ID NO: 990:

CAAUAAACUG AUGAGGCCGA AAGGCCGAAA GCUGGU                                    36

(2) INFORMATION FOR SEQ ID NO: 991:

(i) SEQUENCE CHARACTERISTICS:
           (A) LENGTH:            36 base pairs
           (B) TYPE:              nucleic acid
           (C) STRANDEDNESS:      single
           (D) TOPOLOGY:          linear (xi) SEQUENCE DESCRIPTION: SEQ ID NO: 991:

CUCAAUACUG AUGAGGCCGA AAGGCCGAAA UAGCUG                                    36

(2) INFORMATION FOR SEQ ID NO: 992:

(i) SEQUENCE CHARACTERISTICS:
           (A) LENGTH:            36 base pairs
           (B) TYPE:              nucleic acid
           (C) STRANDEDNESS:      single
           (D) TOPOLOGY:          linear (xi) SEQUENCE DESCRIPTION: SEQ ID NO: 992:

ACUCAAUCUG AUGAGGCCGA AAGGCCGAAA AUAGCU                                    36

(2) INFORMATION FOR SEQ ID NO: 993:

(i) SEQUENCE CHARACTERISTICS:
           (A) LENGTH:            36 base pairs
           (B) TYPE:              nucleic acid
           (C) STRANDEDNESS:      single
           (D) TOPOLOGY:          linear (xi) SEQUENCE DESCRIPTION: SEQ ID NO: 993:

CACUCAACUG AUGAGGCCGA AAGGCCGAAA AAUAGC                                    36

(2) INFORMATION FOR SEQ ID NO: 994:

(i) SEQUENCE CHARACTERISTICS:
           (A) LENGTH:            36 base pairs
           (B) TYPE:              nucleic acid
           (C) STRANDEDNESS:      single
           (D) TOPOLOGY:          linear (xi) SEQUENCE DESCRIPTION: SEQ ID NO: 994:

GACACUCCUG AUGAGGCCGA AAGGCCGAAA UAAAUA                                    36

(2) INFORMATION FOR SEQ ID NO: 995:
```

```
    (i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 995:

CAUAAACUG AUGAGGCCGA AAGGCCGAAA CACUCA                              36

(2) INFORMATION FOR SEQ ID NO: 996:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 996:

UACAUAACUG AUGAGGCCGA AAGGCCGAAA GACACU                             36

(2) INFORMATION FOR SEQ ID NO: 997:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 997:

CUACAUACUG AUGAGGCCGA AAGGCCGAAA AGACAC                             36

(2) INFORMATION FOR SEQ ID NO: 998:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 998:

CCUACAUCUG AUGAGGCCGA AAGGCCGAAA AAGACA                             36

(2) INFORMATION FOR SEQ ID NO: 999:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 999:

GCCUACACUG AUGAGGCCGA AAGGCCGAAA AAAGAC                             36

(2) INFORMATION FOR SEQ ID NO: 1000:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1000:

UUUAGCCCUG AUGAGGCCGA AAGGCCGAAA CAUAAA                             36

(2) INFORMATION FOR SEQ ID NO: 1001:

(i) SEQUENCE CHARACTERISTICS:
```

```
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1001:

GUUCAUUCUG AUGAGGCCGA AAGGCCGAAA GCCUAC                          36

(2) INFORMATION FOR SEQ ID NO: 1002:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1002:

AGAGACCCUG AUGAGGCCGA AAGGCCGAAA UGUUCA                          36

(2) INFORMATION FOR SEQ ID NO: 1003:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1003:

GGCCAGACUG AUGAGGCCGA AAGGCCGAAA CCUAUG                          36

(2) INFORMATION FOR SEQ ID NO: 1004:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1004:

GAGGCCACUG AUGAGGCCGA AAGGCCGAAA GACCUA                          36

(2) INFORMATION FOR SEQ ID NO: 1005:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1005:

GCUCCGUCUG AUGAGGCCGA AAGGCCGAAA GGCCAG                          36

(2) INFORMATION FOR SEQ ID NO: 1006:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1006:

GGACUGGCUG AUGAGGCCGA AAGGCCGAAA GCUCCG                          36

(2) INFORMATION FOR SEQ ID NO: 1007:

(i) SEQUENCE CHARACTERISTICS:
            (A) LENGTH:            36 base pairs
```

```
        (B) TYPE:               nucleic acid
        (C) STRANDEDNESS:       single
        (D) TOPOLOGY:           linear (xi) SEQUENCE DESCRIPTION: SEQ ID NO: 1007:

UGACAUGCUG AUGAGGCCGA AAGGCCGAAA CUGGGA                              36

(2) INFORMATION FOR SEQ ID NO: 1008:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1008:

UGAAUGUCUG AUGAGGCCGA AAGGCCGAAA CAUGGA                              36

(2) INFORMATION FOR SEQ ID NO: 1009:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1009:

GACCUUGCUG AUGAGGCCGA AAGGCCGAAA UGUGAC                              36

(2) INFORMATION FOR SEQ ID NO: 1010:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1010:

UGACCUUCUG AUGAGGCCGA AAGGCCGAAA AUGUGA                              36

(2) INFORMATION FOR SEQ ID NO: 1011:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1011:

ACCUGGUCUG AUGAGGCCGA AAGGCCGAAA CCUUGA                              36

(2) INFORMATION FOR SEQ ID NO: 1012:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1012:

ACAACUGCUG AUGAGGCCGA AAGGCCGAAA CCUGGU                              36

(2) INFORMATION FOR SEQ ID NO: 1013:

(i) SEQUENCE CHARACTERISTICS:
        (A) LENGTH:             36 base pairs
        (B) TYPE:               nucleic acid
```

```
            (C) STRANDEDNESS:        single
            (D) TOPOLOGY:            linear (xi) SEQUENCE DESCRIPTION: SEQ ID NO: 1013:

CCUGUACCUG AUGAGGCCGA AAGGCCGAAA CUGUAC                              36

(2) INFORMATION FOR SEQ ID NO: 1014:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1014:

CAACCUGCUG AUGAGGCCGA AAGGCCGAAA CAACUG                              36

(2) INFORMATION FOR SEQ ID NO: 1015:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1015:

AGUGUACCUG AUGAGGCCGA AAGGCCGAAA CCUGUA                              36

(2) INFORMATION FOR SEQ ID NO: 1016:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1016:

UGCAGUGCUG AUGAGGCCGA AAGGCCGAAA CAACCU                              36

(2) INFORMATION FOR SEQ ID NO: 1017:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1017:

CCCAUUUCUG AUGAGGCCGA AAGGCCGAAA UCUUUU                              36

(2) INFORMATION FOR SEQ ID NO: 1018:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1018:

CAAUGAGCUG AUGAGGCCGA AAGGCCGAAA GUCCCA                              36

(2) INFORMATION FOR SEQ ID NO: 1019:

(i) SEQUENCE CHARACTERISTICS:
            (A) LENGTH:              36 base pairs
            (B) TYPE:                nucleic acid
            (C) STRANDEDNESS:        single
```

(D) TOPOLOGY:           linear (xi) SEQUENCE DESCRIPTION: SEQ ID NO: 1019:

CCAAUGACUG AUGAGGCCGA AAGGCCGAAA AGUCCC                                    36

(2) INFORMATION FOR SEQ ID NO: 1020:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1020:

GGCCAAUCUG AUGAGGCCGA AAGGCCGAAA GAAGUC                                    36

(2) INFORMATION FOR SEQ ID NO: 1021:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1021:

GUUGGCCCUG AUGAGGCCGA AAGGCCGAAA UGAGAA                                    36

(2) INFORMATION FOR SEQ ID NO: 1022:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1022:

CUGGGGACUG AUGAGGCCGA AAGGCCGAAA GGCAGG                                    36

(2) INFORMATION FOR SEQ ID NO: 1023:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1023:

UCUGGGGCUG AUGAGGCCGA AAGGCCGAAA AGGCAG                                    36

(2) INFORMATION FOR SEQ ID NO: 1024:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1024:

UUCUGGGCUG AUGAGGCCGA AAGGCCGAAA AAGGCA                                    36

(2) INFORMATION FOR SEQ ID NO: 1025:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1025:

AUAGAAACUG AUGAGGCCGA AAGGCCGAAA UCACUC                          36

(2) INFORMATION FOR SEQ ID NO: 1026:

(i) SEQUENCE CHARACTERISTICS:
        (A) LENGTH:         36 base pairs
        (B) TYPE:           nucleic acid
        (C) STRANDEDNESS:   single
        (D) TOPOLOGY:      linear (xi) SEQUENCE DESCRIPTION: SEQ ID NO: 1026:

GAUAGAACUG AUGAGGCCGA AAGGCCGAAA AUCACU                          36

(2) INFORMATION FOR SEQ ID NO: 1027:

(i) SEQUENCE CHARACTERISTICS:
        (A) LENGTH:         36 base pairs
        (B) TYPE:           nucleic acid
        (C) STRANDEDNESS:   single
        (D) TOPOLOGY:      linear (xi) SEQUENCE DESCRIPTION: SEQ ID NO: 1027:

CGAUAGACUG AUGAGGCCGA AAGGCCGAAA AAUCAC                          36

(2) INFORMATION FOR SEQ ID NO: 1028:

(i) SEQUENCE CHARACTERISTICS:
        (A) LENGTH:         36 base pairs
        (B) TYPE:           nucleic acid
        (C) STRANDEDNESS:   single
        (D) TOPOLOGY:      linear (xi) SEQUENCE DESCRIPTION: SEQ ID NO: 1028:

CCGAUAGCUG AUGAGGCCGA AAGGCCGAAA AAAUCA                          36

(2) INFORMATION FOR SEQ ID NO: 1029:

(i) SEQUENCE CHARACTERISTICS:
        (A) LENGTH:         36 base pairs
        (B) TYPE:           nucleic acid
        (C) STRANDEDNESS:   single
        (D) TOPOLOGY:      linear (xi) SEQUENCE DESCRIPTION: SEQ ID NO: 1029:

GCCGAUACUG AUGAGGCCGA AAGGCCGAAA AAAAUC                          36

(2) INFORMATION FOR SEQ ID NO: 1030:

(i) SEQUENCE CHARACTERISTICS:
        (A) LENGTH:         36 base pairs
        (B) TYPE:           nucleic acid
        (C) STRANDEDNESS:   single
        (D) TOPOLOGY:      linear (xi) SEQUENCE DESCRIPTION: SEQ ID NO: 1030:

GUGCCGACUG AUGAGGCCGA AAGGCCGAAA GAAAAA                          36

(2) INFORMATION FOR SEQ ID NO: 1031:

(i) SEQUENCE CHARACTERISTICS:
        (A) LENGTH:         36 base pairs
        (B) TYPE:           nucleic acid
        (C) STRANDEDNESS:   single
        (D) TOPOLOGY:      linear (xi) SEQUENCE DESCRIPTION: SEQ ID NO: 1031:

UUGUGCCCUG AUGAGGCCGA AAGGCCGAAA UAGAAA     36

(2) INFORMATION FOR SEQ ID NO: 1032:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO: 1032:

GUCCAUACUG AUGAGGCCGA AAGGCCGAAA GUGCUU     36

(2) INFORMATION FOR SEQ ID NO: 1033:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO: 1033:

CAGUCCACUG AUGAGGCCGA AAGGCCGAAA UAGUGC     36

(2) INFORMATION FOR SEQ ID NO: 1034:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO: 1034:

GAACCAUCUG AUGAGGCCGA AAGGCCGAAA CCAGUC     36

(2) INFORMATION FOR SEQ ID NO: 1035:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO: 1035:

ACCUGUGCUG AUGAGGCCGA AAGGCCGAAA CCAUUA     36

(2) INFORMATION FOR SEQ ID NO: 1036:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO: 1036:

AACCUGUCUG AUGAGGCCGA AAGGCCGAAA ACCAUU     36

(2) INFORMATION FOR SEQ ID NO: 1037:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO: 1037:

AUCUCUGCUG AUGAGGCCGA AAGGCCGAAA CCUGUG                36

(2) INFORMATION FOR SEQ ID NO: 1038:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1038:

AAUCUCUCUG AUGAGGCCGA AAGGCCGAAA ACCUGU                36

(2) INFORMATION FOR SEQ ID NO: 1039:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1039:

ACUGGGUCUG AUGAGGCCGA AAGGCCGAAA UCUCUG                36

(2) INFORMATION FOR SEQ ID NO: 1040:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1040:

CACUGGGCUG AUGAGGCCGA AAGGCCGAAA AUCUCU                36

(2) INFORMATION FOR SEQ ID NO: 1041:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1041:

GAGGAAUCUG AUGAGGCCGA AAGGCCGAAA GGCCUC                36

(2) INFORMATION FOR SEQ ID NO: 1042:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1042:

GGAGGAACUG AUGAGGCCGA AAGGCCGAAA AGGCCU                36

(2) INFORMATION FOR SEQ ID NO: 1043:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1043:

```
AGGGAGGCUG AUGAGGCCGA AAGGCCGAAA UAAGGC                                    36

(2) INFORMATION FOR SEQ ID NO: 1044:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO: 1044:

AAGGGAGCUG AUGAGGCCGA AAGGCCGAAA AUAAGG                                    36

(2) INFORMATION FOR SEQ ID NO: 1045:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO: 1045:

GGGAAGGCUG AUGAGGCCGA AAGGCCGAAA GGAAUA                                    36

(2) INFORMATION FOR SEQ ID NO: 1046:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO: 1046:

UGGGGGGCUG AUGAGGCCGA AAGGCCGAAA GGGAGG                                    36

(2) INFORMATION FOR SEQ ID NO: 1047:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO: 1047:

UUGGGGGCUG AUGAGGCCGA AAGGCCGAAA AGGGAG                                    36

(2) INFORMATION FOR SEQ ID NO: 1048:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO: 1048:

GCUAACACUG AUGAGGCCGA AAGGCCGAAA GGUGUC                                    36

(2) INFORMATION FOR SEQ ID NO: 1049:

(i) SEQUENCE CHARACTERISTICS:
         (A) LENGTH:          36 base pairs
         (B) TYPE:            nucleic acid
         (C) STRANDEDNESS:    single
         (D) TOPOLOGY:        linear (xi) SEQUENCE DESCRIPTION: SEQ ID NO: 1049:

GGCUAACCUG AUGAGGCCGA AAGGCCGAAA AGGUGU                                    36
```

(2) INFORMATION FOR SEQ ID NO: 1050:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1050:

GGUGGCUCUG AUGAGGCCGA AAGGCCGAAA CAAAGG                    36

(2) INFORMATION FOR SEQ ID NO: 1051:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1051:

AGGUGGCCUG AUGAGGCCGA AAGGCCGAAA ACAAAG                    36

(2) INFORMATION FOR SEQ ID NO: 1052:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1052:

GGGUGGGCUG AUGAGGCCGA AAGGCCGAAA GGUGGC                    36

(2) INFORMATION FOR SEQ ID NO: 1053:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1053:

AGAAAUGCUG AUGAGGCCGA AAGGCCGAAA UGUGGG                    36

(2) INFORMATION FOR SEQ ID NO: 1054:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1054:

UGGCAGACUG AUGAGGCCGA AAGGCCGAAA UGUAUG                    36

(2) INFORMATION FOR SEQ ID NO: 1055:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1055:

CUGGCAGCUG AUGAGGCCGA AAGGCCGAAA AUGUAU                    36

(2) INFORMATION FOR SEQ ID NO: 1056:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1056:

ACUGGCACUG AUGAGGCCGA AAGGCCGAAA AAUGUA                                      36

(2) INFORMATION FOR SEQ ID NO: 1057:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1057:

CAUUGUGCUG AUGAGGCCGA AAGGCCGAAA CACUGG                                      36

(2) INFORMATION FOR SEQ ID NO: 1058:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1058:

UCAUUGUCUG AUGAGGCCGA AAGGCCGAAA ACACUG                                      36

(2) INFORMATION FOR SEQ ID NO: 1059:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1059:

GACCGCUCUG AUGAGGCCGA AAGGCCGAAA GUGUCA                                      36

(2) INFORMATION FOR SEQ ID NO: 1060:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1060:

CAGACAUCUG AUGAGGCCGA AAGGCCGAAA CCGCUG                                      36

(2) INFORMATION FOR SEQ ID NO: 1061:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1061:

AUGUCCACUG AUGAGGCCGA AAGGCCGAAA CAUGAC                                      36

(2) INFORMATION FOR SEQ ID NO: 1062:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO: 1062:

UUGGGCACUG AUGAGGCCGA AAGGCCGAAA UUCCCU                                      36

(2) INFORMATION FOR SEQ ID NO: 1063:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO: 1063:

CAAGGCACUG AUGAGGCCGA AAGGCCGAAA GCUUGG                                      36

(2) INFORMATION FOR SEQ ID NO: 1064:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO: 1064:

AGAGGACCUG AUGAGGCCGA AAGGCCGAAA GGCAUA                                      36

(2) INFORMATION FOR SEQ ID NO: 1065:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO: 1065:

ACAAGAGCUG AUGAGGCCGA AAGGCCGAAA CAAGGC                                      36

(2) INFORMATION FOR SEQ ID NO: 1066:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO: 1066:

AGGACAACUG AUGAGGCCGA AAGGCCGAAA GGACAA                                      36

(2) INFORMATION FOR SEQ ID NO: 1067:

(i) SEQUENCE CHARACTERISTICS:
        (A) LENGTH:        36 base pairs
        (B) TYPE:          nucleic acid
        (C) STRANDEDNESS:  single
        (D) TOPOLOGY:      linear (xi) SEQUENCE DESCRIPTION: SEQ ID NO: 1067:

ACAGGACCUG AUGAGGCCGA AAGGCCGAAA GAGGAC                                      36

(2) INFORMATION FOR SEQ ID NO: 1068:

```
    (i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1068:

CAAACAGCUG AUGAGGCCGA AAGGCCGAAA CAAGAG                           36

(2) INFORMATION FOR SEQ ID NO: 1069:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1069:

AAAUGCACUG AUGAGGCCGA AAGGCCGAAA CAGGAC                           36

(2) INFORMATION FOR SEQ ID NO: 1070:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1070:

GAAAUGCCUG AUGAGGCCGA AAGGCCGAAA ACAGGA                           36

(2) INFORMATION FOR SEQ ID NO: 1071:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1071:

CCAGUGACUG AUGAGGCCGA AAGGCCGAAA UGCAAA                           36

(2) INFORMATION FOR SEQ ID NO: 1072:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1072:

CCCAGUGCUG AUGAGGCCGA AAGGCCGAAA AUGCAA                           36

(2) INFORMATION FOR SEQ ID NO: 1073:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1073:

UCCCAGUCUG AUGAGGCCGA AAGGCCGAAA AAUGCA                           36

(2) INFORMATION FOR SEQ ID NO: 1074:
```

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1074:

AUAGUGCCUG AUGAGGCCGA AAGGCCGAAA GCUCCC                          36

(2) INFORMATION FOR SEQ ID NO: 1075:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1075:

GCUGCAACUG AUGAGGCCGA AAGGCCGAAA GUGCAA                          36

(2) INFORMATION FOR SEQ ID NO: 1076:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1076:

GAGCUGCCUG AUGAGGCCGA AAGGCCGAAA UAGUGC                          36

(2) INFORMATION FOR SEQ ID NO: 1077:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1077:

GAAACUGCUG AUGAGGCCGA AAGGCCGAAA GCUGCA                          36

(2) INFORMATION FOR SEQ ID NO: 1078:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1078:

UGCAGGACUG AUGAGGCCGA AAGGCCGAAA CUGGAG                          36

(2) INFORMATION FOR SEQ ID NO: 1079:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1079:

CUGCAGGCUG AUGAGGCCGA AAGGCCGAAA ACUGGA                          36

(2) INFORMATION FOR SEQ ID NO: 1080:

(i) SEQUENCE CHARACTERISTICS:

```
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1080:

ACUGCAGCUG AUGAGGCCGA AAGGCCGAAA AACUGG                              36

(2) INFORMATION FOR SEQ ID NO: 1081:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1081:

GGACCCUCUG AUGAGGCCGA AAGGCCGAAA UCACUG                              36

(2) INFORMATION FOR SEQ ID NO: 1082:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1082:

CUUGCAGCUG AUGAGGCCGA AAGGCCGAAA CCCUGA                              36

(2) INFORMATION FOR SEQ ID NO: 1083:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1083:

CCUCCAACUG AUGAGGCCGA AAGGCCGAAA CCUUGG                              36

(2) INFORMATION FOR SEQ ID NO: 1084:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1084:

GUCCUCCCUG AUGAGGCCGA AAGGCCGAAA UACCUU                              36

(2) INFORMATION FOR SEQ ID NO: 1085:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1085:

UGGGAGGCUG AUGAGGCCGA AAGGCCGAAA GUCCUC                              36

(2) INFORMATION FOR SEQ ID NO: 1086:

(i) SEQUENCE CHARACTERISTICS:
            (A) LENGTH:           36 base pairs
```

```
            (B) TYPE:              nucleic acid
            (C) STRANDEDNESS:      single
            (D) TOPOLOGY:          linear (xi) SEQUENCE DESCRIPTION: SEQ ID NO: 1086:

AAGCUGGCUG AUGAGGCCGA AAGGCCGAAA GGGAGU                          36

(2) INFORMATION FOR SEQ ID NO: 1087:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1087:

CCUUCCACUG AUGAGGCCGA AAGGCCGAAA GCUGGG                          36

(2) INFORMATION FOR SEQ ID NO: 1088:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1088:

CCCUUCCCUG AUGAGGCCGA AAGGCCGAAA AGCUGG                          36

(2) INFORMATION FOR SEQ ID NO: 1089:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1089:

CGCGGAUCUG AUGAGGCCGA AAGGCCGAAA CCCUUC                          36

(2) INFORMATION FOR SEQ ID NO: 1090:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1090:

ACACGCGCUG AUGAGGCCGA AAGGCCGAAA UGACCC                          36

(2) INFORMATION FOR SEQ ID NO: 1091:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1091:

CUACACACUG AUGAGGCCGA AAGGCCGAAA CACACA                          36

(2) INFORMATION FOR SEQ ID NO: 1092:

(i) SEQUENCE CHARACTERISTICS:
            (A) LENGTH:            36 base pairs
            (B) TYPE:              nucleic acid
```

```
            (C) STRANDEDNESS:        single
            (D) TOPOLOGY:            linear (xi) SEQUENCE DESCRIPTION: SEQ ID NO: 1092:

GCUUGUCCUG AUGAGGCCGA AAGGCCGAAA CACAUA                           36

(2) INFORMATION FOR SEQ ID NO: 1093:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1093:

AGAGCGACUG AUGAGGCCGA AAGGCCGAAA GCUUGU                           36

(2) INFORMATION FOR SEQ ID NO: 1094:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1094:

ACAGAGCCUG AUGAGGCCGA AAGGCCGAAA GAGCUU                           36

(2) INFORMATION FOR SEQ ID NO: 1095:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1095:

GGUGACACUG AUGAGGCCGA AAGGCCGAAA GCGAGA                           36

(2) INFORMATION FOR SEQ ID NO: 1096:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1096:

CCUGGGUCUG AUGAGGCCGA AAGGCCGAAA CAGAGC                           36

(2) INFORMATION FOR SEQ ID NO: 1097:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1097:

GAACCAUCUG AUGAGGCCGA AAGGCCGAAA UUGCAC                           36

(2) INFORMATION FOR SEQ ID NO: 1098:

(i) SEQUENCE CHARACTERISTICS:
            (A) LENGTH:              36 base pairs
            (B) TYPE:                nucleic acid
            (C) STRANDEDNESS:        single
```

```
         (D) TOPOLOGY:            linear (xi) SEQUENCE DESCRIPTION: SEQ ID NO: 1098:

UGCAGUCUG AUGAGGCCGA AAGGCCGAAA CCAUGA                              36

(2) INFORMATION FOR SEQ ID NO: 1099:

(i) SEQUENCE CHARACTERISTICS:
         (A) LENGTH:             36 base pairs
         (B) TYPE:               nucleic acid
         (C) STRANDEDNESS:       single
         (D) TOPOLOGY:           linear (xi) SEQUENCE DESCRIPTION: SEQ ID NO: 1099:

CUGCAGUCUG AUGAGGCCGA AAGGCCGAAA ACCAUG                             36

(2) INFORMATION FOR SEQ ID NO: 1100:

(i) SEQUENCE CHARACTERISTICS:
         (A) LENGTH:             36 base pairs
         (B) TYPE:               nucleic acid
         (C) STRANDEDNESS:       single
         (D) TOPOLOGY:           linear (xi) SEQUENCE DESCRIPTION: SEQ ID NO: 1100:

AGGUCAACUG AUGAGGCCGA AAGGCCGAAA CUGCAG                             36

(2) INFORMATION FOR SEQ ID NO: 1101:

(i) SEQUENCE CHARACTERISTICS:
         (A) LENGTH:             36 base pairs
         (B) TYPE:               nucleic acid
         (C) STRANDEDNESS:       single
         (D) TOPOLOGY:           linear (xi) SEQUENCE DESCRIPTION: SEQ ID NO: 1101:

AAAGGUCCUG AUGAGGCCGA AAGGCCGAAA GACUGC                             36

(2) INFORMATION FOR SEQ ID NO: 1102:

(i) SEQUENCE CHARACTERISTICS:
         (A) LENGTH:             36 base pairs
         (B) TYPE:               nucleic acid
         (C) STRANDEDNESS:       single
         (D) TOPOLOGY:           linear (xi) SEQUENCE DESCRIPTION: SEQ ID NO: 1102:

AGCCCAACUG AUGAGGCCGA AAGGCCGAAA GGUCAA                             36

(2) INFORMATION FOR SEQ ID NO: 1103:

(i) SEQUENCE CHARACTERISTICS:
         (A) LENGTH:             36 base pairs
         (B) TYPE:               nucleic acid
         (C) STRANDEDNESS:       single
         (D) TOPOLOGY:           linear (xi) SEQUENCE DESCRIPTION: SEQ ID NO: 1103:

GAGCCCACUG AUGAGGCCGA AAGGCCGAAA AGGUCA                             36

(2) INFORMATION FOR SEQ ID NO: 1104:

(i) SEQUENCE CHARACTERISTICS:
         (A) LENGTH:             36 base pairs
         (B) TYPE:               nucleic acid
         (C) STRANDEDNESS:       single
         (D) TOPOLOGY:           linear
```

(xi) SEQUENCE DESCRIPTION: SEQ ID NO: 1104:

UGAGCCCCUG AUGAGGCCGA AAGGCCGAAA AAGGUC                                  36

(2) INFORMATION FOR SEQ ID NO: 1105:

(i) SEQUENCE CHARACTERISTICS:
                (A) LENGTH:             36 base pairs
                (B) TYPE:               nucleic acid
                (C) STRANDEDNESS:       single
                (D) TOPOLOGY:           linear (xi) SEQUENCE DESCRIPTION: SEQ ID NO: 1105:

AUCACUUCUG AUGAGGCCGA AAGGCCGAAA GCCCAA                                  36

(2) INFORMATION FOR SEQ ID NO: 1106:

(i) SEQUENCE CHARACTERISTICS:
                (A) LENGTH:             36 base pairs
                (B) TYPE:               nucleic acid
                (C) STRANDEDNESS:       single
                (D) TOPOLOGY:           linear (xi) SEQUENCE DESCRIPTION: SEQ ID NO: 1106:

GUGGGAGCUG AUGAGGCCGA AAGGCCGAAA UCACUU                                  36

(2) INFORMATION FOR SEQ ID NO: 1107:

(i) SEQUENCE CHARACTERISTICS:
                (A) LENGTH:             36 base pairs
                (B) TYPE:               nucleic acid
                (C) STRANDEDNESS:       single
                (D) TOPOLOGY:           linear (xi) SEQUENCE DESCRIPTION: SEQ ID NO: 1107:

GAGGUGGCUG AUGAGGCCGA AAGGCCGAAA GGAUCA                                  36

(2) INFORMATION FOR SEQ ID NO: 1108:

(i) SEQUENCE CHARACTERISTICS:
                (A) LENGTH:             36 base pairs
                (B) TYPE:               nucleic acid
                (C) STRANDEDNESS:       single
                (D) TOPOLOGY:           linear (xi) SEQUENCE DESCRIPTION: SEQ ID NO: 1108:

GGAGGCUCUG AUGAGGCCGA AAGGCCGAAA GGUGGG                                  36

(2) INFORMATION FOR SEQ ID NO: 1109:

(i) SEQUENCE CHARACTERISTICS:
                (A) LENGTH:             36 base pairs
                (B) TYPE:               nucleic acid
                (C) STRANDEDNESS:       single
                (D) TOPOLOGY:           linear (xi) SEQUENCE DESCRIPTION: SEQ ID NO: 1109:

UACUCAGCUG AUGAGGCCGA AAGGCCGAAA GGCUGA                                  36

(2) INFORMATION FOR SEQ ID NO: 1110:

(i) SEQUENCE CHARACTERISTICS:
                (A) LENGTH:             36 base pairs
                (B) TYPE:               nucleic acid
                (C) STRANDEDNESS:       single
                (D) TOPOLOGY:           linear (xi) SEQUENCE DESCRIPTION: SEQ ID NO: 1110:

UCCCAGCCUG AUGAGGCCGA AAGGCCGAAA CUCAGG                                    36

(2) INFORMATION FOR SEQ ID NO: 1111:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1111:

GUGAGCCCUG AUGAGGCCGA AAGGCCGAAA UGGUCC                                    36

(2) INFORMATION FOR SEQ ID NO: 1112:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1112:

GUGUUGUCUG AUGAGGCCGA AAGGCCGAAA GCCUAU                                    36

(2) INFORMATION FOR SEQ ID NO: 1113:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1113:

AAAAUCACUG AUGAGGCCGA AAGGCCGAAA UUUGCC                                    36

(2) INFORMATION FOR SEQ ID NO: 1114:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1114:

AAAAAUCCUG AUGAGGCCGA AAGGCCGAAA AUUUGC                                    36

(2) INFORMATION FOR SEQ ID NO: 1115:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1115:

AAAAAAACUG AUGAGGCCGA AAGGCCGAAA UCAAAU                                    36

(2) INFORMATION FOR SEQ ID NO: 1116:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1116:

AAAAAAACUG AUGAGGCCGA AAGGCCGAAA AUCAAA                36

(2) INFORMATION FOR SEQ ID NO: 1117:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1117:

AAAAAAACUG AUGAGGCCGA AAGGCCGAAA AAUCAA                 36

(2) INFORMATION FOR SEQ ID NO: 1118:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1118:

AAAAAAACUG AUGAGGCCGA AAGGCCGAAA AAAUCA                 36

(2) INFORMATION FOR SEQ ID NO: 1119:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1119:

AAAAAAACUG AUGAGGCCGA AAGGCCGAAA AAAAUC                 36

(2) INFORMATION FOR SEQ ID NO: 1120:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1120:

AAAAAAACUG AUGAGGCCGA AAGGCCGAAA AAAAAU                 36

(2) INFORMATION FOR SEQ ID NO: 1121:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1121:

AAAAAAACUG AUGAGGCCGA AAGGCCGAAA AAAAAA                 36

(2) INFORMATION FOR SEQ ID NO: 1122:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1122:

```
AAAAAAACUG AUGAGGCCGA AAGGCCGAAA AAAAAA                                     36

(2) INFORMATION FOR SEQ ID NO: 1123:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1123:

GAAAAAACUG AUGAGGCCGA AAGGCCGAAA AAAAAA                                     36

(2) INFORMATION FOR SEQ ID NO: 1124:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1124:

UGAAAAACUG AUGAGGCCGA AAGGCCGAAA AAAAAA                                     36

(2) INFORMATION FOR SEQ ID NO: 1125:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1125:

CUGAAAACUG AUGAGGCCGA AAGGCCGAAA AAAAAA                                     36

(2) INFORMATION FOR SEQ ID NO: 1126:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1126:

UCUGAAACUG AUGAGGCCGA AAGGCCGAAA AAAAAA                                     36

(2) INFORMATION FOR SEQ ID NO: 1127:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1127:

CUCUGAACUG AUGAGGCCGA AAGGCCGAAA AAAAAA                                     36

(2) INFORMATION FOR SEQ ID NO: 1128:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1128:

UCUCUGACUG AUGAGGCCGA AAGGCCGAAA AAAAAA                                     36
```

(2) INFORMATION FOR SEQ ID NO: 1129:

(i) SEQUENCE CHARACTERISTICS:
        (A) LENGTH:            36 base pairs
        (B) TYPE:              nucleic acid
        (C) STRANDEDNESS:     single
        (D) TOPOLOGY:         linear (xi) SEQUENCE DESCRIPTION: SEQ ID NO: 1129:

GUCUCUGCUG AUGAGGCCGA AAGGCCGAAA AAAAAA                           36

(2) INFORMATION FOR SEQ ID NO: 1130:

(i) SEQUENCE CHARACTERISTICS:
        (A) LENGTH:            36 base pairs
        (B) TYPE:              nucleic acid
        (C) STRANDEDNESS:     single
        (D) TOPOLOGY:         linear (xi) SEQUENCE DESCRIPTION: SEQ ID NO: 1130:

CGUCUCUCUG AUGAGGCCGA AAGGCCGAAA AAAAAA                           36

(2) INFORMATION FOR SEQ ID NO: 1131:

(i) SEQUENCE CHARACTERISTICS:
        (A) LENGTH:            36 base pairs
        (B) TYPE:              nucleic acid
        (C) STRANDEDNESS:     single
        (D) TOPOLOGY:         linear (xi) SEQUENCE DESCRIPTION: SEQ ID NO: 1131:

GUUGCGACUG AUGAGGCCGA AAGGCCGAAA CCCCGU                           36

(2) INFORMATION FOR SEQ ID NO: 1132:

(i) SEQUENCE CHARACTERISTICS:
        (A) LENGTH:            36 base pairs
        (B) TYPE:              nucleic acid
        (C) STRANDEDNESS:     single
        (D) TOPOLOGY:         linear (xi) SEQUENCE DESCRIPTION: SEQ ID NO: 1132:

AUGUUGCCUG AUGAGGCCGA AAGGCCGAAA GACCCC                           36

(2) INFORMATION FOR SEQ ID NO: 1133:

(i) SEQUENCE CHARACTERISTICS:
        (A) LENGTH:            36 base pairs
        (B) TYPE:              nucleic acid
        (C) STRANDEDNESS:     single
        (D) TOPOLOGY:         linear (xi) SEQUENCE DESCRIPTION: SEQ ID NO: 1133:

UCUGGGCCUG AUGAGGCCGA AAGGCCGAAA UGUUGC                           36

(2) INFORMATION FOR SEQ ID NO: 1134:

(i) SEQUENCE CHARACTERISTICS:
        (A) LENGTH:            36 base pairs
        (B) TYPE:              nucleic acid
        (C) STRANDEDNESS:     single
        (D) TOPOLOGY:         linear (xi) SEQUENCE DESCRIPTION: SEQ ID NO: 1134:

ACAAAGGCUG AUGAGGCCGA AAGGCCGAAA GUCUGG                           36

(2) INFORMATION FOR SEQ ID NO: 1135:

(i) SEQUENCE CHARACTERISTICS:
        (A) LENGTH:         36 base pairs
        (B) TYPE:           nucleic acid
        (C) STRANDEDNESS:  single
        (D) TOPOLOGY:      linear (xi) SEQUENCE DESCRIPTION: SEQ ID NO: 1135:

CACAAAGCUG AUGAGGCCGA AAGGCCGAAA AGUCUG                           36

(2) INFORMATION FOR SEQ ID NO: 1136:

(i) SEQUENCE CHARACTERISTICS:
        (A) LENGTH:         36 base pairs
        (B) TYPE:           nucleic acid
        (C) STRANDEDNESS:  single
        (D) TOPOLOGY:      linear (xi) SEQUENCE DESCRIPTION: SEQ ID NO: 1136:

UAACACACUG AUGAGGCCGA AAGGCCGAAA GGAAGU                           36

(2) INFORMATION FOR SEQ ID NO: 1137:

(i) SEQUENCE CHARACTERISTICS:
        (A) LENGTH:         36 base pairs
        (B) TYPE:           nucleic acid
        (C) STRANDEDNESS:  single
        (D) TOPOLOGY:      linear (xi) SEQUENCE DESCRIPTION: SEQ ID NO: 1137:

CUAACACCUG AUGAGGCCGA AAGGCCGAAA AGGAAG                           36

(2) INFORMATION FOR SEQ ID NO: 1138:

(i) SEQUENCE CHARACTERISTICS:
        (A) LENGTH:         36 base pairs
        (B) TYPE:           nucleic acid
        (C) STRANDEDNESS:  single
        (D) TOPOLOGY:      linear (xi) SEQUENCE DESCRIPTION: SEQ ID NO: 1138:

AUUAACUCUG AUGAGGCCGA AAGGCCGAAA CACAAA                           36

(2) INFORMATION FOR SEQ ID NO: 1139:

(i) SEQUENCE CHARACTERISTICS:
        (A) LENGTH:         36 base pairs
        (B) TYPE:           nucleic acid
        (C) STRANDEDNESS:  single
        (D) TOPOLOGY:      linear (xi) SEQUENCE DESCRIPTION: SEQ ID NO: 1139:

UAUUAACCUG AUGAGGCCGA AAGGCCGAAA ACACAA                           36

(2) INFORMATION FOR SEQ ID NO: 1140:

(i) SEQUENCE CHARACTERISTICS:
        (A) LENGTH:         36 base pairs
        (B) TYPE:           nucleic acid
        (C) STRANDEDNESS:  single
        (D) TOPOLOGY:      linear (xi) SEQUENCE DESCRIPTION: SEQ ID NO: 1140:

CUUUAUUCUG AUGAGGCCGA AAGGCCGAAA CUAACA                           36

(2) INFORMATION FOR SEQ ID NO: 1141:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1141:

GCUUUAUCUG AUGAGGCCGA AAGGCCGAAA ACUAAC                                     36

(2) INFORMATION FOR SEQ ID NO: 1142:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1142:

AAAGCUUCUG AUGAGGCCGA AAGGCCGAAA UUAACU                                     36

(2) INFORMATION FOR SEQ ID NO: 1143:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1143:

GUUGAGACUG AUGAGGCCGA AAGGCCGAAA GCUUUA                                     36

(2) INFORMATION FOR SEQ ID NO: 1144:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1144:

AGUUGAGCUG AUGAGGCCGA AAGGCCGAAA AGCUUU                                     36

(2) INFORMATION FOR SEQ ID NO: 1145:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1145:

CAGUUGACUG AUGAGGCCGA AAGGCCGAAA AAGCUU                                     36

(2) INFORMATION FOR SEQ ID NO: 1146:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1146:

GGCAGUUCUG AUGAGGCCGA AAGGCCGAAA GAAAGC                                     36

(2) INFORMATION FOR SEQ ID NO: 1147:

```
    (i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1147:

CAACGGUCUG AUGAGGCCGA AAGGCCGAAA CCAGGG                                     36

(2) INFORMATION FOR SEQ ID NO: 1148:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1148:

AGCAGAGCUG AUGAGGCCGA AAGGCCGAAA CCACUG                                     36

(2) INFORMATION FOR SEQ ID NO: 1149:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1149:

AGGAGCACUG AUGAGGCCGA AAGGCCGAAA GAACCA                                     36

(2) INFORMATION FOR SEQ ID NO: 1150:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1150:

UGUGGAGCUG AUGAGGCCGA AAGGCCGAAA GCAGAG                                     36

(2) INFORMATION FOR SEQ ID NO: 1151:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1151:

CGACCCUCUG AUGAGGCCGA AAGGCCGAAA UGAGAA                                     36

(2) INFORMATION FOR SEQ ID NO: 1152:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1152:

AGGCUACCUG AUGAGGCCGA AAGGCCGAAA GUGUGC                                     36

(2) INFORMATION FOR SEQ ID NO: 1153:
```

(i) SEQUENCE CHARACTERISTICS:
           (A) LENGTH:         36 base pairs
           (B) TYPE:           nucleic acid
           (C) STRANDEDNESS:   single
           (D) TOPOLOGY:       linear (xi) SEQUENCE DESCRIPTION: SEQ ID NO: 1153:

CCAGGCUCUG AUGAGGCCGA AAGGCCGAAA GGUCCU                                   36

(2) INFORMATION FOR SEQ ID NO: 1154:

(i) SEQUENCE CHARACTERISTICS:
           (A) LENGTH:         36 base pairs
           (B) TYPE:           nucleic acid
           (C) STRANDEDNESS:   single
           (D) TOPOLOGY:       linear (xi) SEQUENCE DESCRIPTION: SEQ ID NO: 1154:

CCAUCACCUG AUGAGGCCGA AAGGCCGAAA GGCCCA                                   36

(2) INFORMATION FOR SEQ ID NO: 1155:

(i) SEQUENCE CHARACTERISTICS:
           (A) LENGTH:         36 base pairs
           (B) TYPE:           nucleic acid
           (C) STRANDEDNESS:   single
           (D) TOPOLOGY:       linear (xi) SEQUENCE DESCRIPTION: SEQ ID NO: 1155:

GGAGCUACUG AUGAGGCCGA AAGGCCGAAA GGCAUG                                   36

(2) INFORMATION FOR SEQ ID NO: 1156:

(i) SEQUENCE CHARACTERISTICS:
           (A) LENGTH:         36 base pairs
           (B) TYPE:           nucleic acid
           (C) STRANDEDNESS:   single
           (D) TOPOLOGY:       linear (xi) SEQUENCE DESCRIPTION: SEQ ID NO: 1156:

CUGCUGGCUG AUGAGGCCGA AAGGCCGAAA GGGGUG                                   36

(2) INFORMATION FOR SEQ ID NO: 1157:

(i) SEQUENCE CHARACTERISTICS:
           (A) LENGTH:         36 base pairs
           (B) TYPE:           nucleic acid
           (C) STRANDEDNESS:   single
           (D) TOPOLOGY:       linear (xi) SEQUENCE DESCRIPTION: SEQ ID NO: 1157:

GGGCCAGCUG AUGAGGCCGA AAGGCCGAAA GCAGAG                                   36

(2) INFORMATION FOR SEQ ID NO: 1158:

(i) SEQUENCE CHARACTERISTICS:
           (A) LENGTH:         36 base pairs
           (B) TYPE:           nucleic acid
           (C) STRANDEDNESS:   single
           (D) TOPOLOGY:       linear (xi) SEQUENCE DESCRIPTION: SEQ ID NO: 1158:

CCAGCAGCUG AUGAGGCCGA AAGGCCGAAA CUGGCA                                   36

(2) INFORMATION FOR SEQ ID NO: 1159:

(i) SEQUENCE CHARACTERISTICS:

```
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1159:

GGGCCAGCUG AUGAGGCCGA AAGGCCGAAA GCAGAG                         36

(2) INFORMATION FOR SEQ ID NO: 1160:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1160:

AGGAGCACUG AUGAGGCCGA AAGGCCGAAA GAACCA                         36

(2) INFORMATION FOR SEQ ID NO: 1161:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1161:

UCCUGGUCUG AUGAGGCCGA AAGGCCGAAA CAUUCC                         36

(2) INFORMATION FOR SEQ ID NO: 1162:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1162:

GGGCCAGCUG AUGAGGCCGA AAGGCCGAAA GCAGAG                         36

(2) INFORMATION FOR SEQ ID NO: 1163:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1163:

GGAAGCGCUG AUGAGGCCGA AAGGCCGAAA CGACUG                         36

(2) INFORMATION FOR SEQ ID NO: 1164:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1164:

AGUGGCUCUG AUGAGGCCGA AAGGCCGAAA CACAGA                         36

(2) INFORMATION FOR SEQ ID NO: 1165:

(i) SEQUENCE CHARACTERISTICS:
            (A) LENGTH:            36 base pairs
```

```
            (B) TYPE:               nucleic acid
            (C) STRANDEDNESS:       single
            (D) TOPOLOGY:           linear (xi) SEQUENCE DESCRIPTION: SEQ ID NO: 1165:

GGUUUUUCUG AUGAGGCCGA AAGGCCGAAA ACAGGA                              36

(2) INFORMATION FOR SEQ ID NO: 1166:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1166:

GCAAAACCUG AUGAGGCCGA AAGGCCGAAA CUUCUG                              36

(2) INFORMATION FOR SEQ ID NO: 1167:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1167:

GGGGCAGCUG AUGAGGCCGA AAGGCCGAAA AGGCUU                              36

(2) INFORMATION FOR SEQ ID NO: 1168:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1168:

CUGCACGCUG AUGAGGCCGA AAGGCCGAAA CCCACC                              36

(2) INFORMATION FOR SEQ ID NO: 1169:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1169:

GCCAGAGCUG AUGAGGCCGA AAGGCCGAAA AGUGGC                              36

(2) INFORMATION FOR SEQ ID NO: 1170:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1170:

GCAAAACCUG AUGAGGCCGA AAGGCCGAAA CUUCUG                              36

(2) INFORMATION FOR SEQ ID NO: 1171:

(i) SEQUENCE CHARACTERISTICS:
            (A) LENGTH:             36 base pairs
            (B) TYPE:               nucleic acid
```

```
            (C) STRANDEDNESS:        single
            (D) TOPOLOGY:            linear (xi) SEQUENCE DESCRIPTION: SEQ ID NO: 1171:

GGAGCAACUG AUGAGGCCGA AAGGCCGAAA CAACUU                              36

(2) INFORMATION FOR SEQ ID NO: 1172:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1172:

AGUUCUCCUG AUGAGGCCGA AAGGCCGAAA AGCACA                              36

(2) INFORMATION FOR SEQ ID NO: 1173:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1173:

UUUAGGACUG AUGAGGCCGA AAGGCCGAAA UGGGUU                              36

(2) INFORMATION FOR SEQ ID NO: 1174:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1174:

UCUUCCUCUG AUGAGGCCGA AAGGCCGAAA GGCAGG                              36

(2) INFORMATION FOR SEQ ID NO: 1175:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1175:

CAGUAGACUG AUGAGGCCGA AAGGCCGAAA AACCCU                              36

(2) INFORMATION FOR SEQ ID NO: 1176:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1176:

UAGGCAGCUG AUGAGGCCGA AAGGCCGAAA GCCCCU                              36

(2) INFORMATION FOR SEQ ID NO: 1177:

(i) SEQUENCE CHARACTERISTICS:
            (A) LENGTH:              36 base pairs
            (B) TYPE:                nucleic acid
            (C) STRANDEDNESS:        single
```

(D) TOPOLOGY: linear (xi) SEQUENCE DESCRIPTION: SEQ ID NO: 1177:

CAGCUCACUG AUGAGGCCGA AAGGCCGAAA CAGCUU                36

(2) INFORMATION FOR SEQ ID NO: 1178:

(i) SEQUENCE CHARACTERISTICS:
      (A) LENGTH:          36 base pairs
      (B) TYPE:            nucleic acid
      (C) STRANDEDNESS:    single
      (D) TOPOLOGY:        linear (xi) SEQUENCE DESCRIPTION: SEQ ID NO: 1178:

GGCUCAGCUG AUGAGGCCGA AAGGCCGAAA UCUCCU                36

(2) INFORMATION FOR SEQ ID NO: 1179:

(i) SEQUENCE CHARACTERISTICS:
      (A) LENGTH:          36 base pairs
      (B) TYPE:            nucleic acid
      (C) STRANDEDNESS:    single
      (D) TOPOLOGY:        linear (xi) SEQUENCE DESCRIPTION: SEQ ID NO: 1179:

GUUCUCACUG AUGAGGCCGA AAGGCCGAAA GCACAG                36

(2) INFORMATION FOR SEQ ID NO: 1180:

(i) SEQUENCE CHARACTERISTICS:
      (A) LENGTH:          36 base pairs
      (B) TYPE:            nucleic acid
      (C) STRANDEDNESS:    single
      (D) TOPOLOGY:        linear (xi) SEQUENCE DESCRIPTION: SEQ ID NO: 1180:

CAGUGUGCUG AUGAGGCCGA AAGGCCGAAA UUGGAC                36

(2) INFORMATION FOR SEQ ID NO: 1181:

(i) SEQUENCE CHARACTERISTICS:
      (A) LENGTH:          36 base pairs
      (B) TYPE:            nucleic acid
      (C) STRANDEDNESS:    single
      (D) TOPOLOGY:        linear (xi) SEQUENCE DESCRIPTION: SEQ ID NO: 1181:

UCAGCUCCUG AUGAGGCCGA AAGGCCGAAA ACAGCU                36

(2) INFORMATION FOR SEQ ID NO: 1182:

(i) SEQUENCE CHARACTERISTICS:
      (A) LENGTH:          36 base pairs
      (B) TYPE:            nucleic acid
      (C) STRANDEDNESS:    single
      (D) TOPOLOGY:        linear (xi) SEQUENCE DESCRIPTION: SEQ ID NO: 1182:

AGCGGACCUG AUGAGGCCGA AAGGCCGAAA CUGCAC                36

(2) INFORMATION FOR SEQ ID NO: 1183:

(i) SEQUENCE CHARACTERISTICS:
      (A) LENGTH:          36 base pairs
      (B) TYPE:            nucleic acid
      (C) STRANDEDNESS:    single
      (D) TOPOLOGY:        linear (xi) SEQUENCE DESCRIPTION: SEQ ID NO: 1183:

CGGGUUGCUG AUGAGGCCGA AAGGCCGAAA GCCAUU         36

(2) INFORMATION FOR SEQ ID NO: 1184:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 1184:

GGGCAGGCUG AUGAGGCCGA AAGGCCGAAA GGCUUC         36

(2) INFORMATION FOR SEQ ID NO: 1185:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 1185:

GGGGCAGCUG AUGAGGCCGA AAGGCCGAAA AGGCUU         36

(2) INFORMATION FOR SEQ ID NO: 1186:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 1186:

ACACGGUCUG AUGAGGCCGA AAGGCCGAAA UGGUAG         36

(2) INFORMATION FOR SEQ ID NO: 1187:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 1187:

AAACGAACUG AUGAGGCCGA AAGGCCGAAA CACGGU         36

(2) INFORMATION FOR SEQ ID NO: 1188:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 1188:

AGAUCGACUG AUGAGGCCGA AAGGCCGAAA GUCCGG         36

(2) INFORMATION FOR SEQ ID NO: 1189:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (xi) SEQUENCE DESCRIPTION: SEQ ID NO: 1189:

CGGGGGGCUG AUGAGGCCGA AAGGCCGAAA AGUGUG 36

(2) INFORMATION FOR SEQ ID NO: 1190:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1190:

CUGCUGGCUG AUGAGGCCGA AAGGCCGAAA GGGGUG 36

(2) INFORMATION FOR SEQ ID NO: 1191:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1191:

CACUGCUCUG AUGAGGCCGA AAGGCCGAAA GAGCUG 36

(2) INFORMATION FOR SEQ ID NO: 1192:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1192:

GCAGGGUCUG AUGAGGCCGA AAGGCCGAAA GGUCCU 36

(2) INFORMATION FOR SEQ ID NO: 1193:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1193:

CAAAGGACUG AUGAGGCCGA AAGGCCGAAA GGUUUC 36

(2) INFORMATION FOR SEQ ID NO: 1194:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1194:

AGUGGCUCUG AUGAGGCCGA AAGGCCGAAA GGGUAA 36

(2) INFORMATION FOR SEQ ID NO: 1195:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1195:

ACACGGUCUG AUGAGGCCGA AAGGCCGAAA UGGUAG                36

(2) INFORMATION FOR SEQ ID NO: 1196:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1196:

CCCCACGCUG AUGAGGCCGA AAGGCCGAAA GCAGCA                36

(2) INFORMATION FOR SEQ ID NO: 1197:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1197:

GGAUGGACUG AUGAGGCCGA AAGGCCGAAA CCUGAG                36

(2) INFORMATION FOR SEQ ID NO: 1198:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1198:

CCCAUGUCUG AUGAGGCCGA AAGGCCGAAA UCUUUC                36

(2) INFORMATION FOR SEQ ID NO: 1199:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1199:

CAUGAGACUG AUGAGGCCGA AAGGCCGAAA UUGGCU                36

(2) INFORMATION FOR SEQ ID NO: 1200:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1200:

GCAUGAGCUG AUGAGGCCGA AAGGCCGAAA AUUGGC                36

(2) INFORMATION FOR SEQ ID NO: 1201:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1201:

```
GGCAUGACUG AUGAGGCCGA AAGGCCGAAA AAUUGG                                36

(2) INFORMATION FOR SEQ ID NO: 1202:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1202:

GCGGCAUCUG AUGAGGCCGA AAGGCCGAAA GAAAUU                                36

(2) INFORMATION FOR SEQ ID NO: 1203:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1203:

CAGCUCACUG AUGAGGCCGA AAGGCCGAAA CAGCUU                                36

(2) INFORMATION FOR SEQ ID NO: 1204:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1204:

UCAGCUCCUG AUGAGGCCGA AAGGCCGAAA ACAGCU                                36

(2) INFORMATION FOR SEQ ID NO: 1205:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1205:

GGUGGCCCUG AUGAGGCCGA AAGGCCGAAA GGCUCG                                36

(2) INFORMATION FOR SEQ ID NO: 1206:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1206:

AGGCUGGCUG AUGAGGCCGA AAGGCCGAAA GAGGUC                                36

(2) INFORMATION FOR SEQ ID NO: 1207:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1207:

AGGACCGCUG AUGAGGCCGA AAGGCCGAAA GCUGAA                                36
```

(2) INFORMATION FOR SEQ ID NO: 1208:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1208:

AAGAUCGCUG AUGAGGCCGA AAGGCCGAAA AGUCCG                          36

(2) INFORMATION FOR SEQ ID NO: 1209:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1209:

GCAGGGUCUG AUGAGGCCGA AAGGCCGAAA GGUCCU                          36

(2) INFORMATION FOR SEQ ID NO: 1210:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1210:

GAGGCAGCUG AUGAGGCCGA AAGGCCGAAA AACAGG                          36

(2) INFORMATION FOR SEQ ID NO: 1211:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1211:

UGAGGUGCUG AUGAGGCCGA AAGGCCGAAA GCCGCC                          36

(2) INFORMATION FOR SEQ ID NO: 1212:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1212:

AGCUGAACUG AUGAGGCCGA AAGGCCGAAA GUUGUA                          36

(2) INFORMATION FOR SEQ ID NO: 1213:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1213:

CGGAGCUCUG AUGAGGCCGA AAGGCCGAAA AAAGUU                          36

(2) INFORMATION FOR SEQ ID NO: 1214:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1214:

UCUCCAGCUG AUGAGGCCGA AAGGCCGAAA UCUGGU                          36

(2) INFORMATION FOR SEQ ID NO: 1215:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1215:

CCAUCACCUG AUGAGGCCGA AAGGCCGAAA GGCCCA                          36

(2) INFORMATION FOR SEQ ID NO: 1216:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1216:

GGAAGCGCUG AUGAGGCCGA AAGGCCGAAA CGACUG                          36

(2) INFORMATION FOR SEQ ID NO: 1217:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1217:

GGCAGGACUG AUGAGGCCGA AAGGCCGAAA CAGGCC                          36

(2) INFORMATION FOR SEQ ID NO: 1218:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1218:

UUCCAGGCUG AUGAGGCCGA AAGGCCGAAA GCAAAA                          36

(2) INFORMATION FOR SEQ ID NO: 1219:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1219:

GGCAGGACUG AUGAGGCCGA AAGGCCGAAA CAGGCC                          36

```
(2) INFORMATION FOR SEQ ID NO: 1220:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1220:

AGGCAGGCUG AUGAGGCCGA AAGGCCGAAA ACAGGC                              36

(2) INFORMATION FOR SEQ ID NO: 1221:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1221:

CUUCCGACUG AUGAGGCCGA AAGGCCGAAA CCUCCA                              36

(2) INFORMATION FOR SEQ ID NO: 1222:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1222:

AGUCUCCCUG AUGAGGCCGA AAGGCCGAAA GCCCAG                              36

(2) INFORMATION FOR SEQ ID NO: 1223:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1223:

CCAGGUACUG AUGAGGCCGA AAGGCCGAAA UCCGAG                              36

(2) INFORMATION FOR SEQ ID NO: 1224:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1224:

GGGUGUCCUG AUGAGGCCGA AAGGCCGAAA GCUUUG                              36

(2) INFORMATION FOR SEQ ID NO: 1225:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1225:

CAACGGUCUG AUGAGGCCGA AAGGCCGAAA CCAGGG                              36

(2) INFORMATION FOR SEQ ID NO: 1226:
```

(i) SEQUENCE CHARACTERISTICS:
    (A) LENGTH:            36 base pairs
    (B) TYPE:              nucleic acid
    (C) STRANDEDNESS:     single
    (D) TOPOLOGY:         linear (xi) SEQUENCE DESCRIPTION: SEQ ID NO: 1226:

GCUGGUACUG AUGAGGCCGA AAGGCCGAAA GGUCUC                            36

(2) INFORMATION FOR SEQ ID NO: 1227:

(i) SEQUENCE CHARACTERISTICS:
        (A) LENGTH:            36 base pairs
        (B) TYPE:              nucleic acid
        (C) STRANDEDNESS:     single
        (D) TOPOLOGY:         linear (xi) SEQUENCE DESCRIPTION: SEQ ID NO: 1227:

CCAGAGGCUG AUGAGGCCGA AAGGCCGAAA GUGGCU                            36

(2) INFORMATION FOR SEQ ID NO: 1228:

(i) SEQUENCE CHARACTERISTICS:
        (A) LENGTH:            36 base pairs
        (B) TYPE:              nucleic acid
        (C) STRANDEDNESS:     single
        (D) TOPOLOGY:         linear (xi) SEQUENCE DESCRIPTION: SEQ ID NO: 1228:

GGGCAGGCUG AUGAGGCCGA AAGGCCGAAA GGCUUC                            36

(2) INFORMATION FOR SEQ ID NO: 1229:

(i) SEQUENCE CHARACTERISTICS:
        (A) LENGTH:            36 base pairs
        (B) TYPE:              nucleic acid
        (C) STRANDEDNESS:     single
        (D) TOPOLOGY:         linear (xi) SEQUENCE DESCRIPTION: SEQ ID NO: 1229:

UCUCCGGCUG AUGAGGCCGA AAGGCCGAAA ACGAAU                            36

(2) INFORMATION FOR SEQ ID NO: 1230:

(i) SEQUENCE CHARACTERISTICS:
        (A) LENGTH:            36 base pairs
        (B) TYPE:              nucleic acid
        (C) STRANDEDNESS:     single
        (D) TOPOLOGY:         linear (xi) SEQUENCE DESCRIPTION: SEQ ID NO: 1230:

CUUGCAUCUG AUGAGGCCGA AAGGCCGAAA GGAAGA                            36

(2) INFORMATION FOR SEQ ID NO: 1231:

(i) SEQUENCE CHARACTERISTICS:
        (A) LENGTH:            36 base pairs
        (B) TYPE:              nucleic acid
        (C) STRANDEDNESS:     single
        (D) TOPOLOGY:         linear (xi) SEQUENCE DESCRIPTION: SEQ ID NO: 1231:

ACGGGUUCUG AUGAGGCCGA AAGGCCGAAA AGCCAU                            36

(2) INFORMATION FOR SEQ ID NO: 1232:

```
        (i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO: 1232:

UCACCUCCUG AUGAGGCCGA AAGGCCGAAA CCAAGG                              36

(2) INFORMATION FOR SEQ ID NO: 1233:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO: 1233:

CCAGAAUCUG AUGAGGCCGA AAGGCCGAAA UUAUAG                              36

(2) INFORMATION FOR SEQ ID NO: 1234:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO: 1234:

GCACCAGCUG AUGAGGCCGA AAGGCCGAAA UGAUUA                              36

(2) INFORMATION FOR SEQ ID NO: 1235:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO: 1235:

AGUUGUACUG AUGAGGCCGA AAGGCCGAAA CUGUUA                              36

(2) INFORMATION FOR SEQ ID NO: 1236:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO: 1236:

AAAGUUGCUG AUGAGGCCGA AAGGCCGAAA GACUGU                              36

(2) INFORMATION FOR SEQ ID NO: 1237:

(i) SEQUENCE CHARACTERISTICS:
            (A) LENGTH:          36 base pairs
            (B) TYPE:            nucleic acid
            (C) STRANDEDNESS:    single
            (D) TOPOLOGY:        linear (xi) SEQUENCE DESCRIPTION: SEQ ID NO: 1237:

AGCUGAACUG AUGAGGCCGA AAGGCCGAAA GUUGUA                              36

(2) INFORMATION FOR SEQ ID NO: 1238:

(i) SEQUENCE CHARACTERISTICS:
```

```
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 1238:

GAGCUGACUG AUGAGGCCGA AAGGCCGAAA AGUUGU                           36

(2) INFORMATION FOR SEQ ID NO: 1239:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 1239:

GGAGCUGCUG AUGAGGCCGA AAGGCCGAAA AAGUUG                           36

(2) INFORMATION FOR SEQ ID NO: 1240:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 1240:

UCUCCAGCUG AUGAGGCCGA AAGGCCGAAA UCUGGU                           36

(2) INFORMATION FOR SEQ ID NO: 1241:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 1241:

UUCCCCACUG AUGAGGCCGA AAGGCCGAAA CUCUCA                           36

(2) INFORMATION FOR SEQ ID NO: 1242:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 1242:

CUUCCGACUG AUGAGGCCGA AAGGCCGAAA CCUCCA                           36

(2) INFORMATION FOR SEQ ID NO: 1243:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 1243:

CCCUUCCCUG AUGAGGCCGA AAGGCCGAAA GACCUC                           36

(2) INFORMATION FOR SEQ ID NO: 1244:

(i) SEQUENCE CHARACTERISTICS:
        (A) LENGTH:              36 base pairs
```

```
            (B) TYPE:              nucleic acid
            (C) STRANDEDNESS:      single
            (D) TOPOLOGY:          linear (xi) SEQUENCE DESCRIPTION: SEQ ID NO: 1244:

UUAUUUCUG AUGAGGCCGA AAGGCCGAAA GAGUGG                                  36

(2) INFORMATION FOR SEQ ID NO: 1245:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1245:

GGCCUGACUG AUGAGGCCGA AAGGCCGAAA UCCAGU                                 36

(2) INFORMATION FOR SEQ ID NO: 1246:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1246:

UUGGCUGCUG AUGAGGCCGA AAGGCCGAAA GGUCCA                                 36

(2) INFORMATION FOR SEQ ID NO: 1247:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1247:

UCAAGAACUG AUGAGGCCGA AAGGCCGAAA GUUGGG                                 36

(2) INFORMATION FOR SEQ ID NO: 1248:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1248:

GCAAAAGCUG AUGAGGCCGA AAGGCCGAAA GCUUCG                                 36

(2) INFORMATION FOR SEQ ID NO: 1249:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1249:

AGCAAAACUG AUGAGGCCGA AAGGCCGAAA AGCUUC                                 36

(2) INFORMATION FOR SEQ ID NO: 1250:

(i) SEQUENCE CHARACTERISTICS:
            (A) LENGTH:            36 base pairs
            (B) TYPE:              nucleic acid
```

```
        (C) STRANDEDNESS:        single
        (D) TOPOLOGY:            linear (xi) SEQUENCE DESCRIPTION: SEQ ID NO: 1250:

AGAGCAACUG AUGAGGCCGA AAGGCCGAAA GAAGCU                                  36

(2) INFORMATION FOR SEQ ID NO: 1251:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 1251:

GGUUUUUCUG AUGAGGCCGA AAGGCCGAAA ACAGGA                                  36

(2) INFORMATION FOR SEQ ID NO: 1252:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 1252:

UGUGGAGCUG AUGAGGCCGA AAGGCCGAAA GCAGAG                                  36

(2) INFORMATION FOR SEQ ID NO: 1253:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 1253:

CUGUUCACUG AUGAGGCCGA AAGGCCGAAA AGCAGC                                  36

(2) INFORMATION FOR SEQ ID NO: 1254:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 1254:

ACUGGUGCUG AUGAGGCCGA AAGGCCGAAA AAAAGU                                  36

(2) INFORMATION FOR SEQ ID NO: 1255:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 1255:

GCACACGCUG AUGAGGCCGA AAGGCCGAAA UGUACC                                  36

(2) INFORMATION FOR SEQ ID NO: 1256:

(i) SEQUENCE CHARACTERISTICS:
        (A) LENGTH:              36 base pairs
        (B) TYPE:                nucleic acid
        (C) STRANDEDNESS:        single
```

(D) TOPOLOGY:            linear (xi) SEQUENCE DESCRIPTION: SEQ ID NO: 1256:

AGCAAAACUG AUGAGGCCGA AAGGCCGAAA AGCUUC                                    36

(2) INFORMATION FOR SEQ ID NO: 1257:

(i) SEQUENCE CHARACTERISTICS:
          (A) LENGTH:              36 base pairs
          (B) TYPE:                nucleic acid
          (C) STRANDEDNESS:        single
          (D) TOPOLOGY:            linear (xi) SEQUENCE DESCRIPTION: SEQ ID NO: 1257:

CUCUCCGCUG AUGAGGCCGA AAGGCCGAAA AACGAA                                    36

(2) INFORMATION FOR SEQ ID NO: 1258:

(i) SEQUENCE CHARACTERISTICS:
          (A) LENGTH:              36 base pairs
          (B) TYPE:                nucleic acid
          (C) STRANDEDNESS:        single
          (D) TOPOLOGY:            linear (xi) SEQUENCE DESCRIPTION: SEQ ID NO: 1258:

AGGACCACUG AUGAGGCCGA AAGGCCGAAA CAGCAC                                    36

(2) INFORMATION FOR SEQ ID NO: 1259:

(i) SEQUENCE CHARACTERISTICS:
          (A) LENGTH:              36 base pairs
          (B) TYPE:                nucleic acid
          (C) STRANDEDNESS:        single
          (D) TOPOLOGY:            linear (xi) SEQUENCE DESCRIPTION: SEQ ID NO: 1259:

CUUGCACCUG AUGAGGCCGA AAGGCCGAAA CCCUUC                                    36

(2) INFORMATION FOR SEQ ID NO: 1260:

(i) SEQUENCE CHARACTERISTICS:
          (A) LENGTH:              36 base pairs
          (B) TYPE:                nucleic acid
          (C) STRANDEDNESS:        single
          (D) TOPOLOGY:            linear (xi) SEQUENCE DESCRIPTION: SEQ ID NO: 1260:

UUCCCCACUG AUGAGGCCGA AAGGCCGAAA CUCUCA                                    36

(2) INFORMATION FOR SEQ ID NO: 1261:

(i) SEQUENCE CHARACTERISTICS:
          (A) LENGTH:              36 base pairs
          (B) TYPE:                nucleic acid
          (C) STRANDEDNESS:        single
          (D) TOPOLOGY:            linear (xi) SEQUENCE DESCRIPTION: SEQ ID NO: 1261:

GGCUCAGCUG AUGAGGCCGA AAGGCCGAAA UCUCCU                                    36

(2) INFORMATION FOR SEQ ID NO: 1262:

(i) SEQUENCE CHARACTERISTICS:
          (A) LENGTH:              36 base pairs
          (B) TYPE:                nucleic acid
          (C) STRANDEDNESS:        single
          (D) TOPOLOGY:            linear (xi) SEQUENCE DESCRIPTION: SEQ ID NO: 1262:

CUGCUGACUG AUGAGGCCGA AAGGCCGAAA CCCCUC          36

(2) INFORMATION FOR SEQ ID NO: 1263:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1263:

CAUUUCACUG AUGAGGCCGA AAGGCCGAAA GUCUGC          36

(2) INFORMATION FOR SEQ ID NO: 1264:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1264:

UCCUCCUCUG AUGAGGCCGA AAGGCCGAAA GCCUUC          36

(2) INFORMATION FOR SEQ ID NO: 1265:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1265:

UUUAGGACUG AUGAGGCCGA AAGGCCGAAA UGGGUU          36

(2) INFORMATION FOR SEQ ID NO: 1266:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1266:

CACUCUCCUG AUGAGGCCGA AAGGCCGAAA GCUCAU          36

(2) INFORMATION FOR SEQ ID NO: 1267:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1267:

UAACUUACUG AUGAGGCCGA AAGGCCGAAA CAUUCA          36

(2) INFORMATION FOR SEQ ID NO: 1268:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear -continued (xi) SEQUENCE DESCRIPTION: SEQ ID NO: 1268:

CACCUUCCUG AUGAGGCCGA AAGGCCGAAA CCCACU                                     36

(2) INFORMATION FOR SEQ ID NO: 1269:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1269:

AGUUGUACUG AUGAGGCCGA AAGGCCGAAA CUGUUA                                     36

(2) INFORMATION FOR SEQ ID NO: 1270:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1270:

AGGUGGGCUG AUGAGGCCGA AAGGCCGAAA GGUGCU                                     36

(2) INFORMATION FOR SEQ ID NO: 1271:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1271:

AGAGUGGCUG AUGAGGCCGA AAGGCCGAAA CAGUAC                                     36

(2) INFORMATION FOR SEQ ID NO: 1272:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1272:

CCACCCCCUG AUGAGGCCGA AAGGCCGAAA UGGGCA                                     36

(2) INFORMATION FOR SEQ ID NO: 1273:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1273:

AGCCACUCUG AUGAGGCCGA AAGGCCGAAA GUCUCC                                     36

(2) INFORMATION FOR SEQ ID NO: 1274:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1274:

GUUCUGUCUG AUGAGGCCGA AAGGCCGAAA CAGCCA                          36

(2) INFORMATION FOR SEQ ID NO: 1275:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1275:

AGUUCUCCUG AUGAGGCCGA AAGGCCGAAA AGCACA                          36

(2) INFORMATION FOR SEQ ID NO: 1276:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1276:

CCUCCCCCUG AUGAGGCCGA AAGGCCGAAA UCUCGC                          36

(2) INFORMATION FOR SEQ ID NO: 1277:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1277:

CCCUUCCCUG AUGAGGCCGA AAGGCCGAAA GACCUC                          36

(2) INFORMATION FOR SEQ ID NO: 1278:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1278:

ACAAAAGCUG AUGAGGCCGA AAGGCCGAAA GGUGGG                          36

(2) INFORMATION FOR SEQ ID NO: 1279:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1279:

CUCUACCCUG AUGAGGCCGA AAGGCCGAAA GGCAGU                          36

(2) INFORMATION FOR SEQ ID NO: 1280:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1280:

```
CAGGGGCCUG AUGAGGCCGA AAGGCCGAAA UAGAGA                                         36

(2) INFORMATION FOR SEQ ID NO: 1281:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1281:

UCCUCCUCUG AUGAGGCCGA AAGGCCGAAA GCCUUC                                         36

(2) INFORMATION FOR SEQ ID NO: 1282:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1282:

UCCUGGUCUG AUGAGGCCGA AAGGCCGAAA CAUUCC                                         36

(2) INFORMATION FOR SEQ ID NO: 1283:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1283:

GGGAGCACUG AUGAGGCCGA AAGGCCGAAA ACAACU                                         36

(2) INFORMATION FOR SEQ ID NO: 1284:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1284:

CAUGAGGCUG AUGAGGCCGA AAGGCCGAAA GAACAG                                         36

(2) INFORMATION FOR SEQ ID NO: 1285:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1285:

GUUCUCACUG AUGAGGCCGA AAGGCCGAAA GCACAG                                         36

(2) INFORMATION FOR SEQ ID NO: 1286:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1286:

GGACCAUCUG AUGAGGCCGA AAGGCCGAAA UUUCAU                                         36
```

(2) INFORMATION FOR SEQ ID NO: 1287:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1287:

GAAUGAUCUG AUGAGGCCGA AAGGCCGAAA UAGUCC                          36

(2) INFORMATION FOR SEQ ID NO: 1288:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1288:

CGGUUAUCUG AUGAGGCCGA AAGGCCGAAA ACAUAA                          36

(2) INFORMATION FOR SEQ ID NO: 1289:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1289:

ACACGGUCUG AUGAGGCCGA AAGGCCGAAA UGGUAG                          36

(2) INFORMATION FOR SEQ ID NO: 1290:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1290:

CGCCUGGCUG AUGAGGCCGA AAGGCCGAAA CCAUGA                          36

(2) INFORMATION FOR SEQ ID NO: 1291:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1291:

CCAGAAUCUG AUGAGGCCGA AAGGCCGAAA UUAUAG                          36

(2) INFORMATION FOR SEQ ID NO: 1292:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1292:

GGCCCACCUG AUGAGGCCGA AAGGCCGAAA UGACCA                          36

```
(2) INFORMATION FOR SEQ ID NO: 1293:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1293:

AGCUGCUCUG AUGAGGCCGA AAGGCCGAAA GGCAUG                              36

(2) INFORMATION FOR SEQ ID NO: 1294:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1294:

AGGUGGGCUG AUGAGGCCGA AAGGCCGAAA GGUGCU                              36

(2) INFORMATION FOR SEQ ID NO: 1295:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1295:

GGUUAUACUG AUGAGGCCGA AAGGCCGAAA CAUAAG                              36

(2) INFORMATION FOR SEQ ID NO: 1296:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1296:

GCGGUUACUG AUGAGGCCGA AAGGCCGAAA AACAUA                              36

(2) INFORMATION FOR SEQ ID NO: 1297:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1297:

UGGCGGUCUG AUGAGGCCGA AAGGCCGAAA UAAACA                              36

(2) INFORMATION FOR SEQ ID NO: 1298:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1298:

AUAUCCUCUG AUGAGGCCGA AAGGCCGAAA UCUUUC                              36
```

```
(2) INFORMATION FOR SEQ ID NO: 1299:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1299:

UAACUUGCUG AUGAGGCCGA AAGGCCGAAA UAUCCU                                36

(2) INFORMATION FOR SEQ ID NO: 1300:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1300:

CCUUCUGCUG AUGAGGCCGA AAGGCCGAAA ACUUGU                                36

(2) INFORMATION FOR SEQ ID NO: 1301:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1301:

GCUCAGGCUG AUGAGGCCGA AAGGCCGAAA GGUGGG                                36

(2) INFORMATION FOR SEQ ID NO: 1302:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1302:

CAAAGGACUG AUGAGGCCGA AAGGCCGAAA GGUUUC                                36

(2) INFORMATION FOR SEQ ID NO: 1303:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1303:

UUCAAAGCUG AUGAGGCCGA AAGGCCGAAA AAGGUU                                36

(2) INFORMATION FOR SEQ ID NO: 1304:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1304:

CCAGGCUCUG AUGAGGCCGA AAGGCCGAAA GGUCCU                                36

(2) INFORMATION FOR SEQ ID NO: 1305:
```

```
    (i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1305:

CCAGAGGCUG AUGAGGCCGA AAGGCCGAAA GUGGCU                            36

(2) INFORMATION FOR SEQ ID NO: 1306:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1306:

GCCAGAGCUG AUGAGGCCGA AAGGCCGAAA AGUGGC                            36

(2) INFORMATION FOR SEQ ID NO: 1307:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1307:

ACAGCCACUG AUGAGGCCGA AAGGCCGAAA GGAAGU                            36

(2) INFORMATION FOR SEQ ID NO: 1308:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1308:

AGAUCGACUG AUGAGGCCGA AAGGCCGAAA GUCCGG                            36

(2) INFORMATION FOR SEQ ID NO: 1309:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1309:

AAGAUCGCUG AUGAGGCCGA AAGGCCGAAA AGUCCG                            36

(2) INFORMATION FOR SEQ ID NO: 1310:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1310:

CCACCCCCUG AUGAGGCCGA AAGGCCGAAA UGGGCA                            36

(2) INFORMATION FOR SEQ ID NO: 1311:
```

```
    (i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1311:

CUCCAGGCUG AUGAGGCCGA AAGGCCGAAA UAUCCG                         36

(2) INFORMATION FOR SEQ ID NO: 1312:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1312:

GCUGGUACUG AUGAGGCCGA AAGGCCGAAA GGUCUC                         36

(2) INFORMATION FOR SEQ ID NO: 1313:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1313:

UGAGGUGCUG AUGAGGCCGA AAGGCCGAAA GCCGCC                         36

(2) INFORMATION FOR SEQ ID NO: 1314:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1314:

GGGCAGGCUG AUGAGGCCGA AAGGCCGAAA GGCUUC                         36

(2) INFORMATION FOR SEQ ID NO: 1315:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1315:

UGGGGACCUG AUGAGGCCGA AAGGCCGAAA UGUCUC                         36

(2) INFORMATION FOR SEQ ID NO: 1316:

(i) SEQUENCE CHARACTERISTICS:
         (A) LENGTH:           36 base pairs
         (B) TYPE:             nucleic acid
         (C) STRANDEDNESS:     single
         (D) TOPOLOGY:         linear (xi) SEQUENCE DESCRIPTION: SEQ ID NO: 1316:

AUUAGAGCUG AUGAGGCCGA AAGGCCGAAA CAAUGC                         36

(2) INFORMATION FOR SEQ ID NO: 1317:

(i) SEQUENCE CHARACTERISTICS:
```

(A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1317:

UCCAGCCCUG AUGAGGCCGA AAGGCCGAAA GGACCA                        36

(2) INFORMATION FOR SEQ ID NO: 1318:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1318:

UUUAUGUCUG AUGAGGCCGA AAGGCCGAAA CUGGUG                        36

(2) INFORMATION FOR SEQ ID NO: 1319:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1319:

UCUCCAGCUG AUGAGGCCGA AAGGCCGAAA UCUGGU                        36

(2) INFORMATION FOR SEQ ID NO: 1320:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1320:

GGCCUGACUG AUGAGGCCGA AAGGCCGAAA UCCAGU                        36

(2) INFORMATION FOR SEQ ID NO: 1321:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1321:

UGAGGGUCUG AUGAGGCCGA AAGGCCGAAA AUGCUG                        36

(2) INFORMATION FOR SEQ ID NO: 1322:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1322:

GCAGAGGCUG AUGAGGCCGA AAGGCCGAAA GCGUGG                        36

(2) INFORMATION FOR SEQ ID NO: 1323:

(i) SEQUENCE CHARACTERISTICS:
        (A) LENGTH:           36 base pairs

```
            (B) TYPE:                nucleic acid
            (C) STRANDEDNESS:        single
            (D) TOPOLOGY:            linear (xi) SEQUENCE DESCRIPTION: SEQ ID NO: 1323:

GGAGCUACUG AUGAGGCCGA AAGGCCGAAA GGCAUG                              36

(2) INFORMATION FOR SEQ ID NO: 1324:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1324:

GGUGGCCCUG AUGAGGCCGA AAGGCCGAAA GGCUCG                              36

(2) INFORMATION FOR SEQ ID NO: 1325:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1325:

AAGAUCGCUG AUGAGGCCGA AAGGCCGAAA AGUCCG                              36

(2) INFORMATION FOR SEQ ID NO: 1326:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1326:

UACUGGACUG AUGAGGCCGA AAGGCCGAAA UCAUGU                              36

(2) INFORMATION FOR SEQ ID NO: 1327:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1327:

CUGAGGCCUG AUGAGGCCGA AAGGCCGAAA CAAGUG                              36

(2) INFORMATION FOR SEQ ID NO: 1328:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1328:

UUUAUGUCUG AUGAGGCCGA AAGGCCGAAA CUGGUG                              36

(2) INFORMATION FOR SEQ ID NO: 1329:

(i) SEQUENCE CHARACTERISTICS:
            (A) LENGTH:              36 base pairs
            (B) TYPE:                nucleic acid
```

```
            (C) STRANDEDNESS:      single
            (D) TOPOLOGY:          linear (xi) SEQUENCE DESCRIPTION: SEQ ID NO: 1329:

AGCUGCUCUG AUGAGGCCGA AAGGCCGAAA GGCAUG                               36

(2) INFORMATION FOR SEQ ID NO: 1330:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1330:

GUCCCUUCUG AUGAGGCCGA AAGGCCGAAA GUUUUA                               36

(2) INFORMATION FOR SEQ ID NO: 1331:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1331:

ACUGAUCCUG AUGAGGCCGA AAGGCCGAAA CUAUAU                               36

(2) INFORMATION FOR SEQ ID NO: 1332:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1332:

UAACUUACUG AUGAGGCCGA AAGGCCGAAA CAUUCA                               36

(2) INFORMATION FOR SEQ ID NO: 1333:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1333:

GAUACCUCUG AUGAGGCCGA AAGGCCGAAA GCAUCA                               36

(2) INFORMATION FOR SEQ ID NO: 1334:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1334:

CUGGUAACUG AUGAGGCCGA AAGGCCGAAA CUCUAA                               36

(2) INFORMATION FOR SEQ ID NO: 1335:

(i) SEQUENCE CHARACTERISTICS:
            (A) LENGTH:            36 base pairs
            (B) TYPE:              nucleic acid
            (C) STRANDEDNESS:      single
```

```
            (D) TOPOLOGY:           linear (xi) SEQUENCE DESCRIPTION: SEQ ID NO: 1335:

AGCUGGUCUG AUGAGGCCGA AAGGCCGAAA AACUCU                                   36

(2) INFORMATION FOR SEQ ID NO: 1336:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1336:

UGGGGACCUG AUGAGGCCGA AAGGCCGAAA UGUCUC                                   36

(2) INFORMATION FOR SEQ ID NO: 1337:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1337:

UAACUUGCUG AUGAGGCCGA AAGGCCGAAA UAUCCU                                   36

(2) INFORMATION FOR SEQ ID NO: 1338:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1338:

GGCUCAGCUG AUGAGGCCGA AAGGCCGAAA UCUCCU                                   36

(2) INFORMATION FOR SEQ ID NO: 1339:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1339:

GGUCCGCCUG AUGAGGCCGA AAGGCCGAAA GCUCCA                                   36

(2) INFORMATION FOR SEQ ID NO: 1340:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1340:

UACUCAACUG AUGAGGCCGA AAGGCCGAAA AAUAGC                                   36

(2) INFORMATION FOR SEQ ID NO: 1341:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear
```

(xi) SEQUENCE DESCRIPTION: SEQ ID NO: 1341:

CCACCCCCUG AUGAGGCCGA AAGGCCGAAA UGGGCA    36

(2) INFORMATION FOR SEQ ID NO: 1342:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1342:

CUCAGAACUG AUGAGGCCGA AAGGCCGAAA ACCACC    36

(2) INFORMATION FOR SEQ ID NO: 1343:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1343:

CCUCUGCCUG AUGAGGCCGA AAGGCCGAAA GCCAGC    36

(2) INFORMATION FOR SEQ ID NO: 1344:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1344:

CCUCCAGCUG AUGAGGCCGA AAGGCCGAAA GGUCAG    36

(2) INFORMATION FOR SEQ ID NO: 1345:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1345:

GGAUGUGCUG AUGAGGCCGA AAGGCCGAAA GGAGCA    36

(2) INFORMATION FOR SEQ ID NO: 1346:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1346:

ACACGGUCUG AUGAGGCCGA AAGGCCGAAA UGGUAG    36

(2) INFORMATION FOR SEQ ID NO: 1347:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1347:

CUGAGGCCUG AUGAGGCCGA AAGGCCGAAA CAAGUG                                    36

(2) INFORMATION FOR SEQ ID NO: 1348:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO: 1348:

UAGCUCUCUG AUGAGGCCGA AAGGCCGAAA GGCUAC                                    36

(2) INFORMATION FOR SEQ ID NO: 1349:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO: 1349:

CAUCAAGCUG AUGAGGCCGA AAGGCCGAAA GAGUUG                                    36

(2) INFORMATION FOR SEQ ID NO: 1350:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO: 1350:

CGGGGGGCUG AUGAGGCCGA AAGGCCGAAA AGUGUG                                    36

(2) INFORMATION FOR SEQ ID NO: 1351:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO: 1351:

AUCCUCCCUG AUGAGGCCGA AAGGCCGAAA GCUGGC                                    36

(2) INFORMATION FOR SEQ ID NO: 1352:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO: 1352:

CUCAAUACUG AUGAGGCCGA AAGGCCGAAA UAGCUG                                    36

(2) INFORMATION FOR SEQ ID NO: 1353:

(i) SEQUENCE CHARACTERISTICS:
            (A) LENGTH:         36 base pairs
            (B) TYPE:           nucleic acid
            (C) STRANDEDNESS:   single
            (D) TOPOLOGY:       linear (xi) SEQUENCE DESCRIPTION: SEQ ID NO: 1353:

GAGGCAGCUG AUGAGGCCGA AAGGCCGAAA AACAGG 36

(2) INFORMATION FOR SEQ ID NO: 1354:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1354:

CAUCAAGCUG AUGAGGCCGA AAGGCCGAAA GAGUUG 36

(2) INFORMATION FOR SEQ ID NO: 1355:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1355:

AACUCUACUG AUGAGGCCGA AAGGCCGAAA UUAAUA 36

(2) INFORMATION FOR SEQ ID NO: 1356:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1356:

UAAUAAACUG AUGAGGCCGA AAGGCCGAAA CAUCAA 36

(2) INFORMATION FOR SEQ ID NO: 1357:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1357:

AUUAAUACUG AUGAGGCCGA AAGGCCGAAA UACAUC 36

(2) INFORMATION FOR SEQ ID NO: 1358:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1358:

AAUUAAUCUG AUGAGGCCGA AAGGCCGAAA AUACAU 36

(2) INFORMATION FOR SEQ ID NO: 1359:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1359:

```
AAAUUAACUG AUGAGGCCGA AAGGCCGAAA AAUACA                                      36

(2) INFORMATION FOR SEQ ID NO: 1360:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1360:

CUAAAUUCUG AUGAGGCCGA AAGGCCGAAA UAAAUA                                      36

(2) INFORMATION FOR SEQ ID NO: 1361:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1361:

AAUUAAUCUG AUGAGGCCGA AAGGCCGAAA AUACAU                                      36

(2) INFORMATION FOR SEQ ID NO: 1362:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1362:

AAUAGAGCUG AUGAGGCCGA AAGGCCGAAA UGAAGU                                      36

(2) INFORMATION FOR SEQ ID NO: 1363:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1363:

AAUUAAUCUG AUGAGGCCGA AAGGCCGAAA AUACAU                                      36

(2) INFORMATION FOR SEQ ID NO: 1364:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1364:

CUAAAUUCUG AUGAGGCCGA AAGGCCGAAA UAAAUA                                      36

(2) INFORMATION FOR SEQ ID NO: 1365:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1365:

GGGAGCACUG AUGAGGCCGA AAGGCCGAAA ACAACU                                      36
```

(2) INFORMATION FOR SEQ ID NO: 1366:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1366:

CUGGUAACUG AUGAGGCCGA AAGGCCGAAA CUCUAA                       36

(2) INFORMATION FOR SEQ ID NO: 1367:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1367:

GCUGGUACUG AUGAGGCCGA AAGGCCGAAA ACUCUA                       36

(2) INFORMATION FOR SEQ ID NO: 1368:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1368:

AGCUGGUCUG AUGAGGCCGA AAGGCCGAAA AACUCU                       36

(2) INFORMATION FOR SEQ ID NO: 1369:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1369:

UAGCUGGCUG AUGAGGCCGA AAGGCCGAAA AAACUC                       36

(2) INFORMATION FOR SEQ ID NO: 1370:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1370:

CAAUAAACUG AUGAGGCCGA AAGGCCGAAA GCUGGU                       36

(2) INFORMATION FOR SEQ ID NO: 1371:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1371:

CUCAAUACUG AUGAGGCCGA AAGGCCGAAA UAGCUG                       36

(2) INFORMATION FOR SEQ ID NO: 1372:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1372:

ACUCAAUCUG AUGAGGCCGA AAGGCCGAAA AUAGCU                    36

(2) INFORMATION FOR SEQ ID NO: 1373:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1373:

UACUCAACUG AUGAGGCCGA AAGGCCGAAA AAUAGC                    36

(2) INFORMATION FOR SEQ ID NO: 1374:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1374:

GGUACUCCUG AUGAGGCCGA AAGGCCGAAA UAAAUA                    36

(2) INFORMATION FOR SEQ ID NO: 1375:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1375:

CAUCAAGCUG AUGAGGCCGA AAGGCCGAAA GAGUUG                    36

(2) INFORMATION FOR SEQ ID NO: 1376:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1376:

AACAUAACUG AUGAGGCCGA AAGGCCGAAA GGCUGC                    36

(2) INFORMATION FOR SEQ ID NO: 1377:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 1377:

AUAAACACUG AUGAGGCCGA AAGGCCGAAA AGAGGC                    36

(2) INFORMATION FOR SEQ ID NO: 1378:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO: 1378:

CUUGCAUCUG AUGAGGCCGA AAGGCCGAAA GGAAGA                                  36

(2) INFORMATION FOR SEQ ID NO: 1379:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO: 1379:

GCCGACACUG AUGAGGCCGA AAGGCCGAAA AAACUU                                  36

(2) INFORMATION FOR SEQ ID NO: 1380:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO: 1380:

UCAGGCCCUG AUGAGGCCGA AAGGCCGAAA CAUAAA                                  36

(2) INFORMATION FOR SEQ ID NO: 1381:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO: 1381:

AGCCACUCUG AUGAGGCCGA AAGGCCGAAA GUCUCC                                  36

(2) INFORMATION FOR SEQ ID NO: 1382:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO: 1382:

AGAGAACCUG AUGAGGCCGA AAGGCCGAAA UGCCAG                                  36

(2) INFORMATION FOR SEQ ID NO: 1383:

(i) SEQUENCE CHARACTERISTICS:
       (A) LENGTH:        36 base pairs
       (B) TYPE:          nucleic acid
       (C) STRANDEDNESS:  single
       (D) TOPOLOGY:      linear (xi) SEQUENCE DESCRIPTION: SEQ ID NO: 1383:

GGAUGGACUG AUGAGGCCGA AAGGCCGAAA CCUGAG                                  36

(2) INFORMATION FOR SEQ ID NO: 1384:

```
       (i) SEQUENCE CHARACTERISTICS:
             (A) LENGTH:              36 base pairs
             (B) TYPE:                nucleic acid
             (C) STRANDEDNESS:        single
             (D) TOPOLOGY:            linear (xi) SEQUENCE DESCRIPTION: SEQ ID NO: 1384:

GCGGCCUCUG AUGAGGCCGA AAGGCCGAAA GAUCCA                              36

(2) INFORMATION FOR SEQ ID NO: 1385:

(i) SEQUENCE CHARACTERISTICS:
             (A) LENGTH:              36 base pairs
             (B) TYPE:                nucleic acid
             (C) STRANDEDNESS:        single
             (D) TOPOLOGY:            linear (xi) SEQUENCE DESCRIPTION: SEQ ID NO: 1385:

CCUCCAGCUG AUGAGGCCGA AAGGCCGAAA GGUCAG                              36

(2) INFORMATION FOR SEQ ID NO: 1386:

(i) SEQUENCE CHARACTERISTICS:
             (A) LENGTH:              36 base pairs
             (B) TYPE:                nucleic acid
             (C) STRANDEDNESS:        single
             (D) TOPOLOGY:            linear (xi) SEQUENCE DESCRIPTION: SEQ ID NO: 1386:

GGUCCGCCUG AUGAGGCCGA AAGGCCGAAA GCUCCA                              36

(2) INFORMATION FOR SEQ ID NO: 1387:

(i) SEQUENCE CHARACTERISTICS:
             (A) LENGTH:              36 base pairs
             (B) TYPE:                nucleic acid
             (C) STRANDEDNESS:        single
             (D) TOPOLOGY:            linear (xi) SEQUENCE DESCRIPTION: SEQ ID NO: 1387:

UGGGAUGCUG AUGAGGCCGA AAGGCCGAAA UGGAUA                              36

(2) INFORMATION FOR SEQ ID NO: 1388:

(i) SEQUENCE CHARACTERISTICS:
             (A) LENGTH:              36 base pairs
             (B) TYPE:                nucleic acid
             (C) STRANDEDNESS:        single
             (D) TOPOLOGY:            linear (xi) SEQUENCE DESCRIPTION: SEQ ID NO: 1388:

UCAGUGUCUG AUGAGGCCGA AAGGCCGAAA AUUGGA                              36

(2) INFORMATION FOR SEQ ID NO: 1389:

(i) SEQUENCE CHARACTERISTICS:
             (A) LENGTH:              36 base pairs
             (B) TYPE:                nucleic acid
             (C) STRANDEDNESS:        single
             (D) TOPOLOGY:            linear (xi) SEQUENCE DESCRIPTION: SEQ ID NO: 1389:

CACCGUGCUG AUGAGGCCGA AAGGCCGAAA UGUGAU                              36

(2) INFORMATION FOR SEQ ID NO: 1390:
```

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1390:

GCACCGUCUG AUGAGGCCGA AAGGCCGAAA AUGUGA                                36

(2) INFORMATION FOR SEQ ID NO: 1391:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1391:

UCCUGGUCUG AUGAGGCCGA AAGGCCGAAA CAUUCC                                36

(2) INFORMATION FOR SEQ ID NO: 1392:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1392:

UCUCCAGCUG AUGAGGCCGA AAGGCCGAAA UCUGGU                                36

(2) INFORMATION FOR SEQ ID NO: 1393:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1393:

CUUGCACCUG AUGAGGCCGA AAGGCCGAAA CCCUUC                                36

(2) INFORMATION FOR SEQ ID NO: 1394:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1394:

CAGCUCACUG AUGAGGCCGA AAGGCCGAAA CAGCUU                                36

(2) INFORMATION FOR SEQ ID NO: 1395:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1395:

AGGCCAUCUG AUGAGGCCGA AAGGCCGAAA CUUAUA                                36

(2) INFORMATION FOR SEQ ID NO: 1396:

(i) SEQUENCE CHARACTERISTICS:

(A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1396:

AGCAGAGCUG AUGAGGCCGA AAGGCCGAAA CCACUG                         36

(2) INFORMATION FOR SEQ ID NO: 1397:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1397:

CCCAUGUCUG AUGAGGCCGA AAGGCCGAAA UCUUUC                         36

(2) INFORMATION FOR SEQ ID NO: 1398:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1398:

CAGGCAGCUG AUGAGGCCGA AAGGCCGAAA GUCUCA                         36

(2) INFORMATION FOR SEQ ID NO: 1399:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1399:

CAAAGGACUG AUGAGGCCGA AAGGCCGAAA GGUUUC                         36

(2) INFORMATION FOR SEQ ID NO: 1400:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1400:

AGGCUGGCUG AUGAGGCCGA AAGGCCGAAA GAGGUC                         36

(2) INFORMATION FOR SEQ ID NO: 1401:

(i) SEQUENCE CHARACTERISTICS:
            (A) LENGTH:           36 base pairs
            (B) TYPE:             nucleic acid
            (C) STRANDEDNESS:     single
            (D) TOPOLOGY:         linear (xi) SEQUENCE DESCRIPTION: SEQ ID NO: 1401:

GCUGGAACUG AUGAGGCCGA AAGGCCGAAA UCGAAA                         36

(2) INFORMATION FOR SEQ ID NO: 1402:

(i) SEQUENCE CHARACTERISTICS:
            (A) LENGTH:           36 base pairs

```
            (B) TYPE:              nucleic acid
            (C) STRANDEDNESS:      single
            (D) TOPOLOGY:          linear (xi) SEQUENCE DESCRIPTION: SEQ ID NO: 1402:

CUGCUGACUG AUGAGGCCGA AAGGCCGAAA GCUGGG                            36

(2) INFORMATION FOR SEQ ID NO: 1403:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1403:

UCUGUUCCUG AUGAGGCCGA AAGGCCGAAA AAGCAG                            36

(2) INFORMATION FOR SEQ ID NO: 1404:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1404:

UUCAAAGCUG AUGAGGCCGA AAGGCCGAAA AAGGUU                            36

(2) INFORMATION FOR SEQ ID NO: 1405:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1405:

UCAGAAGCUG AUGAGGCCGA AAGGCCGAAA CCACCU                            36

(2) INFORMATION FOR SEQ ID NO: 1406:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1406:

CUCAGAACUG AUGAGGCCGA AAGGCCGAAA ACCACC                            36

(2) INFORMATION FOR SEQ ID NO: 1407:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1407:

CAGUAGACUG AUGAGGCCGA AAGGCCGAAA AACCCU                            36

(2) INFORMATION FOR SEQ ID NO: 1408:

(i) SEQUENCE CHARACTERISTICS:
            (A) LENGTH:            36 base pairs
            (B) TYPE:              nucleic acid
```

```
            (C) STRANDEDNESS:        single
            (D) TOPOLOGY:            linear (xi) SEQUENCE DESCRIPTION: SEQ ID NO: 1408:

CUUAUGACUG AUGAGGCCGA AAGGCCGAAA AAAGCA                                    36

(2) INFORMATION FOR SEQ ID NO: 1409:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1409:

GCCGACACUG AUGAGGCCGA AAGGCCGAAA AAACUU                                    36

(2) INFORMATION FOR SEQ ID NO: 1410:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1410:

GGGGCAACUG AUGAGGCCGA AAGGCCGAAA GAGAAU                                    36

(2) INFORMATION FOR SEQ ID NO: 1411:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1411:

UUGUGUCCUG AUGAGGCCGA AAGGCCGAAA CUGGAU                                    36

(2) INFORMATION FOR SEQ ID NO: 1412:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1412:

GUCCACACUG AUGAGGCCGA AAGGCCGAAA GUGUUU                                    36

(2) INFORMATION FOR SEQ ID NO: 1413:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 1413:

CAGCUCACUG AUGAGGCCGA AAGGCCGAAA CAGCUU                                    36

(2) INFORMATION FOR SEQ ID NO: 1414:

(i) SEQUENCE CHARACTERISTICS:
            (A) LENGTH:             36 base pairs
            (B) TYPE:               nucleic acid
            (C) STRANDEDNESS:       single
```

(D) TOPOLOGY:           linear (xi) SEQUENCE DESCRIPTION: SEQ ID NO: 1414:

GCAUCCUCUG AUGAGGCCGA AAGGCCGAAA CCAGUA                           36

(2) INFORMATION FOR SEQ ID NO: 1415:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1415:

ACGUAUGCUG AUGAGGCCGA AAGGCCGAAA CCAUUC                           36

(2) INFORMATION FOR SEQ ID NO: 1416:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1416:

GGCCUGACUG AUGAGGCCGA AAGGCCGAAA UCCAGU                           36

(2) INFORMATION FOR SEQ ID NO: 1417:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1417:

AACCCUCCUG AUGAGGCCGA AAGGCCGAAA CCCAUG                           36

(2) INFORMATION FOR SEQ ID NO: 1418:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1418:

AAACUCUCUG AUGAGGCCGA AAGGCCGAAA AUUAAU                           36

(2) INFORMATION FOR SEQ ID NO: 1419:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1419:

GCUGGUACUG AUGAGGCCGA AAGGCCGAAA ACUCUA                           36

(2) INFORMATION FOR SEQ ID NO: 1420:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1420:

AGCUGGUCUG AUGAGGCCGA AAGGCCGAAA AACUCU					36

(2) INFORMATION FOR SEQ ID NO: 1421:

(i) SEQUENCE CHARACTERISTICS:
        (A) LENGTH:			36 base pairs
        (B) TYPE:			nucleic acid
        (C) STRANDEDNESS:		single
        (D) TOPOLOGY:			linear (xi) SEQUENCE DESCRIPTION: SEQ ID NO: 1421:

GGGCAGGCUG AUGAGGCCGA AAGGCCGAAA GGCUUC					36

(2) INFORMATION FOR SEQ ID NO: 1422:

(i) SEQUENCE CHARACTERISTICS:
        (A) LENGTH:			36 base pairs
        (B) TYPE:			nucleic acid
        (C) STRANDEDNESS:		single
        (D) TOPOLOGY:			linear (xi) SEQUENCE DESCRIPTION: SEQ ID NO: 1422:

GGGGCAGCUG AUGAGGCCGA AAGGCCGAAA AGGCUU					36

(2) INFORMATION FOR SEQ ID NO: 1423:

(i) SEQUENCE CHARACTERISTICS:
        (A) LENGTH:			36 base pairs
        (B) TYPE:			nucleic acid
        (C) STRANDEDNESS:		single
        (D) TOPOLOGY:			linear (xi) SEQUENCE DESCRIPTION: SEQ ID NO: 1423:

AGGCAGGCUG AUGAGGCCGA AAGGCCGAAA ACAGGC					36

(2) INFORMATION FOR SEQ ID NO: 1424:

(i) SEQUENCE CHARACTERISTICS:
        (A) LENGTH:			36 base pairs
        (B) TYPE:			nucleic acid
        (C) STRANDEDNESS:		single
        (D) TOPOLOGY:			linear (xi) SEQUENCE DESCRIPTION: SEQ ID NO: 1424:

GAGGCAGCUG AUGAGGCCGA AAGGCCGAAA AACAGG					36

(2) INFORMATION FOR SEQ ID NO: 1425:

(i) SEQUENCE CHARACTERISTICS:
        (A) LENGTH:			36 base pairs
        (B) TYPE:			nucleic acid
        (C) STRANDEDNESS:		single
        (D) TOPOLOGY:			linear (xi) SEQUENCE DESCRIPTION: SEQ ID NO: 1425:

GGGCAGGCUG AUGAGGCCGA AAGGCCGAAA GGCUUC					36

(2) INFORMATION FOR SEQ ID NO: 1426:

(i) SEQUENCE CHARACTERISTICS:
        (A) LENGTH:			36 base pairs
        (B) TYPE:			nucleic acid
        (C) STRANDEDNESS:		single
        (D) TOPOLOGY:			linear (xi) SEQUENCE DESCRIPTION: SEQ ID NO: 1426:

GGGGGGGCUG AUGAGGCCGA AAGGCCGAAA GUGUGG                     36

(2) INFORMATION FOR SEQ ID NO: 1427:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1427:

CGGGGGGCUG AUGAGGCCGA AAGGCCGAAA AGUGUG                     36

(2) INFORMATION FOR SEQ ID NO: 1428:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1428:

GCUGGUACUG AUGAGGCCGA AAGGCCGAAA GGUCUC                     36

(2) INFORMATION FOR SEQ ID NO: 1429:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1429:

GGAUCACCUG AUGAGGCCGA AAGGCCGAAA CGGUGA                     36

(2) INFORMATION FOR SEQ ID NO: 1430:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1430:

GGUGGCUCUG AUGAGGCCGA AAGGCCGAAA CAUUGG                     36

(2) INFORMATION FOR SEQ ID NO: 1431:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1431:

GACUGGUCUG AUGAGGCCGA AAGGCCGAAA AAAAAG                     36

(2) INFORMATION FOR SEQ ID NO: 1432:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1432:

```
AGGUGGGCUG AUGAGGCCGA AAGGCCGAAA GGUGCU                    36

(2) INFORMATION FOR SEQ ID NO: 1433:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1433:

ACAAAAGCUG AUGAGGCCGA AAGGCCGAAA GGUGGG                    36

(2) INFORMATION FOR SEQ ID NO: 1434:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1434:

UGGGAUGCUG AUGAGGCCGA AAGGCCGAAA UGGAUA                    36

(2) INFORMATION FOR SEQ ID NO: 1435:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1435:

CUGGUAACUG AUGAGGCCGA AAGGCCGAAA CUCUAA                    36

(2) INFORMATION FOR SEQ ID NO: 1436:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1436:

GCUGGUACUG AUGAGGCCGA AAGGCCGAAA ACUCUA                    36

(2) INFORMATION FOR SEQ ID NO: 1437:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1437:

CAUUGGGCUG AUGAGGCCGA AAGGCCGAAA CAAAAG                    36

(2) INFORMATION FOR SEQ ID NO: 1438:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1438:
```

```
UGAGGGUCUG AUGAGGCCGA AAGGCCGAAA AUGCUG                                    36

(2) INFORMATION FOR SEQ ID NO: 1439:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1439:

GAUACCUCUG AUGAGGCCGA AAGGCCGAAA GCAUCA                                    36

(2) INFORMATION FOR SEQ ID NO: 1440:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1440:

CACAGCGCUG AUGAGGCCGA AAGGCCGAAA CUGCUG                                    36

(2) INFORMATION FOR SEQ ID NO: 1441:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1441:

AGGACCACUG AUGAGGCCGA AAGGCCGAAA CAGCAC                                    36

(2) INFORMATION FOR SEQ ID NO: 1442:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1442:

UUUGACACUG AUGAGGCCGA AAGGCCGAAA CUUCAC                                    36

(2) INFORMATION FOR SEQ ID NO: 1443:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1443:

CAGGCCACUG AUGAGGCCGA AAGGCCGAAA ACUUAU                                    36

(2) INFORMATION FOR SEQ ID NO: 1444:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1444:

AGAGAACCUG AUGAGGCCGA AAGGCCGAAA UGCCAG                                    36
```

(2) INFORMATION FOR SEQ ID NO: 1445:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 1445:

AUUAGAGCUG AUGAGGCCGA AAGGCCGAAA CAAUGC                    36

(2) INFORMATION FOR SEQ ID NO: 1446:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 1446:

AGGAGCACUG AUGAGGCCGA AAGGCCGAAA GAACCA                    36

(2) INFORMATION FOR SEQ ID NO: 1447:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 1447:

GCAGAGCCUG AUGAGGCCGA AAGGCCGAAA AAGAAG                    36

(2) INFORMATION FOR SEQ ID NO: 1448:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 1448:

CAUUGGGCUG AUGAGGCCGA AAGGCCGAAA CAAAAG                    36

(2) INFORMATION FOR SEQ ID NO: 1449:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 1449:

AAACGAACUG AUGAGGCCGA AAGGCCGAAA CACGGU                    36

(2) INFORMATION FOR SEQ ID NO: 1450:

(i) SEQUENCE CHARACTERISTICS:
        (A) LENGTH:        36 base pairs
        (B) TYPE:          nucleic acid
        (C) STRANDEDNESS:  single
        (D) TOPOLOGY:     linear (xi) SEQUENCE DESCRIPTION: SEQ ID NO: 1450:

GGGAUGGCUG AUGAGGCCGA AAGGCCGAAA GCUGGA                    36

(2) INFORMATION FOR SEQ ID NO: 1451:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1451:

CCAGGUACUG AUGAGGCCGA AAGGCCGAAA UCCGAG                                        36

(2) INFORMATION FOR SEQ ID NO: 1452:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1452:

CACAGCGCUG AUGAGGCCGA AAGGCCGAAA CUGCUG                                        36

(2) INFORMATION FOR SEQ ID NO: 1453:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1453:

UCCUGGUCUG AUGAGGCCGA AAGGCCGAAA CAUUCC                                        36

(2) INFORMATION FOR SEQ ID NO: 1454:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1454:

GCAGGGUCUG AUGAGGCCGA AAGGCCGAAA GGUCCU                                        36

(2) INFORMATION FOR SEQ ID NO: 1455:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1455:

GCUGGAACUG AUGAGGCCGA AAGGCCGAAA UCGAAA                                        36

(2) INFORMATION FOR SEQ ID NO: 1456:

(i) SEQUENCE CHARACTERISTICS:
        (A) LENGTH:          36 base pairs
        (B) TYPE:            nucleic acid
        (C) STRANDEDNESS:    single
        (D) TOPOLOGY:        linear (xi) SEQUENCE DESCRIPTION: SEQ ID NO: 1456:

AGGCUACCUG AUGAGGCCGA AAGGCCGAAA GUGUGC                                        36

(2) INFORMATION FOR SEQ ID NO: 1457:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1457:

AGGACCGCUG AUGAGGCCGA AAGGCCGAAA GCUGAA                                    36

(2) INFORMATION FOR SEQ ID NO: 1458:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1458:

GGCAGGACUG AUGAGGCCGA AAGGCCGAAA CAGGCC                                    36

(2) INFORMATION FOR SEQ ID NO: 1459:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1459:

CUGCUGACUG AUGAGGCCGA AAGGCCGAAA GCUGGG                                    36

(2) INFORMATION FOR SEQ ID NO: 1460:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1460:

GAGGCAGCUG AUGAGGCCGA AAGGCCGAAA AACAGG                                    36

(2) INFORMATION FOR SEQ ID NO: 1461:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1461:

GCAUCCUCUG AUGAGGCCGA AAGGCCGAAA CCAGUA                                    36

(2) INFORMATION FOR SEQ ID NO: 1462:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1462:

CUUGCACCUG AUGAGGCCGA AAGGCCGAAA CCCUUC                                    36

(2) INFORMATION FOR SEQ ID NO: 1463:

```
   (i) SEQUENCE CHARACTERISTICS:
       (A) LENGTH:          36 base pairs
       (B) TYPE:            nucleic acid
       (C) STRANDEDNESS:    single
       (D) TOPOLOGY:        linear (xi) SEQUENCE DESCRIPTION: SEQ ID NO: 1463:

CCUCGGACUG AUGAGGCCGA AAGGCCGAAA CAUUAG                              36

(2) INFORMATION FOR SEQ ID NO: 1464:

(i) SEQUENCE CHARACTERISTICS:
       (A) LENGTH:          36 base pairs
       (B) TYPE:            nucleic acid
       (C) STRANDEDNESS:    single
       (D) TOPOLOGY:        linear (xi) SEQUENCE DESCRIPTION: SEQ ID NO: 1464:

GGCCUCGCUG AUGAGGCCGA AAGGCCGAAA GACAUU                              36

(2) INFORMATION FOR SEQ ID NO: 1465:

(i) SEQUENCE CHARACTERISTICS:
       (A) LENGTH:          36 base pairs
       (B) TYPE:            nucleic acid
       (C) STRANDEDNESS:    single
       (D) TOPOLOGY:        linear (xi) SEQUENCE DESCRIPTION: SEQ ID NO: 1465:

GGGCAGGCUG AUGAGGCCGA AAGGCCGAAA GGCUUC                              36

(2) INFORMATION FOR SEQ ID NO: 1466:

(i) SEQUENCE CHARACTERISTICS:
       (A) LENGTH:          36 base pairs
       (B) TYPE:            nucleic acid
       (C) STRANDEDNESS:    single
       (D) TOPOLOGY:        linear (xi) SEQUENCE DESCRIPTION: SEQ ID NO: 1466:

AGGCUGGCUG AUGAGGCCGA AAGGCCGAAA GAGGUC                              36

(2) INFORMATION FOR SEQ ID NO: 1467:

(i) SEQUENCE CHARACTERISTICS:
       (A) LENGTH:          36 base pairs
       (B) TYPE:            nucleic acid
       (C) STRANDEDNESS:    single
       (D) TOPOLOGY:        linear (xi) SEQUENCE DESCRIPTION: SEQ ID NO: 1467:

CUGCUGACUG AUGAGGCCGA AAGGCCGAAA GCUGGG                              36

(2) INFORMATION FOR SEQ ID NO: 1468:

(i) SEQUENCE CHARACTERISTICS:
       (A) LENGTH:          36 base pairs
       (B) TYPE:            nucleic acid
       (C) STRANDEDNESS:    single
       (D) TOPOLOGY:        linear (xi) SEQUENCE DESCRIPTION: SEQ ID NO: 1468:

CCCUUCCCUG AUGAGGCCGA AAGGCCGAAA GACCUC                              36

(2) INFORMATION FOR SEQ ID NO: 1469:
```

```
    (i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1469:

CUUGCACCUG AUGAGGCCGA AAGGCCGAAA CCCUUC                              36

(2) INFORMATION FOR SEQ ID NO: 1470:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1470:

GCACACGCUG AUGAGGCCGA AAGGCCGAAA UGUACC                              36

(2) INFORMATION FOR SEQ ID NO: 1471:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1471:

CUGCACGCUG AUGAGGCCGA AAGGCCGAAA CCCACC                              36

(2) INFORMATION FOR SEQ ID NO: 1472:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1472:

GGUACUCCUG AUGAGGCCGA AAGGCCGAAA UAAAUA                              36

(2) INFORMATION FOR SEQ ID NO: 1473:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1473:

AGAUCGACUG AUGAGGCCGA AAGGCCGAAA GUCCGG                              36

(2) INFORMATION FOR SEQ ID NO: 1474:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1474:

GCAGGGUCUG AUGAGGCCGA AAGGCCGAAA GGUCCU                              36

(2) INFORMATION FOR SEQ ID NO: 1475:

(i) SEQUENCE CHARACTERISTICS:
```

```
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1475:

AGCGGCACUG AUGAGGCCGA AAGGCCGAAA GCAAAA                              36

(2) INFORMATION FOR SEQ ID NO: 1476:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1476:

CCUGUUUCUG AUGAGGCCGA AAGGCCGAAA CAGACU                              36

(2) INFORMATION FOR SEQ ID NO: 1477:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1477:

GGACCAUCUG AUGAGGCCGA AAGGCCGAAA UUUCAU                              36

(2) INFORMATION FOR SEQ ID NO: 1478:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1478:

CGCCUGGCUG AUGAGGCCGA AAGGCCGAAA CCAUGA                              36

(2) INFORMATION FOR SEQ ID NO: 1479:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1479:

CUGCACGCUG AUGAGGCCGA AAGGCCGAAA CCCACC                              36

(2) INFORMATION FOR SEQ ID NO: 1480:

(i) SEQUENCE CHARACTERISTICS:
            (A) LENGTH:              36 base pairs
            (B) TYPE:                nucleic acid
            (C) STRANDEDNESS:        single
            (D) TOPOLOGY:            linear (xi) SEQUENCE DESCRIPTION: SEQ ID NO: 1480:

GGGUCAGCUG AUGAGGCCGA AAGGCCGAAA CCGGAG                              36

(2) INFORMATION FOR SEQ ID NO: 1481:

(i) SEQUENCE CHARACTERISTICS:
            (A) LENGTH:              36 base pairs
```

```
            (B) TYPE:              nucleic acid
            (C) STRANDEDNESS:      single
            (D) TOPOLOGY:          linear (xi) SEQUENCE DESCRIPTION: SEQ ID NO: 1481:

AAAGUUGCUG AUGAGGCCGA AAGGCCGAAA GACUGU                                36

(2) INFORMATION FOR SEQ ID NO: 1482:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1482:

CCUCCAGCUG AUGAGGCCGA AAGGCCGAAA GGUCAG                                36

(2) INFORMATION FOR SEQ ID NO: 1483:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1483:

AAGUCCGCUG AUGAGGCCGA AAGGCCGAAA GGCUCC                                36

(2) INFORMATION FOR SEQ ID NO: 1484:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1484:

UGGGAGCCUG AUGAGGCCGA AAGGCCGAAA AAGGCA                                36

(2) INFORMATION FOR SEQ ID NO: 1485:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1485:

AUGAUUACUG AUGAGGCCGA AAGGCCGAAA GUCCAG                                36

(2) INFORMATION FOR SEQ ID NO: 1486:

(i) SEQUENCE CHARACTERISTICS:
            (A) LENGTH:            36 base pairs
            (B) TYPE:              nucleic acid
            (C) STRANDEDNESS:      single
            (D) TOPOLOGY:          linear (xi) SEQUENCE DESCRIPTION: SEQ ID NO: 1486:

UCAGAAGCUG AUGAGGCCGA AAGGCCGAAA CCACCU                                36

(2) INFORMATION FOR SEQ ID NO: 1487:

(i) SEQUENCE CHARACTERISTICS:
            (A) LENGTH:            36 base pairs
            (B) TYPE:              nucleic acid
```

```
            (C) STRANDEDNESS:         single
            (D) TOPOLOGY:             linear (xi) SEQUENCE DESCRIPTION: SEQ ID NO: 1487:

CAGGCAGCUG AUGAGGCCGA AAGGCCGAAA GUCUCA                              36

(2) INFORMATION FOR SEQ ID NO: 1488:

(i) SEQUENCE CHARACTERISTICS:
            (A) LENGTH:               36 base pairs
            (B) TYPE:                 nucleic acid
            (C) STRANDEDNESS:         single
            (D) TOPOLOGY:             linear (xi) SEQUENCE DESCRIPTION: SEQ ID NO: 1488:

GGUGGCUCUG AUGAGGCCGA AAGGCCGAAA CAUUGG                              36

(2) INFORMATION FOR SEQ ID NO: 1489:

(i) SEQUENCE CHARACTERISTICS:
            (A) LENGTH:               36 base pairs
            (B) TYPE:                 nucleic acid
            (C) STRANDEDNESS:         single
            (D) TOPOLOGY:             linear (xi) SEQUENCE DESCRIPTION: SEQ ID NO: 1489:

AACAUAACUG AUGAGGCCGA AAGGCCGAAA GGCUGC                              36

(2) INFORMATION FOR SEQ ID NO: 1490:

(i) SEQUENCE CHARACTERISTICS:
            (A) LENGTH:               36 base pairs
            (B) TYPE:                 nucleic acid
            (C) STRANDEDNESS:         single
            (D) TOPOLOGY:             linear (xi) SEQUENCE DESCRIPTION: SEQ ID NO: 1490:

UCACAGUCUG AUGAGGCCGA AAGGCCGAAA CUUGGC                              36

(2) INFORMATION FOR SEQ ID NO: 1491:

(i) SEQUENCE CHARACTERISTICS:
            (A) LENGTH:               36 base pairs
            (B) TYPE:                 nucleic acid
            (C) STRANDEDNESS:         single
            (D) TOPOLOGY:             linear (xi) SEQUENCE DESCRIPTION: SEQ ID NO: 1491:

CUUGGCUCUG AUGAGGCCGA AAGGCCGAAA AGGUCC                              36

(2) INFORMATION FOR SEQ ID NO: 1492:

(i) SEQUENCE CHARACTERISTICS:
            (A) LENGTH:               36 base pairs
            (B) TYPE:                 nucleic acid
            (C) STRANDEDNESS:         single
            (D) TOPOLOGY:             linear (xi) SEQUENCE DESCRIPTION: SEQ ID NO: 1492:

GUGAUGGCUG AUGAGGCCGA AAGGCCGAAA GCGGAA                              36

(2) INFORMATION FOR SEQ ID NO: 1493:

(i) SEQUENCE CHARACTERISTICS:
            (A) LENGTH:               36 base pairs
            (B) TYPE:                 nucleic acid
            (C) STRANDEDNESS:         single
```

(D) TOPOLOGY:           linear (xi) SEQUENCE DESCRIPTION: SEQ ID NO: 1493:

AAGAUCGCUG AUGAGGCCGA AAGGCCGAAA AGUCCG                              36

(2) INFORMATION FOR SEQ ID NO: 1494:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1494:

AAAACUCCUG AUGAGGCCGA AAGGCCGAAA AAUUAA                              36

(2) INFORMATION FOR SEQ ID NO: 1495:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1495:

AAUAGAGCUG AUGAGGCCGA AAGGCCGAAA UGAAGU                              36

(2) INFORMATION FOR SEQ ID NO: 1496:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1496:

CAAUAGACUG AUGAGGCCGA AAGGCCGAAA AUGAAG                              36

(2) INFORMATION FOR SEQ ID NO: 1497:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1497:

UAAUAAACUG AUGAGGCCGA AAGGCCGAAA CAUCAA                              36

(2) INFORMATION FOR SEQ ID NO: 1498:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1498:

AAAUUAACUG AUGAGGCCGA AAGGCCGAAA AAUACA                              36

(2) INFORMATION FOR SEQ ID NO: 1499:

(i) SEQUENCE CHARACTERISTICS:
        (A) LENGTH:             36 base pairs
        (B) TYPE:               nucleic acid
        (C) STRANDEDNESS:       single
        (D) TOPOLOGY:           linear (xi) SEQUENCE DESCRIPTION: SEQ ID NO: 1499:

AGCAAAACUG AUGAGGCCGA AAGGCCGAAA AGCUUC                36

(2) INFORMATION FOR SEQ ID NO: 1500:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1500:

AGAGCAACUG AUGAGGCCGA AAGGCCGAAA GAAGCU                36

(2) INFORMATION FOR SEQ ID NO: 1501:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1501:

AAAUUAACUG AUGAGGCCGA AAGGCCGAAA AAUACA                36

(2) INFORMATION FOR SEQ ID NO: 1502:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1502:

AAAUUAACUG AUGAGGCCGA AAGGCCGAAA AAUACA                36

(2) INFORMATION FOR SEQ ID NO: 1503:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1503:

GACAUUACUG AUGAGGCCGA AAGGCCGAAA GAACAA                36

(2) INFORMATION FOR SEQ ID NO: 1504:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1504:

UGACCAGCUG AUGAGGCCGA AAGGCCGAAA GAGAAA                36

(2) INFORMATION FOR SEQ ID NO: 1505:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1505:

CUUAUGACUG AUGAGGCCGA AAGGCCGAAA AAAGCA                       36

(2) INFORMATION FOR SEQ ID NO: 1506:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1506:

UCUAAAUCUG AUGAGGCCGA AAGGCCGAAA AUAAAU                       36

(2) INFORMATION FOR SEQ ID NO: 1507:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1507:

CUCCGGACUG AUGAGGCCGA AAGGCCGAAA CGAAUA                       36

(2) INFORMATION FOR SEQ ID NO: 1508:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1508:

UCUCCGGCUG AUGAGGCCGA AAGGCCGAAA ACGAAU                       36

(2) INFORMATION FOR SEQ ID NO: 1509:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1509:

CUCUCCGCUG AUGAGGCCGA AAGGCCGAAA AACGAA                       36

(2) INFORMATION FOR SEQ ID NO: 1510:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1510:

CGACCCUCUG AUGAGGCCGA AAGGCCGAAA UGAGAA                       36

(2) INFORMATION FOR SEQ ID NO: 1511:

(i) SEQUENCE CHARACTERISTICS:
        (A) LENGTH:         36 base pairs
        (B) TYPE:           nucleic acid
        (C) STRANDEDNESS:   single
        (D) TOPOLOGY:       linear (xi) SEQUENCE DESCRIPTION: SEQ ID NO: 1511:

```
CUUCCGACUG AUGAGGCCGA AAGGCCGAAA CCUCCA                              36

(2) INFORMATION FOR SEQ ID NO: 1512:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1512:

CCCUUCCCUG AUGAGGCCGA AAGGCCGAAA GACCUC                              36

(2) INFORMATION FOR SEQ ID NO: 1513:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1513:

UGGGGACCUG AUGAGGCCGA AAGGCCGAAA UGUCUC                              36

(2) INFORMATION FOR SEQ ID NO: 1514:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1514:

GCAGAGGCUG AUGAGGCCGA AAGGCCGAAA GCGUGG                              36

(2) INFORMATION FOR SEQ ID NO: 1515:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1515:

CACAGCGCUG AUGAGGCCGA AAGGCCGAAA CUGCUG                              36

(2) INFORMATION FOR SEQ ID NO: 1516:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1516:

UGACACACUG AUGAGGCCGA AAGGCCGAAA GUCACU                              36

(2) INFORMATION FOR SEQ ID NO: 1517:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1517:
```

```
UUGAUUCCUG AUGAGGCCGA AAGGCCGAAA AGGAAA                                    36

(2) INFORMATION FOR SEQ ID NO: 1518:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1518:

AGUGGCUCUG AUGAGGCCGA AAGGCCGAAA CACAGA                                    36

(2) INFORMATION FOR SEQ ID NO: 1519:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1519:

AAUUAAUCUG AUGAGGCCGA AAGGCCGAAA AUACAU                                    36

(2) INFORMATION FOR SEQ ID NO: 1520:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1520:

CUUUAUUCUG AUGAGGCCGA AAGGCCGAAA UUCAAA                                    36

(2) INFORMATION FOR SEQ ID NO: 1521:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1521:

CCUCUGCCUG AUGAGGCCGA AAGGCCGAAA GCCAGC                                    36

(2) INFORMATION FOR SEQ ID NO: 1522:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1522:

AAAACUUCUG AUGAGGCCGA AAGGCCGAAA UUGAUU                                    36

(2) INFORMATION FOR SEQ ID NO: 1523:

(i) SEQUENCE CHARACTERISTICS:
        (A) LENGTH:           36 base pairs
        (B) TYPE:             nucleic acid
        (C) STRANDEDNESS:     single
        (D) TOPOLOGY:         linear (xi) SEQUENCE DESCRIPTION: SEQ ID NO: 1523:

GCUGGUACUG AUGAGGCCGA AAGGCCGAAA ACUCUA                                    36
```

(2) INFORMATION FOR SEQ ID NO: 1524:

(i) SEQUENCE CHARACTERISTICS:
        (A) LENGTH:         36 base pairs
        (B) TYPE:           nucleic acid
        (C) STRANDEDNESS:   single
        (D) TOPOLOGY:      linear (xi) SEQUENCE DESCRIPTION: SEQ ID NO: 1524:

AGUAGAGCUG AUGAGGCCGA AAGGCCGAAA ACCCUC                      36

(2) INFORMATION FOR SEQ ID NO: 1525:

(i) SEQUENCE CHARACTERISTICS:
        (A) LENGTH:         36 base pairs
        (B) TYPE:           nucleic acid
        (C) STRANDEDNESS:   single
        (D) TOPOLOGY:      linear (xi) SEQUENCE DESCRIPTION: SEQ ID NO: 1525:

CAGCUCACUG AUGAGGCCGA AAGGCCGAAA CAGCUU                      36

(2) INFORMATION FOR SEQ ID NO: 1526:

(i) SEQUENCE CHARACTERISTICS:
        (A) LENGTH:         36 base pairs
        (B) TYPE:           nucleic acid
        (C) STRANDEDNESS:   single
        (D) TOPOLOGY:      linear (xi) SEQUENCE DESCRIPTION: SEQ ID NO: 1526:

GGCAAUACUG AUGAGGCCGA AAGGCCGAAA GAAUGA                      36

(2) INFORMATION FOR SEQ ID NO: 1527:

(i) SEQUENCE CHARACTERISTICS:
        (A) LENGTH:         52 base pairs
        (B) TYPE:           nucleic acid
        (C) STRANDEDNESS:   single
        (D) TOPOLOGY:      linear (xi) SEQUENCE DESCRIPTION: SEQ ID NO: 1527:

GGGCCGGGAG AAGCUGACCA GAGAAACACA CGUUGUGGUA CAUUACCUGG UA        52

(2) INFORMATION FOR SEQ ID NO: 1528:

(i) SEQUENCE CHARACTERISTICS:
        (A) LENGTH:         52 base pairs
        (B) TYPE:           nucleic acid
        (C) STRANDEDNESS:   single
        (D) TOPOLOGY:      linear (xi) SEQUENCE DESCRIPTION: SEQ ID NO: 1528:

GGAGUGCGAG AAGCGCACCA GAGAAACACA CGUUGUGGUA CAUUACCUGG UA        52

(2) INFORMATION FOR SEQ ID NO: 1529:

(i) SEQUENCE CHARACTERISTICS:
        (A) LENGTH:         52 base pairs
        (B) TYPE:           nucleic acid
        (C) STRANDEDNESS:   single
        (D) TOPOLOGY:      linear (xi) SEQUENCE DESCRIPTION: SEQ ID NO: 1529:

CCCAUCAGAG AAGUUUACCA GAGAAACACA CGUUGUGGUA CAUUACCUGG UA        52

(2) INFORMATION FOR SEQ ID NO: 1530:

(i) SEQUENCE CHARACTERISTICS:
        (A) LENGTH:        52 base pairs
        (B) TYPE:          nucleic acid
        (C) STRANDEDNESS:  single
        (D) TOPOLOGY:     linear (xi) SEQUENCE DESCRIPTION: SEQ ID NO: 1530:

GCCCUUGGAG AAGCAGACCA GAGAAACACA CGUUGUGGUA CAUUACCUGG UA        52

(2) INFORMATION FOR SEQ ID NO: 1531:

(i) SEQUENCE CHARACTERISTICS:
        (A) LENGTH:        52 base pairs
        (B) TYPE:          nucleic acid
        (C) STRANDEDNESS:  single
        (D) TOPOLOGY:     linear (xi) SEQUENCE DESCRIPTION: SEQ ID NO: 1531:

UGUUCUCAAG AAGCUCACCA GAGAAACACA CGUUGUGGUA CAUUACCUGG UA        52

(2) INFORMATION FOR SEQ ID NO: 1532:

(i) SEQUENCE CHARACTERISTICS:
        (A) LENGTH:        52 base pairs
        (B) TYPE:          nucleic acid
        (C) STRANDEDNESS:  single
        (D) TOPOLOGY:     linear (xi) SEQUENCE DESCRIPTION: SEQ ID NO: 1532:

AGACUGGGAG AAGCCCACCA GAGAAACACA CGUUGUGGUA CAUUACCUGG UA        52

(2) INFORMATION FOR SEQ ID NO: 1533:

(i) SEQUENCE CHARACTERISTICS:
        (A) LENGTH:        52 base pairs
        (B) TYPE:          nucleic acid
        (C) STRANDEDNESS:  single
        (D) TOPOLOGY:     linear (xi) SEQUENCE DESCRIPTION: SEQ ID NO: 1533:

CUGCACACAG AAGCCGACCA GAGAAACACA CGUUGUGGUA CAUUACCUGG UA        52

(2) INFORMATION FOR SEQ ID NO: 1534:

(i) SEQUENCE CHARACTERISTICS:
        (A) LENGTH:        52 base pairs
        (B) TYPE:          nucleic acid
        (C) STRANDEDNESS:  single
        (D) TOPOLOGY:     linear (xi) SEQUENCE DESCRIPTION: SEQ ID NO: 1534:

ACAUUGGAAG AAGCUGACCA GAGAAACACA CGUUGUGGUA CAUUACCUGG UA        52

(2) INFORMATION FOR SEQ ID NO: 1535:

(i) SEQUENCE CHARACTERISTICS:
        (A) LENGTH:        52 base pairs
        (B) TYPE:          nucleic acid
        (C) STRANDEDNESS:  single
        (D) TOPOLOGY:     linear (xi) SEQUENCE DESCRIPTION: SEQ ID NO: 1535:

CCCCGAUGAG AAGUGGACCA GAGAAACACA CGUUGUGGUA CAUUACCUGG UA        52

```
(2) INFORMATION FOR SEQ ID NO: 1536:

(i) SEQUENCE CHARACTERISTICS:
        (A) LENGTH:         52 base pairs
        (B) TYPE:           nucleic acid
        (C) STRANDEDNESS:   single
        (D) TOPOLOGY:       linear (xi) SEQUENCE DESCRIPTION: SEQ ID NO: 1536:

AUGACUGCAG AAGCUAACCA GAGAAACACA CGUUGUGGUA CAUUACCUGG UA            52

(2) INFORMATION FOR SEQ ID NO: 1537:

(i) SEQUENCE CHARACTERISTICS:
        (A) LENGTH:         52 base pairs
        (B) TYPE:           nucleic acid
        (C) STRANDEDNESS:   single
        (D) TOPOLOGY:       linear (xi) SEQUENCE DESCRIPTION: SEQ ID NO: 1537:

CUGUUGUAAG AAGUAUACCA GAGAAACACA CGUUGUGGUA CAUUACCUGG UA            52

(2) INFORMATION FOR SEQ ID NO: 1538:

(i) SEQUENCE CHARACTERISTICS:
        (A) LENGTH:         52 base pairs
        (B) TYPE:           nucleic acid
        (C) STRANDEDNESS:   single
        (D) TOPOLOGY:       linear (xi) SEQUENCE DESCRIPTION: SEQ ID NO: 1538:

ACCCAAUAAG AAGCAAACCA GAGAAACACA CGUUGUGGUA CAUUACCUGG UA            52

(2) INFORMATION FOR SEQ ID NO: 1539:

(i) SEQUENCE CHARACTERISTICS:
        (A) LENGTH:         52 base pairs
        (B) TYPE:           nucleic acid
        (C) STRANDEDNESS:   single
        (D) TOPOLOGY:       linear (xi) SEQUENCE DESCRIPTION: SEQ ID NO: 1539:

UUCUGUAAAG AAGUGGACCA GAGAAACACA CGUUGUGGUA CAUUACCUGG UA            52

(2) INFORMATION FOR SEQ ID NO: 1540:

(i) SEQUENCE CHARACTERISTICS:
        (A) LENGTH:         52 base pairs
        (B) TYPE:           nucleic acid
        (C) STRANDEDNESS:   single
        (D) TOPOLOGY:       linear (xi) SEQUENCE DESCRIPTION: SEQ ID NO: 1540:

GGUCAGUAAG AAGCAGACCA GAGAAACACA CGUUGUGGUA CAUUACCUGG UA            52

(2) INFORMATION FOR SEQ ID NO: 1541:

(i) SEQUENCE CHARACTERISTICS:
        (A) LENGTH:         52 base pairs
        (B) TYPE:           nucleic acid
        (C) STRANDEDNESS:   single
        (D) TOPOLOGY:       linear (xi) SEQUENCE DESCRIPTION: SEQ ID NO: 1541:

GGGUUGGGAG AAGUAGACCA GAGAAACACA CGUUGUGGUA CAUUACCUGG UA            52

(2) INFORMATION FOR SEQ ID NO: 1542:
```

(i) SEQUENCE CHARACTERISTICS:
            (A) LENGTH:         52 base pairs
            (B) TYPE:           nucleic acid
            (C) STRANDEDNESS:   single
            (D) TOPOLOGY:       linear (xi) SEQUENCE DESCRIPTION: SEQ ID NO: 1542:

ACCUGUACAG AAGUACACCA GAGAAACACA CGUUGUGGUA CAUUACCUGG UA           52

(2) INFORMATION FOR SEQ ID NO: 1543:

(i) SEQUENCE CHARACTERISTICS:
            (A) LENGTH:         52 base pairs
            (B) TYPE:           nucleic acid
            (C) STRANDEDNESS:   single
            (D) TOPOLOGY:       linear (xi) SEQUENCE DESCRIPTION: SEQ ID NO: 1543:

AAGGUCAAAG AAGCAGACCA GAGAAACACA CGUUGUGGUA CAUUACCUGG UA           52

(2) INFORMATION FOR SEQ ID NO: 1544:

(i) SEQUENCE CHARACTERISTICS:
            (A) LENGTH:         16 base pairs
            (B) TYPE:           nucleic acid
            (C) STRANDEDNESS:   single
            (D) TOPOLOGY:       linear (xi) SEQUENCE DESCRIPTION: SEQ ID NO: 1544:

CAGCAGCCCC CGGCCC                                                  16

(2) INFORMATION FOR SEQ ID NO: 1545:

(i) SEQUENCE CHARACTERISTICS:
            (A) LENGTH:         16 base pairs
            (B) TYPE:           nucleic acid
            (C) STRANDEDNESS:   single
            (D) TOPOLOGY:       linear (xi) SEQUENCE DESCRIPTION: SEQ ID NO: 1545:

GCGCUGCCCG CACUCC                                                  16

(2) INFORMATION FOR SEQ ID NO: 1546:

(i) SEQUENCE CHARACTERISTICS:
            (A) LENGTH:         16 base pairs
            (B) TYPE:           nucleic acid
            (C) STRANDEDNESS:   single
            (D) TOPOLOGY:       linear (xi) SEQUENCE DESCRIPTION: SEQ ID NO: 1546:

AAACUGCCCU GAUGGG                                                  16

(2) INFORMATION FOR SEQ ID NO: 1547:

(i) SEQUENCE CHARACTERISTICS:
            (A) LENGTH:         16 base pairs
            (B) TYPE:           nucleic acid
            (C) STRANDEDNESS:   single
            (D) TOPOLOGY:       linear (xi) SEQUENCE DESCRIPTION: SEQ ID NO: 1547:

CUGCGGCCCC AAGGGC                                                  16

(2) INFORMATION FOR SEQ ID NO: 1548:

```
    (i) SEQUENCE CHARACTERISTICS:
        (A) LENGTH:          16 base pairs
        (B) TYPE:            nucleic acid
        (C) STRANDEDNESS:    single
        (D) TOPOLOGY:        linear (xi) SEQUENCE DESCRIPTION: SEQ ID NO: 1548:

GAGCUGUUUG AGAACA                                                   16

(2) INFORMATION FOR SEQ ID NO: 1549:

(i) SEQUENCE CHARACTERISTICS:
        (A) LENGTH:          16 base pairs
        (B) TYPE:            nucleic acid
        (C) STRANDEDNESS:    single
        (D) TOPOLOGY:        linear (xi) SEQUENCE DESCRIPTION: SEQ ID NO: 1549:

GGGCUGUUCC CAGUCU                                                   16

(2) INFORMATION FOR SEQ ID NO: 1550:

(i) SEQUENCE CHARACTERISTICS:
        (A) LENGTH:          16 base pairs
        (B) TYPE:            nucleic acid
        (C) STRANDEDNESS:    single
        (D) TOPOLOGY:        linear (xi) SEQUENCE DESCRIPTION: SEQ ID NO: 1550:

CGGCUGACGU GUGCAG                                                   16

(2) INFORMATION FOR SEQ ID NO: 1551:

(i) SEQUENCE CHARACTERISTICS:
        (A) LENGTH:          16 base pairs
        (B) TYPE:            nucleic acid
        (C) STRANDEDNESS:    single
        (D) TOPOLOGY:        linear (xi) SEQUENCE DESCRIPTION: SEQ ID NO: 1551:

CAGCAGACUC CAAUGU                                                   16

(2) INFORMATION FOR SEQ ID NO: 1552:

(i) SEQUENCE CHARACTERISTICS:
        (A) LENGTH:          16 base pairs
        (B) TYPE:            nucleic acid
        (C) STRANDEDNESS:    single
        (D) TOPOLOGY:        linear (xi) SEQUENCE DESCRIPTION: SEQ ID NO: 1552:

CCACUGCCCA UCGGGG                                                   16

(2) INFORMATION FOR SEQ ID NO: 1553:

(i) SEQUENCE CHARACTERISTICS:
        (A) LENGTH:          16 base pairs
        (B) TYPE:            nucleic acid
        (C) STRANDEDNESS:    single
        (D) TOPOLOGY:        linear (xi) SEQUENCE DESCRIPTION: SEQ ID NO: 1553:

UAGCAGCCGC AGUCAU                                                   16

(2) INFORMATION FOR SEQ ID NO: 1554:

(i) SEQUENCE CHARACTERISTICS:
```

```
            (A) LENGTH:            16 base pairs
            (B) TYPE:              nucleic acid
            (C) STRANDEDNESS:      single
            (D) TOPOLOGY:          linear (xi) SEQUENCE DESCRIPTION: SEQ ID NO: 1554:

AUACAGACUA CAACAG                                                    16

(2) INFORMATION FOR SEQ ID NO: 1555:

(i) SEQUENCE CHARACTERISTICS:
            (A) LENGTH:            16 base pairs
            (B) TYPE:              nucleic acid
            (C) STRANDEDNESS:      single
            (D) TOPOLOGY:          linear (xi) SEQUENCE DESCRIPTION: SEQ ID NO: 1555:

UUGCUGCCUA UUGGGU                                                    16

(2) INFORMATION FOR SEQ ID NO: 1556:

(i) SEQUENCE CHARACTERISTICS:
            (A) LENGTH:            16 base pairs
            (B) TYPE:              nucleic acid
            (C) STRANDEDNESS:      single
            (D) TOPOLOGY:          linear (xi) SEQUENCE DESCRIPTION: SEQ ID NO: 1556:

CCACAGACUU ACAGAA                                                    16

(2) INFORMATION FOR SEQ ID NO: 1557:

(i) SEQUENCE CHARACTERISTICS:
            (A) LENGTH:            16 base pairs
            (B) TYPE:              nucleic acid
            (C) STRANDEDNESS:      single
            (D) TOPOLOGY:          linear (xi) SEQUENCE DESCRIPTION: SEQ ID NO: 1557:

CUGCUGUCUA CUGACC                                                    16

(2) INFORMATION FOR SEQ ID NO: 1558:

(i) SEQUENCE CHARACTERISTICS:
            (A) LENGTH:            16 base pairs
            (B) TYPE:              nucleic acid
            (C) STRANDEDNESS:      single
            (D) TOPOLOGY:          linear (xi) SEQUENCE DESCRIPTION: SEQ ID NO: 1558:

CUACUGACCC CAACCC                                                    16

(2) INFORMATION FOR SEQ ID NO: 1559:

(i) SEQUENCE CHARACTERISTICS:
            (A) LENGTH:            16 base pairs
            (B) TYPE:              nucleic acid
            (C) STRANDEDNESS:      single
            (D) TOPOLOGY:          linear (xi) SEQUENCE DESCRIPTION: SEQ ID NO: 1559:

GUACAGUUGU ACAGGU                                                    16

(2) INFORMATION FOR SEQ ID NO: 1560:

(i) SEQUENCE CHARACTERISTICS:
            (A) LENGTH:            16 base pairs
```

```
        (B) TYPE:               nucleic acid
        (C) STRANDEDNESS:       single
        (D) TOPOLOGY:           linear (xi) SEQUENCE DESCRIPTION: SEQ ID NO: 1560:

CUGCAGUCUU GACCUU                                                            16

(2) INFORMATION FOR SEQ ID NO: 1561:

(i) SEQUENCE CHARACTERISTICS:
        (A) LENGTH:             52 base pairs
        (B) TYPE:               nucleic acid
        (C) STRANDEDNESS:       single
        (D) TOPOLOGY:           linear (xi) SEQUENCE DESCRIPTION: SEQ ID NO: 1561:

GGGAUCACAG AAGUGAACCA GAGAAACACA CGUUGUGGUA CAUUACCUGG UA                    52

(2) INFORMATION FOR SEQ ID NO: 1562:

(i) SEQUENCE CHARACTERISTICS:
        (A) LENGTH:             52 base pairs
        (B) TYPE:               nucleic acid
        (C) STRANDEDNESS:       single
        (D) TOPOLOGY:           linear (xi) SEQUENCE DESCRIPTION: SEQ ID NO: 1562:

UGAGGAAGAG AAGUUCACCA GAGAAACACA CGUUGUGGUA CAUUACCUGG UA                    52

(2) INFORMATION FOR SEQ ID NO: 1563:

(i) SEQUENCE CHARACTERISTICS:
        (A) LENGTH:             52 base pairs
        (B) TYPE:               nucleic acid
        (C) STRANDEDNESS:       single
        (D) TOPOLOGY:           linear (xi) SEQUENCE DESCRIPTION: SEQ ID NO: 1563:

UCAGCUCAAG AAGCUUACCA GAGAAACACA CGUUGUGGUA CAUUACCUGG UA                    52

(2) INFORMATION FOR SEQ ID NO: 1564:

(i) SEQUENCE CHARACTERISTICS:
        (A) LENGTH:             52 base pairs
        (B) TYPE:               nucleic acid
        (C) STRANDEDNESS:       single
        (D) TOPOLOGY:           linear (xi) SEQUENCE DESCRIPTION: SEQ ID NO: 1564:

GCACAGCGAG AAGCUGACCA GAGAAACACA CGUUGUGGUA CAUUACCUGG UA                    52

(2) INFORMATION FOR SEQ ID NO: 1565:

(i) SEQUENCE CHARACTERISTICS:
        (A) LENGTH:             52 base pairs
        (B) TYPE:               nucleic acid
        (C) STRANDEDNESS:       single
        (D) TOPOLOGY:           linear (xi) SEQUENCE DESCRIPTION: SEQ ID NO: 1565:

AAGCGGACAG AAGCACACCA GAGAAACACA CGUUGUGGUA CAUUACCUGG UA                    52

(2) INFORMATION FOR SEQ ID NO: 1566:

(i) SEQUENCE CHARACTERISTICS:
        (A) LENGTH:             52 base pairs
        (B) TYPE:               nucleic acid
```

```
            (C) STRANDEDNESS:        single
            (D) TOPOLOGY:            linear (xi) SEQUENCE DESCRIPTION: SEQ ID NO: 1566:

AGAGCUGGAG AAGCGGACCA GAGAAACACA CGUUGUGGUA CAUUACCUGG UA              52

(2) INFORMATION FOR SEQ ID NO: 1567:

(i) SEQUENCE CHARACTERISTICS:
            (A) LENGTH:             52 base pairs
            (B) TYPE:               nucleic acid
            (C) STRANDEDNESS:       single
            (D) TOPOLOGY:           linear (xi) SEQUENCE DESCRIPTION: SEQ ID NO: 1567:

UCUCCUGGAG AAGCAUACCA GAGAAACACA CGUUGUGGUA CAUUACCUGG UA              52

(2) INFORMATION FOR SEQ ID NO: 1568:

(i) SEQUENCE CHARACTERISTICS:
            (A) LENGTH:             52 base pairs
            (B) TYPE:               nucleic acid
            (C) STRANDEDNESS:       single
            (D) TOPOLOGY:           linear (xi) SEQUENCE DESCRIPTION: SEQ ID NO: 1568:

UCUACCAAAG AAGUGGACCA GAGAAACACA CGUUGUGGUA CAUUACCUGG UA              52

(2) INFORMATION FOR SEQ ID NO: 1569:

(i) SEQUENCE CHARACTERISTICS:
            (A) LENGTH:             52 base pairs
            (B) TYPE:               nucleic acid
            (C) STRANDEDNESS:       single
            (D) TOPOLOGY:           linear (xi) SEQUENCE DESCRIPTION: SEQ ID NO: 1569:

AGGAUCUGAG AAGCUAACCA GAGAAACACA CGUUGUGGUA CAUUACCUGG UA              52

(2) INFORMATION FOR SEQ ID NO: 1570:

(i) SEQUENCE CHARACTERISTICS:
            (A) LENGTH:             52 base pairs
            (B) TYPE:               nucleic acid
            (C) STRANDEDNESS:       single
            (D) TOPOLOGY:           linear (xi) SEQUENCE DESCRIPTION: SEQ ID NO: 1570:

AAGUUGUAAG AAGUUAACCA GAGAAACACA CGUUGUGGUA CAUUACCUGG UA              52

(2) INFORMATION FOR SEQ ID NO: 1571:

(i) SEQUENCE CHARACTERISTICS:
            (A) LENGTH:             52 base pairs
            (B) TYPE:               nucleic acid
            (C) STRANDEDNESS:       single
            (D) TOPOLOGY:           linear (xi) SEQUENCE DESCRIPTION: SEQ ID NO: 1571:

CCCAAGCAAG AAGUCUACCA GAGAAACACA CGUUGUGGUA CAUUACCUGG UA              52

(2) INFORMATION FOR SEQ ID NO: 1572:

(i) SEQUENCE CHARACTERISTICS:
            (A) LENGTH:             52 base pairs
            (B) TYPE:               nucleic acid
            (C) STRANDEDNESS:       single
```

(D) TOPOLOGY:           linear (xi) SEQUENCE DESCRIPTION: SEQ ID NO: 1572:

AUUUCAGAAG AAGCUGACCA GAGAAACACA CGUUGUGGUA CAUUACCUGG UA          52

(2) INFORMATION FOR SEQ ID NO: 1573:

(i) SEQUENCE CHARACTERISTICS:
            (A) LENGTH:             52 base pairs
            (B) TYPE:               nucleic acid
            (C) STRANDEDNESS:       single
            (D) TOPOLOGY:           linear (xi) SEQUENCE DESCRIPTION: SEQ ID NO: 1573:

UGCCUUCCAG AAGCAGACCA GAGAAACACA CGUUGUGGUA CAUUACCUGG UA          52

(2) INFORMATION FOR SEQ ID NO: 1574:

(i) SEQUENCE CHARACTERISTICS:
            (A) LENGTH:             52 base pairs
            (B) TYPE:               nucleic acid
            (C) STRANDEDNESS:       single
            (D) TOPOLOGY:           linear (xi) SEQUENCE DESCRIPTION: SEQ ID NO: 1574:

CCCCGAUGAG AAGCAGACCA GAGAAACACA CGUUGUGGUA CAUUACCUGG UA          52

(2) INFORMATION FOR SEQ ID NO: 1575:

(i) SEQUENCE CHARACTERISTICS:
            (A) LENGTH:             52 base pairs
            (B) TYPE:               nucleic acid
            (C) STRANDEDNESS:       single
            (D) TOPOLOGY:           linear (xi) SEQUENCE DESCRIPTION: SEQ ID NO: 1575:

ACAUAAGAAG AAGCCAACCA GAGAAACACA CGUUGUGGUA CAUUACCUGG UA          52

(2) INFORMATION FOR SEQ ID NO: 1576:

(i) SEQUENCE CHARACTERISTICS:
            (A) LENGTH:             52 base pairs
            (B) TYPE:               nucleic acid
            (C) STRANDEDNESS:       single
            (D) TOPOLOGY:           linear (xi) SEQUENCE DESCRIPTION: SEQ ID NO: 1576:

GUCCACCGAG AAGUAGACCA GAGAAACACA CGUUGUGGUA CAUUACCUGG UA          52

(2) INFORMATION FOR SEQ ID NO: 1577:

(i) SEQUENCE CHARACTERISTICS:
            (A) LENGTH:             52 base pairs
            (B) TYPE:               nucleic acid
            (C) STRANDEDNESS:       single
            (D) TOPOLOGY:           linear (xi) SEQUENCE DESCRIPTION: SEQ ID NO: 1577:

AGAAUGAAAG AAGCGUACCA GAGAAACACA CGUUGUGGUA CAUUACCUGG UA          52

(2) INFORMATION FOR SEQ ID NO: 1578:

(i) SEQUENCE CHARACTERISTICS:
            (A) LENGTH:             16 base pairs
            (B) TYPE:               nucleic acid
            (C) STRANDEDNESS:       single
            (D) TOPOLOGY:           linear (xi) SEQUENCE DESCRIPTION: SEQ ID NO: 1578:

UCACCGUUGU GAUCCC                                              16

(2) INFORMATION FOR SEQ ID NO: 1579:

(i) SEQUENCE CHARACTERISTICS:
        (A) LENGTH:             16 base pairs
        (B) TYPE:               nucleic acid
        (C) STRANDEDNESS:       single
        (D) TOPOLOGY:           linear (xi) SEQUENCE DESCRIPTION: SEQ ID NO: 1579:

GAACUGUUCU UCCUCA                                              16

(2) INFORMATION FOR SEQ ID NO: 1580:

(i) SEQUENCE CHARACTERISTICS:
        (A) LENGTH:             16 base pairs
        (B) TYPE:               nucleic acid
        (C) STRANDEDNESS:       single
        (D) TOPOLOGY:           linear (xi) SEQUENCE DESCRIPTION: SEQ ID NO: 1580:

AAGCUGUUUG AGCUGA                                              16

(2) INFORMATION FOR SEQ ID NO: 1581:

(i) SEQUENCE CHARACTERISTICS:
        (A) LENGTH:             16 base pairs
        (B) TYPE:               nucleic acid
        (C) STRANDEDNESS:       single
        (D) TOPOLOGY:           linear (xi) SEQUENCE DESCRIPTION: SEQ ID NO: 1581:

CAGCAGUCCG CUGUGC                                              16

(2) INFORMATION FOR SEQ ID NO: 1582:

(i) SEQUENCE CHARACTERISTICS:
        (A) LENGTH:             16 base pairs
        (B) TYPE:               nucleic acid
        (C) STRANDEDNESS:       single
        (D) TOPOLOGY:           linear (xi) SEQUENCE DESCRIPTION: SEQ ID NO: 1582:

GUGCAGUCGU CCGCUU                                              16

(2) INFORMATION FOR SEQ ID NO: 1583:

(i) SEQUENCE CHARACTERISTICS:
        (A) LENGTH:             16 base pairs
        (B) TYPE:               nucleic acid
        (C) STRANDEDNESS:       single
        (D) TOPOLOGY:           linear (xi) SEQUENCE DESCRIPTION: SEQ ID NO: 1583:

CCGCGGACCC AGCUCU                                              16

(2) INFORMATION FOR SEQ ID NO: 1584:

(i) SEQUENCE CHARACTERISTICS:
        (A) LENGTH:             16 base pairs
        (B) TYPE:               nucleic acid
        (C) STRANDEDNESS:       single
        (D) TOPOLOGY:           linear (xi) SEQUENCE DESCRIPTION: SEQ ID NO: 1584:

AUGCCGACCC AGGAGA                                                       16

(2) INFORMATION FOR SEQ ID NO: 1585:

(i) SEQUENCE CHARACTERISTICS:
        (A) LENGTH:         16 base pairs
        (B) TYPE:           nucleic acid
        (C) STRANDEDNESS:   single
        (D) TOPOLOGY:       linear (xi) SEQUENCE DESCRIPTION: SEQ ID NO: 1585:

CCACUGCCUU GGUAGA                                                       16

(2) INFORMATION FOR SEQ ID NO: 1586:

(i) SEQUENCE CHARACTERISTICS:
        (A) LENGTH:         16 base pairs
        (B) TYPE:           nucleic acid
        (C) STRANDEDNESS:   single
        (D) TOPOLOGY:       linear (xi) SEQUENCE DESCRIPTION: SEQ ID NO: 1586:

UAGCGGACCA GAUCCU                                                       16

(2) INFORMATION FOR SEQ ID NO: 1587:

(i) SEQUENCE CHARACTERISTICS:
        (A) LENGTH:         16 base pairs
        (B) TYPE:           nucleic acid
        (C) STRANDEDNESS:   single
        (D) TOPOLOGY:       linear (xi) SEQUENCE DESCRIPTION: SEQ ID NO: 1587:

UAACAGUCUA CAACUU                                                       16

(2) INFORMATION FOR SEQ ID NO: 1588:

(i) SEQUENCE CHARACTERISTICS:
        (A) LENGTH:         16 base pairs
        (B) TYPE:           nucleic acid
        (C) STRANDEDNESS:   single
        (D) TOPOLOGY:       linear (xi) SEQUENCE DESCRIPTION: SEQ ID NO: 1588:

AGACGGACUG CUUGGG                                                       16

(2) INFORMATION FOR SEQ ID NO: 1589:

(i) SEQUENCE CHARACTERISTICS:
        (A) LENGTH:         16 base pairs
        (B) TYPE:           nucleic acid
        (C) STRANDEDNESS:   single
        (D) TOPOLOGY:       linear (xi) SEQUENCE DESCRIPTION: SEQ ID NO: 1589:

CAGCAGACUC UGAAAU                                                       16

(2) INFORMATION FOR SEQ ID NO: 1590:

(i) SEQUENCE CHARACTERISTICS:
        (A) LENGTH:         16 base pairs
        (B) TYPE:           nucleic acid
        (C) STRANDEDNESS:   single
        (D) TOPOLOGY:       linear (xi) SEQUENCE DESCRIPTION: SEQ ID NO: 1590:

```
CUGCAGACGG AAGGCA                                                      16

(2) INFORMATION FOR SEQ ID NO: 1591:

(i) SEQUENCE CHARACTERISTICS:
        (A) LENGTH:           16 base pairs
        (B) TYPE:             nucleic acid
        (C) STRANDEDNESS:     single
        (D) TOPOLOGY:         linear (xi) SEQUENCE DESCRIPTION: SEQ ID NO: 1591:

CUGCUGCCCA UCGGGG                                                      16

(2) INFORMATION FOR SEQ ID NO: 1592:

(i) SEQUENCE CHARACTERISTICS:
        (A) LENGTH:           16 base pairs
        (B) TYPE:             nucleic acid
        (C) STRANDEDNESS:     single
        (D) TOPOLOGY:         linear (xi) SEQUENCE DESCRIPTION: SEQ ID NO: 1592:

UGGCAGCCUC UUAUGU                                                      16

(2) INFORMATION FOR SEQ ID NO: 1593:

(i) SEQUENCE CHARACTERISTICS:
        (A) LENGTH:           16 base pairs
        (B) TYPE:             nucleic acid
        (C) STRANDEDNESS:     single
        (D) TOPOLOGY:         linear (xi) SEQUENCE DESCRIPTION: SEQ ID NO: 1593:

CUACAGCCCG GUGGAC                                                      16

(2) INFORMATION FOR SEQ ID NO: 1594:

(i) SEQUENCE CHARACTERISTICS:
        (A) LENGTH:           16 base pairs
        (B) TYPE:             nucleic acid
        (C) STRANDEDNESS:     single
        (D) TOPOLOGY:         linear (xi) SEQUENCE DESCRIPTION: SEQ ID NO: 1594:

ACGCUGACUU CAUUCU                                                      16

(2) INFORMATION FOR SEQ ID NO: 1595:

(i) SEQUENCE CHARACTERISTICS:
        (A) LENGTH:           52 base pairs
        (B) TYPE:             nucleic acid
        (C) STRANDEDNESS:     single
        (D) TOPOLOGY:         linear (xi) SEQUENCE DESCRIPTION: SEQ ID NO: 1595:

AAAGUGCAAG AAGCAGACCA GAGAAACACA CGUUGUGGUA CAUUACCUGG UA              52

(2) INFORMATION FOR SEQ ID NO: 1596:

(i) SEQUENCE CHARACTERISTICS:
        (A) LENGTH:           52 base pairs
        (B) TYPE:             nucleic acid
        (C) STRANDEDNESS:     single
        (D) TOPOLOGY:         linear (xi) SEQUENCE DESCRIPTION: SEQ ID NO: 1596:
```

GGAGCAGAAG AAGCAUACCA GAGAAACACA CGUUGUGGUA CAUUACCUGG UA         52

(2) INFORMATION FOR SEQ ID NO: 1597:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1597:

GGGAUCACAG AAGCGAACCA GAGAAACACA CGUUGUGGUA CAUUACCUGG UA         52

(2) INFORMATION FOR SEQ ID NO: 1598:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1598:

GCACAGUGAG AAGCUGACCA GAGAAACACA CGUUGUGGUA CAUUACCUGG UA         52

(2) INFORMATION FOR SEQ ID NO: 1599:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1599:

AAGCCGAGAG AAGCGUACCA GAGAAACACA CGUUGUGGUA CAUUACCUGG UA         52

(2) INFORMATION FOR SEQ ID NO: 1600:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1600:

UUCCACCAAG AAGCGCACCA GAGAAACACA CGUUGUGGUA CAUUACCUGG UA         52

(2) INFORMATION FOR SEQ ID NO: 1601:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1601:

CAUUCUUGAG AAGUGAACCA GAGAAACACA CGUUGUGGUA CAUUACCUGG UA         52

(2) INFORMATION FOR SEQ ID NO: 1602:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1602:

UCUCCAGGAG AAGCAUACCA GAGAAACACA CGUUGUGGUA CAUUACCUGG UA         52

(2) INFORMATION FOR SEQ ID NO: 1603:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1603:

UCCACUGAAG AAGUGGACCA GAGAAACACA CGUUGUGGUA CAUUACCUGG UA           52

(2) INFORMATION FOR SEQ ID NO: 1604:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1604:

AGGGUCUGAG AAGCCAACCA GAGAAACACA CGUUGUGGUA CAUUACCUGG UA           52

(2) INFORMATION FOR SEQ ID NO: 1605:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1605:

ACCUCCAAAG AAGCAGACCA GAGAAACACA CGUUGUGGUA CAUUACCUGG UA           52

(2) INFORMATION FOR SEQ ID NO: 1606:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1606:

AUGUAAGAAG AAGCUGACCA GAGAAACACA CGUUGUGGUA CAUUACCUGG UA           52

(2) INFORMATION FOR SEQ ID NO: 1607:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1607:

UGCUUUCCAG AAGCAGACCA GAGAAACACA CGUUGUGGUA CAUUACCUGG UA           52

(2) INFORMATION FOR SEQ ID NO: 1608:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1608:

UCCCGAUAAG AAGCGGACCA GAGAAACACA CGUUGUGGUA CAUUACCUGG UA           52

(2) INFORMATION FOR SEQ ID NO: 1609:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1609:

GCCCACCAAG AAGUAGACCA GAGAAACACA CGUUGUGGUA CAUUACCUGG UA            52

(2) INFORMATION FOR SEQ ID NO: 1610:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1610:

AGAAGGAAAG AAGCCUACCA GAGAAACACA CGUUGUGGUA CAUUACCUGG UA            52

(2) INFORMATION FOR SEQ ID NO: 1611:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1611:

GAGUUGGGAG AAGUGUACCA GAGAAACACA CGUUGUGGUA CAUUACCUGG UA            52

(2) INFORMATION FOR SEQ ID NO: 1612:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1612:

AGACUCCAAG AAGUGGACCA GAGAAACACA CGUUGUGGUA CAUUACCUGG UA            52

(2) INFORMATION FOR SEQ ID NO: 1613:

(i) SEQUENCE CHARACTERISTICS:
        (A) LENGTH:          52 base pairs
        (B) TYPE:            nucleic acid
        (C) STRANDEDNESS:    single
        (D) TOPOLOGY:        linear (xi) SEQUENCE DESCRIPTION: SEQ ID NO: 1613:

CCUCCCACAG AAGCUUACCA GAGAAACACA CGUUGUGGUA CAUUACCUGG UA            52

(2) INFORMATION FOR SEQ ID NO: 1614:

(i) SEQUENCE CHARACTERISTICS:
        (A) LENGTH:          16 base pairs
        (B) TYPE:            nucleic acid
        (C) STRANDEDNESS:    single
        (D) TOPOLOGY:        linear (xi) SEQUENCE DESCRIPTION: SEQ ID NO: 1614:

CUGCUGCCUG CACUUU                                                   16

```
(2) INFORMATION FOR SEQ ID NO: 1615:

(i) SEQUENCE CHARACTERISTICS:
        (A) LENGTH:              16 base pairs
        (B) TYPE:                nucleic acid
        (C) STRANDEDNESS:        single
        (D) TOPOLOGY:            linear (xi) SEQUENCE DESCRIPTION: SEQ ID NO: 1615:

AUGCUGCCUC UGCUCC                                                       16

(2) INFORMATION FOR SEQ ID NO: 1616:

(i) SEQUENCE CHARACTERISTICS:
        (A) LENGTH:              16 base pairs
        (B) TYPE:                nucleic acid
        (C) STRANDEDNESS:        single
        (D) TOPOLOGY:            linear (xi) SEQUENCE DESCRIPTION: SEQ ID NO: 1616:

UCGCCGUUGU GAUCCC                                                       16

(2) INFORMATION FOR SEQ ID NO: 1617:

(i) SEQUENCE CHARACTERISTICS:
        (A) LENGTH:              16 base pairs
        (B) TYPE:                nucleic acid
        (C) STRANDEDNESS:        single
        (D) TOPOLOGY:            linear (xi) SEQUENCE DESCRIPTION: SEQ ID NO: 1617:

CAGCAGACCA CUGUGC                                                       16

(2) INFORMATION FOR SEQ ID NO: 1618:

(i) SEQUENCE CHARACTERISTICS:
        (A) LENGTH:              16 base pairs
        (B) TYPE:                nucleic acid
        (C) STRANDEDNESS:        single
        (D) TOPOLOGY:            linear (xi) SEQUENCE DESCRIPTION: SEQ ID NO: 1618:

ACGCAGUCCU CGGCUU                                                       16

(2) INFORMATION FOR SEQ ID NO: 1619:

(i) SEQUENCE CHARACTERISTICS:
        (A) LENGTH:              16 base pairs
        (B) TYPE:                nucleic acid
        (C) STRANDEDNESS:        single
        (D) TOPOLOGY:            linear (xi) SEQUENCE DESCRIPTION: SEQ ID NO: 1619:

GCGCUGCCUG GUGGAA                                                       16

(2) INFORMATION FOR SEQ ID NO: 1620:

(i) SEQUENCE CHARACTERISTICS:
        (A) LENGTH:              16 base pairs
        (B) TYPE:                nucleic acid
        (C) STRANDEDNESS:        single
        (D) TOPOLOGY:            linear (xi) SEQUENCE DESCRIPTION: SEQ ID NO: 1620:

UCACUGUUCA AGAAUG                                                       16

(2) INFORMATION FOR SEQ ID NO: 1621:
```

(i) SEQUENCE CHARACTERISTICS:
    (A) LENGTH:        16 base pairs
    (B) TYPE:          nucleic acid
    (C) STRANDEDNESS:  single
    (D) TOPOLOGY:      linear (xi) SEQUENCE DESCRIPTION: SEQ ID NO: 1621:

AUGCUGACCC UGGAGA                                               16

(2) INFORMATION FOR SEQ ID NO: 1622:

(i) SEQUENCE CHARACTERISTICS:
        (A) LENGTH:        16 base pairs
        (B) TYPE:          nucleic acid
        (C) STRANDEDNESS:  single
        (D) TOPOLOGY:      linear (xi) SEQUENCE DESCRIPTION: SEQ ID NO: 1622:

CCACUGCCUC AGUGGA                                               16

(2) INFORMATION FOR SEQ ID NO: 1623:

(i) SEQUENCE CHARACTERISTICS:
        (A) LENGTH:        16 base pairs
        (B) TYPE:          nucleic acid
        (C) STRANDEDNESS:  single
        (D) TOPOLOGY:      linear (xi) SEQUENCE DESCRIPTION: SEQ ID NO: 1623:

UGGCGGACCA GACCCU                                               16

(2) INFORMATION FOR SEQ ID NO: 1624:

(i) SEQUENCE CHARACTERISTICS:
        (A) LENGTH:        16 base pairs
        (B) TYPE:          nucleic acid
        (C) STRANDEDNESS:  single
        (D) TOPOLOGY:      linear (xi) SEQUENCE DESCRIPTION: SEQ ID NO: 1624:

CUGCGGCCUU GGAGGU                                               16

(2) INFORMATION FOR SEQ ID NO: 1625:

(i) SEQUENCE CHARACTERISTICS:
        (A) LENGTH:        16 base pairs
        (B) TYPE:          nucleic acid
        (C) STRANDEDNESS:  single
        (D) TOPOLOGY:      linear (xi) SEQUENCE DESCRIPTION: SEQ ID NO: 1625:

CAGCAGACUC UUACAU                                               16

(2) INFORMATION FOR SEQ ID NO: 1626:

(i) SEQUENCE CHARACTERISTICS:
        (A) LENGTH:        16 base pairs
        (B) TYPE:          nucleic acid
        (C) STRANDEDNESS:  single
        (D) TOPOLOGY:      linear (xi) SEQUENCE DESCRIPTION: SEQ ID NO: 1626:

CUGCAGCCGG AAAGCA                                               16

(2) INFORMATION FOR SEQ ID NO: 1627:

(i) SEQUENCE CHARACTERISTICS:
           (A) LENGTH:           16 base pairs
           (B) TYPE:             nucleic acid
           (C) STRANDEDNESS:     single
           (D) TOPOLOGY:         linear (xi) SEQUENCE DESCRIPTION: SEQ ID NO: 1627:

CCGCUGCCUA UCGGGA                                                     16

(2) INFORMATION FOR SEQ ID NO: 1628:

(i) SEQUENCE CHARACTERISTICS:
           (A) LENGTH:           16 base pairs
           (B) TYPE:             nucleic acid
           (C) STRANDEDNESS:     single
           (D) TOPOLOGY:         linear (xi) SEQUENCE DESCRIPTION: SEQ ID NO: 1628:

CUACAGCCUG GUGGGC                                                     16

(2) INFORMATION FOR SEQ ID NO: 1629:

(i) SEQUENCE CHARACTERISTICS:
           (A) LENGTH:           16 base pairs
           (B) TYPE:             nucleic acid
           (C) STRANDEDNESS:     single
           (D) TOPOLOGY:         linear (xi) SEQUENCE DESCRIPTION: SEQ ID NO: 1629:

AGGCUGACUU CCUUCU                                                     16

(2) INFORMATION FOR SEQ ID NO: 1630:

(i) SEQUENCE CHARACTERISTICS:
           (A) LENGTH:           16 base pairs
           (B) TYPE:             nucleic acid
           (C) STRANDEDNESS:     single
           (D) TOPOLOGY:         linear (xi) SEQUENCE DESCRIPTION: SEQ ID NO: 1630:

ACACUGUCCC CAACUC                                                     16

(2) INFORMATION FOR SEQ ID NO: 1631:

(i) SEQUENCE CHARACTERISTICS:
           (A) LENGTH:           16 base pairs
           (B) TYPE:             nucleic acid
           (C) STRANDEDNESS:     single
           (D) TOPOLOGY:         linear (xi) SEQUENCE DESCRIPTION: SEQ ID NO: 1631:

CCACAGCCUG GAGUCU                                                     16

(2) INFORMATION FOR SEQ ID NO: 1632:

(i) SEQUENCE CHARACTERISTICS:
           (A) LENGTH:           16 base pairs
           (B) TYPE:             nucleic acid
           (C) STRANDEDNESS:     single
           (D) TOPOLOGY:         linear (xi) SEQUENCE DESCRIPTION: SEQ ID NO: 1632:

AAGCUGUUGU GGGAGG                                                     16

(2) INFORMATION FOR SEQ ID NO: 1633:

(i) SEQUENCE CHARACTERISTICS:

```
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1633:

GAUCCAAUUC ACACUGA                                                    17

(2) INFORMATION FOR SEQ ID NO: 1634:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1634:

GCUGACUUCC UUCUCUA                                                    17

(2) INFORMATION FOR SEQ ID NO: 1635:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1635:

GAACUGCUCU UCCUCUU                                                    17

(2) INFORMATION FOR SEQ ID NO: 1636:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1636:

CCUCUGCUCC UGGUCCU                                                    17

(2) INFORMATION FOR SEQ ID NO: 1637:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1637:

CUGAAGCUCA GAUAUAC                                                    17

(2) INFORMATION FOR SEQ ID NO: 1638:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1638:

CUCAAGGUAC AAGCCCC                                                    17

(2) INFORMATION FOR SEQ ID NO: 1639:

(i) SEQUENCE CHARACTERISTICS:
            (A) LENGTH:              17 base pairs
```

```
        (B) TYPE:              nucleic acid
        (C) STRANDEDNESS:      single
        (D) TOPOLOGY:          linear (xi) SEQUENCE DESCRIPTION: SEQ ID NO: 1639:

GAGAACCUCG GCCUGGG                                                17

(2) INFORMATION FOR SEQ ID NO: 1640:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1640:

CCCCGCCUCC CUGAGCC                                                17

(2) INFORMATION FOR SEQ ID NO: 1641:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1641:

CCGUGCCUUU AGCUCCC                                                17

(2) INFORMATION FOR SEQ ID NO: 1642:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1642:

CAAUGGCUUC AACCCGU                                                17

(2) INFORMATION FOR SEQ ID NO: 1643:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1643:

CCUCUGCUCC UGGUCCU                                                17

(2) INFORMATION FOR SEQ ID NO: 1644:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1644:

CUCCUGGUCC UGGUCGC                                                17

(2) INFORMATION FOR SEQ ID NO: 1645:

(i) SEQUENCE CHARACTERISTICS:
        (A) LENGTH:            17 base pairs
        (B) TYPE:              nucleic acid
```

```
            (C) STRANDEDNESS:        single
            (D) TOPOLOGY:            linear (xi) SEQUENCE DESCRIPTION: SEQ ID NO: 1645:

GGACUGCUUG GGGAACU                                              17

(2) INFORMATION FOR SEQ ID NO: 1646:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1646:

UCCUACCUUU GUUCCCA                                              17

(2) INFORMATION FOR SEQ ID NO: 1647:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1647:

GACACUGUCC CCAACUC                                              17

(2) INFORMATION FOR SEQ ID NO: 1648:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1648:

GUUGUGAUCC CCGGGCC                                              17

(2) INFORMATION FOR SEQ ID NO: 1649:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1649:

CCAGACCUUG GAACUCC                                              17

(2) INFORMATION FOR SEQ ID NO: 1650:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1650:

ACCCGGCUCC ACCUCAA                                              17

(2) INFORMATION FOR SEQ ID NO: 1651:

(i) SEQUENCE CHARACTERISTICS:
            (A) LENGTH:              17 base pairs
            (B) TYPE:                nucleic acid
            (C) STRANDEDNESS:        single
```

(D) TOPOLOGY:           linear (xi) SEQUENCE DESCRIPTION: SEQ ID NO: 1651:

AUUUCUUUCA CGAGUCA                                                    17

(2) INFORMATION FOR SEQ ID NO: 1652:

(i) SEQUENCE CHARACTERISTICS:
                (A) LENGTH:             17 base pairs
                (B) TYPE:               nucleic acid
                (C) STRANDEDNESS:       single
                (D) TOPOLOGY:           linear (xi) SEQUENCE DESCRIPTION: SEQ ID NO: 1652:

UGAACAGUAC UUCCCCC                                                    17

(2) INFORMATION FOR SEQ ID NO: 1653:

(i) SEQUENCE CHARACTERISTICS:
                (A) LENGTH:             17 base pairs
                (B) TYPE:               nucleic acid
                (C) STRANDEDNESS:       single
                (D) TOPOLOGY:           linear (xi) SEQUENCE DESCRIPTION: SEQ ID NO: 1653:

GAAGCCUUCC UGCCUCG                                                    17

(2) INFORMATION FOR SEQ ID NO: 1654:

(i) SEQUENCE CHARACTERISTICS:
                (A) LENGTH:             17 base pairs
                (B) TYPE:               nucleic acid
                (C) STRANDEDNESS:       single
                (D) TOPOLOGY:           linear (xi) SEQUENCE DESCRIPTION: SEQ ID NO: 1654:

GGGUGGAUCC GUGCAGG                                                    17

(2) INFORMATION FOR SEQ ID NO: 1655:

(i) SEQUENCE CHARACTERISTICS:
                (A) LENGTH:             17 base pairs
                (B) TYPE:               nucleic acid
                (C) STRANDEDNESS:       single
                (D) TOPOLOGY:           linear (xi) SEQUENCE DESCRIPTION: SEQ ID NO: 1655:

CAGCCCCUAA UCUGACC                                                    17

(2) INFORMATION FOR SEQ ID NO: 1656:

(i) SEQUENCE CHARACTERISTICS:
                (A) LENGTH:             17 base pairs
                (B) TYPE:               nucleic acid
                (C) STRANDEDNESS:       single
                (D) TOPOLOGY:           linear (xi) SEQUENCE DESCRIPTION: SEQ ID NO: 1656:

GACCAAGUAA CUGUGAA                                                    17

(2) INFORMATION FOR SEQ ID NO: 1657:

(i) SEQUENCE CHARACTERISTICS:
                (A) LENGTH:             17 base pairs
                (B) TYPE:               nucleic acid
                (C) STRANDEDNESS:       single
                (D) TOPOLOGY:           linear (xi) SEQUENCE DESCRIPTION: SEQ ID NO: 1657:

CAAGCUGUUG UGGGAGG        17

(2) INFORMATION FOR SEQ ID NO: 1658:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1658:

CUGAAGCUCG ACACCCC        17

(2) INFORMATION FOR SEQ ID NO: 1659:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1659:

GGCCCCCUAC CUUAGGA        17

(2) INFORMATION FOR SEQ ID NO: 1660:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1660:

CACUGCCUCA GUGGAGG        17

(2) INFORMATION FOR SEQ ID NO: 1661:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1661:

GAGCCAAUUU CUCAUGC        17

(2) INFORMATION FOR SEQ ID NO: 1662:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1662:

GAAGCCUUCC UGCCUCG        17

(2) INFORMATION FOR SEQ ID NO: 1663:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1663:

GAAGCUCUUC AAGCUGA                                                   17

(2) INFORMATION FOR SEQ ID NO: 1664:

(i) SEQUENCE CHARACTERISTICS:
       (A) LENGTH:           17 base pairs
       (B) TYPE:             nucleic acid
       (C) STRANDEDNESS:     single
       (D) TOPOLOGY:         linear (xi) SEQUENCE DESCRIPTION: SEQ ID NO: 1664:

CGGAGGAUCA CAAACGA                                                   17

(2) INFORMATION FOR SEQ ID NO: 1665:

(i) SEQUENCE CHARACTERISTICS:
       (A) LENGTH:           17 base pairs
       (B) TYPE:             nucleic acid
       (C) STRANDEDNESS:     single
       (D) TOPOLOGY:         linear (xi) SEQUENCE DESCRIPTION: SEQ ID NO: 1665:

ACUGUGCUUU GAGAACU                                                   17

(2) INFORMATION FOR SEQ ID NO: 1666:

(i) SEQUENCE CHARACTERISTICS:
       (A) LENGTH:           17 base pairs
       (B) TYPE:             nucleic acid
       (C) STRANDEDNESS:     single
       (D) TOPOLOGY:         linear (xi) SEQUENCE DESCRIPTION: SEQ ID NO: 1666:

UGUGCUAUAU GGUCCUC                                                   17

(2) INFORMATION FOR SEQ ID NO: 1667:

(i) SEQUENCE CHARACTERISTICS:
       (A) LENGTH:           17 base pairs
       (B) TYPE:             nucleic acid
       (C) STRANDEDNESS:     single
       (D) TOPOLOGY:         linear (xi) SEQUENCE DESCRIPTION: SEQ ID NO: 1667:

AAGCUCUUCA AGCUGAG                                                   17

(2) INFORMATION FOR SEQ ID NO: 1668:

(i) SEQUENCE CHARACTERISTICS:
       (A) LENGTH:           17 base pairs
       (B) TYPE:             nucleic acid
       (C) STRANDEDNESS:     single
       (D) TOPOLOGY:         linear (xi) SEQUENCE DESCRIPTION: SEQ ID NO: 1668:

CACGCAGUCC UCGGCUU                                                   17

(2) INFORMATION FOR SEQ ID NO: 1669:

(i) SEQUENCE CHARACTERISTICS:
       (A) LENGTH:           17 base pairs
       (B) TYPE:             nucleic acid
       (C) STRANDEDNESS:     single
       (D) TOPOLOGY:         linear (xi) SEQUENCE DESCRIPTION: SEQ ID NO: 1669:

CAAUGGCUUC AACCCGU 17

(2) INFORMATION FOR SEQ ID NO: 1670:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1670:

UUACCCCUCA CCCACCU 17

(2) INFORMATION FOR SEQ ID NO: 1671:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1671:

AGAAGCCUUC CUGCCUC 17

(2) INFORMATION FOR SEQ ID NO: 1672:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1672:

ACCCACCUCA CAGGGUA 17

(2) INFORMATION FOR SEQ ID NO: 1673:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1673:

CGCUGUGUUU UGGAGCU 17

(2) INFORMATION FOR SEQ ID NO: 1674:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1674:

GUGGUGCUUC UGAACAG 17

(2) INFORMATION FOR SEQ ID NO: 1675:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1675:

```
GCACCCCUCC CAGCGCA                                                      17

(2) INFORMATION FOR SEQ ID NO: 1676:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1676:

CCUCGGCUUC UGCCACC                                                      17

(2) INFORMATION FOR SEQ ID NO: 1677:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1677:

UCCCUGUUUA AAAACCA                                                      17

(2) INFORMATION FOR SEQ ID NO: 1678:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1678:

AAGAACCUCA UCCUGCG                                                      17

(2) INFORMATION FOR SEQ ID NO: 1679:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1679:

GGGUACUUCC CCCAGGC                                                      17

(2) INFORMATION FOR SEQ ID NO: 1680:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1680:

CUCGGCUUCU GCCACCA                                                      17

(2) INFORMATION FOR SEQ ID NO: 1681:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1681:

GCCACCAUCA CUGUGUA                                                      17
```

(2) INFORMATION FOR SEQ ID NO: 1682:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1682:

GUGCUGCUCC GUGGGAA                                      17

(2) INFORMATION FOR SEQ ID NO: 1683:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1683:

GAAAAUGUUC CAACCAC                                      17

(2) INFORMATION FOR SEQ ID NO: 1684:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1684:

GGGAGUAUCA CCAGGGA                                      17

(2) INFORMATION FOR SEQ ID NO: 1685:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1685:

GAGCCAAUUU CUCAUGC                                      17

(2) INFORMATION FOR SEQ ID NO: 1686:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1686:

AGCCAAUUUC UCAUGCU                                      17

(2) INFORMATION FOR SEQ ID NO: 1687:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1687:

GCCAAUUUCU CAUGCUU                                      17

(2) INFORMATION FOR SEQ ID NO: 1688:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 1688:

CAAUUUCUCA UGCUUCA                                            17

(2) INFORMATION FOR SEQ ID NO: 1689:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 1689:

GUCACUGUUC AAGAAUG                                            17

(2) INFORMATION FOR SEQ ID NO: 1690:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 1690:

UCACUGUUCA AGAAUGU                                            17

(2) INFORMATION FOR SEQ ID NO: 1691:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 1691:

GAACUGCUCU UCCUCUU                                            17

(2) INFORMATION FOR SEQ ID NO: 1692:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 1692:

GCACCCCUCC CAGCGCA                                            17

(2) INFORMATION FOR SEQ ID NO: 1693:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 1693:

AGGCAGCUCC GGACUUU                                            17

```
(2) INFORMATION FOR SEQ ID NO: 1694:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1694:

CCAGACCUUG GAACUCC                                                    17

(2) INFORMATION FOR SEQ ID NO: 1695:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1695:

CGGACUUUCG AUCUUCC                                                    17

(2) INFORMATION FOR SEQ ID NO: 1696:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1696:

GCCUGUUUCC UGCCUCU                                                    17

(2) INFORMATION FOR SEQ ID NO: 1697:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1697:

CAGCAUUUAC CCCUCAC                                                    17

(2) INFORMATION FOR SEQ ID NO: 1698:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1698:

CUACAACUUU UCAGCUC                                                    17

(2) INFORMATION FOR SEQ ID NO: 1699:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1699:

CAACUUUUCA GCUCCCA                                                    17

(2) INFORMATION FOR SEQ ID NO: 1700:
```

```
    (i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1700:

CUCCUGGUCC UGGUCGC                                                    17

(2) INFORMATION FOR SEQ ID NO: 1701:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1701:

UCCUGCCUCG GGGUGGA                                                    17

(2) INFORMATION FOR SEQ ID NO: 1702:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1702:

ACUGUGCUUU GAGAACU                                                    17

(2) INFORMATION FOR SEQ ID NO: 1703:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1703:

UCUUGUGUUC CCUGGAA                                                    17

(2) INFORMATION FOR SEQ ID NO: 1704:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1704:

CUUGUGUUCC CUGGAAG                                                    17

(2) INFORMATION FOR SEQ ID NO: 1705:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1705:

AGGCCUGUUU CCUGCCU                                                    17

(2) INFORMATION FOR SEQ ID NO: 1706:
```

(i) SEQUENCE CHARACTERISTICS:
    (A) LENGTH:           17 base pairs
    (B) TYPE:             nucleic acid
    (C) STRANDEDNESS:     single
    (D) TOPOLOGY:         linear (xi) SEQUENCE DESCRIPTION: SEQ ID NO: 1706:

GGCCUGUUUC CUGCCUC                                                      17

(2) INFORMATION FOR SEQ ID NO: 1707:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1707:

CUCCUGGUCC UGGUCGC                                                      17

(2) INFORMATION FOR SEQ ID NO: 1708:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1708:

UCCUGCCUCU GAAGCUC                                                      17

(2) INFORMATION FOR SEQ ID NO: 1709:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1709:

GCUCAGAUAU ACCUGGA                                                      17

(2) INFORMATION FOR SEQ ID NO: 1710:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1710:

CCUGGGGUUG GAGACUA                                                      17

(2) INFORMATION FOR SEQ ID NO: 1711:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1711:

CUGACAGUUA UUUAUUG                                                      17

(2) INFORMATION FOR SEQ ID NO: 1712:

(i) SEQUENCE CHARACTERISTICS:

```
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1712:

GCUCACCUUU AGCAGCU                                                17

(2) INFORMATION FOR SEQ ID NO: 1713:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1713:

CAAUGGCUUC AACCCGU                                                17

(2) INFORMATION FOR SEQ ID NO: 1714:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1714:

CCAUGCUUCC UCUGACA                                                17

(2) INFORMATION FOR SEQ ID NO: 1715:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1715:

GACCACCUCC CCACCUA                                                17

(2) INFORMATION FOR SEQ ID NO: 1716:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1716:

CUCUUCCUCU UGCGAAG                                                17

(2) INFORMATION FOR SEQ ID NO: 1717:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1717:

AAUGGCUUCA ACCCGUG                                                17

(2) INFORMATION FOR SEQ ID NO: 1718:

(i) SEQUENCE CHARACTERISTICS:
            (A) LENGTH:            17 base pairs
```

```
        (B) TYPE:              nucleic acid
        (C) STRANDEDNESS:      single
        (D) TOPOLOGY:          linear (xi) SEQUENCE DESCRIPTION: SEQ ID NO: 1718:

GACCAAGUAA CUGUGAA                                              17

(2) INFORMATION FOR SEQ ID NO: 1719:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1719:

UGUGUAUUCG UUCCCAG                                              17

(2) INFORMATION FOR SEQ ID NO: 1720:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1720:

GCAGAGAUUU UGUGUCA                                              17

(2) INFORMATION FOR SEQ ID NO: 1721:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1721:

UUGAGAAUCU ACAACUU                                              17

(2) INFORMATION FOR SEQ ID NO: 1722:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1722:

GAGAAUCUAC AACUUUU                                              17

(2) INFORMATION FOR SEQ ID NO: 1723:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1723:

CUACAACUUU UCAGCUC                                              17

(2) INFORMATION FOR SEQ ID NO: 1724:

(i) SEQUENCE CHARACTERISTICS:
        (A) LENGTH:            17 base pairs
        (B) TYPE:              nucleic acid
```

```
         (C) STRANDEDNESS:        single
         (D) TOPOLOGY:            linear (xi) SEQUENCE DESCRIPTION: SEQ ID NO: 1724:

UACAACUUUU CAGCUCC                                              17

(2) INFORMATION FOR SEQ ID NO: 1725:

(i) SEQUENCE CHARACTERISTICS:
         (A) LENGTH:              17 base pairs
         (B) TYPE:                nucleic acid
         (C) STRANDEDNESS:        single
         (D) TOPOLOGY:            linear (xi) SEQUENCE DESCRIPTION: SEQ ID NO: 1725:

ACAACUUUUC AGCUCCC                                              17

(2) INFORMATION FOR SEQ ID NO: 1726:

(i) SEQUENCE CHARACTERISTICS:
         (A) LENGTH:              17 base pairs
         (B) TYPE:                nucleic acid
         (C) STRANDEDNESS:        single
         (D) TOPOLOGY:            linear (xi) SEQUENCE DESCRIPTION: SEQ ID NO: 1726:

UUCGUGAUCG UGGCGUC                                              17

(2) INFORMATION FOR SEQ ID NO: 1727:

(i) SEQUENCE CHARACTERISTICS:
         (A) LENGTH:              17 base pairs
         (B) TYPE:                nucleic acid
         (C) STRANDEDNESS:        single
         (D) TOPOLOGY:            linear (xi) SEQUENCE DESCRIPTION: SEQ ID NO: 1727:

GUGGGAGUAU CACCAGG                                              17

(2) INFORMATION FOR SEQ ID NO: 1728:

(i) SEQUENCE CHARACTERISTICS:
         (A) LENGTH:              17 base pairs
         (B) TYPE:                nucleic acid
         (C) STRANDEDNESS:        single
         (D) TOPOLOGY:            linear (xi) SEQUENCE DESCRIPTION: SEQ ID NO: 1728:

CCGGAGGUCU CAGAAGG                                              17

(2) INFORMATION FOR SEQ ID NO: 1729:

(i) SEQUENCE CHARACTERISTICS:
         (A) LENGTH:              17 base pairs
         (B) TYPE:                nucleic acid
         (C) STRANDEDNESS:        single
         (D) TOPOLOGY:            linear (xi) SEQUENCE DESCRIPTION: SEQ ID NO: 1729:

GGAGGUCUCA GAAGGGG                                              17

(2) INFORMATION FOR SEQ ID NO: 1730:

(i) SEQUENCE CHARACTERISTICS:
         (A) LENGTH:              17 base pairs
         (B) TYPE:                nucleic acid
         (C) STRANDEDNESS:        single
```

```
          (D) TOPOLOGY:            linear (xi) SEQUENCE DESCRIPTION: SEQ ID NO: 1730:

CCUACCUUUG UUCCCAA                                              17

(2) INFORMATION FOR SEQ ID NO: 1731:

(i) SEQUENCE CHARACTERISTICS:
          (A) LENGTH:              17 base pairs
          (B) TYPE:                nucleic acid
          (C) STRANDEDNESS:        single
          (D) TOPOLOGY:            linear (xi) SEQUENCE DESCRIPTION: SEQ ID NO: 1731:

AGAGGGGUCU CAGCAGA                                              17

(2) INFORMATION FOR SEQ ID NO: 1732:

(i) SEQUENCE CHARACTERISTICS:
          (A) LENGTH:              17 base pairs
          (B) TYPE:                nucleic acid
          (C) STRANDEDNESS:        single
          (D) TOPOLOGY:            linear (xi) SEQUENCE DESCRIPTION: SEQ ID NO: 1732:

AGGGGAAUCC AGCCCCU                                              17

(2) INFORMATION FOR SEQ ID NO: 1733:

(i) SEQUENCE CHARACTERISTICS:
          (A) LENGTH:              17 base pairs
          (B) TYPE:                nucleic acid
          (C) STRANDEDNESS:        single
          (D) TOPOLOGY:            linear (xi) SEQUENCE DESCRIPTION: SEQ ID NO: 1733:

CCCCAACUCU UGUUGAU                                              17

(2) INFORMATION FOR SEQ ID NO: 1734:

(i) SEQUENCE CHARACTERISTICS:
          (A) LENGTH:              17 base pairs
          (B) TYPE:                nucleic acid
          (C) STRANDEDNESS:        single
          (D) TOPOLOGY:            linear (xi) SEQUENCE DESCRIPTION: SEQ ID NO: 1734:

ACGACGCUUC UUUUGCU                                              17

(2) INFORMATION FOR SEQ ID NO: 1735:

(i) SEQUENCE CHARACTERISTICS:
          (A) LENGTH:              17 base pairs
          (B) TYPE:                nucleic acid
          (C) STRANDEDNESS:        single
          (D) TOPOLOGY:            linear (xi) SEQUENCE DESCRIPTION: SEQ ID NO: 1735:

CGACGCUUCU UUUGCUC                                              17

(2) INFORMATION FOR SEQ ID NO: 1736:

(i) SEQUENCE CHARACTERISTICS:
          (A) LENGTH:              17 base pairs
          (B) TYPE:                nucleic acid
          (C) STRANDEDNESS:        single
          (D) TOPOLOGY:            linear
```

(xi) SEQUENCE DESCRIPTION: SEQ ID NO: 1736:

ACGCUUCUUU UGCUCUG                                              17

(2) INFORMATION FOR SEQ ID NO: 1737:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1737:

CUUUUGCUCU GCGGCCU                                              17

(2) INFORMATION FOR SEQ ID NO: 1738:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1738:

AUCCAAUUCA CACUGAA                                              17

(2) INFORMATION FOR SEQ ID NO: 1739:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1739:

UUGGGCUUCU CCACAGG                                              17

(2) INFORMATION FOR SEQ ID NO: 1740:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1740:

GGGCUUCUCC ACAGGUC                                              17

(2) INFORMATION FOR SEQ ID NO: 1741:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1741:

UUGGAACUCC AUGUGCU                                              17

(2) INFORMATION FOR SEQ ID NO: 1742:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1742:

GCGGGCUUCG UGAUCGU                                                          17

(2) INFORMATION FOR SEQ ID NO: 1743:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1743:

CUCCUGGUCC UGGUCGC                                                          17

(2) INFORMATION FOR SEQ ID NO: 1744:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1744:

UGUGCUAUAU GGUCCUC                                                          17

(2) INFORMATION FOR SEQ ID NO: 1745:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1745:

GGAAAGAUCA UACGGGU                                                          17

(2) INFORMATION FOR SEQ ID NO: 1746:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1746:

GUCACUGUUC AAGAAUG                                                          17

(2) INFORMATION FOR SEQ ID NO: 1747:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1747:

CAGAGAUUUU GUGUCAG                                                          17

(2) INFORMATION FOR SEQ ID NO: 1748:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1748:

AGAGGGGUCU CAGCAGA                                                              17

(2) INFORMATION FOR SEQ ID NO: 1749:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1749:

AGCAGACUCU UACAUGC                                                              17

(2) INFORMATION FOR SEQ ID NO: 1750:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1750:

AACAGAGUCU GGGGAAA                                                              17

(2) INFORMATION FOR SEQ ID NO: 1751:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1751:

GUAUUCGUUC CCAGAGC                                                              17

(2) INFORMATION FOR SEQ ID NO: 1752:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1752:

UCGGUGCUCA GGUAUCC                                                              17

(2) INFORMATION FOR SEQ ID NO: 1753:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1753:

UCAGGCCUAA GAGGACU                                                              17

(2) INFORMATION FOR SEQ ID NO: 1754:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1754:

```
UAGCAGCUCA ACAAUGG                                                17

(2) INFORMATION FOR SEQ ID NO: 1755:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1755:

AGGGUACUUC CCCCAGG                                                17

(2) INFORMATION FOR SEQ ID NO: 1756:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1756:

GGGUACUUCC CCCAGGC                                                17

(2) INFORMATION FOR SEQ ID NO: 1757:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1757:

GAUGGUGUCC CGCUGCC                                                17

(2) INFORMATION FOR SEQ ID NO: 1758:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1758:

CUGCCUAUCG GGAUGGU                                                17

(2) INFORMATION FOR SEQ ID NO: 1759:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1759:

UGGAGACUAA CUGGAUG                                                17

(2) INFORMATION FOR SEQ ID NO: 1760:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1760:

CUGGCUGUCA CAGGACA                                                17
```

(2) INFORMATION FOR SEQ ID NO: 1761:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 1761:

CUGUGCUUUG AGAACUG                                      17

(2) INFORMATION FOR SEQ ID NO: 1762:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 1762:

UUCGUGAUCG UGGCGUC                                      17

(2) INFORMATION FOR SEQ ID NO: 1763:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 1763:

CGAACUAUCG AGUGGAC                                      17

(2) INFORMATION FOR SEQ ID NO: 1764:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 1764:

GGGUACUUCC CCCAGGC                                      17

(2) INFORMATION FOR SEQ ID NO: 1765:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 1765:

ACCCACCUCC UCUGGCU                                      17

(2) INFORMATION FOR SEQ ID NO: 1766:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 1766:

AUACUUGUAG CCUCAGG                                      17

(2) INFORMATION FOR SEQ ID NO: 1767:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1767:

AGAAGGCUCA GGAGGAG                                                          17

(2) INFORMATION FOR SEQ ID NO: 1768:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1768:

GGGAGUAUCA CCAGGGA                                                          17

(2) INFORMATION FOR SEQ ID NO: 1769:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1769:

AGGGUACUUC CCCCAGG                                                          17

(2) INFORMATION FOR SEQ ID NO: 1770:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1770:

ACUGCUCUUC CUCUUGC                                                          17

(2) INFORMATION FOR SEQ ID NO: 1771:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1771:

CCUGGGGUUG GAGACUA                                                          17

(2) INFORMATION FOR SEQ ID NO: 1772:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1772:

CGUGAAAUUA UGGUCAA                                                          17

(2) INFORMATION FOR SEQ ID NO: 1773:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1773:

GAAAAUGUUC CAACCAC                                                    17

(2) INFORMATION FOR SEQ ID NO: 1774:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1774:

UGGGUCAUAA UUGUUGG                                                    17

(2) INFORMATION FOR SEQ ID NO: 1775:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1775:

GCCACCAUCA CUGUGUA                                                    17

(2) INFORMATION FOR SEQ ID NO: 1776:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1776:

GUCCUGGUCG CCGUUGU                                                    17

(2) INFORMATION FOR SEQ ID NO: 1777:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1777:

ACCUGGGUCA UAAUUGU                                                    17

(2) INFORMATION FOR SEQ ID NO: 1778:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1778:

CUGAUCAUUG CGGGCUU                                                    17

(2) INFORMATION FOR SEQ ID NO: 1779:

```
    (i) SEQUENCE CHARACTERISTICS:
         (A) LENGTH:           17 base pairs
         (B) TYPE:             nucleic acid
         (C) STRANDEDNESS:     single
         (D) TOPOLOGY:         linear (xi) SEQUENCE DESCRIPTION: SEQ ID NO: 1779:

GUGGCCCUCU GCUCGUA                                                  17

(2) INFORMATION FOR SEQ ID NO: 1780:

(i) SEQUENCE CHARACTERISTICS:
         (A) LENGTH:           17 base pairs
         (B) TYPE:             nucleic acid
         (C) STRANDEDNESS:     single
         (D) TOPOLOGY:         linear (xi) SEQUENCE DESCRIPTION: SEQ ID NO: 1780:

UGGGAAGUCC CUGUUUA                                                  17

(2) INFORMATION FOR SEQ ID NO: 1781:

(i) SEQUENCE CHARACTERISTICS:
         (A) LENGTH:           17 base pairs
         (B) TYPE:             nucleic acid
         (C) STRANDEDNESS:     single
         (D) TOPOLOGY:         linear (xi) SEQUENCE DESCRIPTION: SEQ ID NO: 1781:

UCCUACCUUU GUUCCCA                                                  17

(2) INFORMATION FOR SEQ ID NO: 1782:

(i) SEQUENCE CHARACTERISTICS:
         (A) LENGTH:           17 base pairs
         (B) TYPE:             nucleic acid
         (C) STRANDEDNESS:     single
         (D) TOPOLOGY:         linear (xi) SEQUENCE DESCRIPTION: SEQ ID NO: 1782:

UUACACCUAU UACCGCC                                                  17

(2) INFORMATION FOR SEQ ID NO: 1783:

(i) SEQUENCE CHARACTERISTICS:
         (A) LENGTH:           17 base pairs
         (B) TYPE:             nucleic acid
         (C) STRANDEDNESS:     single
         (D) TOPOLOGY:         linear (xi) SEQUENCE DESCRIPTION: SEQ ID NO: 1783:

ACACCUAUUA CCGCCAG                                                  17

(2) INFORMATION FOR SEQ ID NO: 1784:

(i) SEQUENCE CHARACTERISTICS:
         (A) LENGTH:           17 base pairs
         (B) TYPE:             nucleic acid
         (C) STRANDEDNESS:     single
         (D) TOPOLOGY:         linear (xi) SEQUENCE DESCRIPTION: SEQ ID NO: 1784:

AGGAAGAUCA GGAUAUA                                                  17

(2) INFORMATION FOR SEQ ID NO: 1785:
```

```
    (i) SEQUENCE CHARACTERISTICS:
         (A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 1785:

CAGGAUAUAC AAGUUAC                                                 17

(2) INFORMATION FOR SEQ ID NO: 1786:

(i) SEQUENCE CHARACTERISTICS:
         (A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 1786:

UACAAGUUAC AGAAGGC                                                 17

(2) INFORMATION FOR SEQ ID NO: 1787:

(i) SEQUENCE CHARACTERISTICS:
         (A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 1787:

CCCCGCCUCC CUGAGCC                                                 17

(2) INFORMATION FOR SEQ ID NO: 1788:

(i) SEQUENCE CHARACTERISTICS:
         (A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 1788:

CUGCACUUUG CCCUGGU                                                 17

(2) INFORMATION FOR SEQ ID NO: 1789:

(i) SEQUENCE CHARACTERISTICS:
         (A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 1789:

GAACAGAUCA AUGGACA                                                 17

(2) INFORMATION FOR SEQ ID NO: 1790:

(i) SEQUENCE CHARACTERISTICS:
         (A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 1790:

GAGAACCUCG GCCUGGG                                                 17

(2) INFORMATION FOR SEQ ID NO: 1791:

(i) SEQUENCE CHARACTERISTICS:
```

```
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1791:

GGGCUUCUCC ACAGGUC                                                      17

(2) INFORMATION FOR SEQ ID NO: 1792:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1792:

GGCCUGUUUC CUGCCUC                                                      17

(2) INFORMATION FOR SEQ ID NO: 1793:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1793:

CUGCUCGUAG ACCUCUC                                                      17

(2) INFORMATION FOR SEQ ID NO: 1794:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1794:

CCCCACCUAC AUACAUU                                                      17

(2) INFORMATION FOR SEQ ID NO: 1795:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1795:

CCGGACUUUC GAUCUUC                                                      17

(2) INFORMATION FOR SEQ ID NO: 1796:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1796:

CUCCUGGUCC UGGUCGC                                                      17

(2) INFORMATION FOR SEQ ID NO: 1797:

(i) SEQUENCE CHARACTERISTICS:
            (A) LENGTH:              17 base pairs
```

```
            (B) TYPE:            nucleic acid
            (C) STRANDEDNESS:    single
            (D) TOPOLOGY:        linear (xi) SEQUENCE DESCRIPTION: SEQ ID NO: 1797:

UCAGAUAUAC CUGGAGA                                                    17

(2) INFORMATION FOR SEQ ID NO: 1798:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 1798:

GAUCACAUUC ACGGUGC                                                    17

(2) INFORMATION FOR SEQ ID NO: 1799:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 1799:

GUCCAUUUAC ACCUAUU                                                    17

(2) INFORMATION FOR SEQ ID NO: 1800:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 1800:

CCUCUGCUCC UGGUCCU                                                    17

(2) INFORMATION FOR SEQ ID NO: 1801:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 1801:

GAGAACCUCG GCCUGGG                                                    17

(2) INFORMATION FOR SEQ ID NO: 1802:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 1802:

GACACUGUCC CCAACUC                                                    17

(2) INFORMATION FOR SEQ ID NO: 1803:

(i) SEQUENCE CHARACTERISTICS:
            (A) LENGTH:          17 base pairs
            (B) TYPE:            nucleic acid
```

```
        (C) STRANDEDNESS:         single
        (D) TOPOLOGY:             linear (xi) SEQUENCE DESCRIPTION: SEQ ID NO: 1803:

AUGGUCCUCA CCUGGAC                                                    17

(2) INFORMATION FOR SEQ ID NO: 1804:

(i) SEQUENCE CHARACTERISTICS:
        (A) LENGTH:               17 base pairs
        (B) TYPE:                 nucleic acid
        (C) STRANDEDNESS:         single
        (D) TOPOLOGY:             linear (xi) SEQUENCE DESCRIPTION: SEQ ID NO: 1804:

UCCCUGUUUA AAAACCA                                                    17

(2) INFORMATION FOR SEQ ID NO: 1805:

(i) SEQUENCE CHARACTERISTICS:
        (A) LENGTH:               17 base pairs
        (B) TYPE:                 nucleic acid
        (C) STRANDEDNESS:         single
        (D) TOPOLOGY:             linear (xi) SEQUENCE DESCRIPTION: SEQ ID NO: 1805:

GCUCAGAUAU ACCUGGA                                                    17

(2) INFORMATION FOR SEQ ID NO: 1806:

(i) SEQUENCE CHARACTERISTICS:
        (A) LENGTH:               17 base pairs
        (B) TYPE:                 nucleic acid
        (C) STRANDEDNESS:         single
        (D) TOPOLOGY:             linear (xi) SEQUENCE DESCRIPTION: SEQ ID NO: 1806:

AACAGAGUCU GGGGAAA                                                    17

(2) INFORMATION FOR SEQ ID NO: 1807:

(i) SEQUENCE CHARACTERISTICS:
        (A) LENGTH:               17 base pairs
        (B) TYPE:                 nucleic acid
        (C) STRANDEDNESS:         single
        (D) TOPOLOGY:             linear (xi) SEQUENCE DESCRIPTION: SEQ ID NO: 1807:

GCGGGCUUCG UGAUCGU                                                    17

(2) INFORMATION FOR SEQ ID NO: 1808:

(i) SEQUENCE CHARACTERISTICS:
        (A) LENGTH:               17 base pairs
        (B) TYPE:                 nucleic acid
        (C) STRANDEDNESS:         single
        (D) TOPOLOGY:             linear (xi) SEQUENCE DESCRIPTION: SEQ ID NO: 1808:

GCCACCAUCA CUGUGUA                                                    17

(2) INFORMATION FOR SEQ ID NO: 1809:

(i) SEQUENCE CHARACTERISTICS:
        (A) LENGTH:               17 base pairs
        (B) TYPE:                 nucleic acid
        (C) STRANDEDNESS:         single
```

```
        (D) TOPOLOGY:           linear (xi) SEQUENCE DESCRIPTION: SEQ ID NO: 1809:

ACCCACCUCA CAGGGUA                                                17

(2) INFORMATION FOR SEQ ID NO: 1810:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 1810:

AGAGGACUCG GAGGGGC                                                17

(2) INFORMATION FOR SEQ ID NO: 1811:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 1811:

CCCCUAAUCU GACCUGC                                                17

(2) INFORMATION FOR SEQ ID NO: 1812:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 1812:

CAUGUGCUAU AUGGUCC                                                17

(2) INFORMATION FOR SEQ ID NO: 1813:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 1813:

UAUCCGGUAG ACACAAG                                                17

(2) INFORMATION FOR SEQ ID NO: 1814:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 1814:

UCACGAGUCA UAUAAAU                                                17

(2) INFORMATION FOR SEQ ID NO: 1815:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear
```

(xi) SEQUENCE DESCRIPTION: SEQ ID NO: 1815:

ACAGUACUUC CCCCAGG                                                          17

(2) INFORMATION FOR SEQ ID NO: 1816:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1816:

CUAAAACUCA AGGUACA                                                          17

(2) INFORMATION FOR SEQ ID NO: 1817:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1817:

GAACAGAUCA AUGGACA                                                          17

(2) INFORMATION FOR SEQ ID NO: 1818:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1818:

AUGUAAGUUA UUGCCUA                                                          17

(2) INFORMATION FOR SEQ ID NO: 1819:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1819:

UGGACGCUCA CCUUUAG                                                          17

(2) INFORMATION FOR SEQ ID NO: 1820:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1820:

GCUCAGAUAU ACCUGGA                                                          17

(2) INFORMATION FOR SEQ ID NO: 1821:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1821:

UGGAGACUAA CUGGAUG                                                              17

(2) INFORMATION FOR SEQ ID NO: 1822:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 1822:

AGAGAUUUUG UGUCAGC                                                              17

(2) INFORMATION FOR SEQ ID NO: 1823:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 1823:

GAGAACCUCG GCCUGGG                                                              17

(2) INFORMATION FOR SEQ ID NO: 1824:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 1824:

UGGAAGCUCU UCAAGCU                                                              17

(2) INFORMATION FOR SEQ ID NO: 1825:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 1825:

AUGUAAGUUA UUGCCUA                                                              17

(2) INFORMATION FOR SEQ ID NO: 1826:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 1826:

CGCUGCCUAU CGGGAUG                                                              17

(2) INFORMATION FOR SEQ ID NO: 1827:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 1827:

CUGCCUAUCG GGAUGGU          17

(2) INFORMATION FOR SEQ ID NO: 1828:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1828:

UAUUGAGUAC CCUGUAC          17

(2) INFORMATION FOR SEQ ID NO: 1829:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1829:

CGGAGGAUCA CAAACGA          17

(2) INFORMATION FOR SEQ ID NO: 1830:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1830:

CCUGACCUCC UGGAGGU          17

(2) INFORMATION FOR SEQ ID NO: 1831:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1831:

CUGGUCCUCC AAUGGCU          17

(2) INFORMATION FOR SEQ ID NO: 1832:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1832:

GCGUCCAUUU ACACCUA          17

(2) INFORMATION FOR SEQ ID NO: 1833:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1833:

AUACUUGUAG CCUCAGG                                                                  17

(2) INFORMATION FOR SEQ ID NO: 1834:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1834:

UGUAGCCUCA GGCCUAA                                                                  17

(2) INFORMATION FOR SEQ ID NO: 1835:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1835:

CCAACUCUUG UUGAUGU                                                                  17

(2) INFORMATION FOR SEQ ID NO: 1836:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1836:

CCUGACCUCC UGGAGGU                                                                  17

(2) INFORMATION FOR SEQ ID NO: 1837:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1837:

UUCCGACUAG GGUCCUG                                                                  17

(2) INFORMATION FOR SEQ ID NO: 1838:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1838:

AGUGCUGUAC CAUGAUC                                                                  17

(2) INFORMATION FOR SEQ ID NO: 1839:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1839:

GCCUGUUUCC UGCCUCU                                                                  17

(2) INFORMATION FOR SEQ ID NO: 1840:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1840:

CCAACUCUUG UUGAUGU                                              17

(2) INFORMATION FOR SEQ ID NO: 1841:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1841:

UUGAGAAUCU ACAACUU                                              17

(2) INFORMATION FOR SEQ ID NO: 1842:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1842:

UGACAGUUAU UUAUUGA                                              17

(2) INFORMATION FOR SEQ ID NO: 1843:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1843:

UGAUGUAUUU AUUAAUU                                              17

(2) INFORMATION FOR SEQ ID NO: 1844:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1844:

GAUGUAUUUA UUAAUUC                                              17

(2) INFORMATION FOR SEQ ID NO: 1845:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1845:

AUGUAUUUAU UAAUUCA                                              17

(2) INFORMATION FOR SEQ ID NO: 1846:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1846:

ACAUUCCUAC CUUUGUU    17

(2) INFORMATION FOR SEQ ID NO: 1847:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1847:

UAUUUAUUAA UUCAGAG    17

(2) INFORMATION FOR SEQ ID NO: 1848:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1848:

UGAUGUAUUU AUUAAUU    17

(2) INFORMATION FOR SEQ ID NO: 1849:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1849:

GAUGUAUUUA UUAAUUC    17

(2) INFORMATION FOR SEQ ID NO: 1850:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1850:

GUAUUUAUUA AUUCAGA    17

(2) INFORMATION FOR SEQ ID NO: 1851:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1851:

CAGUUAUUUA UUGAGUA    17

```
(2) INFORMATION FOR SEQ ID NO: 1852:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 1852:

UGUGCUAUAU GGUCCUC                                                  17

(2) INFORMATION FOR SEQ ID NO: 1853:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 1853:

UCUCUAUUAC CCCUGCU                                                  17

(2) INFORMATION FOR SEQ ID NO: 1854:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 1854:

AUUUCUUUCA CGAGUCA                                                  17

(2) INFORMATION FOR SEQ ID NO: 1855:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 1855:

GAAAAUGUUC CAACCAC                                                  17

(2) INFORMATION FOR SEQ ID NO: 1856:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 1856:

UGACAGUUAU UUAUUGA                                                  17

(2) INFORMATION FOR SEQ ID NO: 1857:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 1857:

ACAGUUAUUU AUUGAGU                                                  17

(2) INFORMATION FOR SEQ ID NO: 1858:
```

(i) SEQUENCE CHARACTERISTICS:
    (A) LENGTH:         17 base pairs
    (B) TYPE:           nucleic acid
    (C) STRANDEDNESS:  single
    (D) TOPOLOGY:      linear (xi) SEQUENCE DESCRIPTION: SEQ ID NO: 1858:

CAGUUAUUUA UUGAGUA                                    17

(2) INFORMATION FOR SEQ ID NO: 1859:

(i) SEQUENCE CHARACTERISTICS:
        (A) LENGTH:         17 base pairs
        (B) TYPE:           nucleic acid
        (C) STRANDEDNESS:  single
        (D) TOPOLOGY:      linear (xi) SEQUENCE DESCRIPTION: SEQ ID NO: 1859:

AGUUAUUUAU UGAGUAC                                    17

(2) INFORMATION FOR SEQ ID NO: 1860:

(i) SEQUENCE CHARACTERISTICS:
        (A) LENGTH:         17 base pairs
        (B) TYPE:           nucleic acid
        (C) STRANDEDNESS:  single
        (D) TOPOLOGY:      linear (xi) SEQUENCE DESCRIPTION: SEQ ID NO: 1860:

UUAUUUAUUG AGUACCC                                    17

(2) INFORMATION FOR SEQ ID NO: 1861:

(i) SEQUENCE CHARACTERISTICS:
        (A) LENGTH:         17 base pairs
        (B) TYPE:           nucleic acid
        (C) STRANDEDNESS:  single
        (D) TOPOLOGY:      linear (xi) SEQUENCE DESCRIPTION: SEQ ID NO: 1861:

CUGACAGUUA UUUAUUG                                    17

(2) INFORMATION FOR SEQ ID NO: 1862:

(i) SEQUENCE CHARACTERISTICS:
        (A) LENGTH:         17 base pairs
        (B) TYPE:           nucleic acid
        (C) STRANDEDNESS:  single
        (D) TOPOLOGY:      linear (xi) SEQUENCE DESCRIPTION: SEQ ID NO: 1862:

GAAUGUCUCC GAGGUCA                                    17

(2) INFORMATION FOR SEQ ID NO: 1863:

(i) SEQUENCE CHARACTERISTICS:
        (A) LENGTH:         17 base pairs
        (B) TYPE:           nucleic acid
        (C) STRANDEDNESS:  single
        (D) TOPOLOGY:      linear (xi) SEQUENCE DESCRIPTION: SEQ ID NO: 1863:

AGACUCUUAC AUGCCAG                                    17

(2) INFORMATION FOR SEQ ID NO: 1864:

```
    (i) SEQUENCE CHARACTERISTICS:
         (A) LENGTH:            17 base pairs
         (B) TYPE:              nucleic acid
         (C) STRANDEDNESS:      single
         (D) TOPOLOGY:          linear (xi) SEQUENCE DESCRIPTION: SEQ ID NO: 1864:

GGGUACUUCC CCCAGGC                                                17

(2) INFORMATION FOR SEQ ID NO: 1865:

(i) SEQUENCE CHARACTERISTICS:
         (A) LENGTH:            17 base pairs
         (B) TYPE:              nucleic acid
         (C) STRANDEDNESS:      single
         (D) TOPOLOGY:          linear (xi) SEQUENCE DESCRIPTION: SEQ ID NO: 1865:

GGGCUUCUCC ACAGGUC                                                17

(2) INFORMATION FOR SEQ ID NO: 1866:

(i) SEQUENCE CHARACTERISTICS:
         (A) LENGTH:            17 base pairs
         (B) TYPE:              nucleic acid
         (C) STRANDEDNESS:      single
         (D) TOPOLOGY:          linear (xi) SEQUENCE DESCRIPTION: SEQ ID NO: 1866:

UUUUGUGUCA GCCACUG                                                17

(2) INFORMATION FOR SEQ ID NO: 1867:

(i) SEQUENCE CHARACTERISTICS:
         (A) LENGTH:            17 base pairs
         (B) TYPE:              nucleic acid
         (C) STRANDEDNESS:      single
         (D) TOPOLOGY:          linear (xi) SEQUENCE DESCRIPTION: SEQ ID NO: 1867:

UGGAGACUAA CUGGAUG                                                17

(2) INFORMATION FOR SEQ ID NO: 1868:

(i) SEQUENCE CHARACTERISTICS:
         (A) LENGTH:            17 base pairs
         (B) TYPE:              nucleic acid
         (C) STRANDEDNESS:      single
         (D) TOPOLOGY:          linear (xi) SEQUENCE DESCRIPTION: SEQ ID NO: 1868:

GAGAACCUCG GCCUGGG                                                17

(2) INFORMATION FOR SEQ ID NO: 1869:

(i) SEQUENCE CHARACTERISTICS:
         (A) LENGTH:            17 base pairs
         (B) TYPE:              nucleic acid
         (C) STRANDEDNESS:      single
         (D) TOPOLOGY:          linear (xi) SEQUENCE DESCRIPTION: SEQ ID NO: 1869:

ACAUACAUUC CUACCUU                                                17

(2) INFORMATION FOR SEQ ID NO: 1870:

(i) SEQUENCE CHARACTERISTICS:
```

```
          (A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 1870:

CUGGACCUCA GGCCACA                                                   17

(2) INFORMATION FOR SEQ ID NO: 1871:

(i) SEQUENCE CHARACTERISTICS:
          (A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 1871:

UCAUGCUUCA CAGAACU                                                   17

(2) INFORMATION FOR SEQ ID NO: 1872:

(i) SEQUENCE CHARACTERISTICS:
          (A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 1872:

ACACAGCUCU CAGUAGU                                                   17

(2) INFORMATION FOR SEQ ID NO: 1873:

(i) SEQUENCE CHARACTERISTICS:
          (A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 1873:

CUCCUGGUCC UGGUCGC                                                   17

(2) INFORMATION FOR SEQ ID NO: 1874:

(i) SEQUENCE CHARACTERISTICS:
          (A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 1874:

AUCCAAUUCA CACUGAA                                                   17

(2) INFORMATION FOR SEQ ID NO: 1875:

(i) SEQUENCE CHARACTERISTICS:
          (A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 1875:

GAUCACAUUC ACGGUGC                                                   17

(2) INFORMATION FOR SEQ ID NO: 1876:

(i) SEQUENCE CHARACTERISTICS:
          (A) LENGTH:             17 base pairs
```

```
              (B) TYPE:                nucleic acid
              (C) STRANDEDNESS:        single
              (D) TOPOLOGY:            linear (xi) SEQUENCE DESCRIPTION: SEQ ID NO: 1876:

AUCACAUUCA CGGUGCU                                                    17

(2) INFORMATION FOR SEQ ID NO: 1877:

(i) SEQUENCE CHARACTERISTICS:
              (A) LENGTH:              17 base pairs
              (B) TYPE:                nucleic acid
              (C) STRANDEDNESS:        single
              (D) TOPOLOGY:            linear (xi) SEQUENCE DESCRIPTION: SEQ ID NO: 1877:

AUCAGGAUAU ACAAGUU                                                    17

(2) INFORMATION FOR SEQ ID NO: 1878:

(i) SEQUENCE CHARACTERISTICS:
              (A) LENGTH:              17 base pairs
              (B) TYPE:                nucleic acid
              (C) STRANDEDNESS:        single
              (D) TOPOLOGY:            linear (xi) SEQUENCE DESCRIPTION: SEQ ID NO: 1878:

GAGCAGGUUA ACAUGUA                                                    17

(2) INFORMATION FOR SEQ ID NO: 1879:

(i) SEQUENCE CHARACTERISTICS:
              (A) LENGTH:              17 base pairs
              (B) TYPE:                nucleic acid
              (C) STRANDEDNESS:        single
              (D) TOPOLOGY:            linear (xi) SEQUENCE DESCRIPTION: SEQ ID NO: 1879:

GGAAAGAUCA UACGGGU                                                    17

(2) INFORMATION FOR SEQ ID NO: 1880:

(i) SEQUENCE CHARACTERISTICS:
              (A) LENGTH:              17 base pairs
              (B) TYPE:                nucleic acid
              (C) STRANDEDNESS:        single
              (D) TOPOLOGY:            linear (xi) SEQUENCE DESCRIPTION: SEQ ID NO: 1880:

ACAGUUAUUU AUUGAGU                                                    17

(2) INFORMATION FOR SEQ ID NO: 1881:

(i) SEQUENCE CHARACTERISTICS:
              (A) LENGTH:              17 base pairs
              (B) TYPE:                nucleic acid
              (C) STRANDEDNESS:        single
              (D) TOPOLOGY:            linear (xi) SEQUENCE DESCRIPTION: SEQ ID NO: 1881:

GCCCUGGUCC UCCAAUG                                                    17

(2) INFORMATION FOR SEQ ID NO: 1882:

(i) SEQUENCE CHARACTERISTICS:
              (A) LENGTH:              17 base pairs
              (B) TYPE:                nucleic acid
```

```
                (C) STRANDEDNESS:       single
                (D) TOPOLOGY:           linear (xi) SEQUENCE DESCRIPTION: SEQ ID NO: 1882:

CAGGAUAUAC AAGUUAC                                                    17

(2) INFORMATION FOR SEQ ID NO: 1883:

(i) SEQUENCE CHARACTERISTICS:
                (A) LENGTH:             17 base pairs
                (B) TYPE:               nucleic acid
                (C) STRANDEDNESS:       single
                (D) TOPOLOGY:           linear (xi) SEQUENCE DESCRIPTION: SEQ ID NO: 1883:

GGAAAGAUCA UACGGGU                                                    17

(2) INFORMATION FOR SEQ ID NO: 1884:

(i) SEQUENCE CHARACTERISTICS:
                (A) LENGTH:             17 base pairs
                (B) TYPE:               nucleic acid
                (C) STRANDEDNESS:       single
                (D) TOPOLOGY:           linear (xi) SEQUENCE DESCRIPTION: SEQ ID NO: 1884:

UUGGGCUUCU CCACAGG                                                    17

(2) INFORMATION FOR SEQ ID NO: 1885:

(i) SEQUENCE CHARACTERISTICS:
                (A) LENGTH:             17 base pairs
                (B) TYPE:               nucleic acid
                (C) STRANDEDNESS:       single
                (D) TOPOLOGY:           linear (xi) SEQUENCE DESCRIPTION: SEQ ID NO: 1885:

GGGUACUUCC CCCAGGC                                                    17

(2) INFORMATION FOR SEQ ID NO: 1886:

(i) SEQUENCE CHARACTERISTICS:
                (A) LENGTH:             17 base pairs
                (B) TYPE:               nucleic acid
                (C) STRANDEDNESS:       single
                (D) TOPOLOGY:           linear (xi) SEQUENCE DESCRIPTION: SEQ ID NO: 1886:

GGGCCUGUCG GUGCUCA                                                    17

(2) INFORMATION FOR SEQ ID NO: 1887:

(i) SEQUENCE CHARACTERISTICS:
                (A) LENGTH:             17 base pairs
                (B) TYPE:               nucleic acid
                (C) STRANDEDNESS:       single
                (D) TOPOLOGY:           linear (xi) SEQUENCE DESCRIPTION: SEQ ID NO: 1887:

CUGCUCGUAG ACCUCUC                                                    17

(2) INFORMATION FOR SEQ ID NO: 1888:

(i) SEQUENCE CHARACTERISTICS:
                (A) LENGTH:             17 base pairs
                (B) TYPE:               nucleic acid
                (C) STRANDEDNESS:       single
```

```
            (D) TOPOLOGY:           linear (xi) SEQUENCE DESCRIPTION: SEQ ID NO: 1888:

CCCUGCCUCC UCCCACA                                                      17

(2) INFORMATION FOR SEQ ID NO: 1889:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 1889:

CCAUCCAUCC CACAGAA                                                      17

(2) INFORMATION FOR SEQ ID NO: 1890:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 1890:

CUUGUGUUCC CUGGAAG                                                      17

(2) INFORMATION FOR SEQ ID NO: 1891:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 1891:

GAACUGCUCU UCCUCUU                                                      17

(2) INFORMATION FOR SEQ ID NO: 1892:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 1892:

GACUUCCUUC UCUAUUA                                                      17

(2) INFORMATION FOR SEQ ID NO: 1893:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 1893:

GCUGAUUUCU UUCACGA                                                      17

(2) INFORMATION FOR SEQ ID NO: 1894:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear
```

(xi) SEQUENCE DESCRIPTION: SEQ ID NO: 1894:

CUGCUCUUCC UCUUGCG					17

(2) INFORMATION FOR SEQ ID NO: 1895:

(i) SEQUENCE CHARACTERISTICS:
        (A) LENGTH:			17 base pairs
        (B) TYPE:			nucleic acid
        (C) STRANDEDNESS:		single
        (D) TOPOLOGY:			linear (xi) SEQUENCE DESCRIPTION: SEQ ID NO: 1895:

UGAUUUCUUU CACGAGU					17

(2) INFORMATION FOR SEQ ID NO: 1896:

(i) SEQUENCE CHARACTERISTICS:
        (A) LENGTH:			17 base pairs
        (B) TYPE:			nucleic acid
        (C) STRANDEDNESS:		single
        (D) TOPOLOGY:			linear (xi) SEQUENCE DESCRIPTION: SEQ ID NO: 1896:

AUUUCUUUCA CGAGUCA					17

(2) INFORMATION FOR SEQ ID NO: 1897:

(i) SEQUENCE CHARACTERISTICS:
        (A) LENGTH:			17 base pairs
        (B) TYPE:			nucleic acid
        (C) STRANDEDNESS:		single
        (D) TOPOLOGY:			linear (xi) SEQUENCE DESCRIPTION: SEQ ID NO: 1897:

UAUCCGGUAG ACACAAG					17

(2) INFORMATION FOR SEQ ID NO: 1898:

(i) SEQUENCE CHARACTERISTICS:
        (A) LENGTH:			17 base pairs
        (B) TYPE:			nucleic acid
        (C) STRANDEDNESS:		single
        (D) TOPOLOGY:			linear (xi) SEQUENCE DESCRIPTION: SEQ ID NO: 1898:

UAAAUACUAU GUGGACG					17

(2) INFORMATION FOR SEQ ID NO: 1899:

(i) SEQUENCE CHARACTERISTICS:
        (A) LENGTH:			17 base pairs
        (B) TYPE:			nucleic acid
        (C) STRANDEDNESS:		single
        (D) TOPOLOGY:			linear (xi) SEQUENCE DESCRIPTION: SEQ ID NO: 1899:

UGUGCUAUAU GGUCCUC					17

(2) INFORMATION FOR SEQ ID NO: 1900:

(i) SEQUENCE CHARACTERISTICS:
        (A) LENGTH:			17 base pairs
        (B) TYPE:			nucleic acid
        (C) STRANDEDNESS:		single
        (D) TOPOLOGY:			linear (xi) SEQUENCE DESCRIPTION: SEQ ID NO: 1900:

CAAUUUCUCA UGCUUCA					17

(2) INFORMATION FOR SEQ ID NO: 1901:

(i) SEQUENCE CHARACTERISTICS:
        (A) LENGTH:			17 base pairs
        (B) TYPE:			nucleic acid
        (C) STRANDEDNESS:		single
        (D) TOPOLOGY:		linear (xi) SEQUENCE DESCRIPTION: SEQ ID NO: 1901:

AUCAGGAUAU ACAAGUU					17

(2) INFORMATION FOR SEQ ID NO: 1902:

(i) SEQUENCE CHARACTERISTICS:
        (A) LENGTH:			17 base pairs
        (B) TYPE:			nucleic acid
        (C) STRANDEDNESS:		single
        (D) TOPOLOGY:		linear (xi) SEQUENCE DESCRIPTION: SEQ ID NO: 1902:

UCAUGCUUCA CAGAACU					17

(2) INFORMATION FOR SEQ ID NO: 1903:

(i) SEQUENCE CHARACTERISTICS:
        (A) LENGTH:			17 base pairs
        (B) TYPE:			nucleic acid
        (C) STRANDEDNESS:		single
        (D) TOPOLOGY:		linear (xi) SEQUENCE DESCRIPTION: SEQ ID NO: 1903:

UUAUUAAUUC AGAGUUC					17

(2) INFORMATION FOR SEQ ID NO: 1904:

(i) SEQUENCE CHARACTERISTICS:
        (A) LENGTH:			17 base pairs
        (B) TYPE:			nucleic acid
        (C) STRANDEDNESS:		single
        (D) TOPOLOGY:		linear (xi) SEQUENCE DESCRIPTION: SEQ ID NO: 1904:

CCUGGGGUUG GAGACUA					17

(2) INFORMATION FOR SEQ ID NO: 1905:

(i) SEQUENCE CHARACTERISTICS:
        (A) LENGTH:			17 base pairs
        (B) TYPE:			nucleic acid
        (C) STRANDEDNESS:		single
        (D) TOPOLOGY:		linear (xi) SEQUENCE DESCRIPTION: SEQ ID NO: 1905:

UCAGAGUUCU GACAGUU					17

(2) INFORMATION FOR SEQ ID NO: 1906:

(i) SEQUENCE CHARACTERISTICS:
        (A) LENGTH:			17 base pairs
        (B) TYPE:			nucleic acid
        (C) STRANDEDNESS:		single
        (D) TOPOLOGY:		linear (xi) SEQUENCE DESCRIPTION: SEQ ID NO: 1906:

CGGAGGAUCA CAAACGA                                                       17

(2) INFORMATION FOR SEQ ID NO: 1907:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1907:

UGAACAGUAC UUCCCCC                                                       17

(2) INFORMATION FOR SEQ ID NO: 1908:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1908:

GAAGCCUUCC UGCCUCG                                                       17

(2) INFORMATION FOR SEQ ID NO: 1909:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1909:

GGCCUGUUUC CUGCCUC                                                       17

(2) INFORMATION FOR SEQ ID NO: 1910:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1910:

GCCUGUUUCC UGCCUCU                                                       17

(2) INFORMATION FOR SEQ ID NO: 1911:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1911:

ACAUUCCUAC CUUUGUU                                                       17

(2) INFORMATION FOR SEQ ID NO: 1912:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1912:

CCCUGCCUCC UCCCACA                                                17

(2) INFORMATION FOR SEQ ID NO: 1913:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1913:

CCUACCUUUG UUCCCAA                                                17

(2) INFORMATION FOR SEQ ID NO: 1914:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1914:

UUACACCUAU UACCGCC                                                17

(2) INFORMATION FOR SEQ ID NO: 1915:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1915:

GUCGCCGUUG UGAUCCC                                                17

(2) INFORMATION FOR SEQ ID NO: 1916:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1916:

ACCUUUGUUC CCAAUGU                                                17

(2) INFORMATION FOR SEQ ID NO: 1917:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1917:

CCUUUGUUCC CAAUGUC                                                17

(2) INFORMATION FOR SEQ ID NO: 1918:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1918:

GACCACCUCC CCACCUA                                                17

(2) INFORMATION FOR SEQ ID NO: 1919:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1919:

ACCUACAUAC AUUCCUA                                              17

(2) INFORMATION FOR SEQ ID NO: 1920:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1920:

ACAUACAUUC CUACCUU                                              17

(2) INFORMATION FOR SEQ ID NO: 1921:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1921:

CAUACAUUCC UACCUUU                                              17

(2) INFORMATION FOR SEQ ID NO: 1922:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1922:

GUCCAUUUAC ACCUAUU                                              17

(2) INFORMATION FOR SEQ ID NO: 1923:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1923:

ACCUUUGUUC CCAAUGU                                              17

(2) INFORMATION FOR SEQ ID NO: 1924:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1924:

CCUUUGUUCC CAAUGUC                                              17

(2) INFORMATION FOR SEQ ID NO: 1925:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1925:

ACAGCAUUUA CCCCUCA                                                      17

(2) INFORMATION FOR SEQ ID NO: 1926:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1926:

UCGGUGCUCA GGUAUCC                                                      17

(2) INFORMATION FOR SEQ ID NO: 1927:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1927:

AGGCAGCUCC GGACUUU                                                      17

(2) INFORMATION FOR SEQ ID NO: 1928:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1928:

CAGAGAUUUU GUGUCAG                                                      17

(2) INFORMATION FOR SEQ ID NO: 1929:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1929:

CCUGCACUUU GCCCUGG                                                      17

(2) INFORMATION FOR SEQ ID NO: 1930:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1930:

CUGCUCGUAG ACCUCUC                                                      17

(2) INFORMATION FOR SEQ ID NO: 1931:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1931:

UGCCUCCUCC CACAGCC                                            17

(2) INFORMATION FOR SEQ ID NO: 1932:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1932:

CUCUUCCUCU UGCGAAG                                            17

(2) INFORMATION FOR SEQ ID NO: 1933:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1933:

UCUCUAUUAC CCCUGCU                                            17

(2) INFORMATION FOR SEQ ID NO: 1934:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1934:

CUCCUGGUCC UGGUCGC                                            17

(2) INFORMATION FOR SEQ ID NO: 1935:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1935:

UGUGCUAUAU GGUCCUC                                            17

(2) INFORMATION FOR SEQ ID NO: 1936:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1936:

GUCCUGGUCG CCGUUGU                                            17

(2) INFORMATION FOR SEQ ID NO: 1937:

(i) SEQUENCE CHARACTERISTICS:
    (A) LENGTH:         17 base pairs
    (B) TYPE:           nucleic acid
    (C) STRANDEDNESS:   single
    (D) TOPOLOGY:       linear (xi) SEQUENCE DESCRIPTION: SEQ ID NO: 1937:

GUGGGAGUAU CACCAGG                                              17

(2) INFORMATION FOR SEQ ID NO: 1938:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1938:

CUUUAGCUCC CGUGGGA                                              17

(2) INFORMATION FOR SEQ ID NO: 1939:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1939:

UGGAGACUAA CUGGAUG                                              17

(2) INFORMATION FOR SEQ ID NO: 1940:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1940:

UCAGAGUUCU GACAGUU                                              17

(2) INFORMATION FOR SEQ ID NO: 1941:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1941:

CUCUCAGUAG UGCUGCU                                              17

(2) INFORMATION FOR SEQ ID NO: 1942:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1942:

UACAACUUUU CAGCUCC                                              17

(2) INFORMATION FOR SEQ ID NO: 1943:

```
    (i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1943:

UCACAGAUCC AAUUCAC                                                  17

(2) INFORMATION FOR SEQ ID NO: 1944:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1944:

GCUCAGGUAU CCAUCCA                                                  17

(2) INFORMATION FOR SEQ ID NO: 1945:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1945:

CCCCACCUAC AUACAUU                                                  17

(2) INFORMATION FOR SEQ ID NO: 1946:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1946:

GCCUGUUUCC UGCCUCU                                                  17

(2) INFORMATION FOR SEQ ID NO: 1947:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1947:

CCACAGGUCA GGGUGCU                                                  17

(2) INFORMATION FOR SEQ ID NO: 1948:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 1948:

AGAAGGGUCC UGCAAGC                                                  17

(2) INFORMATION FOR SEQ ID NO: 1949:

(i) SEQUENCE CHARACTERISTICS:
```

```
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1949:

ACUAGGGUCC UGAAGCU                                                17

(2) INFORMATION FOR SEQ ID NO: 1950:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1950:

UCAGGCCUAA GAGGACU                                                17

(2) INFORMATION FOR SEQ ID NO: 1951:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1951:

AGGGUACUUC CCCCAGG                                                17

(2) INFORMATION FOR SEQ ID NO: 1952:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1952:

GACCACCUCC CCACCUA                                                17

(2) INFORMATION FOR SEQ ID NO: 1953:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1953:

CCCUACCUUA GGAAGGU                                                17

(2) INFORMATION FOR SEQ ID NO: 1954:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 1954:

CCUACCUUAG GAAGGUG                                                17

(2) INFORMATION FOR SEQ ID NO: 1955:

(i) SEQUENCE CHARACTERISTICS:
            (A) LENGTH:            17 base pairs
```

```
            (B) TYPE:                nucleic acid
            (C) STRANDEDNESS:        single
            (D) TOPOLOGY:            linear (xi) SEQUENCE DESCRIPTION: SEQ ID NO: 1955:

GGAAAGAUCA UACGGGU                                                    17

(2) INFORMATION FOR SEQ ID NO: 1956:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1956:

AAGAUCAUAC GGGUUUG                                                    17

(2) INFORMATION FOR SEQ ID NO: 1957:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1957:

GGGUGGAUCC GUGCAGG                                                    17

(2) INFORMATION FOR SEQ ID NO: 1958:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1958:

GUCCCUGUUU AAAAACC                                                    17

(2) INFORMATION FOR SEQ ID NO: 1959:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1959:

GACGAACUAU CGAGUGG                                                    17

(2) INFORMATION FOR SEQ ID NO: 1960:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 1960:

CGGACUUUCG AUCUUCC                                                    17

(2) INFORMATION FOR SEQ ID NO: 1961:

(i) SEQUENCE CHARACTERISTICS:
            (A) LENGTH:              17 base pairs
            (B) TYPE:                nucleic acid
```

```
        (C) STRANDEDNESS:        single
        (D) TOPOLOGY:            linear (xi) SEQUENCE DESCRIPTION: SEQ ID NO: 1961:

CUUUUGCUCU GCGGCCU                                                    17

(2) INFORMATION FOR SEQ ID NO: 1962:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 1962:

UUCUCUAUUA CCCCUGC                                                    17

(2) INFORMATION FOR SEQ ID NO: 1963:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 1963:

CGUGAAAUUA UGGUCAA                                                    17

(2) INFORMATION FOR SEQ ID NO: 1964:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 1964:

CUCAUGCUUC ACAGAAC                                                    17

(2) INFORMATION FOR SEQ ID NO: 1965:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 1965:

UCAUGCUUCA CAGAACU                                                    17

(2) INFORMATION FOR SEQ ID NO: 1966:

(i) SEQUENCE CHARACTERISTICS:
        (A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 1966:

GCUCCCAUCC UGACCCU                                                    17

(2) INFORMATION FOR SEQ ID NO: 1967:

(i) SEQUENCE CHARACTERISTICS:
        (A) LENGTH:              17 base pairs
        (B) TYPE:                nucleic acid
        (C) STRANDEDNESS:        single
```

(D) TOPOLOGY:           linear (xi) SEQUENCE DESCRIPTION: SEQ ID NO: 1967:

CGGACUUUCG AUCUUCC                                                    17

(2) INFORMATION FOR SEQ ID NO: 1968:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 1968:

CCUGACCUCC UGGAGGU                                                    17

(2) INFORMATION FOR SEQ ID NO: 1969:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 1969:

UACAACUUUU CAGCUCC                                                    17

(2) INFORMATION FOR SEQ ID NO: 1970:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 1970:

CAACUUUUCA GCUCCCA                                                    17

(2) INFORMATION FOR SEQ ID NO: 1971:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 1971:

UCGGUGCUCA GGUAUCC                                                    17

(2) INFORMATION FOR SEQ ID NO: 1972:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 1972:

CACAGGGUAC UUCCCCC                                                    17

(2) INFORMATION FOR SEQ ID NO: 1973:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 1973:

GCACCCCUCC CAGCGCA                                                17

(2) INFORMATION FOR SEQ ID NO: 1974:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1974:

UUACCCCUCA CCCACCU                                                17

(2) INFORMATION FOR SEQ ID NO: 1975:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1975:

UUCGAUCUUC CGACUAG                                                17

(2) INFORMATION FOR SEQ ID NO: 1976:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1976:

UCUUGUGUUC CCUGGAA                                                17

(2) INFORMATION FOR SEQ ID NO: 1977:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1977:

GGGCCUGUCG GUGCUCA                                                17

(2) INFORMATION FOR SEQ ID NO: 1978:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1978:

UGGAGUCUCC CAGCACC                                                17

(2) INFORMATION FOR SEQ ID NO: 1979:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1979:

AGGCAGCUCC GGACUUU                                                17

(2) INFORMATION FOR SEQ ID NO: 1980:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1980:

GGCUGACUUC CUUCUCU                                                17

(2) INFORMATION FOR SEQ ID NO: 1981:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1981:

GAACUGCUCU UCCUCUU                                                17

(2) INFORMATION FOR SEQ ID NO: 1982:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1982:

GGCUGACUUC CUUCUCU                                                17

(2) INFORMATION FOR SEQ ID NO: 1983:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1983:

GUUGAUGUAU UUAUUAA                                                17

(2) INFORMATION FOR SEQ ID NO: 1984:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1984:

CUGCUCUUCC UCUUGCG                                                17

(2) INFORMATION FOR SEQ ID NO: 1985:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 1985:

UGAUGUAUUU AUUAAUU                                                              17

(2) INFORMATION FOR SEQ ID NO: 1986:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1986:

GAACUGCUCU UCCUCUU                                                              17

(2) INFORMATION FOR SEQ ID NO: 1987:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1987:

ACUUCCUUCU CUAUUAC                                                              17

(2) INFORMATION FOR SEQ ID NO: 1988:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1988:

UUCCUUCUCU AUUACCC                                                              17

(2) INFORMATION FOR SEQ ID NO: 1989:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1989:

AUGUAUUUAU UAAUUCA                                                              17

(2) INFORMATION FOR SEQ ID NO: 1990:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1990:

UGUGUAUUCG UUCCCAG                                                              17

(2) INFORMATION FOR SEQ ID NO: 1991:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1991:

```
GUAUUUAUUA AUUCAGA                                                17

(2) INFORMATION FOR SEQ ID NO: 1992:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1992:

UAUUUAUUAA UUCAGAG                                                17

(2) INFORMATION FOR SEQ ID NO: 1993:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1993:

CUCUUCCUCU UGCGAAG                                                17

(2) INFORMATION FOR SEQ ID NO: 1994:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1994:

CUUCCUCUUG CGAAGAC                                                17

(2) INFORMATION FOR SEQ ID NO: 1995:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1995:

AUUUCUUUCA CGAGUCA                                                17

(2) INFORMATION FOR SEQ ID NO: 1996:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1996:

UUUUGUGUCA GCCACUG                                                17

(2) INFORMATION FOR SEQ ID NO: 1997:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 1997:

GAUGGUGUCC CGCUGCC                                                17
```

(2) INFORMATION FOR SEQ ID NO: 1998:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1998:

UGGAGUCUCC CAGCACC                                        17

(2) INFORMATION FOR SEQ ID NO: 1999:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 1999:

CAGUACUUCC CCCAGGC                                        17

(2) INFORMATION FOR SEQ ID NO: 2000:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 2000:

ACCAUGCUUC CUCUGAC                                        17

(2) INFORMATION FOR SEQ ID NO: 2001:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 2001:

CCGGACUUUC GAUCUUC                                        17

(2) INFORMATION FOR SEQ ID NO: 2002:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 2002:

UGCUUCCUCU GACAUGG                                        17

(2) INFORMATION FOR SEQ ID NO: 2003:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 2003:

CUUUCCUUUG AAUCAAU                                        17

(2) INFORMATION FOR SEQ ID NO: 2004:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 2004:

UUUUGUGUCA GCCACUG 17

(2) INFORMATION FOR SEQ ID NO: 2005:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 2005:

UGUGUAUUCG UUCCCAG 17

(2) INFORMATION FOR SEQ ID NO: 2006:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 2006:

CUUUGAAUCA AUAAAGU 17

(2) INFORMATION FOR SEQ ID NO: 2007:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 2007:

UGGAAGCUCU UCAAGCU 17

(2) INFORMATION FOR SEQ ID NO: 2008:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 2008:

GAAUCAAUAA AGUUUUA 17

(2) INFORMATION FOR SEQ ID NO: 2009:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 2009:

UGGAAGCUCU UCAAGCU 17

(2) INFORMATION FOR SEQ ID NO: 2010:

(i) SEQUENCE CHARACTERISTICS:
        (A) LENGTH:          17 base pairs
        (B) TYPE:            nucleic acid
        (C) STRANDEDNESS:   single
        (D) TOPOLOGY:       linear (xi) SEQUENCE DESCRIPTION: SEQ ID NO: 2010:

UAUAUGGUCC UCACCUG                                        17

(2) INFORMATION FOR SEQ ID NO: 2011:

(i) SEQUENCE CHARACTERISTICS:
        (A) LENGTH:          17 base pairs
        (B) TYPE:            nucleic acid
        (C) STRANDEDNESS:   single
        (D) TOPOLOGY:       linear (xi) SEQUENCE DESCRIPTION: SEQ ID NO: 2011:

GAAGCUCUUC AAGCUGA                                        17

(2) INFORMATION FOR SEQ ID NO: 2012:

(i) SEQUENCE CHARACTERISTICS:
        (A) LENGTH:          38 base pairs
        (B) TYPE:            nucleic acid
        (C) STRANDEDNESS:   single
        (D) TOPOLOGY:       linear (xi) SEQUENCE DESCRIPTION: SEQ ID NO: 2012:

UCAGUGUGCU GAUGAGGCCG AAAGGCCGAA AUUGGAUC              38

(2) INFORMATION FOR SEQ ID NO: 2013:

(i) SEQUENCE CHARACTERISTICS:
        (A) LENGTH:          38 base pairs
        (B) TYPE:            nucleic acid
        (C) STRANDEDNESS:   single
        (D) TOPOLOGY:       linear (xi) SEQUENCE DESCRIPTION: SEQ ID NO: 2013:

UAGAGAAGCU GAUGAGGCCG AAAGGCCGAA AAGUCAGC              38

(2) INFORMATION FOR SEQ ID NO: 2014:

(i) SEQUENCE CHARACTERISTICS:
        (A) LENGTH:          38 base pairs
        (B) TYPE:            nucleic acid
        (C) STRANDEDNESS:   single
        (D) TOPOLOGY:       linear (xi) SEQUENCE DESCRIPTION: SEQ ID NO: 2014:

AAGAGGAACU GAUGAGGCCG AAAGGCCGAA AGCAGUUC              38

(2) INFORMATION FOR SEQ ID NO: 2015:

(i) SEQUENCE CHARACTERISTICS:
        (A) LENGTH:          38 base pairs
        (B) TYPE:            nucleic acid
        (C) STRANDEDNESS:   single
        (D) TOPOLOGY:       linear (xi) SEQUENCE DESCRIPTION: SEQ ID NO: 2015:

AGGACCAGCU GAUGAGGCCG AAAGGCCGAA AGCAGAGG              38

(2) INFORMATION FOR SEQ ID NO: 2016:

(i) SEQUENCE CHARACTERISTICS:
    (A) LENGTH:          38 base pairs
    (B) TYPE:            nucleic acid
    (C) STRANDEDNESS:    single
    (D) TOPOLOGY:        linear (xi) SEQUENCE DESCRIPTION: SEQ ID NO: 2016:

GUAUAUCUCU GAUGAGGCCG AAAGGCCGAA AGCUUCAG                                38

(2) INFORMATION FOR SEQ ID NO: 2017:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2017:

GGGGCUUGCU GAUGAGGCCG AAAGGCCGAA ACCUUGAG                                38

(2) INFORMATION FOR SEQ ID NO: 2018:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2018:

CCCAGGCCCU GAUGAGGCCG AAAGGCCGAA AGGUUCUC                                38

(2) INFORMATION FOR SEQ ID NO: 2019:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2019:

GGCUCAGGCU GAUGAGGCCG AAAGGCCGAA AGGCGGGG                                38

(2) INFORMATION FOR SEQ ID NO: 2020:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2020:

GGGAGCUACU GAUGAGGCCG AAAGGCCGAA AGGCACGG                                38

(2) INFORMATION FOR SEQ ID NO: 2021:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2021:

ACGGGUUGCU GAUGAGGCCG AAAGGCCGAA AGCCAUUG                                38

(2) INFORMATION FOR SEQ ID NO: 2022:

(i) SEQUENCE CHARACTERISTICS:
        (A) LENGTH:             38 base pairs
        (B) TYPE:               nucleic acid
        (C) STRANDEDNESS:       single
        (D) TOPOLOGY:           linear (xi) SEQUENCE DESCRIPTION: SEQ ID NO: 2022:

AGGACCAGCU GAUGAGGCCG AAAGGCCGAA AGCAGAGG                                      38

(2) INFORMATION FOR SEQ ID NO: 2023:

(i) SEQUENCE CHARACTERISTICS:
        (A) LENGTH:             38 base pairs
        (B) TYPE:               nucleic acid
        (C) STRANDEDNESS:       single
        (D) TOPOLOGY:           linear (xi) SEQUENCE DESCRIPTION: SEQ ID NO: 2023:

GCGACCAGCU GAUGAGGCCG AAAGGCCGAA ACCAGGAG                                      38

(2) INFORMATION FOR SEQ ID NO: 2024:

(i) SEQUENCE CHARACTERISTICS:
        (A) LENGTH:             38 base pairs
        (B) TYPE:               nucleic acid
        (C) STRANDEDNESS:       single
        (D) TOPOLOGY:           linear (xi) SEQUENCE DESCRIPTION: SEQ ID NO: 2024:

AGUUCCCCCU GAUGAGGCCG AAAGGCCGAA AGCAGUCC                                      38

(2) INFORMATION FOR SEQ ID NO: 2025:

(i) SEQUENCE CHARACTERISTICS:
        (A) LENGTH:             38 base pairs
        (B) TYPE:               nucleic acid
        (C) STRANDEDNESS:       single
        (D) TOPOLOGY:           linear (xi) SEQUENCE DESCRIPTION: SEQ ID NO: 2025:

UGGGAACACU GAUGAGGCCG AAAGGCCGAA AGGUAGGA                                      38

(2) INFORMATION FOR SEQ ID NO: 2026:

(i) SEQUENCE CHARACTERISTICS:
        (A) LENGTH:             38 base pairs
        (B) TYPE:               nucleic acid
        (C) STRANDEDNESS:       single
        (D) TOPOLOGY:           linear (xi) SEQUENCE DESCRIPTION: SEQ ID NO: 2026:

GAGUUGGGCU GAUGAGGCCG AAAGGCCGAA ACAGUGUC                                      38

(2) INFORMATION FOR SEQ ID NO: 2027:

(i) SEQUENCE CHARACTERISTICS:
        (A) LENGTH:             38 base pairs
        (B) TYPE:               nucleic acid
        (C) STRANDEDNESS:       single
        (D) TOPOLOGY:           linear (xi) SEQUENCE DESCRIPTION: SEQ ID NO: 2027:

GGCCCGGGCU GAUGAGGCCG AAAGGCCGAA AUCACAAC                                      38

(2) INFORMATION FOR SEQ ID NO: 2028:

(i) SEQUENCE CHARACTERISTICS:

```
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2028:

GGAGUUCCCU GAUGAGGCCG AAAGGCCGAA AGGUCUGG                         38

(2) INFORMATION FOR SEQ ID NO: 2029:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2029:

UUGAGGUGCU GAUGAGGCCG AAAGGCCGAA AGCCGGGU                         38

(2) INFORMATION FOR SEQ ID NO: 2030:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2030:

UGACUCGUCU GAUGAGGCCG AAAGGCCGAA AAAGAAAU                         38

(2) INFORMATION FOR SEQ ID NO: 2031:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2031:

GGGGGAAGCU GAUGAGGCCG AAAGGCCGAA ACUGUUCA                         38

(2) INFORMATION FOR SEQ ID NO: 2032:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2032:

CGAGGCAGCU GAUGAGGCCG AAAGGCCGAA AAGGCUUC                         38

(2) INFORMATION FOR SEQ ID NO: 2033:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2033:

CCUGCACGCU GAUGAGGCCG AAAGGCCGAA AUCCACCC                         38

(2) INFORMATION FOR SEQ ID NO: 2034:

(i) SEQUENCE CHARACTERISTICS:
            (A) LENGTH:              38 base pairs
```

```
              (B) TYPE:               nucleic acid
              (C) STRANDEDNESS:       single
              (D) TOPOLOGY:           linear (xi) SEQUENCE DESCRIPTION: SEQ ID NO: 2034:

GGUCAGAUCU GAUGAGGCCG AAAGGCCGAA AGGGGCUG                              38

(2) INFORMATION FOR SEQ ID NO: 2035:

(i) SEQUENCE CHARACTERISTICS:
              (A) LENGTH:             38 base pairs
              (B) TYPE:               nucleic acid
              (C) STRANDEDNESS:       single
              (D) TOPOLOGY:           linear (xi) SEQUENCE DESCRIPTION: SEQ ID NO: 2035:

UUCACAGUCU GAUGAGGCCG AAAGGCCGAA ACUUGGUC                              38

(2) INFORMATION FOR SEQ ID NO: 2036:

(i) SEQUENCE CHARACTERISTICS:
              (A) LENGTH:             38 base pairs
              (B) TYPE:               nucleic acid
              (C) STRANDEDNESS:       single
              (D) TOPOLOGY:           linear (xi) SEQUENCE DESCRIPTION: SEQ ID NO: 2036:

CCUCCCACCU GAUGAGGCCG AAAGGCCGAA ACAGCUUG                              38

(2) INFORMATION FOR SEQ ID NO: 2037:

(i) SEQUENCE CHARACTERISTICS:
              (A) LENGTH:             38 base pairs
              (B) TYPE:               nucleic acid
              (C) STRANDEDNESS:       single
              (D) TOPOLOGY:           linear (xi) SEQUENCE DESCRIPTION: SEQ ID NO: 2037:

GGGGUGUCCU GAUGAGGCCG AAAGGCCGAA AGCUUCAG                              38

(2) INFORMATION FOR SEQ ID NO: 2038:

(i) SEQUENCE CHARACTERISTICS:
              (A) LENGTH:             38 base pairs
              (B) TYPE:               nucleic acid
              (C) STRANDEDNESS:       single
              (D) TOPOLOGY:           linear (xi) SEQUENCE DESCRIPTION: SEQ ID NO: 2038:

UCCUAAGGCU GAUGAGGCCG AAAGGCCGAA AGGGGGCC                              38

(2) INFORMATION FOR SEQ ID NO: 2039:

(i) SEQUENCE CHARACTERISTICS:
              (A) LENGTH:             38 base pairs
              (B) TYPE:               nucleic acid
              (C) STRANDEDNESS:       single
              (D) TOPOLOGY:           linear (xi) SEQUENCE DESCRIPTION: SEQ ID NO: 2039:

CCUCCACUCU GAUGAGGCCG AAAGGCCGAA AGGCAGUG                              38

(2) INFORMATION FOR SEQ ID NO: 2040:

(i) SEQUENCE CHARACTERISTICS:
              (A) LENGTH:             38 base pairs
              (B) TYPE:               nucleic acid
```

```
            (C) STRANDEDNESS:        single
            (D) TOPOLOGY:            linear (xi) SEQUENCE DESCRIPTION: SEQ ID NO: 2040:

GCAUGAGACU GAUGAGGCCG AAAGGCCGAA AUUGGCUC                              38

(2) INFORMATION FOR SEQ ID NO: 2041:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2041:

CGAGGCAGCU GAUGAGGCCG AAAGGCCGAA AAGGCUUC                              38

(2) INFORMATION FOR SEQ ID NO: 2042:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2042:

UCAGCUUGCU GAUGAGGCCG AAAGGCCGAA AGAGCUUC                              38

(2) INFORMATION FOR SEQ ID NO: 2043:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2043:

UCGUUUGUCU GAUGAGGCCG AAAGGCCGAA AUCCUCCG                              38

(2) INFORMATION FOR SEQ ID NO: 2044:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2044:

AGUUCUCACU GAUGAGGCCG AAAGGCCGAA AGCACAGU                              38

(2) INFORMATION FOR SEQ ID NO: 2045:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2045:

GAGGACCACU GAUGAGGCCG AAAGGCCGAA AUAGCACA                              38

(2) INFORMATION FOR SEQ ID NO: 2046:

(i) SEQUENCE CHARACTERISTICS:
            (A) LENGTH:              38 base pairs
            (B) TYPE:                nucleic acid
            (C) STRANDEDNESS:        single
```

(D) TOPOLOGY:          linear (xi) SEQUENCE DESCRIPTION: SEQ ID NO: 2046:

CUCAGCUUCU GAUGAGGCCG AAAGGCCGAA AAGAGCUU                                    38

(2) INFORMATION FOR SEQ ID NO: 2047:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2047:

AAGCCGAGCU GAUGAGGCCG AAAGGCCGAA ACUGCGUG                                    38

(2) INFORMATION FOR SEQ ID NO: 2048:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2048:

ACGGUUGCU GAUGAGGCCG AAAGGCCGAA AGCCAUUG                                     38

(2) INFORMATION FOR SEQ ID NO: 2049:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2049:

AGGUGGGUCU GAUGAGGCCG AAAGGCCGAA AGGGGUAA                                    38

(2) INFORMATION FOR SEQ ID NO: 2050:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2050:

GAGGCAGGCU GAUGAGGCCG AAAGGCCGAA AGGCUUCU                                    38

(2) INFORMATION FOR SEQ ID NO: 2051:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2051:

UACCCUGUCU GAUGAGGCCG AAAGGCCGAA AGGUGGGU                                    38

(2) INFORMATION FOR SEQ ID NO: 2052:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2052:

AGCUCCAACU GAUGAGGCCG AAAGGCCGAA ACACAGCG                                    38

(2) INFORMATION FOR SEQ ID NO: 2053:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2053:

CUGUUCAGCU GAUGAGGCCG AAAGGCCGAA AGCACCAC                                    38

(2) INFORMATION FOR SEQ ID NO: 2054:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2054:

UGCGCUGGCU GAUGAGGCCG AAAGGCCGAA AGGGGUGC                                    38

(2) INFORMATION FOR SEQ ID NO: 2055:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2055:

GGUGGCAGCU GAUGAGGCCG AAAGGCCGAA AGCCGAGG                                    38

(2) INFORMATION FOR SEQ ID NO: 2056:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2056:

UGGUUUUUCU GAUGAGGCCG AAAGGCCGAA AACAGGGA                                    38

(2) INFORMATION FOR SEQ ID NO: 2057:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2057:

CGCAGGAUCU GAUGAGGCCG AAAGGCCGAA AGGUUCUU                                    38

(2) INFORMATION FOR SEQ ID NO: 2058:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2058:

GCCUGGGGCU GAUGAGGCCG AAAGGCCGAA AAGUACCC                                    38

(2) INFORMATION FOR SEQ ID NO: 2059:

(i) SEQUENCE CHARACTERISTICS:
           (A) LENGTH:         38 base pairs
           (B) TYPE:           nucleic acid
           (C) STRANDEDNESS:   single
           (D) TOPOLOGY:       linear (xi) SEQUENCE DESCRIPTION: SEQ ID NO: 2059:

UGGUGGCACU GAUGAGGCCG AAAGGCCGAA AAGCCGAG                                    38

(2) INFORMATION FOR SEQ ID NO: 2060:

(i) SEQUENCE CHARACTERISTICS:
           (A) LENGTH:         38 base pairs
           (B) TYPE:           nucleic acid
           (C) STRANDEDNESS:   single
           (D) TOPOLOGY:       linear (xi) SEQUENCE DESCRIPTION: SEQ ID NO: 2060:

UACACAGUCU GAUGAGGCCG AAAGGCCGAA AUGGUGGC                                    38

(2) INFORMATION FOR SEQ ID NO: 2061:

(i) SEQUENCE CHARACTERISTICS:
           (A) LENGTH:         38 base pairs
           (B) TYPE:           nucleic acid
           (C) STRANDEDNESS:   single
           (D) TOPOLOGY:       linear (xi) SEQUENCE DESCRIPTION: SEQ ID NO: 2061:

UUCCCACGCU GAUGAGGCCG AAAGGCCGAA AGCAGCAC                                    38

(2) INFORMATION FOR SEQ ID NO: 2062:

(i) SEQUENCE CHARACTERISTICS:
           (A) LENGTH:         38 base pairs
           (B) TYPE:           nucleic acid
           (C) STRANDEDNESS:   single
           (D) TOPOLOGY:       linear (xi) SEQUENCE DESCRIPTION: SEQ ID NO: 2062:

GUGGUUGGCU GAUGAGGCCG AAAGGCCGAA ACAUUUUC                                    38

(2) INFORMATION FOR SEQ ID NO: 2063:

(i) SEQUENCE CHARACTERISTICS:
           (A) LENGTH:         38 base pairs
           (B) TYPE:           nucleic acid
           (C) STRANDEDNESS:   single
           (D) TOPOLOGY:       linear (xi) SEQUENCE DESCRIPTION: SEQ ID NO: 2063:

UCCCUGGUCU GAUGAGGCCG AAAGGCCGAA AUACUCCC                                    38

(2) INFORMATION FOR SEQ ID NO: 2064:

(i) SEQUENCE CHARACTERISTICS:
           (A) LENGTH:         38 base pairs
           (B) TYPE:           nucleic acid
           (C) STRANDEDNESS:   single
           (D) TOPOLOGY:       linear (xi) SEQUENCE DESCRIPTION: SEQ ID NO: 2064:

GCAUGAGACU GAUGAGGCCG AAAGGCCGAA AUUGGCUC                                38

(2) INFORMATION FOR SEQ ID NO: 2065:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2065:

AGCAUGAGCU GAUGAGGCCG AAAGGCCGAA AAUUGGCU                                38

(2) INFORMATION FOR SEQ ID NO: 2066:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2066:

AAGCAUGACU GAUGAGGCCG AAAGGCCGAA AAAUUGGC                                38

(2) INFORMATION FOR SEQ ID NO: 2067:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2067:

UGAAGCAUCU GAUGAGGCCG AAAGGCCGAA AGAAAUUG                                38

(2) INFORMATION FOR SEQ ID NO: 2068:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2068:

CAUUCUUGCU GAUGAGGCCG AAAGGCCGAA ACAGUGAC                                38

(2) INFORMATION FOR SEQ ID NO: 2069:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2069:

ACAUUCUUCU GAUGAGGCCG AAAGGCCGAA AACAGUGA                                38

(2) INFORMATION FOR SEQ ID NO: 2070:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2070:

```
AAGAGGAACU GAUGAGGCCG AAAGGCCGAA AGCAGUUC                                     38

(2) INFORMATION FOR SEQ ID NO: 2071:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2071:

UGCGCUGGCU GAUGAGGCCG AAAGGCCGAA AGGGGUGC                                     38

(2) INFORMATION FOR SEQ ID NO: 2072:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2072:

AAAGUCCGCU GAUGAGGCCG AAAGGCCGAA AGCUGCCU                                     38

(2) INFORMATION FOR SEQ ID NO: 2073:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2073:

GGAGUUCCCU GAUGAGGCCG AAAGGCCGAA AGGUCUGG                                     38

(2) INFORMATION FOR SEQ ID NO: 2074:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2074:

GGAAGAUCCU GAUGAGGCCG AAAGGCCGAA AAAGUCCG                                     38

(2) INFORMATION FOR SEQ ID NO: 2075:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2075:

AGAGGCAGCU GAUGAGGCCG AAAGGCCGAA AAACAGGC                                     38

(2) INFORMATION FOR SEQ ID NO: 2076:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2076:

GUGAGGGGCU GAUGAGGCCG AAAGGCCGAA AAAUGCUG                                     38
```

(2) INFORMATION FOR SEQ ID NO: 2077:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2077:

GAGCUGAACU GAUGAGGCCG AAAGGCCGAA AGUUGUAG                                38

(2) INFORMATION FOR SEQ ID NO: 2078:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2078:

UGGGAGCUCU GAUGAGGCCG AAAGGCCGAA AAAAGUUG                                38

(2) INFORMATION FOR SEQ ID NO: 2079:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2079:

GCGACCAGCU GAUGAGGCCG AAAGGCCGAA ACCAGGAG                                38

(2) INFORMATION FOR SEQ ID NO: 2080:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2080:

UCCACCCCCU GAUGAGGCCG AAAGGCCGAA AGGCAGGA                                38

(2) INFORMATION FOR SEQ ID NO: 2081:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2081:

AGUUCUCACU GAUGAGGCCG AAAGGCCGAA AGCACAGU                                38

(2) INFORMATION FOR SEQ ID NO: 2082:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2082:

UUCCAGGGCU GAUGAGGCCG AAAGGCCGAA ACACAAGA                                38

(2) INFORMATION FOR SEQ ID NO: 2083:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2083:

CUUCCAGGCU GAUGAGGCCG AAAGGCCGAA AACACAAG                                  38

(2) INFORMATION FOR SEQ ID NO: 2084:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2084:

AGGCAGGACU GAUGAGGCCG AAAGGCCGAA ACAGGCCU                                  38

(2) INFORMATION FOR SEQ ID NO: 2085:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2085:

GAGGCAGGCU GAUGAGGCCG AAAGGCCGAA AACAGGCC                                  38

(2) INFORMATION FOR SEQ ID NO: 2086:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2086:

GCGACCAGCU GAUGAGGCCG AAAGGCCGAA ACCAGGAG                                  38

(2) INFORMATION FOR SEQ ID NO: 2087:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2087:

GAGCUUCACU GAUGAGGCCG AAAGGCCGAA AGGCAGGA                                  38

(2) INFORMATION FOR SEQ ID NO: 2088:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2088:

UCCAGGUACU GAUGAGGCCG AAAGGCCGAA AUCUGAGC                                  38

(2) INFORMATION FOR SEQ ID NO: 2089:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2089:

UAGUCUCCCU GAUGAGGCCG AAAGGCCGAA ACCCCAGG                                38

(2) INFORMATION FOR SEQ ID NO: 2090:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2090:

CAAUAAAUCU GAUGAGGCCG AAAGGCCGAA ACUGUCAG                                38

(2) INFORMATION FOR SEQ ID NO: 2091:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2091:

AGCUGCUACU GAUGAGGCCG AAAGGCCGAA AGGUGAGC                                38

(2) INFORMATION FOR SEQ ID NO: 2092:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2092:

ACGGGUUGCU GAUGAGGCCG AAAGGCCGAA AGCCAUUG                                38

(2) INFORMATION FOR SEQ ID NO: 2093:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2093:

UGUCAGAGCU GAUGAGGCCG AAAGGCCGAA AAGCAUGG                                38

(2) INFORMATION FOR SEQ ID NO: 2094:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2094:

UAGGUGGGCU GAUGAGGCCG AAAGGCCGAA AGGUGGUC                                38

(2) INFORMATION FOR SEQ ID NO: 2095:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2095:

CUUCGCAACU GAUGAGGCCG AAAGGCCGAA AGGAAGAG                              38

(2) INFORMATION FOR SEQ ID NO: 2096:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2096:

CACGGGUUCU GAUGAGGCCG AAAGGCCGAA AAGCCAUU                              38

(2) INFORMATION FOR SEQ ID NO: 2097:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2097:

UUCACAGUCU GAUGAGGCCG AAAGGCCGAA ACUUGGUC                              38

(2) INFORMATION FOR SEQ ID NO: 2098:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2098:

CUGGGAACCU GAUGAGGCCG AAAGGCCGAA AAUACACA                              38

(2) INFORMATION FOR SEQ ID NO: 2099:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2099:

UGACACAACU GAUGAGGCCG AAAGGCCGAA AUCUCUGC                              38

(2) INFORMATION FOR SEQ ID NO: 2100:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2100:

AAGUUGUACU GAUGAGGCCG AAAGGCCGAA AUUCUCAA                              38

(2) INFORMATION FOR SEQ ID NO: 2101:

```
        (i) SEQUENCE CHARACTERISTICS:
            (A) LENGTH:          38 base pairs
            (B) TYPE:            nucleic acid
            (C) STRANDEDNESS:    single
            (D) TOPOLOGY:        linear (xi) SEQUENCE DESCRIPTION: SEQ ID NO: 2101:

AAAAGUUGCU GAUGAGGCCG AAAGGCCGAA AGAUUCUC                          38

(2) INFORMATION FOR SEQ ID NO: 2102:

(i) SEQUENCE CHARACTERISTICS:
            (A) LENGTH:          38 base pairs
            (B) TYPE:            nucleic acid
            (C) STRANDEDNESS:    single
            (D) TOPOLOGY:        linear (xi) SEQUENCE DESCRIPTION: SEQ ID NO: 2102:

GAGCUGAACU GAUGAGGCCG AAAGGCCGAA AGUUGUAG                          38

(2) INFORMATION FOR SEQ ID NO: 2103:

(i) SEQUENCE CHARACTERISTICS:
            (A) LENGTH:          38 base pairs
            (B) TYPE:            nucleic acid
            (C) STRANDEDNESS:    single
            (D) TOPOLOGY:        linear (xi) SEQUENCE DESCRIPTION: SEQ ID NO: 2103:

GGAGCUGACU GAUGAGGCCG AAAGGCCGAA AAGUUGUA                          38

(2) INFORMATION FOR SEQ ID NO: 2104:

(i) SEQUENCE CHARACTERISTICS:
            (A) LENGTH:          38 base pairs
            (B) TYPE:            nucleic acid
            (C) STRANDEDNESS:    single
            (D) TOPOLOGY:        linear (xi) SEQUENCE DESCRIPTION: SEQ ID NO: 2104:

GGGAGCUGCU GAUGAGGCCG AAAGGCCGAA AAAGUUGU                          38

(2) INFORMATION FOR SEQ ID NO: 2105:

(i) SEQUENCE CHARACTERISTICS:
            (A) LENGTH:          38 base pairs
            (B) TYPE:            nucleic acid
            (C) STRANDEDNESS:    single
            (D) TOPOLOGY:        linear (xi) SEQUENCE DESCRIPTION: SEQ ID NO: 2105:

GACGCCACCU GAUGAGGCCG AAAGGCCGAA AUCACGAA                          38

(2) INFORMATION FOR SEQ ID NO: 2106:

(i) SEQUENCE CHARACTERISTICS:
            (A) LENGTH:          38 base pairs
            (B) TYPE:            nucleic acid
            (C) STRANDEDNESS:    single
            (D) TOPOLOGY:        linear (xi) SEQUENCE DESCRIPTION: SEQ ID NO: 2106:

CCUGGUGACU GAUGAGGCCG AAAGGCCGAA ACUCCCAC                          38

(2) INFORMATION FOR SEQ ID NO: 2107:

(i) SEQUENCE CHARACTERISTICS:
```

```
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2107:

CCUUCUGACU GAUGAGGCCG AAAGGCCGAA ACCUCCGG                              38

(2) INFORMATION FOR SEQ ID NO: 2108:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2108:

CCCCUUCUCU GAUGAGGCCG AAAGGCCGAA AGACCUCC                              38

(2) INFORMATION FOR SEQ ID NO: 2109:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2109:

UUGGGAACCU GAUGAGGCCG AAAGGCCGAA AAGGUAGG                              38

(2) INFORMATION FOR SEQ ID NO: 2110:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2110:

UCUGCUGACU GAUGAGGCCG AAAGGCCGAA ACCCCUCU                              38

(2) INFORMATION FOR SEQ ID NO: 2111:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2111:

AGGGGCUGCU GAUGAGGCCG AAAGGCCGAA AUUCCCCU                              38

(2) INFORMATION FOR SEQ ID NO: 2112:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2112:

AUCAACAACU GAUGAGGCCG AAAGGCCGAA AGUUGGGG                              38

(2) INFORMATION FOR SEQ ID NO: 2113:

(i) SEQUENCE CHARACTERISTICS:
            (A) LENGTH:            38 base pairs
```

(B) TYPE:                nucleic acid
        (C) STRANDEDNESS:        single
        (D) TOPOLOGY:            linear (xi) SEQUENCE DESCRIPTION: SEQ ID NO: 2113:

AGCAAAAGCU GAUGAGGCCG AAAGGCCGAA AGCGUCGU                                    38

(2) INFORMATION FOR SEQ ID NO: 2114:

(i) SEQUENCE CHARACTERISTICS:
        (A) LENGTH:              38 base pairs
        (B) TYPE:                nucleic acid
        (C) STRANDEDNESS:        single
        (D) TOPOLOGY:            linear (xi) SEQUENCE DESCRIPTION: SEQ ID NO: 2114:

GAGCAAAACU GAUGAGGCCG AAAGGCCGAA AAGCGUCG                                    38

(2) INFORMATION FOR SEQ ID NO: 2115:

(i) SEQUENCE CHARACTERISTICS:
        (A) LENGTH:              38 base pairs
        (B) TYPE:                nucleic acid
        (C) STRANDEDNESS:        single
        (D) TOPOLOGY:            linear (xi) SEQUENCE DESCRIPTION: SEQ ID NO: 2115:

CAGAGCAACU GAUGAGGCCG AAAGGCCGAA AGAAGCGU                                    38

(2) INFORMATION FOR SEQ ID NO: 2116:

(i) SEQUENCE CHARACTERISTICS:
        (A) LENGTH:              38 base pairs
        (B) TYPE:                nucleic acid
        (C) STRANDEDNESS:        single
        (D) TOPOLOGY:            linear (xi) SEQUENCE DESCRIPTION: SEQ ID NO: 2116:

AGGCCGCACU GAUGAGGCCG AAAGGCCGAA AGCAAAAG                                    38

(2) INFORMATION FOR SEQ ID NO: 2117:

(i) SEQUENCE CHARACTERISTICS:
        (A) LENGTH:              38 base pairs
        (B) TYPE:                nucleic acid
        (C) STRANDEDNESS:        single
        (D) TOPOLOGY:            linear (xi) SEQUENCE DESCRIPTION: SEQ ID NO: 2117:

UUCAGUGUCU GAUGAGGCCG AAAGGCCGAA AAUUGGAU                                    38

(2) INFORMATION FOR SEQ ID NO: 2118:

(i) SEQUENCE CHARACTERISTICS:
        (A) LENGTH:              38 base pairs
        (B) TYPE:                nucleic acid
        (C) STRANDEDNESS:        single
        (D) TOPOLOGY:            linear (xi) SEQUENCE DESCRIPTION: SEQ ID NO: 2118:

CCUGUGGACU GAUGAGGCCG AAAGGCCGAA AGCCCAA                                     38

(2) INFORMATION FOR SEQ ID NO: 2119:

(i) SEQUENCE CHARACTERISTICS:
        (A) LENGTH:              38 base pairs
        (B) TYPE:                nucleic acid

```
            (C) STRANDEDNESS:         single
            (D) TOPOLOGY:             linear (xi) SEQUENCE DESCRIPTION: SEQ ID NO: 2119:

GACCUGUGCU GAUGAGGCCG AAAGGCCGAA AGAAGCCC                              38

(2) INFORMATION FOR SEQ ID NO: 2120:

(i) SEQUENCE CHARACTERISTICS:
            (A) LENGTH:               38 base pairs
            (B) TYPE:                 nucleic acid
            (C) STRANDEDNESS:         single
            (D) TOPOLOGY:             linear (xi) SEQUENCE DESCRIPTION: SEQ ID NO: 2120:

AGCACAUGCU GAUGAGGCCG AAAGGCCGAA AGUUCCAA                              38

(2) INFORMATION FOR SEQ ID NO: 2121:

(i) SEQUENCE CHARACTERISTICS:
            (A) LENGTH:               38 base pairs
            (B) TYPE:                 nucleic acid
            (C) STRANDEDNESS:         single
            (D) TOPOLOGY:             linear (xi) SEQUENCE DESCRIPTION: SEQ ID NO: 2121:

ACGAUCACCU GAUGAGGCCG AAAGGCCGAA AAGCCCGC                              38

(2) INFORMATION FOR SEQ ID NO: 2122:

(i) SEQUENCE CHARACTERISTICS:
            (A) LENGTH:               38 base pairs
            (B) TYPE:                 nucleic acid
            (C) STRANDEDNESS:         single
            (D) TOPOLOGY:             linear (xi) SEQUENCE DESCRIPTION: SEQ ID NO: 2122:

GCGACCAGCU GAUGAGGCCG AAAGGCCGAA ACCAGGAG                              38

(2) INFORMATION FOR SEQ ID NO: 2123:

(i) SEQUENCE CHARACTERISTICS:
            (A) LENGTH:               38 base pairs
            (B) TYPE:                 nucleic acid
            (C) STRANDEDNESS:         single
            (D) TOPOLOGY:             linear (xi) SEQUENCE DESCRIPTION: SEQ ID NO: 2123:

GAGGACCACU GAUGAGGCCG AAAGGCCGAA AUAGCACA                              38

(2) INFORMATION FOR SEQ ID NO: 2124:

(i) SEQUENCE CHARACTERISTICS:
            (A) LENGTH:               38 base pairs
            (B) TYPE:                 nucleic acid
            (C) STRANDEDNESS:         single
            (D) TOPOLOGY:             linear (xi) SEQUENCE DESCRIPTION: SEQ ID NO: 2124:

ACCCGUAUCU GAUGAGGCCG AAAGGCCGAA AUCUUUCC                              38

(2) INFORMATION FOR SEQ ID NO: 2125:

(i) SEQUENCE CHARACTERISTICS:
            (A) LENGTH:               38 base pairs
            (B) TYPE:                 nucleic acid
            (C) STRANDEDNESS:         single
```

(D) TOPOLOGY:         linear (xi) SEQUENCE DESCRIPTION: SEQ ID NO: 2125:

CAUUCUUGCU GAUGAGGCCG AAAGGCCGAA ACAGUGAC                                38

(2) INFORMATION FOR SEQ ID NO: 2126:

(i) SEQUENCE CHARACTERISTICS:
          (A) LENGTH:           38 base pairs
          (B) TYPE:             nucleic acid
          (C) STRANDEDNESS:     single
          (D) TOPOLOGY:         linear (xi) SEQUENCE DESCRIPTION: SEQ ID NO: 2126:

CUGACACACU GAUGAGGCCG AAAGGCCGAA AAUCUCUG                                38

(2) INFORMATION FOR SEQ ID NO: 2127:

(i) SEQUENCE CHARACTERISTICS:
          (A) LENGTH:           38 base pairs
          (B) TYPE:             nucleic acid
          (C) STRANDEDNESS:     single
          (D) TOPOLOGY:         linear (xi) SEQUENCE DESCRIPTION: SEQ ID NO: 2127:

UCUGCUGACU GAUGAGGCCG AAAGGCCGAA ACCCCUCU                                38

(2) INFORMATION FOR SEQ ID NO: 2128:

(i) SEQUENCE CHARACTERISTICS:
          (A) LENGTH:           38 base pairs
          (B) TYPE:             nucleic acid
          (C) STRANDEDNESS:     single
          (D) TOPOLOGY:         linear (xi) SEQUENCE DESCRIPTION: SEQ ID NO: 2128:

GCAUGUAACU GAUGAGGCCG AAAGGCCGAA AGUCUGCU                                38

(2) INFORMATION FOR SEQ ID NO: 2129:

(i) SEQUENCE CHARACTERISTICS:
          (A) LENGTH:           38 base pairs
          (B) TYPE:             nucleic acid
          (C) STRANDEDNESS:     single
          (D) TOPOLOGY:         linear (xi) SEQUENCE DESCRIPTION: SEQ ID NO: 2129:

UUUCCCCACU GAUGAGGCCG AAAGGCCGAA ACUCUGUU                                38

(2) INFORMATION FOR SEQ ID NO: 2130:

(i) SEQUENCE CHARACTERISTICS:
          (A) LENGTH:           38 base pairs
          (B) TYPE:             nucleic acid
          (C) STRANDEDNESS:     single
          (D) TOPOLOGY:         linear (xi) SEQUENCE DESCRIPTION: SEQ ID NO: 2130:

GCUCUGGGCU GAUGAGGCCG AAAGGCCGAA ACGAAUAC                                38

(2) INFORMATION FOR SEQ ID NO: 2131:

(i) SEQUENCE CHARACTERISTICS:
          (A) LENGTH:           38 base pairs
          (B) TYPE:             nucleic acid
          (C) STRANDEDNESS:     single
          (D) TOPOLOGY:         linear (xi) SEQUENCE DESCRIPTION: SEQ ID NO: 2131:

GGAUACCUCU GAUGAGGCCG AAAGGCCGAA AGCACCGA                              38

(2) INFORMATION FOR SEQ ID NO: 2132:

(i) SEQUENCE CHARACTERISTICS:
        (A) LENGTH:              38 base pairs
        (B) TYPE:                nucleic acid
        (C) STRANDEDNESS:        single
        (D) TOPOLOGY:            linear (xi) SEQUENCE DESCRIPTION: SEQ ID NO: 2132:

AGUCCUCUCU GAUGAGGCCG AAAGGCCGAA AGGCCUGA                              38

(2) INFORMATION FOR SEQ ID NO: 2133:

(i) SEQUENCE CHARACTERISTICS:
        (A) LENGTH:              38 base pairs
        (B) TYPE:                nucleic acid
        (C) STRANDEDNESS:        single
        (D) TOPOLOGY:            linear (xi) SEQUENCE DESCRIPTION: SEQ ID NO: 2133:

CCAUUGUUCU GAUGAGGCCG AAAGGCCGAA AGCUGCUA                              38

(2) INFORMATION FOR SEQ ID NO: 2134:

(i) SEQUENCE CHARACTERISTICS:
        (A) LENGTH:              38 base pairs
        (B) TYPE:                nucleic acid
        (C) STRANDEDNESS:        single
        (D) TOPOLOGY:            linear (xi) SEQUENCE DESCRIPTION: SEQ ID NO: 2134:

CCUGGGGCU GAUGAGGCCG AAAGGCCGAA AGUACCCU                               38

(2) INFORMATION FOR SEQ ID NO: 2135:

(i) SEQUENCE CHARACTERISTICS:
        (A) LENGTH:              38 base pairs
        (B) TYPE:                nucleic acid
        (C) STRANDEDNESS:        single
        (D) TOPOLOGY:            linear (xi) SEQUENCE DESCRIPTION: SEQ ID NO: 2135:

GCCUGGGGCU GAUGAGGCCG AAAGGCCGAA AAGUACCC                              38

(2) INFORMATION FOR SEQ ID NO: 2136:

(i) SEQUENCE CHARACTERISTICS:
        (A) LENGTH:              38 base pairs
        (B) TYPE:                nucleic acid
        (C) STRANDEDNESS:        single
        (D) TOPOLOGY:            linear (xi) SEQUENCE DESCRIPTION: SEQ ID NO: 2136:

GGCAGCGGCU GAUGAGGCCG AAAGGCCGAA ACACCAUC                              38

(2) INFORMATION FOR SEQ ID NO: 2137:

(i) SEQUENCE CHARACTERISTICS:
        (A) LENGTH:              38 base pairs
        (B) TYPE:                nucleic acid
        (C) STRANDEDNESS:        single
        (D) TOPOLOGY:            linear -continued (xi) SEQUENCE DESCRIPTION: SEQ ID NO: 2137:

ACCAUCCCCU GAUGAGGCCG AAAGGCCGAA AUAGGCAG                              38

(2) INFORMATION FOR SEQ ID NO: 2138:

(i) SEQUENCE CHARACTERISTICS:
       (A) LENGTH:           38 base pairs
       (B) TYPE:             nucleic acid
       (C) STRANDEDNESS:     single
       (D) TOPOLOGY:         linear (xi) SEQUENCE DESCRIPTION: SEQ ID NO: 2138:

CAUCCAGUCU GAUGAGGCCG AAAGGCCGAA AGUCUCCA                              38

(2) INFORMATION FOR SEQ ID NO: 2139:

(i) SEQUENCE CHARACTERISTICS:
       (A) LENGTH:           38 base pairs
       (B) TYPE:             nucleic acid
       (C) STRANDEDNESS:     single
       (D) TOPOLOGY:         linear (xi) SEQUENCE DESCRIPTION: SEQ ID NO: 2139:

UGUCCUGUCU GAUGAGGCCG AAAGGCCGAA ACAGCCAG                              38

(2) INFORMATION FOR SEQ ID NO: 2140:

(i) SEQUENCE CHARACTERISTICS:
       (A) LENGTH:           38 base pairs
       (B) TYPE:             nucleic acid
       (C) STRANDEDNESS:     single
       (D) TOPOLOGY:         linear (xi) SEQUENCE DESCRIPTION: SEQ ID NO: 2140:

CAGUUCUCCU GAUGAGGCCG AAAGGCCGAA AAGCACAG                              38

(2) INFORMATION FOR SEQ ID NO: 2141:

(i) SEQUENCE CHARACTERISTICS:
       (A) LENGTH:           38 base pairs
       (B) TYPE:             nucleic acid
       (C) STRANDEDNESS:     single
       (D) TOPOLOGY:         linear (xi) SEQUENCE DESCRIPTION: SEQ ID NO: 2141:

GACGCCACCU GAUGAGGCCG AAAGGCCGAA AUCACGAA                              38

(2) INFORMATION FOR SEQ ID NO: 2142:

(i) SEQUENCE CHARACTERISTICS:
       (A) LENGTH:           38 base pairs
       (B) TYPE:             nucleic acid
       (C) STRANDEDNESS:     single
       (D) TOPOLOGY:         linear (xi) SEQUENCE DESCRIPTION: SEQ ID NO: 2142:

GUCCACUCCU GAUGAGGCCG AAAGGCCGAA AUAGUUCG                              38

(2) INFORMATION FOR SEQ ID NO: 2143:

(i) SEQUENCE CHARACTERISTICS:
       (A) LENGTH:           38 base pairs
       (B) TYPE:             nucleic acid
       (C) STRANDEDNESS:     single
       (D) TOPOLOGY:         linear (xi) SEQUENCE DESCRIPTION: SEQ ID NO: 2143:

GCCUGGGGCU GAUGAGGCCG AAAGGCCGAA AAGUACCC                                 38

(2) INFORMATION FOR SEQ ID NO: 2144:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2144:

AGCCAGAGCU GAUGAGGCCG AAAGGCCGAA AGGUGGGU                                 38

(2) INFORMATION FOR SEQ ID NO: 2145:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2145:

CCUGAGGCCU GAUGAGGCCG AAAGGCCGAA ACAAGUAU                                 38

(2) INFORMATION FOR SEQ ID NO: 2146:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2146:

CUCCUCCUCU GAUGAGGCCG AAAGGCCGAA AGCCUUCU                                 38

(2) INFORMATION FOR SEQ ID NO: 2147:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2147:

UCCCUGGUCU GAUGAGGCCG AAAGGCCGAA AUACUCCC                                 38

(2) INFORMATION FOR SEQ ID NO: 2148:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2148:

CCUGGGGCU GAUGAGGCCG AAAGGCCGAA AGUACCCU                                  38

(2) INFORMATION FOR SEQ ID NO: 2149:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2149:

```
GCAAGAGGCU GAUGAGGCCG AAAGGCCGAA AGAGCAGU                              38

(2) INFORMATION FOR SEQ ID NO: 2150:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2150:

UAGUCUCCCU GAUGAGGCCG AAAGGCCGAA ACCCCAGG                              38

(2) INFORMATION FOR SEQ ID NO: 2151:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2151:

UUGACCAUCU GAUGAGGCCG AAAGGCCGAA AUUUCACG                              38

(2) INFORMATION FOR SEQ ID NO: 2152:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2152:

GUGGUUGGCU GAUGAGGCCG AAAGGCCGAA ACAUUUUC                              38

(2) INFORMATION FOR SEQ ID NO: 2153:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2153:

CCAACAAUCU GAUGAGGCCG AAAGGCCGAA AUGACCCA                              38

(2) INFORMATION FOR SEQ ID NO: 2154:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2154:

UACACAGUCU GAUGAGGCCG AAAGGCCGAA AUGGUGGC                              38

(2) INFORMATION FOR SEQ ID NO: 2155:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2155:

ACAACGGCCU GAUGAGGCCG AAAGGCCGAA ACCAGGAC                              38
```

(2) INFORMATION FOR SEQ ID NO: 2156:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2156:

ACAAUUAUCU GAUGAGGCCG AAAGGCCGAA ACCCAGGU                           38

(2) INFORMATION FOR SEQ ID NO: 2157:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2157:

AAGCCCGCCU GAUGAGGCCG AAAGGCCGAA AUGAUCAG                           38

(2) INFORMATION FOR SEQ ID NO: 2158:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2158:

UACGAGCACU GAUGAGGCCG AAAGGCCGAA AGGGCCAC                           38

(2) INFORMATION FOR SEQ ID NO: 2159:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2159:

UAAACAGGCU GAUGAGGCCG AAAGGCCGAA ACUUCCCA                           38

(2) INFORMATION FOR SEQ ID NO: 2160:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2160:

UGGGAACACU GAUGAGGCCG AAAGGCCGAA AGGUAGGA                           38

(2) INFORMATION FOR SEQ ID NO: 2161:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2161:

GGCGGUAACU GAUGAGGCCG AAAGGCCGAA AGGUGUAA                           38

(2) INFORMATION FOR SEQ ID NO: 2162:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2162:

CUGGCGGUCU GAUGAGGCCG AAAGGCCGAA AUAGGUGU                    38

(2) INFORMATION FOR SEQ ID NO: 2163:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2163:

UAUAUCCUCU GAUGAGGCCG AAAGGCCGAA AUCUUCCU                    38

(2) INFORMATION FOR SEQ ID NO: 2164:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2164:

GUAACUUGCU GAUGAGGCCG AAAGGCCGAA AUAUCCUG                    38

(2) INFORMATION FOR SEQ ID NO: 2165:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2165:

GCCUUCUGCU GAUGAGGCCG AAAGGCCGAA AACUUGUA                    38

(2) INFORMATION FOR SEQ ID NO: 2166:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2166:

GGCUCAGGCU GAUGAGGCCG AAAGGCCGAA AGGCGGGG                    38

(2) INFORMATION FOR SEQ ID NO: 2167:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 2167:

ACCAGGGCCU GAUGAGGCCG AAAGGCCGAA AAGUGCAG                    38

(2) INFORMATION FOR SEQ ID NO: 2168:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2168:

UGUCCAUUCU GAUGAGGCCG AAAGGCCGAA AUCUGUUC                                      38

(2) INFORMATION FOR SEQ ID NO: 2169:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2169:

CCCAGGCCCU GAUGAGGCCG AAAGGCCGAA AGGUUCUC                                      38

(2) INFORMATION FOR SEQ ID NO: 2170:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2170:

GACCUGUGCU GAUGAGGCCG AAAGGCCGAA AGAAGCCC                                      38

(2) INFORMATION FOR SEQ ID NO: 2171:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2171:

GAGGCAGGCU GAUGAGGCCG AAAGGCCGAA AACAGGCC                                      38

(2) INFORMATION FOR SEQ ID NO: 2172:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2172:

GAGAGGUCCU GAUGAGGCCG AAAGGCCGAA ACGAGCAG                                      38

(2) INFORMATION FOR SEQ ID NO: 2173:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2173:

AAUGUAUGCU GAUGAGGCCG AAAGGCCGAA AGGUGGGG                                      38

(2) INFORMATION FOR SEQ ID NO: 2174:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2174:

GAAGAUCGCU GAUGAGGCCG AAAGGCCGAA AAGUCCGG                                   38

(2) INFORMATION FOR SEQ ID NO: 2175:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2175:

GCGACCAGCU GAUGAGGCCG AAAGGCCGAA ACCAGGAG                                   38

(2) INFORMATION FOR SEQ ID NO: 2176:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2176:

UCUCCAGGCU GAUGAGGCCG AAAGGCCGAA AUAUCUGA                                   38

(2) INFORMATION FOR SEQ ID NO: 2177:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2177:

GCACCGUGCU GAUGAGGCCG AAAGGCCGAA AUGUGAUC                                   38

(2) INFORMATION FOR SEQ ID NO: 2178:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2178:

AAUAGGUGCU GAUGAGGCCG AAAGGCCGAA AAAUGGAC                                   38

(2) INFORMATION FOR SEQ ID NO: 2179:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2179:

AGGACCAGCU GAUGAGGCCG AAAGGCCGAA AGCAGAGG                                   38

(2) INFORMATION FOR SEQ ID NO: 2180:

```
    (i) SEQUENCE CHARACTERISTICS:
         (A) LENGTH:          38 base pairs
         (B) TYPE:            nucleic acid
         (C) STRANDEDNESS:    single
         (D) TOPOLOGY:        linear (xi) SEQUENCE DESCRIPTION: SEQ ID NO: 2180:

CCCAGGCCCU GAUGAGGCCG AAAGGCCGAA AGGUUCUC                            38

(2) INFORMATION FOR SEQ ID NO: 2181:

(i) SEQUENCE CHARACTERISTICS:
         (A) LENGTH:          38 base pairs
         (B) TYPE:            nucleic acid
         (C) STRANDEDNESS:    single
         (D) TOPOLOGY:        linear (xi) SEQUENCE DESCRIPTION: SEQ ID NO: 2181:

GAGUUGGGCU GAUGAGGCCG AAAGGCCGAA ACAGUGUC                            38

(2) INFORMATION FOR SEQ ID NO: 2182:

(i) SEQUENCE CHARACTERISTICS:
         (A) LENGTH:          38 base pairs
         (B) TYPE:            nucleic acid
         (C) STRANDEDNESS:    single
         (D) TOPOLOGY:        linear (xi) SEQUENCE DESCRIPTION: SEQ ID NO: 2182:

GUCCAGGUCU GAUGAGGCCG AAAGGCCGAA AGGACCAU                            38

(2) INFORMATION FOR SEQ ID NO: 2183:

(i) SEQUENCE CHARACTERISTICS:
         (A) LENGTH:          38 base pairs
         (B) TYPE:            nucleic acid
         (C) STRANDEDNESS:    single
         (D) TOPOLOGY:        linear (xi) SEQUENCE DESCRIPTION: SEQ ID NO: 2183:

UGGUUUUUCU GAUGAGGCCG AAAGGCCGAA AACAGGGA                            38

(2) INFORMATION FOR SEQ ID NO: 2184:

(i) SEQUENCE CHARACTERISTICS:
         (A) LENGTH:          38 base pairs
         (B) TYPE:            nucleic acid
         (C) STRANDEDNESS:    single
         (D) TOPOLOGY:        linear (xi) SEQUENCE DESCRIPTION: SEQ ID NO: 2184:

UCCAGGUACU GAUGAGGCCG AAAGGCCGAA AUCUGAGC                            38

(2) INFORMATION FOR SEQ ID NO: 2185:

(i) SEQUENCE CHARACTERISTICS:
         (A) LENGTH:          38 base pairs
         (B) TYPE:            nucleic acid
         (C) STRANDEDNESS:    single
         (D) TOPOLOGY:        linear (xi) SEQUENCE DESCRIPTION: SEQ ID NO: 2185:

UUUCCCCACU GAUGAGGCCG AAAGGCCGAA ACUCUGUU                            38

(2) INFORMATION FOR SEQ ID NO: 2186:

(i) SEQUENCE CHARACTERISTICS:
```

```
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2186:

ACGAUCACCU GAUGAGGCCG AAAGGCCGAA AAGCCCGC                              38

(2) INFORMATION FOR SEQ ID NO: 2187:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2187:

UACACAGUCU GAUGAGGCCG AAAGGCCGAA AUGGUGGC                              38

(2) INFORMATION FOR SEQ ID NO: 2188:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2188:

UACCCUGUCU GAUGAGGCCG AAAGGCCGAA AGGUGGGU                              38

(2) INFORMATION FOR SEQ ID NO: 2189:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2189:

GCCCCUCCCU GAUGAGGCCG AAAGGCCGAA AGUCCUCU                              38

(2) INFORMATION FOR SEQ ID NO: 2190:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2190:

GCAGGUCACU GAUGAGGCCG AAAGGCCGAA AUUAGGGG                              38

(2) INFORMATION FOR SEQ ID NO: 2191:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2191:

GGACCAUACU GAUGAGGCCG AAAGGCCGAA AGCACAUG                              38

(2) INFORMATION FOR SEQ ID NO: 2192:

(i) SEQUENCE CHARACTERISTICS:
            (A) LENGTH:            38 base pairs
```

(B) TYPE:            nucleic acid
            (C) STRANDEDNESS:    single
            (D) TOPOLOGY:        linear (xi) SEQUENCE DESCRIPTION: SEQ ID NO: 2192:

CUUGUGUCCU GAUGAGGCCG AAAGGCCGAA ACCGGAUA                                    38

(2) INFORMATION FOR SEQ ID NO: 2193:

(i) SEQUENCE CHARACTERISTICS:
            (A) LENGTH:          38 base pairs
            (B) TYPE:            nucleic acid
            (C) STRANDEDNESS:    single
            (D) TOPOLOGY:        linear (xi) SEQUENCE DESCRIPTION: SEQ ID NO: 2193:

AUUUAUAUCU GAUGAGGCCG AAAGGCCGAA ACUCGUGA                                    38

(2) INFORMATION FOR SEQ ID NO: 2194:

(i) SEQUENCE CHARACTERISTICS:
            (A) LENGTH:          38 base pairs
            (B) TYPE:            nucleic acid
            (C) STRANDEDNESS:    single
            (D) TOPOLOGY:        linear (xi) SEQUENCE DESCRIPTION: SEQ ID NO: 2194:

CCUGGGGGCU GAUGAGGCCG AAAGGCCGAA AGUACUGU                                    38

(2) INFORMATION FOR SEQ ID NO: 2195:

(i) SEQUENCE CHARACTERISTICS:
            (A) LENGTH:          38 base pairs
            (B) TYPE:            nucleic acid
            (C) STRANDEDNESS:    single
            (D) TOPOLOGY:        linear (xi) SEQUENCE DESCRIPTION: SEQ ID NO: 2195:

UGUACCUUCU GAUGAGGCCG AAAGGCCGAA AGUUUUAG                                    38

(2) INFORMATION FOR SEQ ID NO: 2196:

(i) SEQUENCE CHARACTERISTICS:
            (A) LENGTH:          38 base pairs
            (B) TYPE:            nucleic acid
            (C) STRANDEDNESS:    single
            (D) TOPOLOGY:        linear (xi) SEQUENCE DESCRIPTION: SEQ ID NO: 2196:

UGUCCAUUCU GAUGAGGCCG AAAGGCCGAA AUCUGUUC                                    38

(2) INFORMATION FOR SEQ ID NO: 2197:

(i) SEQUENCE CHARACTERISTICS:
            (A) LENGTH:          38 base pairs
            (B) TYPE:            nucleic acid
            (C) STRANDEDNESS:    single
            (D) TOPOLOGY:        linear (xi) SEQUENCE DESCRIPTION: SEQ ID NO: 2197:

UAGGCAAUCU GAUGAGGCCG AAAGGCCGAA ACUUACAU                                    38

(2) INFORMATION FOR SEQ ID NO: 2198:

(i) SEQUENCE CHARACTERISTICS:
            (A) LENGTH:          38 base pairs
            (B) TYPE:            nucleic acid

```
          (C) STRANDEDNESS:        single
          (D) TOPOLOGY:            linear (xi) SEQUENCE DESCRIPTION: SEQ ID NO: 2198:

CUAAAGGUCU GAUGAGGCCG AAAGGCCGAA AGCGUCCA                              38

(2) INFORMATION FOR SEQ ID NO: 2199:

(i) SEQUENCE CHARACTERISTICS:
          (A) LENGTH:             38 base pairs
          (B) TYPE:               nucleic acid
          (C) STRANDEDNESS:       single
          (D) TOPOLOGY:           linear (xi) SEQUENCE DESCRIPTION: SEQ ID NO: 2199:

UCCAGGUACU GAUGAGGCCG AAAGGCCGAA AUCUGAGC                              38

(2) INFORMATION FOR SEQ ID NO: 2200:

(i) SEQUENCE CHARACTERISTICS:
          (A) LENGTH:             38 base pairs
          (B) TYPE:               nucleic acid
          (C) STRANDEDNESS:       single
          (D) TOPOLOGY:           linear (xi) SEQUENCE DESCRIPTION: SEQ ID NO: 2200:

CAUCCAGUCU GAUGAGGCCG AAAGGCCGAA AGUCUCCA                              38

(2) INFORMATION FOR SEQ ID NO: 2201:

(i) SEQUENCE CHARACTERISTICS:
          (A) LENGTH:             38 base pairs
          (B) TYPE:               nucleic acid
          (C) STRANDEDNESS:       single
          (D) TOPOLOGY:           linear (xi) SEQUENCE DESCRIPTION: SEQ ID NO: 2201:

GCUGACACCU GAUGAGGCCG AAAGGCCGAA AAAUCUCU                              38

(2) INFORMATION FOR SEQ ID NO: 2202:

(i) SEQUENCE CHARACTERISTICS:
          (A) LENGTH:             38 base pairs
          (B) TYPE:               nucleic acid
          (C) STRANDEDNESS:       single
          (D) TOPOLOGY:           linear (xi) SEQUENCE DESCRIPTION: SEQ ID NO: 2202:

CCCAGGCCCU GAUGAGGCCG AAAGGCCGAA AGGUUCUC                              38

(2) INFORMATION FOR SEQ ID NO: 2203:

(i) SEQUENCE CHARACTERISTICS:
          (A) LENGTH:             38 base pairs
          (B) TYPE:               nucleic acid
          (C) STRANDEDNESS:       single
          (D) TOPOLOGY:           linear (xi) SEQUENCE DESCRIPTION: SEQ ID NO: 2203:

AGCUUGAACU GAUGAGGCCG AAAGGCCGAA AGCUUCCA                              38

(2) INFORMATION FOR SEQ ID NO: 2204:

(i) SEQUENCE CHARACTERISTICS:
          (A) LENGTH:             38 base pairs
          (B) TYPE:               nucleic acid
          (C) STRANDEDNESS:       single
```

(D) TOPOLOGY:         linear (xi) SEQUENCE DESCRIPTION: SEQ ID NO: 2204:

UAGGCAAUCU GAUGAGGCCG AAAGGCCGAA ACUUACAU                                38

(2) INFORMATION FOR SEQ ID NO: 2205:

(i) SEQUENCE CHARACTERISTICS:
            (A) LENGTH:           38 base pairs
            (B) TYPE:             nucleic acid
            (C) STRANDEDNESS:     single
            (D) TOPOLOGY:         linear (xi) SEQUENCE DESCRIPTION: SEQ ID NO: 2205:

CAUCCCGACU GAUGAGGCCG AAAGGCCGAA AGGCAGCG                                38

(2) INFORMATION FOR SEQ ID NO: 2206:

(i) SEQUENCE CHARACTERISTICS:
            (A) LENGTH:           38 base pairs
            (B) TYPE:             nucleic acid
            (C) STRANDEDNESS:     single
            (D) TOPOLOGY:         linear (xi) SEQUENCE DESCRIPTION: SEQ ID NO: 2206:

ACCAUCCCCU GAUGAGGCCG AAAGGCCGAA AUAGGCAG                                38

(2) INFORMATION FOR SEQ ID NO: 2207:

(i) SEQUENCE CHARACTERISTICS:
            (A) LENGTH:           38 base pairs
            (B) TYPE:             nucleic acid
            (C) STRANDEDNESS:     single
            (D) TOPOLOGY:         linear (xi) SEQUENCE DESCRIPTION: SEQ ID NO: 2207:

GUACAGGGCU GAUGAGGCCG AAAGGCCGAA ACUCAAUA                                38

(2) INFORMATION FOR SEQ ID NO: 2208:

(i) SEQUENCE CHARACTERISTICS:
            (A) LENGTH:           38 base pairs
            (B) TYPE:             nucleic acid
            (C) STRANDEDNESS:     single
            (D) TOPOLOGY:         linear (xi) SEQUENCE DESCRIPTION: SEQ ID NO: 2208:

UCGUUUGUCU GAUGAGGCCG AAAGGCCGAA AUCCUCCG                                38

(2) INFORMATION FOR SEQ ID NO: 2209:

(i) SEQUENCE CHARACTERISTICS:
            (A) LENGTH:           38 base pairs
            (B) TYPE:             nucleic acid
            (C) STRANDEDNESS:     single
            (D) TOPOLOGY:         linear (xi) SEQUENCE DESCRIPTION: SEQ ID NO: 2209:

ACCUCCAGCU GAUGAGGCCG AAAGGCCGAA AGGUCAGG                                38

(2) INFORMATION FOR SEQ ID NO: 2210:

(i) SEQUENCE CHARACTERISTICS:
            (A) LENGTH:           38 base pairs
            (B) TYPE:             nucleic acid
            (C) STRANDEDNESS:     single
            (D) TOPOLOGY:         linear (xi) SEQUENCE DESCRIPTION: SEQ ID NO: 2210:

AGCCAUUGCU GAUGAGGCCG AAAGGCCGAA AGGACCAG                               38

(2) INFORMATION FOR SEQ ID NO: 2211:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2211:

UAGGUGUACU GAUGAGGCCG AAAGGCCGAA AUGGACGC                               38

(2) INFORMATION FOR SEQ ID NO: 2212:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2212:

CCUGAGGCCU GAUGAGGCCG AAAGGCCGAA ACAAGUAU                               38

(2) INFORMATION FOR SEQ ID NO: 2213:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2213:

UUAGGCCUCU GAUGAGGCCG AAAGGCCGAA AGGCUACA                               38

(2) INFORMATION FOR SEQ ID NO: 2214:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2214:

ACAUCAACCU GAUGAGGCCG AAAGGCCGAA AGAGUUGG                               38

(2) INFORMATION FOR SEQ ID NO: 2215:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2215:

ACCUCCAGCU GAUGAGGCCG AAAGGCCGAA AGGUCAGG                               38

(2) INFORMATION FOR SEQ ID NO: 2216:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2216:

CAGGACCCCU GAUGAGGCCG AAAGGCCGAA AGUCGGAA                                      38

(2) INFORMATION FOR SEQ ID NO: 2217:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2217:

GAUCAUGGCU GAUGAGGCCG AAAGGCCGAA ACAGCACU                                      38

(2) INFORMATION FOR SEQ ID NO: 2218:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2218:

AGAGGCAGCU GAUGAGGCCG AAAGGCCGAA AAACAGGC                                      38

(2) INFORMATION FOR SEQ ID NO: 2219:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2219:

ACAUCAACCU GAUGAGGCCG AAAGGCCGAA AGAGUUGG                                      38

(2) INFORMATION FOR SEQ ID NO: 2220:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2220:

AAGUUGUACU GAUGAGGCCG AAAGGCCGAA AUUCUCAA                                      38

(2) INFORMATION FOR SEQ ID NO: 2221:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2221:

UCAAUAAACU GAUGAGGCCG AAAGGCCGAA AACUGUCA                                      38

(2) INFORMATION FOR SEQ ID NO: 2222:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2222:

AAUUAAUACU GAUGAGGCCG AAAGGCCGAA AUACAUCA                    38

(2) INFORMATION FOR SEQ ID NO: 2223:

(i) SEQUENCE CHARACTERISTICS:
        (A) LENGTH:         38 base pairs
        (B) TYPE:           nucleic acid
        (C) STRANDEDNESS:  single
        (D) TOPOLOGY:      linear (xi) SEQUENCE DESCRIPTION: SEQ ID NO: 2223:

GAAUUAAUCU GAUGAGGCCG AAAGGCCGAA AAUACAUC                    38

(2) INFORMATION FOR SEQ ID NO: 2224:

(i) SEQUENCE CHARACTERISTICS:
        (A) LENGTH:         38 base pairs
        (B) TYPE:           nucleic acid
        (C) STRANDEDNESS:  single
        (D) TOPOLOGY:      linear (xi) SEQUENCE DESCRIPTION: SEQ ID NO: 2224:

UGAAUUAACU GAUGAGGCCG AAAGGCCGAA AAAUACAU                    38

(2) INFORMATION FOR SEQ ID NO: 2225:

(i) SEQUENCE CHARACTERISTICS:
        (A) LENGTH:         38 base pairs
        (B) TYPE:           nucleic acid
        (C) STRANDEDNESS:  single
        (D) TOPOLOGY:      linear (xi) SEQUENCE DESCRIPTION: SEQ ID NO: 2225:

AACAAAGGCU GAUGAGGCCG AAAGGCCGAA AGGAAUGU                    38

(2) INFORMATION FOR SEQ ID NO: 2226:

(i) SEQUENCE CHARACTERISTICS:
        (A) LENGTH:         38 base pairs
        (B) TYPE:           nucleic acid
        (C) STRANDEDNESS:  single
        (D) TOPOLOGY:      linear (xi) SEQUENCE DESCRIPTION: SEQ ID NO: 2226:

CUCUGAAUCU GAUGAGGCCG AAAGGCCGAA AAUAAAUA                    38

(2) INFORMATION FOR SEQ ID NO: 2227:

(i) SEQUENCE CHARACTERISTICS:
        (A) LENGTH:         38 base pairs
        (B) TYPE:           nucleic acid
        (C) STRANDEDNESS:  single
        (D) TOPOLOGY:      linear (xi) SEQUENCE DESCRIPTION: SEQ ID NO: 2227:

AAUUAAUACU GAUGAGGCCG AAAGGCCGAA AUACAUCA                    38

(2) INFORMATION FOR SEQ ID NO: 2228:

(i) SEQUENCE CHARACTERISTICS:
        (A) LENGTH:         38 base pairs
        (B) TYPE:           nucleic acid
        (C) STRANDEDNESS:  single
        (D) TOPOLOGY:      linear (xi) SEQUENCE DESCRIPTION: SEQ ID NO: 2228:

```
GAAUUAAUCU GAUGAGGCCG AAAGGCCGAA AAUACAUC                                      38

(2) INFORMATION FOR SEQ ID NO: 2229:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2229:

UCUGAAUUCU GAUGAGGCCG AAAGGCCGAA AUAAAUAC                                      38

(2) INFORMATION FOR SEQ ID NO: 2230:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2230:

UACUCAAUCU GAUGAGGCCG AAAGGCCGAA AAUAACUG                                      38

(2) INFORMATION FOR SEQ ID NO: 2231:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2231:

GAGGACCACU GAUGAGGCCG AAAGGCCGAA AUAGCACA                                      38

(2) INFORMATION FOR SEQ ID NO: 2232:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2232:

AGCAGGGGCU GAUGAGGCCG AAAGGCCGAA AAUAGAGA                                      38

(2) INFORMATION FOR SEQ ID NO: 2233:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2233:

UGACUCGUCU GAUGAGGCCG AAAGGCCGAA AAAGAAAU                                      38

(2) INFORMATION FOR SEQ ID NO: 2234:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2234:

GUGGUUGGCU GAUGAGGCCG AAAGGCCGAA ACAUUUUC                                      38
```

(2) INFORMATION FOR SEQ ID NO: 2235:

(i) SEQUENCE CHARACTERISTICS:
        (A) LENGTH:         38 base pairs
        (B) TYPE:           nucleic acid
        (C) STRANDEDNESS:  single
        (D) TOPOLOGY:      linear (xi) SEQUENCE DESCRIPTION: SEQ ID NO: 2235:

UCAAUAAACU GAUGAGGCCG AAAGGCCGAA AACUGUCA                    38

(2) INFORMATION FOR SEQ ID NO: 2236:

(i) SEQUENCE CHARACTERISTICS:
        (A) LENGTH:         38 base pairs
        (B) TYPE:           nucleic acid
        (C) STRANDEDNESS:  single
        (D) TOPOLOGY:      linear (xi) SEQUENCE DESCRIPTION: SEQ ID NO: 2236:

ACUCAAUACU GAUGAGGCCG AAAGGCCGAA AUAACUGU                    38

(2) INFORMATION FOR SEQ ID NO: 2237:

(i) SEQUENCE CHARACTERISTICS:
        (A) LENGTH:         38 base pairs
        (B) TYPE:           nucleic acid
        (C) STRANDEDNESS:  single
        (D) TOPOLOGY:      linear (xi) SEQUENCE DESCRIPTION: SEQ ID NO: 2237:

UACUCAAUCU GAUGAGGCCG AAAGGCCGAA AAUAACUG                    38

(2) INFORMATION FOR SEQ ID NO: 2238:

(i) SEQUENCE CHARACTERISTICS:
        (A) LENGTH:         38 base pairs
        (B) TYPE:           nucleic acid
        (C) STRANDEDNESS:  single
        (D) TOPOLOGY:      linear (xi) SEQUENCE DESCRIPTION: SEQ ID NO: 2238:

GUACUCAACU GAUGAGGCCG AAAGGCCGAA AAAUAACU                    38

(2) INFORMATION FOR SEQ ID NO: 2239:

(i) SEQUENCE CHARACTERISTICS:
        (A) LENGTH:         38 base pairs
        (B) TYPE:           nucleic acid
        (C) STRANDEDNESS:  single
        (D) TOPOLOGY:      linear (xi) SEQUENCE DESCRIPTION: SEQ ID NO: 2239:

GGGUACUCCU GAUGAGGCCG AAAGGCCGAA AUAAAUAA                    38

(2) INFORMATION FOR SEQ ID NO: 2240:

(i) SEQUENCE CHARACTERISTICS:
        (A) LENGTH:         38 base pairs
        (B) TYPE:           nucleic acid
        (C) STRANDEDNESS:  single
        (D) TOPOLOGY:      linear (xi) SEQUENCE DESCRIPTION: SEQ ID NO: 2240:

CAAUAAAUCU GAUGAGGCCG AAAGGCCGAA ACUGUCAG                    38

```
(2) INFORMATION FOR SEQ ID NO: 2241:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2241:

UGACCUCGCU GAUGAGGCCG AAAGGCCGAA AGACAUUC                                38

(2) INFORMATION FOR SEQ ID NO: 2242:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2242:

CUGGCAUGCU GAUGAGGCCG AAAGGCCGAA AAGAGUCU                                38

(2) INFORMATION FOR SEQ ID NO: 2243:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2243:

GCCUGGGGCU GAUGAGGCCG AAAGGCCGAA AAGUACCC                                38

(2) INFORMATION FOR SEQ ID NO: 2244:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2244:

GACCUGUGCU GAUGAGGCCG AAAGGCCGAA AGAAGCCC                                38

(2) INFORMATION FOR SEQ ID NO: 2245:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2245:

CAGUGGCUCU GAUGAGGCCG AAAGGCCGAA ACACAAAA                                38

(2) INFORMATION FOR SEQ ID NO: 2246:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2246:

CAUCCAGUCU GAUGAGGCCG AAAGGCCGAA AGUCUCCA                                38
```

(2) INFORMATION FOR SEQ ID NO: 2247:

(i) SEQUENCE CHARACTERISTICS:
        (A) LENGTH:        38 base pairs
        (B) TYPE:          nucleic acid
        (C) STRANDEDNESS:   single
        (D) TOPOLOGY:      linear (xi) SEQUENCE DESCRIPTION: SEQ ID NO: 2247:

CCCAGGCCCU GAUGAGGCCG AAAGGCCGAA AGGUUCUC                    38

(2) INFORMATION FOR SEQ ID NO: 2248:

(i) SEQUENCE CHARACTERISTICS:
        (A) LENGTH:        38 base pairs
        (B) TYPE:          nucleic acid
        (C) STRANDEDNESS:   single
        (D) TOPOLOGY:      linear (xi) SEQUENCE DESCRIPTION: SEQ ID NO: 2248:

AAGGUAGGCU GAUGAGGCCG AAAGGCCGAA AUGUAUGU                    38

(2) INFORMATION FOR SEQ ID NO: 2249:

(i) SEQUENCE CHARACTERISTICS:
        (A) LENGTH:        38 base pairs
        (B) TYPE:          nucleic acid
        (C) STRANDEDNESS:   single
        (D) TOPOLOGY:      linear (xi) SEQUENCE DESCRIPTION: SEQ ID NO: 2249:

UGUGGCCUCU GAUGAGGCCG AAAGGCCGAA AGGUCCAG                    38

(2) INFORMATION FOR SEQ ID NO: 2250:

(i) SEQUENCE CHARACTERISTICS:
        (A) LENGTH:        38 base pairs
        (B) TYPE:          nucleic acid
        (C) STRANDEDNESS:   single
        (D) TOPOLOGY:      linear (xi) SEQUENCE DESCRIPTION: SEQ ID NO: 2250:

AGUUCUGUCU GAUGAGGCCG AAAGGCCGAA AAGCAUGA                    38

(2) INFORMATION FOR SEQ ID NO: 2251:

(i) SEQUENCE CHARACTERISTICS:
        (A) LENGTH:        38 base pairs
        (B) TYPE:          nucleic acid
        (C) STRANDEDNESS:   single
        (D) TOPOLOGY:      linear (xi) SEQUENCE DESCRIPTION: SEQ ID NO: 2251:

ACUACUGACU GAUGAGGCCG AAAGGCCGAA AGCUGUGU                    38

(2) INFORMATION FOR SEQ ID NO: 2252:

(i) SEQUENCE CHARACTERISTICS:
        (A) LENGTH:        38 base pairs
        (B) TYPE:          nucleic acid
        (C) STRANDEDNESS:   single
        (D) TOPOLOGY:      linear (xi) SEQUENCE DESCRIPTION: SEQ ID NO: 2252:

GCGACCAGCU GAUGAGGCCG AAAGGCCGAA ACCAGGAG                    38

(2) INFORMATION FOR SEQ ID NO: 2253:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2253:

UUCAGUGUCU GAUGAGGCCG AAAGGCCGAA AAUUGGAU                                    38

(2) INFORMATION FOR SEQ ID NO: 2254:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2254:

GCACCGUGCU GAUGAGGCCG AAAGGCCGAA AUGUGAUC                                    38

(2) INFORMATION FOR SEQ ID NO: 2255:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2255:

AGCACCGUCU GAUGAGGCCG AAAGGCCGAA AAUGUGAU                                    38

(2) INFORMATION FOR SEQ ID NO: 2256:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2256:

AACUUGUACU GAUGAGGCCG AAAGGCCGAA AUCCUGAU                                    38

(2) INFORMATION FOR SEQ ID NO: 2257:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2257:

UACAUGUUCU GAUGAGGCCG AAAGGCCGAA ACCUGCUC                                    38

(2) INFORMATION FOR SEQ ID NO: 2258:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2258:

ACCCGUAUCU GAUGAGGCCG AAAGGCCGAA AUCUUUCC                                    38

(2) INFORMATION FOR SEQ ID NO: 2259:

```
    (i) SEQUENCE CHARACTERISTICS:
         (A) LENGTH:           38 base pairs
         (B) TYPE:             nucleic acid
         (C) STRANDEDNESS:     single
         (D) TOPOLOGY:         linear (xi) SEQUENCE DESCRIPTION: SEQ ID NO: 2259:

ACUCAAUACU GAUGAGGCCG AAAGGCCGAA AUAACUGU                          38

(2) INFORMATION FOR SEQ ID NO: 2260:

(i) SEQUENCE CHARACTERISTICS:
         (A) LENGTH:           38 base pairs
         (B) TYPE:             nucleic acid
         (C) STRANDEDNESS:     single
         (D) TOPOLOGY:         linear (xi) SEQUENCE DESCRIPTION: SEQ ID NO: 2260:

CAUUGGAGCU GAUGAGGCCG AAAGGCCGAA ACCAGGGC                          38

(2) INFORMATION FOR SEQ ID NO: 2261:

(i) SEQUENCE CHARACTERISTICS:
         (A) LENGTH:           38 base pairs
         (B) TYPE:             nucleic acid
         (C) STRANDEDNESS:     single
         (D) TOPOLOGY:         linear (xi) SEQUENCE DESCRIPTION: SEQ ID NO: 2261:

GUAACUUGCU GAUGAGGCCG AAAGGCCGAA AUAUCCUG                          38

(2) INFORMATION FOR SEQ ID NO: 2262:

(i) SEQUENCE CHARACTERISTICS:
         (A) LENGTH:           38 base pairs
         (B) TYPE:             nucleic acid
         (C) STRANDEDNESS:     single
         (D) TOPOLOGY:         linear (xi) SEQUENCE DESCRIPTION: SEQ ID NO: 2262:

ACCCGUAUCU GAUGAGGCCG AAAGGCCGAA AUCUUUCC                          38

(2) INFORMATION FOR SEQ ID NO: 2263:

(i) SEQUENCE CHARACTERISTICS:
         (A) LENGTH:           38 base pairs
         (B) TYPE:             nucleic acid
         (C) STRANDEDNESS:     single
         (D) TOPOLOGY:         linear (xi) SEQUENCE DESCRIPTION: SEQ ID NO: 2263:

CCUGUGGACU GAUGAGGCCG AAAGGCCGAA AAGCCCAA                          38

(2) INFORMATION FOR SEQ ID NO: 2264:

(i) SEQUENCE CHARACTERISTICS:
         (A) LENGTH:           38 base pairs
         (B) TYPE:             nucleic acid
         (C) STRANDEDNESS:     single
         (D) TOPOLOGY:         linear (xi) SEQUENCE DESCRIPTION: SEQ ID NO: 2264:

GCCUGGGGCU GAUGAGGCCG AAAGGCCGAA AAGUACCC                          38

(2) INFORMATION FOR SEQ ID NO: 2265:

(i) SEQUENCE CHARACTERISTICS:
```

```
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2265:

UGAGCACCCU GAUGAGGCCG AAAGGCCGAA ACAGGCCC                              38

(2) INFORMATION FOR SEQ ID NO: 2266:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2266:

GAGAGGUCCU GAUGAGGCCG AAAGGCCGAA ACGAGCAG                              38

(2) INFORMATION FOR SEQ ID NO: 2267:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2267:

UGUGGGAGCU GAUGAGGCCG AAAGGCCGAA AGGCAGGG                              38

(2) INFORMATION FOR SEQ ID NO: 2268:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2268:

UUCUGUGGCU GAUGAGGCCG AAAGGCCGAA AUGGAUGG                              38

(2) INFORMATION FOR SEQ ID NO: 2269:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2269:

CUUCCAGGCU GAUGAGGCCG AAAGGCCGAA AACACAAG                              38

(2) INFORMATION FOR SEQ ID NO: 2270:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2270:

AAGAGGAACU GAUGAGGCCG AAAGGCCGAA AGCAGUUC                              38

(2) INFORMATION FOR SEQ ID NO: 2271:

(i) SEQUENCE CHARACTERISTICS:
            (A) LENGTH:              38 base pairs
```

```
        (B) TYPE:              nucleic acid
        (C) STRANDEDNESS:      single
        (D) TOPOLOGY:          linear (xi) SEQUENCE DESCRIPTION: SEQ ID NO: 2271:

UAAUAGAGCU GAUGAGGCCG AAAGGCCGAA AGGAAGUC                              38

(2) INFORMATION FOR SEQ ID NO: 2272:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2272:

UCGUGAAACU GAUGAGGCCG AAAGGCCGAA AAAUCAGC                              38

(2) INFORMATION FOR SEQ ID NO: 2273:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2273:

CGCAAGAGCU GAUGAGGCCG AAAGGCCGAA AAGAGCAG                              38

(2) INFORMATION FOR SEQ ID NO: 2274:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2274:

ACUCGUGACU GAUGAGGCCG AAAGGCCGAA AGAAAUCA                              38

(2) INFORMATION FOR SEQ ID NO: 2275:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2275:

UGACUCGUCU GAUGAGGCCG AAAGGCCGAA AAAGAAAU                              38

(2) INFORMATION FOR SEQ ID NO: 2276:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2276:

CUUGUGUCCU GAUGAGGCCG AAAGGCCGAA ACCGGAUA                              38

(2) INFORMATION FOR SEQ ID NO: 2277:

(i) SEQUENCE CHARACTERISTICS:
        (A) LENGTH:            38 base pairs
        (B) TYPE:              nucleic acid
```

```
            (C) STRANDEDNESS:        single
            (D) TOPOLOGY:            linear (xi) SEQUENCE DESCRIPTION: SEQ ID NO: 2277:

CGUCCACACU GAUGAGGCCG AAAGGCCGAA AGUAUUUA                            38

(2) INFORMATION FOR SEQ ID NO: 2278:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2278:

GAGGACCACU GAUGAGGCCG AAAGGCCGAA AUAGCACA                            38

(2) INFORMATION FOR SEQ ID NO: 2279:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2279:

UGAAGCAUCU GAUGAGGCCG AAAGGCCGAA AGAAAUUG                            38

(2) INFORMATION FOR SEQ ID NO: 2280:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2280:

AACUUGUACU GAUGAGGCCG AAAGGCCGAA AUCCUGAU                            38

(2) INFORMATION FOR SEQ ID NO: 2281:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2281:

AGUUCUGUCU GAUGAGGCCG AAAGGCCGAA AAGCAUGA                            38

(2) INFORMATION FOR SEQ ID NO: 2282:

(i) SEQUENCE CHARACTERISTICS:
            (A) LENGTH:              38 base pairs
            (B) TYPE:                nucleic acid
            (C) STRANDEDNESS:        single
            (D) TOPOLOGY:            linear (xi) SEQUENCE DESCRIPTION: SEQ ID NO: 2282:

GAACUCUGCU GAUGAGGCCG AAAGGCCGAA AUUAAUAA                            38

(2) INFORMATION FOR SEQ ID NO: 2283:

(i) SEQUENCE CHARACTERISTICS:
            (A) LENGTH:              38 base pairs
            (B) TYPE:                nucleic acid
            (C) STRANDEDNESS:        single
```

(D) TOPOLOGY:          linear (xi) SEQUENCE DESCRIPTION: SEQ ID NO: 2283:

UAGUCUCCCU GAUGAGGCCG AAAGGCCGAA ACCCCAGG                         38

(2) INFORMATION FOR SEQ ID NO: 2284:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2284:

AACUGUCACU GAUGAGGCCG AAAGGCCGAA AACUCUGA                         38

(2) INFORMATION FOR SEQ ID NO: 2285:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2285:

UCGUUUGUCU GAUGAGGCCG AAAGGCCGAA AUCCUCCG                         38

(2) INFORMATION FOR SEQ ID NO: 2286:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2286:

GGGGGAAGCU GAUGAGGCCG AAAGGCCGAA ACUGUUCA                         38

(2) INFORMATION FOR SEQ ID NO: 2287:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2287:

CGAGGCAGCU GAUGAGGCCG AAAGGCCGAA AAGGCUUC                         38

(2) INFORMATION FOR SEQ ID NO: 2288:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2288:

GAGGCAGGCU GAUGAGGCCG AAAGGCCGAA AACAGGCC                         38

(2) INFORMATION FOR SEQ ID NO: 2289:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2289:

AGAGGCAGCU GAUGAGGCCG AAAGGCCGAA AAACAGGC                                    38

(2) INFORMATION FOR SEQ ID NO: 2290:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2290:

AACAAAGGCU GAUGAGGCCG AAAGGCCGAA AGGAAUGU                                    38

(2) INFORMATION FOR SEQ ID NO: 2291:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2291:

UGUGGGAGCU GAUGAGGCCG AAAGGCCGAA AGGCAGGG                                    38

(2) INFORMATION FOR SEQ ID NO: 2292:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2292:

UUGGGAACCU GAUGAGGCCG AAAGGCCGAA AAGGUAGG                                    38

(2) INFORMATION FOR SEQ ID NO: 2293:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2293:

GGCGGUAACU GAUGAGGCCG AAAGGCCGAA AGGUGUAA                                    38

(2) INFORMATION FOR SEQ ID NO: 2294:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2294:

GGGAUCACCU GAUGAGGCCG AAAGGCCGAA ACGGCGAC                                    38

(2) INFORMATION FOR SEQ ID NO: 2295:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2295:

ACAUUGGGCU GAUGAGGCCG AAAGGCCGAA ACAAAGGU                                    38

(2) INFORMATION FOR SEQ ID NO: 2296:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2296:

GACAUUGGCU GAUGAGGCCG AAAGGCCGAA AACAAAGG                                    38

(2) INFORMATION FOR SEQ ID NO: 2297:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2297:

UAGGUGGGCU GAUGAGGCCG AAAGGCCGAA AGGUGGUC                                    38

(2) INFORMATION FOR SEQ ID NO: 2298:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2298:

UAGGAAUGCU GAUGAGGCCG AAAGGCCGAA AUGUAGGU                                    38

(2) INFORMATION FOR SEQ ID NO: 2299:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2299:

AAGGUAGGCU GAUGAGGCCG AAAGGCCGAA AUGUAUGU                                    38

(2) INFORMATION FOR SEQ ID NO: 2300:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2300:

AAAGGUAGCU GAUGAGGCCG AAAGGCCGAA AAUGUAUG                                    38

(2) INFORMATION FOR SEQ ID NO: 2301:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2301:

AAUAGGUGCU GAUGAGGCCG AAAGGCCGAA AAAUGGAC                                    38

(2) INFORMATION FOR SEQ ID NO: 2302:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2302:

ACAUUGGGCU GAUGAGGCCG AAAGGCCGAA ACAAAGGU                                    38

(2) INFORMATION FOR SEQ ID NO: 2303:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2303:

GACAUUGGCU GAUGAGGCCG AAAGGCCGAA AACAAAGG                                    38

(2) INFORMATION FOR SEQ ID NO: 2304:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2304:

UGAGGGUCU GAUGAGGCCG AAAGGCCGAA AAUGCUGU                                     38

(2) INFORMATION FOR SEQ ID NO: 2305:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2305:

GGAUACCUCU GAUGAGGCCG AAAGGCCGAA AGCACCGA                                    38

(2) INFORMATION FOR SEQ ID NO: 2306:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2306:

AAAGUCCGCU GAUGAGGCCG AAAGGCCGAA AGCUGCCU                                    38

(2) INFORMATION FOR SEQ ID NO: 2307:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2307:

```
CUGACACACU GAUGAGGCCG AAAGGCCGAA AAUCUCUG                                    38

(2) INFORMATION FOR SEQ ID NO: 2308:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2308:

CCAGGGCACU GAUGAGGCCG AAAGGCCGAA AGUGCAGG                                    38

(2) INFORMATION FOR SEQ ID NO: 2309:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2309:

GAGAGGUCCU GAUGAGGCCG AAAGGCCGAA ACGAGCAG                                    38

(2) INFORMATION FOR SEQ ID NO: 2310:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2310:

GGCUGUGGCU GAUGAGGCCG AAAGGCCGAA AGGAGGCA                                    38

(2) INFORMATION FOR SEQ ID NO: 2311:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2311:

CUUCGCAACU GAUGAGGCCG AAAGGCCGAA AGGAAGAG                                    38

(2) INFORMATION FOR SEQ ID NO: 2312:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2312:

AGCAGGGGCU GAUGAGGCCG AAAGGCCGAA AAUAGAGA                                    38

(2) INFORMATION FOR SEQ ID NO: 2313:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2313:

GCGACCAGCU GAUGAGGCCG AAAGGCCGAA ACCAGGAG                                    38
```

(2) INFORMATION FOR SEQ ID NO: 2314:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2314:

GAGGACCACU GAUGAGGCCG AAAGGCCGAA AUAGCACA                  38

(2) INFORMATION FOR SEQ ID NO: 2315:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2315:

ACAACGGCCU GAUGAGGCCG AAAGGCCGAA ACCAGGAC                  38

(2) INFORMATION FOR SEQ ID NO: 2316:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2316:

CCUGGUGACU GAUGAGGCCG AAAGGCCGAA ACUCCCAC                  38

(2) INFORMATION FOR SEQ ID NO: 2317:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2317:

UCCCACGGCU GAUGAGGCCG AAAGGCCGAA AGCUAAAG                  38

(2) INFORMATION FOR SEQ ID NO: 2318:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2318:

CAUCCAGUCU GAUGAGGCCG AAAGGCCGAA AGUCUCCA                  38

(2) INFORMATION FOR SEQ ID NO: 2319:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2319:

AACUGUCACU GAUGAGGCCG AAAGGCCGAA AACUCUGA                  38

(2) INFORMATION FOR SEQ ID NO: 2320:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2320:

AGCAGCACCU GAUGAGGCCG AAAGGCCGAA ACUGAGAG                        38

(2) INFORMATION FOR SEQ ID NO: 2321:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2321:

GGAGCUGACU GAUGAGGCCG AAAGGCCGAA AAGUUGUA                        38

(2) INFORMATION FOR SEQ ID NO: 2322:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2322:

GUGAAUUGCU GAUGAGGCCG AAAGGCCGAA AUCUGUGA                        38

(2) INFORMATION FOR SEQ ID NO: 2323:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2323:

UGGAUGGACU GAUGAGGCCG AAAGGCCGAA ACCUGAGC                        38

(2) INFORMATION FOR SEQ ID NO: 2324:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2324:

AAUGUAUGCU GAUGAGGCCG AAAGGCCGAA AGGUGGGG                        38

(2) INFORMATION FOR SEQ ID NO: 2325:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2325:

AGAGGCAGCU GAUGAGGCCG AAAGGCCGAA AAACAGGC                        38

```
(2) INFORMATION FOR SEQ ID NO: 2326:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2326:

AGCACCCUCU GAUGAGGCCG AAAGGCCGAA ACCUGUGG                               38

(2) INFORMATION FOR SEQ ID NO: 2327:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2327:

GCUUGCAGCU GAUGAGGCCG AAAGGCCGAA ACCCUUCU                               38

(2) INFORMATION FOR SEQ ID NO: 2328:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2328:

AGCUUCAGCU GAUGAGGCCG AAAGGCCGAA ACCCUAGU                               38

(2) INFORMATION FOR SEQ ID NO: 2329:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2329:

AGUCCUCUCU GAUGAGGCCG AAAGGCCGAA AGGCCUGA                               38

(2) INFORMATION FOR SEQ ID NO: 2330:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2330:

CCUGGGGCU GAUGAGGCCG AAAGGCCGAA AGUACCCU                                38

(2) INFORMATION FOR SEQ ID NO: 2331:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2331:

UAGGUGGGCU GAUGAGGCCG AAAGGCCGAA AGGUGGUC                               38

(2) INFORMATION FOR SEQ ID NO: 2332:
```

(i) SEQUENCE CHARACTERISTICS:
    (A) LENGTH:          38 base pairs
    (B) TYPE:            nucleic acid
    (C) STRANDEDNESS:    single
    (D) TOPOLOGY:        linear (xi) SEQUENCE DESCRIPTION: SEQ ID NO: 2332:

ACCUUCCUCU GAUGAGGCCG AAAGGCCGAA AGGUAGGG                      38

(2) INFORMATION FOR SEQ ID NO: 2333:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2333:

CACCUUCCCU GAUGAGGCCG AAAGGCCGAA AAGGUAGG                      38

(2) INFORMATION FOR SEQ ID NO: 2334:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2334:

ACCCGUAUCU GAUGAGGCCG AAAGGCCGAA AUCUUUCC                      38

(2) INFORMATION FOR SEQ ID NO: 2335:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2335:

CAAACCCGCU GAUGAGGCCG AAAGGCCGAA AUGAUCUU                      38

(2) INFORMATION FOR SEQ ID NO: 2336:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2336:

CCUGCACGCU GAUGAGGCCG AAAGGCCGAA AUCCACCC                      38

(2) INFORMATION FOR SEQ ID NO: 2337:

(i) SEQUENCE CHARACTERISTICS:
        (A) LENGTH:          38 base pairs
        (B) TYPE:            nucleic acid
        (C) STRANDEDNESS:    single
        (D) TOPOLOGY:        linear (xi) SEQUENCE DESCRIPTION: SEQ ID NO: 2337:

GGUUUUUACU GAUGAGGCCG AAAGGCCGAA ACAGGGAC                      38

(2) INFORMATION FOR SEQ ID NO: 2338:

```
    (i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2338:

CCACUCGACU GAUGAGGCCG AAAGGCCGAA AGUUCGUC                              38

(2) INFORMATION FOR SEQ ID NO: 2339:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2339:

GGAAGAUCCU GAUGAGGCCG AAAGGCCGAA AAAGUCCG                              38

(2) INFORMATION FOR SEQ ID NO: 2340:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2340:

AGGCCGCACU GAUGAGGCCG AAAGGCCGAA AGCAAAAG                              38

(2) INFORMATION FOR SEQ ID NO: 2341:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2341:

GCAGGGUCU GAUGAGGCCG AAAGGCCGAA AUAGAGAA                               38

(2) INFORMATION FOR SEQ ID NO: 2342:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2342:

UUGACCAUCU GAUGAGGCCG AAAGGCCGAA AUUUCACG                              38

(2) INFORMATION FOR SEQ ID NO: 2343:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2343:

GUUCUGUGCU GAUGAGGCCG AAAGGCCGAA AGCAUGAG                              38

(2) INFORMATION FOR SEQ ID NO: 2344:

(i) SEQUENCE CHARACTERISTICS:
```

(A) LENGTH:           38 base pairs
            (B) TYPE:             nucleic acid
            (C) STRANDEDNESS:     single
            (D) TOPOLOGY:         linear (xi) SEQUENCE DESCRIPTION: SEQ ID NO: 2344:

AGUUCUGUCU GAUGAGGCCG AAAGGCCGAA AAGCAUGA                              38

(2) INFORMATION FOR SEQ ID NO: 2345:

(i) SEQUENCE CHARACTERISTICS:
            (A) LENGTH:           38 base pairs
            (B) TYPE:             nucleic acid
            (C) STRANDEDNESS:     single
            (D) TOPOLOGY:         linear (xi) SEQUENCE DESCRIPTION: SEQ ID NO: 2345:

AGGGUCAGCU GAUGAGGCCG AAAGGCCGAA AUGGGAGC                              38

(2) INFORMATION FOR SEQ ID NO: 2346:

(i) SEQUENCE CHARACTERISTICS:
            (A) LENGTH:           38 base pairs
            (B) TYPE:             nucleic acid
            (C) STRANDEDNESS:     single
            (D) TOPOLOGY:         linear (xi) SEQUENCE DESCRIPTION: SEQ ID NO: 2346:

GGAAGAUCCU GAUGAGGCCG AAAGGCCGAA AAAGUCCG                              38

(2) INFORMATION FOR SEQ ID NO: 2347:

(i) SEQUENCE CHARACTERISTICS:
            (A) LENGTH:           38 base pairs
            (B) TYPE:             nucleic acid
            (C) STRANDEDNESS:     single
            (D) TOPOLOGY:         linear (xi) SEQUENCE DESCRIPTION: SEQ ID NO: 2347:

ACCUCCAGCU GAUGAGGCCG AAAGGCCGAA AGGUCAGG                              38

(2) INFORMATION FOR SEQ ID NO: 2348:

(i) SEQUENCE CHARACTERISTICS:
            (A) LENGTH:           38 base pairs
            (B) TYPE:             nucleic acid
            (C) STRANDEDNESS:     single
            (D) TOPOLOGY:         linear (xi) SEQUENCE DESCRIPTION: SEQ ID NO: 2348:

GGAGCUGACU GAUGAGGCCG AAAGGCCGAA AAGUUGUA                              38

(2) INFORMATION FOR SEQ ID NO: 2349:

(i) SEQUENCE CHARACTERISTICS:
            (A) LENGTH:           38 base pairs
            (B) TYPE:             nucleic acid
            (C) STRANDEDNESS:     single
            (D) TOPOLOGY:         linear (xi) SEQUENCE DESCRIPTION: SEQ ID NO: 2349:

UGGGAGCUCU GAUGAGGCCG AAAGGCCGAA AAAAGUUG                              38

(2) INFORMATION FOR SEQ ID NO: 2350:

(i) SEQUENCE CHARACTERISTICS:
            (A) LENGTH:           38 base pairs

```
        (B) TYPE:              nucleic acid
        (C) STRANDEDNESS:      single
        (D) TOPOLOGY:          linear (xi) SEQUENCE DESCRIPTION: SEQ ID NO: 2350:

GGAUACCUCU GAUGAGGCCG AAAGGCCGAA AGCACCGA                              38

(2) INFORMATION FOR SEQ ID NO: 2351:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2351:

GGGGGAAGCU GAUGAGGCCG AAAGGCCGAA ACCCUGUG                              38

(2) INFORMATION FOR SEQ ID NO: 2352:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2352:

UGCGCUGGCU GAUGAGGCCG AAAGGCCGAA AGGGGUGC                              38

(2) INFORMATION FOR SEQ ID NO: 2353:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2353:

AGGUGGGUCU GAUGAGGCCG AAAGGCCGAA AGGGGUAA                              38

(2) INFORMATION FOR SEQ ID NO: 2354:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2354:

CUAGUCGGCU GAUGAGGCCG AAAGGCCGAA AGAUCGAA                              38

(2) INFORMATION FOR SEQ ID NO: 2355:

(i) SEQUENCE CHARACTERISTICS:
        (A) LENGTH:            38 base pairs
        (B) TYPE:              nucleic acid
        (C) STRANDEDNESS:      single
        (D) TOPOLOGY:          linear (xi) SEQUENCE DESCRIPTION: SEQ ID NO: 2355:

UUCCAGGGCU GAUGAGGCCG AAAGGCCGAA ACACAAGA                              38

(2) INFORMATION FOR SEQ ID NO: 2356:

(i) SEQUENCE CHARACTERISTICS:
        (A) LENGTH:            38 base pairs
        (B) TYPE:              nucleic acid
```

```
            (C) STRANDEDNESS:        single
            (D) TOPOLOGY:            linear (xi) SEQUENCE DESCRIPTION: SEQ ID NO: 2356:

UGAGCACCCU GAUGAGGCCG AAAGGCCGAA ACAGGCCC                              38

(2) INFORMATION FOR SEQ ID NO: 2357:

(i) SEQUENCE CHARACTERISTICS:
            (A) LENGTH:             38 base pairs
            (B) TYPE:               nucleic acid
            (C) STRANDEDNESS:       single
            (D) TOPOLOGY:           linear (xi) SEQUENCE DESCRIPTION: SEQ ID NO: 2357:

GGUGCUGGCU GAUGAGGCCG AAAGGCCGAA AGACUCCA                              38

(2) INFORMATION FOR SEQ ID NO: 2358:

(i) SEQUENCE CHARACTERISTICS:
            (A) LENGTH:             38 base pairs
            (B) TYPE:               nucleic acid
            (C) STRANDEDNESS:       single
            (D) TOPOLOGY:           linear (xi) SEQUENCE DESCRIPTION: SEQ ID NO: 2358:

AAAGUCCGCU GAUGAGGCCG AAAGGCCGAA AGCUGCCU                              38

(2) INFORMATION FOR SEQ ID NO: 2359:

(i) SEQUENCE CHARACTERISTICS:
            (A) LENGTH:             38 base pairs
            (B) TYPE:               nucleic acid
            (C) STRANDEDNESS:       single
            (D) TOPOLOGY:           linear (xi) SEQUENCE DESCRIPTION: SEQ ID NO: 2359:

AGAGAAGGCU GAUGAGGCCG AAAGGCCGAA AGUCAGCC                              38

(2) INFORMATION FOR SEQ ID NO: 2360:

(i) SEQUENCE CHARACTERISTICS:
            (A) LENGTH:             38 base pairs
            (B) TYPE:               nucleic acid
            (C) STRANDEDNESS:       single
            (D) TOPOLOGY:           linear (xi) SEQUENCE DESCRIPTION: SEQ ID NO: 2360:

AAGAGGAACU GAUGAGGCCG AAAGGCCGAA AGCAGUUC                              38

(2) INFORMATION FOR SEQ ID NO: 2361:

(i) SEQUENCE CHARACTERISTICS:
            (A) LENGTH:             38 base pairs
            (B) TYPE:               nucleic acid
            (C) STRANDEDNESS:       single
            (D) TOPOLOGY:           linear (xi) SEQUENCE DESCRIPTION: SEQ ID NO: 2361:

AGAGAAGGCU GAUGAGGCCG AAAGGCCGAA AGUCAGCC                              38

(2) INFORMATION FOR SEQ ID NO: 2362:

(i) SEQUENCE CHARACTERISTICS:
            (A) LENGTH:             38 base pairs
            (B) TYPE:               nucleic acid
            (C) STRANDEDNESS:       single
```

(D) TOPOLOGY:          linear (xi) SEQUENCE DESCRIPTION: SEQ ID NO: 2362:

UUAAUAAACU GAUGAGGCCG AAAGGCCGAA ACAUCAAC                                    38

(2) INFORMATION FOR SEQ ID NO: 2363:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2363:

CGCAAGAGCU GAUGAGGCCG AAAGGCCGAA AAGAGCAG                                    38

(2) INFORMATION FOR SEQ ID NO: 2364:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2364:

AAUUAAUACU GAUGAGGCCG AAAGGCCGAA AUACAUCA                                    38

(2) INFORMATION FOR SEQ ID NO: 2365:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2365:

AAGAGGAACU GAUGAGGCCG AAAGGCCGAA AGCAGUUC                                    38

(2) INFORMATION FOR SEQ ID NO: 2366:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2366:

GUAAUAGACU GAUGAGGCCG AAAGGCCGAA AAGGAAGU                                    38

(2) INFORMATION FOR SEQ ID NO: 2367:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2367:

GGGUAAUACU GAUGAGGCCG AAAGGCCGAA AGAAGGAA                                    38

(2) INFORMATION FOR SEQ ID NO: 2368:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 2368:

UGAAUUAACU GAUGAGGCCG AAAGGCCGAA AAAUACAU                                38

(2) INFORMATION FOR SEQ ID NO: 2369:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2369:

CUGGGAACCU GAUGAGGCCG AAAGGCCGAA AAUACACA                                38

(2) INFORMATION FOR SEQ ID NO: 2370:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2370:

UCUGAAUUCU GAUGAGGCCG AAAGGCCGAA AUAAAUAC                                38

(2) INFORMATION FOR SEQ ID NO: 2371:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2371:

CUCUGAAUCU GAUGAGGCCG AAAGGCCGAA AAUAAAUA                                38

(2) INFORMATION FOR SEQ ID NO: 2372:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2372:

CUUCGCAACU GAUGAGGCCG AAAGGCCGAA AGGAAGAG                                38

(2) INFORMATION FOR SEQ ID NO: 2373:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2373:

GUCUUCGCCU GAUGAGGCCG AAAGGCCGAA AGAGGAAG                                38

(2) INFORMATION FOR SEQ ID NO: 2374:

(i) SEQUENCE CHARACTERISTICS:
        (A) LENGTH:         38 base pairs
        (B) TYPE:           nucleic acid
        (C) STRANDEDNESS:   single
        (D) TOPOLOGY:       linear (xi) SEQUENCE DESCRIPTION: SEQ ID NO: 2374:

UGACUCGUCU GAUGAGGCCG AAAGGCCGAA AAAGAAAU					38

(2) INFORMATION FOR SEQ ID NO: 2375:

(i) SEQUENCE CHARACTERISTICS:
        (A) LENGTH:					38 base pairs
        (B) TYPE:					nucleic acid
        (C) STRANDEDNESS:		single
        (D) TOPOLOGY:				linear (xi) SEQUENCE DESCRIPTION: SEQ ID NO: 2375:

CAGUGGCUCU GAUGAGGCCG AAAGGCCGAA ACACAAAA					38

(2) INFORMATION FOR SEQ ID NO: 2376:

(i) SEQUENCE CHARACTERISTICS:
        (A) LENGTH:					38 base pairs
        (B) TYPE:					nucleic acid
        (C) STRANDEDNESS:		single
        (D) TOPOLOGY:				linear (xi) SEQUENCE DESCRIPTION: SEQ ID NO: 2376:

GGCAGCGGCU GAUGAGGCCG AAAGGCCGAA ACACCAUC					38

(2) INFORMATION FOR SEQ ID NO: 2377:

(i) SEQUENCE CHARACTERISTICS:
        (A) LENGTH:					38 base pairs
        (B) TYPE:					nucleic acid
        (C) STRANDEDNESS:		single
        (D) TOPOLOGY:				linear (xi) SEQUENCE DESCRIPTION: SEQ ID NO: 2377:

GGUGCUGGCU GAUGAGGCCG AAAGGCCGAA AGACUCCA					38

(2) INFORMATION FOR SEQ ID NO: 2378:

(i) SEQUENCE CHARACTERISTICS:
        (A) LENGTH:					38 base pairs
        (B) TYPE:					nucleic acid
        (C) STRANDEDNESS:		single
        (D) TOPOLOGY:				linear (xi) SEQUENCE DESCRIPTION: SEQ ID NO: 2378:

GCCUGGGGCU GAUGAGGCCG AAAGGCCGAA AAGUACUG					38

(2) INFORMATION FOR SEQ ID NO: 2379:

(i) SEQUENCE CHARACTERISTICS:
        (A) LENGTH:					38 base pairs
        (B) TYPE:					nucleic acid
        (C) STRANDEDNESS:		single
        (D) TOPOLOGY:				linear (xi) SEQUENCE DESCRIPTION: SEQ ID NO: 2379:

GUCAGAGGCU GAUGAGGCCG AAAGGCCGAA AGCAUGGU					38

(2) INFORMATION FOR SEQ ID NO: 2380:

(i) SEQUENCE CHARACTERISTICS:
        (A) LENGTH:					38 base pairs
        (B) TYPE:					nucleic acid
        (C) STRANDEDNESS:		single
        (D) TOPOLOGY:				linear (xi) SEQUENCE DESCRIPTION: SEQ ID NO: 2380:

GAAGAUCGCU GAUGAGGCCG AAAGGCCGAA AAGUCCGG                                    38

(2) INFORMATION FOR SEQ ID NO: 2381:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2381:

CCAUGUCACU GAUGAGGCCG AAAGGCCGAA AGGAAGCA                                    38

(2) INFORMATION FOR SEQ ID NO: 2382:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2382:

AUUGAUUCCU GAUGAGGCCG AAAGGCCGAA AAGGAAAG                                    38

(2) INFORMATION FOR SEQ ID NO: 2383:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2383:

CAGUGGCUCU GAUGAGGCCG AAAGGCCGAA ACACAAAA                                    38

(2) INFORMATION FOR SEQ ID NO: 2384:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2384:

CUGGGAACCU GAUGAGGCCG AAAGGCCGAA AAUACACA                                    38

(2) INFORMATION FOR SEQ ID NO: 2385:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2385:

ACUUUAUUCU GAUGAGGCCG AAAGGCCGAA AUUCAAAG                                    38

(2) INFORMATION FOR SEQ ID NO: 2386:

(i) SEQUENCE CHARACTERISTICS:
        (A) LENGTH:        38 base pairs
        (B) TYPE:          nucleic acid
        (C) STRANDEDNESS:  single
        (D) TOPOLOGY:      linear (xi) SEQUENCE DESCRIPTION: SEQ ID NO: 2386:

```
                                                            -continued
AGCUUGAACU GAUGAGGCCG AAAGGCCGAA AGCUUCCA                                38

(2) INFORMATION FOR SEQ ID NO: 2387:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2387:

UAAAACUUCU GAUGAGGCCG AAAGGCCGAA AUUGAUUC                                 38

(2) INFORMATION FOR SEQ ID NO: 2388:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2388:

AGCUUGAACU GAUGAGGCCG AAAGGCCGAA AGCUUCCA                                 38

(2) INFORMATION FOR SEQ ID NO: 2389:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2389:

CAGGUGAGCU GAUGAGGCCG AAAGGCCGAA ACCAUAUA                                 38

(2) INFORMATION FOR SEQ ID NO: 2390:

(i) SEQUENCE CHARACTERISTICS:
        (A) LENGTH:           38 base pairs
        (B) TYPE:             nucleic acid
        (C) STRANDEDNESS:     single
        (D) TOPOLOGY:         linear (xi) SEQUENCE DESCRIPTION: SEQ ID NO: 2390:

UCAGCUUGCU GAUGAGGCCG AAAGGCCGAA AGAGCUUC                                 38
```